(12) United States Patent
Burkin et al.

(10) Patent No.: US 10,537,553 B2
(45) Date of Patent: Jan. 21, 2020

(54) METHODS OF TREATING MUSCULAR DYSTROPHY

(71) Applicant: Board of Regents of the Nevada System of Higher Education, on Behalf of the University of Nevada, Reno, Reno, NV (US)

(72) Inventors: Dean Burkin, Sparks, NV (US); Ryan Wuebbles, Sparks, NV (US)

(73) Assignee: BOARD OF REGENTS OF THE NEVADA SYSTEM OF HIGHER EDUCATION ON BEHALF OF THE UNIVERSITY OF NEVADA, RENO, Reno, NV (US)

(*) Notice: Subject to any disclaimer, the term of this patent is extended or adjusted under 35 U.S.C. 154(b) by 0 days.

(21) Appl. No.: 16/236,244

(22) Filed: Dec. 28, 2018

(65) Prior Publication Data

US 2019/0240195 A1 Aug. 8, 2019

Related U.S. Application Data

(60) Continuation of application No. 15/961,408, filed on Apr. 24, 2018, now Pat. No. 10,206,903, which is a continuation of application No. 15/619,256, filed on Jun. 9, 2017, now Pat. No. 9,980,943, which is a division of application No. 14/776,898, filed as application No. PCT/US2014/029085 on Mar. 14, 2014, now Pat. No. 9,707,210.

(60) Provisional application No. 61/798,479, filed on Mar. 15, 2013.

(51) Int. Cl.
*A61K 31/404* (2006.01)
*A61K 45/06* (2006.01)

(52) U.S. Cl.
CPC ............ *A61K 31/404* (2013.01); *A61K 45/06* (2013.01)

(58) Field of Classification Search
CPC ............................ A61K 31/404; A61K 45/06
USPC ........................................................ 424/93.7
See application file for complete search history.

(56) References Cited

U.S. PATENT DOCUMENTS

| 5,444,158 | A | 8/1995 | Engvall et al. |
|---|---|---|---|
| 6,294,356 | B1 | 9/2001 | Jones et al. |
| 6,566,074 | B1 | 5/2003 | Goetinck |
| 6,632,790 | B1 | 10/2003 | Yurchenco |
| 6,638,907 | B1 | 10/2003 | Kortesmaa et al. |
| 6,682,911 | B1 | 1/2004 | Burgeson et al. |
| 6,693,169 | B1 | 2/2004 | Brunken et al. |
| 6,858,395 | B2 | 2/2005 | Kaufman |
| 6,933,280 | B2 | 8/2005 | Castillo et al. |
| 7,078,379 | B2 | 7/2006 | Rüegg |
| 8,193,145 | B2 | 6/2012 | Burkin et al. |
| 9,248,185 | B2 | 2/2016 | Rubin et al. |
| 9,566,310 | B2 | 2/2017 | Burkin et al. |
| 9,707,210 | B2 | 7/2017 | Burkin et al. |
| 9,782,417 | B2 | 10/2017 | Rubin et al. |
| 9,980,943 | B2 | 5/2018 | Burkin et al. |
| 10,028,992 | B2 | 7/2018 | Burkin et al. |
| 2002/0111309 | A1 | 8/2002 | Castillo et al. |
| 2002/0192710 | A1 | 12/2002 | Kaufman |
| 2003/0013648 | A1 | 1/2003 | Castillo et al. |
| 2003/0224981 | A1 | 12/2003 | Ruegg |
| 2003/0232431 | A1 | 12/2003 | Law |
| 2004/0014665 | A1 | 1/2004 | Boutaud |
| 2005/0069985 | A1 | 3/2005 | Kaufman |
| 2005/0165039 | A1 | 7/2005 | Meissner et al. |
| 2005/0244384 | A1 | 11/2005 | Law |
| 2006/0014281 | A1 | 1/2006 | Conti et al. |
| 2006/0014287 | A1 | 1/2006 | Sherwood et al. |
| 2006/0105455 | A1 | 5/2006 | Guarino et al. |
| 2006/0223888 | A1 | 10/2006 | Abbott et al. |
| 2007/0025972 | A1 | 2/2007 | Rodriguez et al. |
| 2007/0154552 | A1 | 7/2007 | Siegal et al. |
| 2009/0092587 | A1 | 4/2009 | Burkin et al. |

(Continued)

FOREIGN PATENT DOCUMENTS

| EP | 1764367 A1 | 3/2007 |
|---|---|---|
| JP | 2005194198 A | 7/2005 |

(Continued)

OTHER PUBLICATIONS

Wagner, Kathryn R., et al.; Current treatment of adult Duchenne muscular dystrophy; Biochimica et Biophysyca Acta; 1772, p. 229-237; 2007.

(Continued)

*Primary Examiner* — Kristin A Vajda
(74) *Attorney, Agent, or Firm* — Schwabe Williamson & Wyatt, P.C.

(57) ABSTRACT

Disclosed herein are α7β1 integrin modulatory agents and methods of using such to treat conditions associated with decreased α7β1 integrin expression or activity, including muscular dystrophy. In one example, methods for treating a subject with muscular dystrophy are disclosed. The methods include administering an effective amount of an α7β1 integrin modulatory agent to the subject with muscular dystrophy, wherein the α7β1 integrin modulatory agent increases α7β1 integrin expression or activity as compared to α7β1 integrin expression or activity prior to treatment, thereby treating the subject with muscular dystrophy. Also disclosed are methods of enhancing muscle regeneration, repair, or maintenance in a subject and methods of enhancing α7β1 integrin expression by use of the disclosed α7β1 integrin modulatory agents. Methods of prospectively preventing or reducing muscle injury or damage in a subject are also disclosed.

20 Claims, 26 Drawing Sheets

(56) References Cited

U.S. PATENT DOCUMENTS

| | | |
|---|---|---|
| 2011/0224128 A1 | 9/2011 | Whalen et al. |
| 2012/0207720 A1 | 8/2012 | Burkin et al. |
| 2014/0072536 A1 | 3/2014 | Burkin et al. |
| 2015/0290276 A1 | 10/2015 | Burkin et al. |
| 2016/0030390 A1 | 2/2016 | Burkin et al. |
| 2017/0224657 A1 | 8/2017 | Burkin et al. |
| 2017/0340606 A1 | 11/2017 | Burkin et al. |
| 2018/0235932 A1 | 8/2018 | Burkin et al. |

FOREIGN PATENT DOCUMENTS

| | | | |
|---|---|---|---|
| WO | 9738729 A1 | 10/1997 | |
| WO | 2007075911 A2 | 7/2007 | |
| WO | 2008021210 A2 | 2/2008 | |
| WO | 2009048778 A2 | 4/2009 | |
| WO | 2010080581 A2 | 7/2010 | |
| WO | 2012174126 A1 | 12/2012 | |
| WO | 2013138623 A1 | 9/2013 | |
| WO | 2014040077 A1 | 3/2014 | |

OTHER PUBLICATIONS

Wang et al., "Binding of Injected Laminin to Developing Kidney Glomerular Mesangial Matrices and Basement Membranes in Vivo," Journal of Histochemistry & Cytochemistry, vol. 46, No. 3, pp. 291-300, 1998.

Wang et al., "Cardiomyopathy Associated with Microcirculation Dysfunction in Laminin α4 Chain-deficient Mice," Journal of Biological Chemistry, vol. 281, No. 1, pp. 213-220, 2006.

Weber-Schuerholz et al., "Muscle regeneration possible mitogenic role of laminin and its proteolytic fragements," European Journal of Cell Biology Supplement, p. 42 (Abstract) Jan. 1, 1990.

Wikipedia, "Agrin," 2 pp., downloaded from the World Wide Web at http://en.wikipedia.org/w/index.php?title=Agrin (marked Sep. 19, 2007).

Wikipedia. "Basil lamina," 2 pp., downloaded from the World Wide Web at http://en.wikipedia.org/w/index.php?title=Basil_lamina (marked Sep. 24, 2007).

Wikipedia, "Bromodeoxyuridine," 1 p., downloaded from the World Wide Web at http://en.wikipedia.org/w/index.php?title=Bromodeoxyuridine (marked May 21, 2007).

Wikipedia, "Cadherin," 1 p., downloaded from the World Wide Web at http://en.wikipedia.org/w/index.php?title=Cadherin (marked Sep. 26, 2007).

Wikipedia, "Cell adhesion molecule," 3 pp., downloaded from the World Wide Web at http://en.wikipedia.org/w/index.php?title=Cell_adhesion_molecule (marked Sep. 19, 2007).

Wikipedia, "Cell cycle," 6 pp, downloaded from the World Wide Web at http://en.wikipedia.org/w/index.php?title=Cell_cycle (marked Sep. 19, 2007).

Wikipedia, "Cyclophosphamide," 3 pp., downloaded from the World Wide Web at http://en.wikipedia.org/w/index.php?title=Cyclophosphamide (marked May 21, 2007).

Wikipedia, "Cytokine," 4 pp., downloaded from the World Wide Web at http://en.wikipedia.org/w/index. php?title=Cytokine (marked Sep. 19, 2007).

Wikipedia, "Dystroglycan," 2 pp., downloaded from the World Wide Web at http://en.wikipedia.org/w/index.php?title=Dystroglycan (marked Sep. 24, 2007).

Wikipedia, "Dystrophin," 2 pp., downloaded from the World Wide Web at http://en.wikipedia.org/w/index.php?title=Dystrophin (marked Sep. 24, 2007).

Wikipedia, "Extracellular matrix," 5 pp., downloaded from the World Wide Web at http://en.wikipedia.org/w/index.php?title=Extracellular_matrix (marked Sep. 19, 2007).

Wikipedia, "Fibroblast," 3 pp., downloaded from the World Wide Web at http://en.wikipedia.org/w/index.php?title=Fibroblast (marked Sep. 24, 2007).

Wikipedia, "Fibronectin," 2 pp., downloaded from the World Wide Web at http://en.wikipedia.org/w/index.php?title=Fibronectin (marked Sep. 24, 2007).

Wikipedia, "Glycoprotein," 3 pp., downloaded from the World Wide Web at http://en.wikipedia.org/w/index.php?title=Glycoprotein (marked May 16, 2007).

Wikipedia, "Green fluorescent protein," 5 pp., downloaded from the World Wide Web at http://en.wikipedia.org/w/Index .php?title=Green_fluorescent_protein (marked Sep. 25, 2007).

Wikipedia, "Growth factor," 3 pp., downloaded from the World Wide Web at http://en.wikipedia.org/w/index.php?title=Growth_factor (marked Sep. 19, 2007).

Wikipedia, "Integrin," 6 pp., downloaded from the World Wide Web at http://en.wikipedia.org/w/index.php?title=Integrin (marked Sep. 19, 2007).

Wikipedia, "Laminin," 2 pp., downloaded from the World Wide Web at http://en.wikipedia.org/w/index.php?title=Laminin (marked May 16, 2007).

Wikipedia, "Merosin," 1 p., downloaded from the World Wide Web at http://en.wikipedia.org/w/index.php?title=Merosin (marked Sep. 21, 2007).

Wikipedia, "Mitosis," 4 pp., downloaded from the World Wide Web at http://en.wikipedia.org/index.php?title=Mitosis (marked Sep. 19, 2007).

Wikipedia, "Muscle fiber," 3 pp., downloaded from the World Wide Web at http://en.wikipedia.org/w/index.php?title=Muscle_tiber (marked Sep. 24, 2007).

Wikipedia, "Muscular Dystrophy," 7 pp., downloaded from the World Wide Web at http://en.wikipedia.org/w/index.php?title=Muscular_Dystrophy (marked May 16, 2007).

Wikipedia, "Myoblast," 1 p., downloaded from the World Wide Web at http://en.wikipedia.org/w/index.php?title=Myoblast (marked Sep. 24, 2007).

Wikipedia, "MyoD," 2 pp., downloaded from the World Wide Web at http://en.wikipedia.org/w/index.php?title=MyoD (marked May 21, 2007).

Wikipedia, "Myofibril," 2 pp., downloaded from the World Wide Web at http://wikipedia.org/w/index.php?title=Myofibril (marked Sep. 24, 2007).

Wikipedia, "Myogenesis," 1 p., downloaded from the World Wide Web at http://en.wikipedia.org/w/index.php?title=Mvogenesis (marked May 21, 2007).

Wikipedia, "Myosin," 5 pp., downloaded from the World Wide Web at http://en.wikipedia.org/w/index.php?title=Myosin (marked May 21, 2007).

Wikipedia, "Nestin (protein)," 3 pp., downloaded from the World Wide Web at http:/en.wikipedia.org/w/index.php?title=Nestin_%28protein (marked Sep. 25, 2007).

Wikipedia, "Neuronal ceroid lipofuscinosis," 6 pp., downloaded from the World Wide Web at http://en.wikipedia.org/w/index.php?title=Neuronal_ceroid_ lipofuscinosis (marked May 21, 2007).

Wikipedia, "Pax genes," 4 pp., downloaded from the World Wide Web at http://en.wikipedia.org/w/index.php?title=Pax_genes (marked May 21, 2007).

Wikipedia, "Protein domains," 17 pp., downloaded from the World Wide Web at http://en.wikipedia.org/w/index.php?title=Protein_domains (marked Sep. 19, 2007).

Wikipedia, "Proteoglycan," 2 pp., downloaded from the World Wide Web at http://en.wikipedia.org/w/index.php?title=Proteoglycan (marked Sep. 19, 2007).

Wikipedia, "Route of administration," 3 pp., downloaded from the World Wide Web at http://en.wikipedia.org/w/index.php?title=Route_of_administration (marked Sep. 24, 2007).

Wikipedia, "Sarcolemma," 1 p., downloaded from the World Wide Web at http://en.wikipedia.org/w/index.php?title=Sarcolemma (marked Sep. 24, 2007).

Wikipedia, "Sarcomere," 3 pp., downloaded from the World Wide Web at http://en.wikipedia.org/w/index.php?title=. Sarcomere (marked Sep. 24, 2007).

Wikipedia, "Satellite cells," 2 pp., downloaded from the World Wide Web at http://en.wikipedia.org/w/index.php?title=Satellite_cells (marked Sep. 19, 2007).

(56) References Cited

OTHER PUBLICATIONS

Wikipedia, "Transcription factor," 8 pp., downloaded from the World Wide Web at http://en.wikipedia.org/w/index.php?title=Transcription_factor (marked Sep. 26, 2007).
Wikipedia, "Utrophin," 2 pp., downloaded from the World Wide Web at http://en.wikipedia.org/w/index.php?title=Utrophin (marked Sep. 25, 2007).
Wikipedia, "Wound healing," 8 pp., downloaded from the World Wide Web at http://en.wikipedia.org/w/index.php?title=Wound_healing (marked Sep. 19, 2007).
Wikipedia, "Zygosity," 3 pp., downloaded from the World Wide Web at http://en.wikipedia.org/w/index.php?title=Zygosity (marked Oct. 2, 2007).
Yurchenco et al., "Loss of basement membrane, receptor and cytoskeletal lattices in laminin-deficient muscular dystrophy," Journal of Cell Science, vol. 117, pp. 735-742, 2004.
Zhu et al., "Stabilization of proteins encapsulated in ijectable poly (lactide-co-clycolide)," Nature Biotechnology, vol. 18, pp. 52-57, 2000.
Allikan et al., "Genetic compensation for sarcoglycan loss by integrin α7β1 in muscle," Journal of Cell Science, vol. 117, pp. 3821-3830, 2004.
Brown et al., "Dystrophic phenotype induced in vitro by antibody blockade of muscle a-dystroglycan-laminin interaction," Journal of Cell Science, 112:209-216, 1999.
Campbell Lab, "Molecular Studies of Muscular Dystrophy," 4 pp., downloaded from the World Wide Web at http://physiology.uiowa.edu/Campbell/Research/Areas/researchareas (marked Sep. 24, 2007).
Chang, "Neuronal Ceroid Lipofuscinoses," 18pp., downloaded from the World Wide Web at http://www.emedicine.com/neuro/topic498.htm (marked May 21, 2007).
Chazalette et al., "α7β Integrin changes in mdx mouse muscles after L-arginine administration," FEBS Letters, vol. 579, pp. 1079-1084, 2005.
Colledge and Froehner, "To Muster a cluster: Anchoring neurotransmitter receptors at synapses," Proc. Natl. Acad. Sci. USA, vol. 95, pp. 3341-3343, 1998.
Colognato et al., "Laminin Polymerization Induces a Receptor-Cytoskeleton Network," Journal of Cell Biology, vol. 145, No. 3, pp. 619-631, 1999.
Database WPI; Week 200557, Thompson Scientific; London, GB; AN 2005-557852, XP-2758735A; Jul. 21, 2005.
Deconinck et al., "Functional protection of dystrophic mouse (mdx) muscles after adenovirus-mediated transfer of a dystrophin minigene," Proc. Natl. Acad. Sci. USA, vol. 93, pp. 3570-3574, 1996.
Dellorusso et al., "Functional correction of adult mdx mousse muscle using gutted adenoviral vectors expressing full-length dystrophin," PNAS, vol. 99, No. 20, pp. 12979-12984, 2002.
Dickson et al., "Co-localization and molecular association of dystrophin with laminin at the surface of mouse and human myotubes," Journal of Cell Science, vol. 103, pp. 1223-1233, 1992.
Duclos et al., "Progressive Muscular Dystrophy in a α-Sarcoglycan-deficient Mice," Journal of Cell Science, vol. 142, No. 6, pp. 1461-1471, 1998.
Ervasti, "Costameres: the Achilles' Heel of Herculean Muscle," Journal of Biological Chemistry, vol. 278, No. 16, pp. 13591-13594, 2003.
From Alchemy to IPO, "Avoiding degradation and phagocytosis," 1 p., downloaded from the World Wide Web at http://books.google.com/books, 2019.
Fu et al., "Protein stability in controlled-release systems," Nature Biotechnology, vol. 18, pp. 24-25, 2000.
Gawlik et al., "Laminin alpha1 chain improves laminin alpha2 chain deficient peripheral neuropathy," Hum. Mol. Genet., vol. 15, No. 18, pp. 2690-2700, 2006.
Gawlik et al., "Laminin alpha1 chain mediated reduction of laminin alpha2 chain deficient muscular dystrophy involves integrin alpha7beta1 and dystroglycan," FEBS Letters, vol. 580, No. 7, pp. 1759-1765, 2006.
Gawlik et al., "Laminin alpha1 chain reduces muscular dystrophy in laminin alpha2 chain deficient mice," Hum. Mol. Genet., vol. 13, No. 16, pp. 1775-1784, 2004.
Gullberg et al., "Laminins during muscle development and in muscular dystrophies," Cell. Mol. Life Sci., vol. 56, No. 5-6, pp. 442-460, 1999.
Guo et al., "Absence of α7 integrin in dystrophin-deficient mice causes a myopathy similar to Duchenne muscular lystrophy," Hum. Mol. Genet., vol. 15, No. 6, pp. 989-998, 2006.
Gurpur, Praveen B., et al.; Valproic acid activates the PI3K/Akt/mTOR pathway in muscle and ameliorates pathology in a mouse model of Duchenne muscular dystrophy; American Journal of Pathology, American Society for Investigative Pathology, US, vol. 174, No. 3; Oct. 6, 2011.
Hager et al., "Laminin {alpha}1 chain corrects male infertility causes by absence of laminin {alpha}2 chain," Am. J. Path., vol. 167, No. 3, pp. 823-833, 2005.
Hashimoto et al., "Development of alginate wound dressings linked with hybrid peptides derived from laminin and elastin," Biomaterials, vol. 25, No. 7-8, pp. 1407-1414, Mar. 1, 2004.
Higuchi et al., "Abnormal Experssion of Laminin Suggests Disturbance of Sarcolemma-Extracellular Matrix Interaction in Japanese Patients with Autosomal Recessive Muscular Dystrophy Deficient in Adhalin," J. Clin. Invest., vol. 94, pp. 601-606, 1994.
Jimenez-Mallebrera et al., "Congenital muscular dystrophy: molecular and cellular aspects," CMLS Cellular and Molecular Life Sciences, vol. 62, No. 7-8, pp. 809-823, Apr. 1, 2005.
Klietsch et al., "Dystrophin-Glycoprotein Complex and Laminin Colocalize to the Sarcolemma and Transverse Tubules of Cardiac Muscle," Circulation Research, vol. 72, No. 2, pp. 349-360, 1993.
Liu, Jianming, et al.; β1D chain increases a7β1 integrin and laminin and protects against sarcolemmal damage in mdx mice. Human Molecular Genetics, vol. 21, No. 7, p. 1592-1603; 2012.
Liu; Development of Research of Laminin; Foreign Medical Sciences (Section of Dermatology and Venereology), No. 6, vol. 26, pp. 352-354; Dec. 31, 2000.
Lowe, "Proteins to the Rescue?" 5 pp., downloaded from the World Wide Web at http://pipeline.corante.com/archives/2004/10/05/proteins_to_the_rescue (marked Sep. 27, 2007).
Milner and Kaufman, "α7β1 Integrin Doe Not Alleviate Disease in a Mouse Model of Limb Girdle Muscular Dystrophy Type 2F," Am. J. Path, vol. 170, No. 2, pp. 609-619, 2007.
Mort, "Multiple modes of drug delivery," Modem Drug Discovery, vol. 3, No. 3, pp. 30-32, 34, 2000.
Murthy et al., "A macromolecular delivery vehicle for protein-based vaccines: Acid-degradable protein-loaded microgels," PNAS, vol. 100, No. 9, pp. 4995-5000, 2003.
Nystom et al., "Extraocular muscle is spared upon complete laminin alpha2 chain deficiency: comparative expression of laminin and integrin isoforms," Matrix Biol., vol. 25, No. 6, pp. 382-385, 2006.
Oecalan et al., "Laminin Alters Cell Shape and Stimulates Motility and Proliferation of Murine Skeletal Myoblasts," Developmental Biology, vol. 125, pp. 158-167, 1988.
Orr-Urtreger et al., "Mice Deficient in the α7 Neuronal Nicotinic Acetylcholine Receptor Lack α-Bungarotoxin Binding Sites and Hippocampal Fast Nicotinic Currents," Joumal of Neuroscience, vol. 17, No. 23, pp. 9165-9171, 1997.
Panisheva, E.K., et al.; "Synthesis and antiviral activity of 5-hydroxyindole derivatives;" XP002759452; Database CA (online) Chemical Abstracts Service, Columbus, OH US; Database accession No. 1989:165602; May 12, 1989.
Pubchem Substance Summary for SID 49643391; Deposit date Mar. 11, 2008; Modify date: Mar. 1, 2012; p. 1-16, p. 1; p. 6-8; Mar. 11, 2008.
Pubchem Bioassay; "qHTS for Activators of Integrin-Mediated Alleviation for Muscular Dystrophy;" retrieved from the Internet; XP002759451; URL:https://pubchem.ncbi.nlm.nih.gov/bioassay/624291#section=Top (retrieved on Jun. 13, 2016).
Rooney et al., "Severe muscular dystrophy in mice that lack dystrophin and a α7 integrin," Journal of Cell Science, vol. 119, pp. 2185-2195, 2006.

(56) References Cited

OTHER PUBLICATIONS

Rooney, J.E., et al.; Laminin-111 protein therapy prevents muscle disease in the mdx mouse model for Duchenne muscular dystrophy; Proceedings of the National Academy of Sciences, vol. 106, No. 19, May 12, 2009.

Rooney, Jachinta E., et al.; Laminin-111 Restores Regenerative Capacity in a Mouse Model for alpha 7 Integrin Congenital Myopathy; American Journal of Pathology; Elsevier Inc., US, vol. 174, No. 1; Jan. 1, 2009.

Pubchem Open Chemistry Database; "Acetic acid 3-acetyl-1-(4-methoxy-phenyl)-2-methyl-1H-indol-5-yl ester;" XP002760284; Database accession No. SID 49643391; Mar. 11, 2008.

Samarel, "Costameres, focal adhesions, and cardiomyocyte mechanotransductions," Am. J. Physiol. Heart Circ. Physiol., vol. 289, pp. H2291-H2301, 2005.

Sher et al., "A Rostrocaudal Muscular Dystrophy Caused by a Defect in Choline Kinase Beta, the First Enzyme in Phosphatidylcholine Biosynthesis," Journal of Biological Chemistry, vol. 281, No. 8, pp. 4938-4948, 2006.

Sorokin et al., "Laminin alpha4 and integrin alpha6 are Upregulated in Regenerating dy/dy Skeletal Muscle: Comparative Expression of Laminin and Integrin Isoforms in Muscles Regenerating after Crush Injury," Experimental cell Research, vol. 256, pp. 500-514, 2000.

Straub et al., "Molecular Pathogenesis of Muscle Degeneration in the δ-Sarcoglycan-Deficient Hamster," American Journal of Pathology, vol. 153, No. 5, pp. 1623-1630, 1998.

Thornell et al., "Fibronectin and laminin related to myocardial damage and repair," Journal of Molecular and Cellular Cardiology, vol. 23, p. S13 (Abstract), Jul. 1, 1991.

Uziyel et al., "Influence of laminin-2 on Schwann cell-axon interactions," Glia., vol. 32, No. 2, pp. 109-121, 2000.

Vachon et al., "Merosin and Laminin in Myogenesis; Specific Requirement for Merosin in Myotube Stability and Survival," Journal of Cell Biology, vol. 134, No. 6, pp. 1483-1497, 1996.

Vachon et al., "Integrins (α7β1) in muscle function and survival," Journal of Clinical Investigation, 100(7); 1870-1881, 1997.

FIG. 1 Quantitative Real-time Analysis in C2C12 cells treated for 24 hours

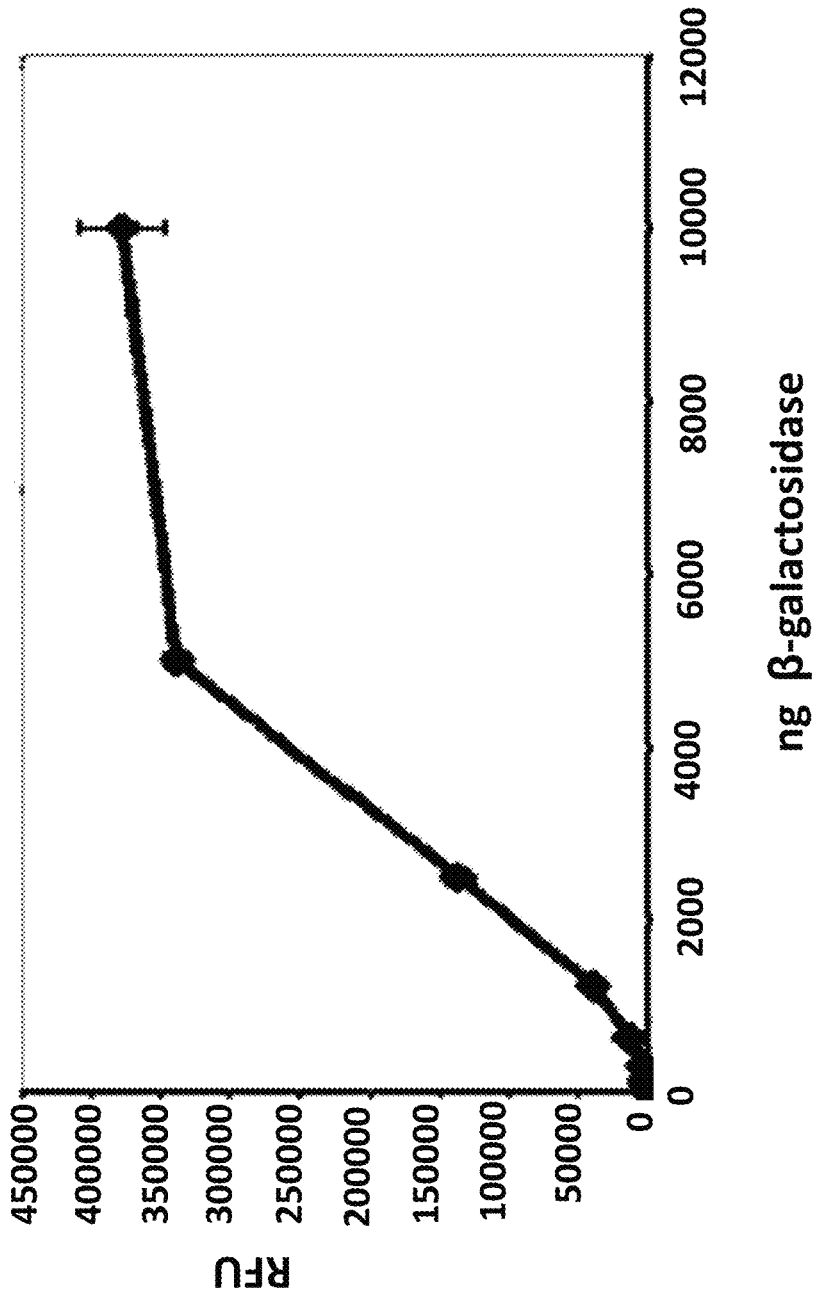

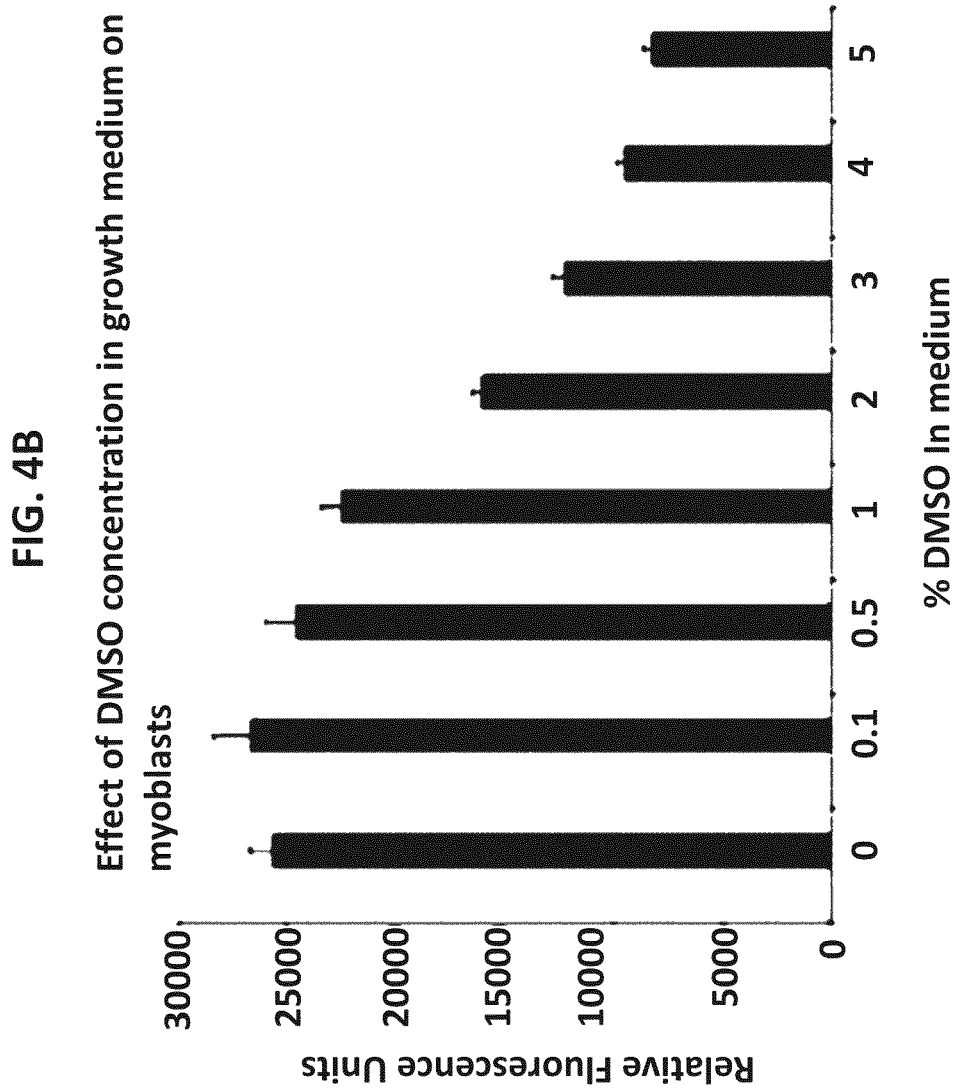

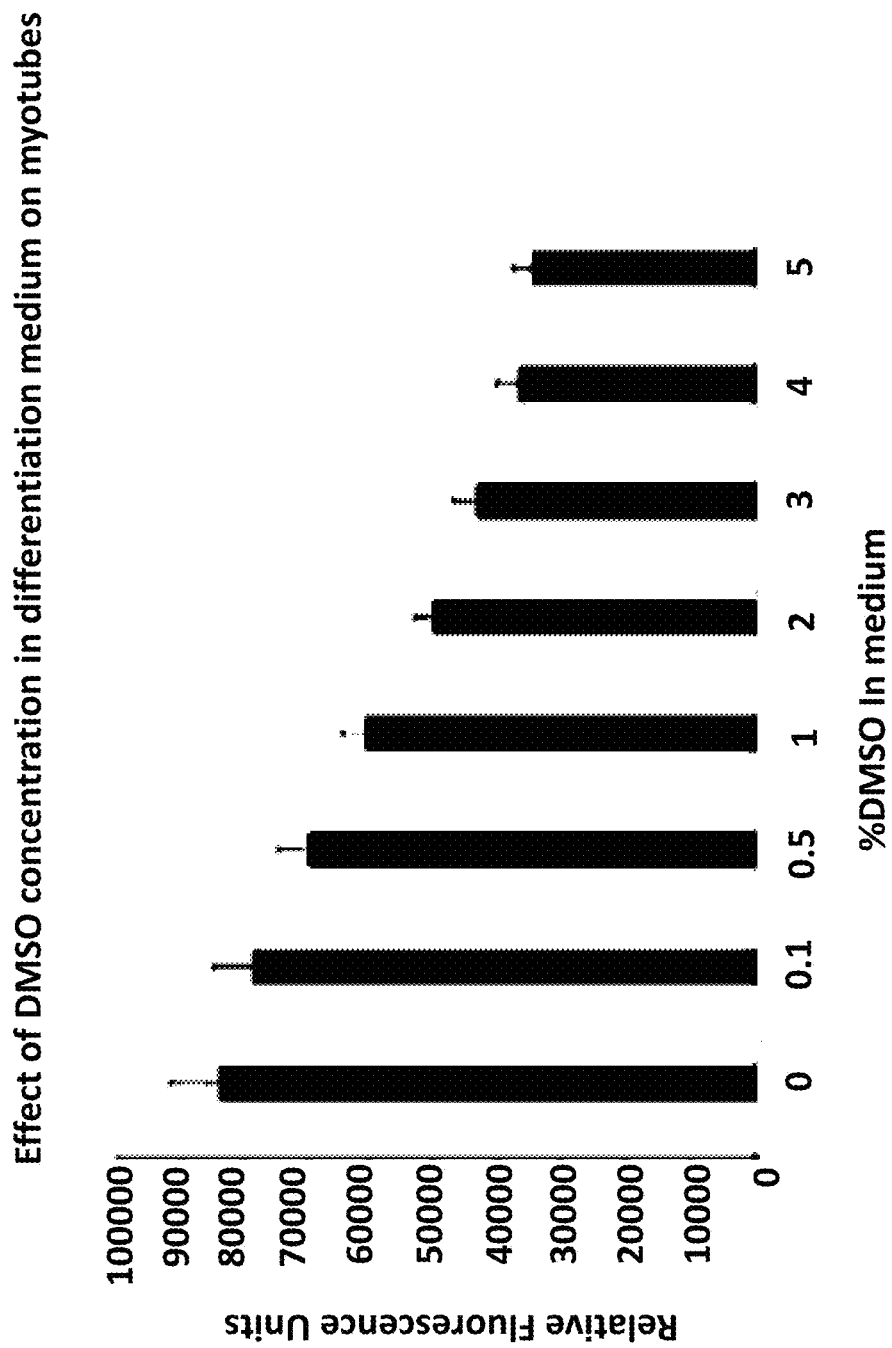

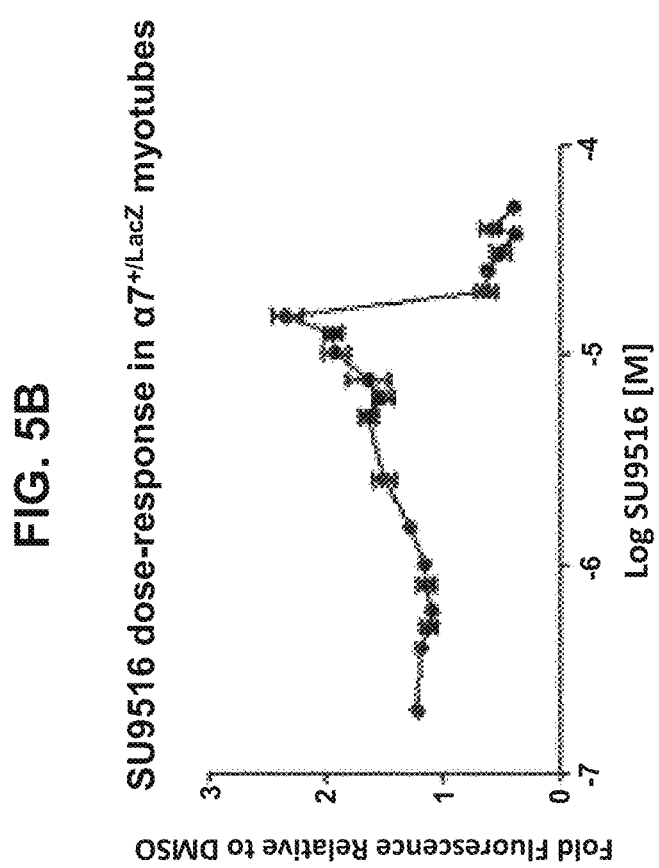

FIG. 6

| Library | Distribution | Curve Classification | | | | | | | | | |
|---|---|---|---|---|---|---|---|---|---|---|---|
| | | 1.1 | 1.2 | 1.3 | 1.4 | 2.1 | 2.2 | 2.3 | 2.4 | 3 | Others |
| MLSMR (368,680) | Cmpd No. | 32 | 108 | 207 | 963 | 140 | 272 | 974 | 2738 | 8327 | 354,919 |
| | % library | 0.001% | 0.029% | 0.056% | 0.26% | 0.04% | 0.074% | 0.26% | 0.74% | 2.26% | 96.27% |

| Curve Class | Description | Asymptotes | Inflection | #pts>SD | Subclass | | Efficacy | r² |
|---|---|---|---|---|---|---|---|---|
| 1 | Complete | 2 | yes | >1 | a | Full Efficacy | >80% | >=0.9 |
| | | | | | b | Partial Efficacy | Min – 80% | >=0.9 |
| | | | | | c | Noisy Full | >80% | <0.9 |
| | | | | | d | Noisy Partial | Min – 80% | <0.9 |
| 2 | Incomplete | 1 | maybe | >1 | a | Potent Incomplete | >80% | >=0.9 |
| | | | | | b | Partial Incomplete | Min – 80% | >=0.9 |
| | | | | | c | Noisy Potent Incomplete | >80% | <0.9 |
| | | | | | d | Noisy Partial Incomplete | Min – 80% | <0.9 |
| 3 | Single Point | 1 | no | 1 | | | >Min | |
| 4 | Inactive | 0 | no | 0 | | | | |

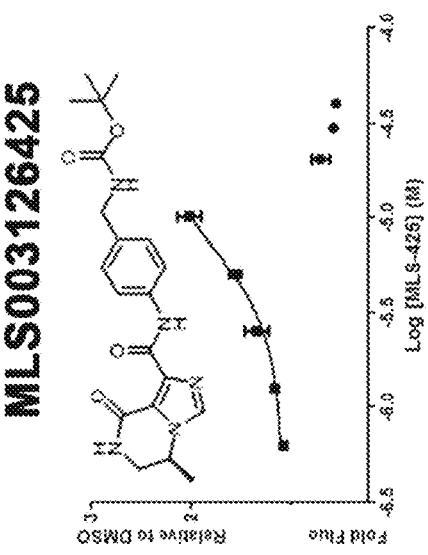
FIG. 7A SU9516
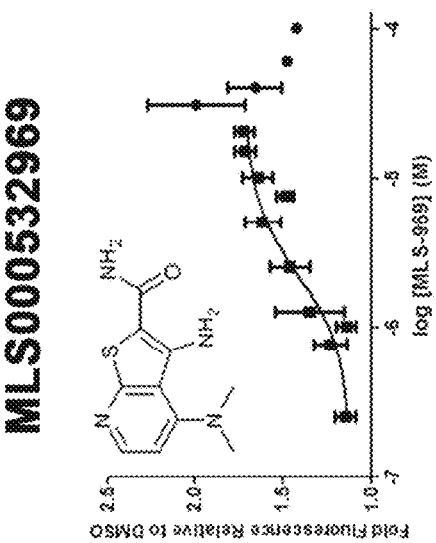
FIG. 7B MLS000532969
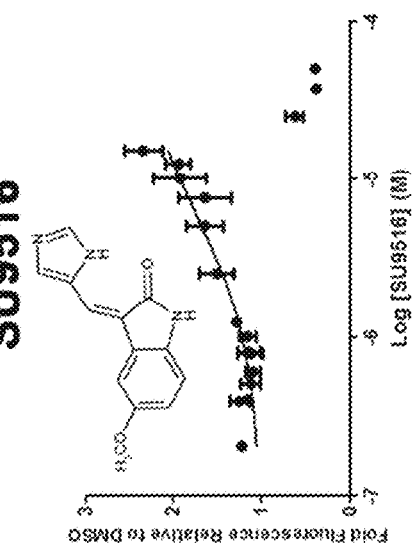
FIG. 7C MLS003126425
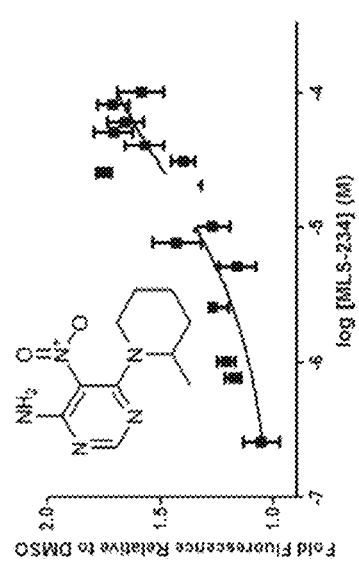
FIG. 7D MLS001060533
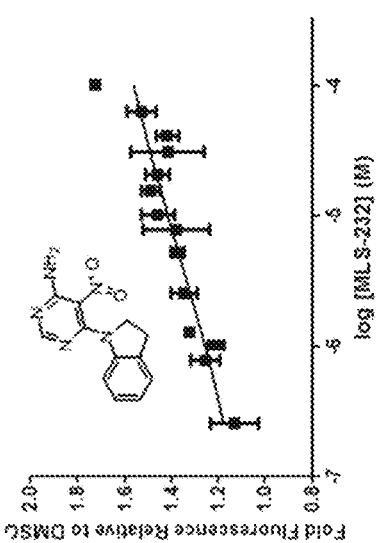
FIG. 7E MLS000683232
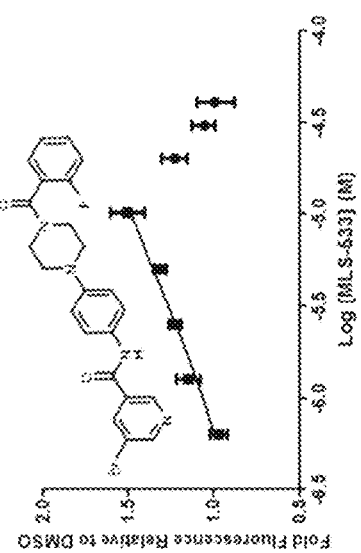
FIG. 7F MLS000683234

SU9516

FIG 12
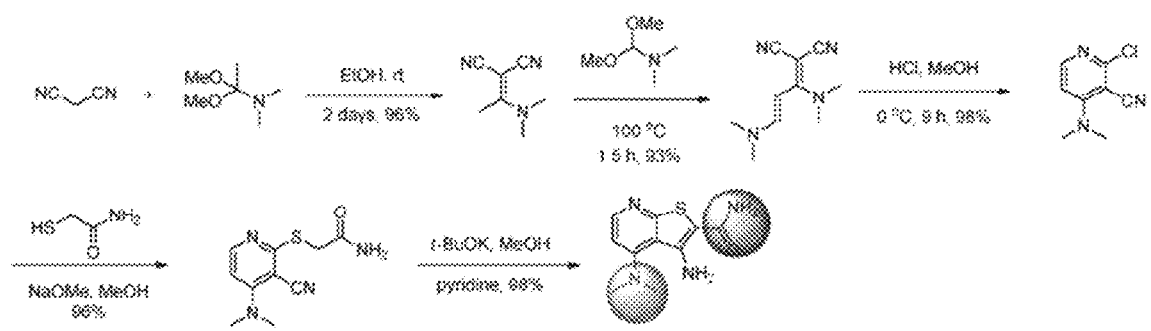
Scheme 1
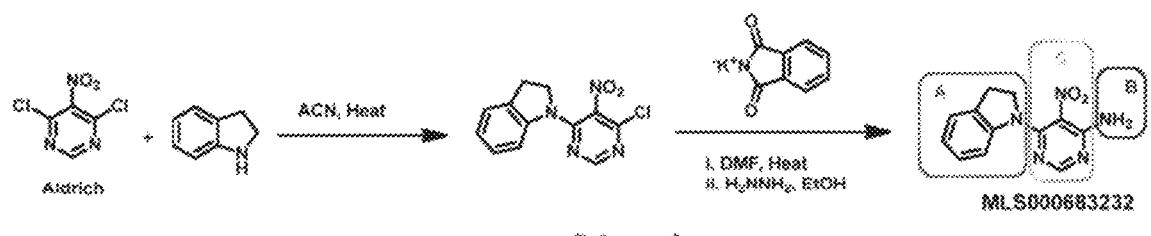
Scheme 2

METHODS OF TREATING MUSCULAR DYSTROPHY

CROSS REFERENCE TO RELATED APPLICATIONS

This is a continuation application of U.S. patent application Ser. No. 15/961,408, which is a continuation application of U.S. patent application Ser. No. 15/619,256, now U.S. Pat. 9,980,943, which is a divisional application of U.S. patent application Ser. No. 14/776,898, now U.S. Pat. 9,707,210, which is the U.S. National Stage of International Application No. PCT/US2014/029085, filed Mar. 14, 2014, which was published in English under PCI Article 21(2), which in turn claims the benefit of U.S. Provisional Patent Application No. 61/798,479, filed on Mar. 15, 2013, each of which is herein incorporated by reference in its entirety.

ACKNOWLEDGMENT OF GOVERNMENT SUPPORT

This invention was made with government support under Grant Numbers R43 AR060030, R21 NS058429-01, and R21 AR060769 awarded by the National Institutes of Health. The government has certain rights in the invention.

FIELD

This disclosure relates to the field of muscular dystrophy and in particular, to compositions and methods for treating muscular dystrophy, such as Duchenne muscular dystrophy, Fukuyama congenital muscular dystrophy or merosin deficient congenital muscular dystrophy type 1A or 1D.

BACKGROUND

Mutations in the α7 integrin gene are responsible for congenital myopathy in man. The α7β1 integrin is also a major modifier of muscle disease progression in various genetic muscle diseases including various types of muscular dystrophy, such as Duchenne muscular dystrophy (DMD), Fukuyama congenital muscular dystrophy (FCMD) and merosin deficient congenital muscular dystrophy type 1A (MDC1A). However, transcriptional regulation of the α7 integrin gene, including such role in muscular dystrophy (e.g., DMD, FCMD and/or MDC1A), remains poorly understood.

Duchenne muscular dystrophy (DMD) is an X-chromosome-linked disease and the most common form of muscular dystrophy. DMD affects 1 in 3500 live male births with patients suffering from chronic muscle degeneration and weakness. Clinical symptoms are first detected between the ages of 2 and 5 years and, by the time the patient is in their teens, the ability for independent ambulation is lost. Death typically occurs in the patient before they are 30 years old due to cardiopulmonary failure.

Fukuyama congenital muscular dystrophy (FCMD) and MDC1A are congenital muscular dystrophies that are heritable neuromuscular disorders. MDC1A is characterized by muscle weakness at birth or in infancy. Affected infants will present with poor muscle tone and few movements. The quality of life and life span of the child is affected through progressive muscle wasting, respiratory compromise, and spinal rigidity. MDC1A is the most common and severe form of congenital muscular dystrophy, accounting for 30-40% of all congenital muscular dystrophy (CMD) diagnosed cases. MDC1A is characterized by congenital hypotonia, distinct joint contractures, and a lack of independent ambulation. Feeding tube placement and positive pressure ventilation is often required for the respiratory problems that occur. Patients afflicted with MDC1A often die before they reach the age of ten years. FCMD is caused by mutations in the fukutin gene, located at human chromosome 9q31. The disease is inherited in an autosomal recessive manner. FCMD is a type of Limb-Girdle muscular dystrophy. Currently there is no cure for DMD, FCMD or MDC1A.

SUMMARY

The muscular dystrophies are a group of diverse, heritable neuromuscular disorders which represent a group of devastating neuromuscular diseases characterized by primary or secondary skeletal muscle involvement. Currently, there are no cures for such diseases.

Disclosed herein are α7β1 integrin expression modulatory agents and methods of using such to treat a condition associated with impaired α7 integrin expression, such as muscular dystrophy. In one embodiment, a method for treating a subject with muscular dystrophy is disclosed. The method includes administering an effective amount of an α7β1 integrin modulatory agent to the subject with muscular dystrophy, wherein the α7β1 integrin modulatory agent is a compound encompassed by any one of Formulas 1-16, or provided by any one of Tables 1-16 and 18, or a combination thereof, wherein the α7β1 integrin modulatory agent increases α7β1 integrin expression or activity as compared to α7β1 integrin expression or activity prior to treatment, thereby treating the subject with muscular dystrophy (such as MDC1A, MDC1D, LGMD, DMD, FCMD or FHMD).

Also disclosed are methods of enhancing muscle regeneration, repair, or maintenance in a subject. In some embodiments, the method includes administering an effective amount of an α7β1 integrin modulatory agent to the subject in need of muscle regeneration, repair or maintenance, wherein the α7β1 integrin modulatory agent comprises a compound encompassed by any one of Formulas 1-16, or provided by any one of Tables 1-16 and 18, or a combination thereof, wherein the α7β1 integrin modulatory agent increases α7β1 integrin expression or activity as compared to α7β1 integrin expression or activity prior to treatment, thereby enhancing muscle regeneration, repair or maintenance in a subject. In a specific embodiment, the present disclosure provides a method for increasing muscle regeneration in a subject. For example, geriatric subjects, subjects suffering from muscle disorders, and subjects suffering front muscle injury, including activity induced muscle injury, such as injury caused by exercise, may benefit from this embodiment.

In yet further embodiments of the disclosed method, the α7β1 integrin modulatory agent is administered in a preventative manner, such as to prevent or reduce muscular damage or injury (such as activity or exercise induced injury). For example, geriatric subjects, subjects prone to muscle damage, or subjects at risk for muscular injury, such as athletes, may be treated in order to eliminate or ameliorate muscular damage, injury, or disease.

Further disclosed are methods of enhancing α7β1 integrin expression. In some embodiments, the method includes contacting a cell with an effective amount of an α7β1 integrin modulatory agent, wherein the α7β1 integrin modulatory agent includes a compound encompassed by any one of Formulas 1-16, or provided by any one of Tables 1-16 and 18, or a combination thereof and increases α7β1 integrin expression in the treated cell relative to α7β1 integrin expression in an untreated cell, thereby enhancing α7β1 integrin expression. The methods of the present disclosure can include administering the α7β1 integrin modulatory agent with one or more additional pharmacological substances, such as a therapeutic agent. In some aspects, the additional therapeutic agent enhances the therapeutic effect of the α7β1 integrin modulatory agent. In further aspects, the therapeutic agent provides independent therapeutic benefit for the condition being treated. In various examples, the additional therapeutic agent is a component of the extracellular matrix, such as an integrin, dystrophin, dystroglycan, utrophin, or a growth factor. In further examples, the therapeutic agent reduces or enhances expression of a substance that enhances the formation or maintenance of the extracellular matrix. In some examples, the therapeutic agent is an additional α7β1 integrin modulatory agent such as laminin-111, a laminin-111 fragment, valproic acid or a valproic acid analog.

In some examples, the α7β1 integrin modulatory agent is applied to a particular area of the subject to be treated. For example, the α7β1 integrin modulatory agent may be injected into a particular area to be treated, such as a muscle. In further examples, the α7β1 integrin modulatory agent is administered such that it is distributed to multiple areas of the subject, such as systemic administration or regional administration.

A α7β1 integrin modulatory agent, can be administered by any suitable method, such as topically, parenterally (such as intravenously or intraperitoneally), or orally. In a specific example, the α7β1 integrin modulatory agent is administered systemically, such as through parenteral administration, such as stomach injection or peritoneal injection.

Although the disclosed methods generally have been described with respect to muscle regeneration, the disclosed methods also may be used to enhance repair or maintenance, or prevent damage to, other tissues and organs. For example, the methods of the present disclosure can be used to treat symptoms of muscular dystrophy stemming from effects to cells or tissue other than skeletal muscle, such as impaired or altered brain function, smooth muscles, or cardiac muscles.

The foregoing and other features of the disclosure will become more apparent from the following detailed description, which proceeds with reference to the accompanying figures.

BRIEF DESCRIPTION OF THE DRAWINGS

FIG. 4A is an image of the relative fluorescence generated by various concentrations of beta-galactosidase from the FDG substrate (FIG. 4A). The effects of DMSO concentrations on α7$^{+/LacZ}$ myoblasts (FIG. 4B) and myotube (FIG. 4C) assays were determined to be unacceptably high at concentrations greater than 1%.

FIGS. 5A and 5B are graphs illustrating dose-response curves for SU9516 on α7$^{+/LacZ}$ myoblasts (FIG. 5A) or myotubes (FIG. 5B). The non-conventional appearance of the curves is thought to be a mechanism of concentration dependent cellular toxicity.

FIG. 6 is an image of a table providing curve classification results from a primary myoblast screen disclosed herein.

FIGS. 7A-7F provide graphs of myotube dose-response and the corresponding chemical structures [SU9516 (FIG. 7A), MLS000532969 (FIG. 7B), MLS003126425 (FIG. 7C), MLS001060533 (FIG. 7D), MLS000683232 (FIG. 7E), and MLS000683234 (FIG. 7F)] for each compound examined wherein n=6-9 over multiple days for all points.

FIG. 12 provides an exemplary synthetic scheme for making specific α7β1 integrin modulatory agents disclosed herein.

DETAILED DESCRIPTION OF SEVERAL EMBODIMENTS

I. Overview of Several Embodiments

Figure 1:
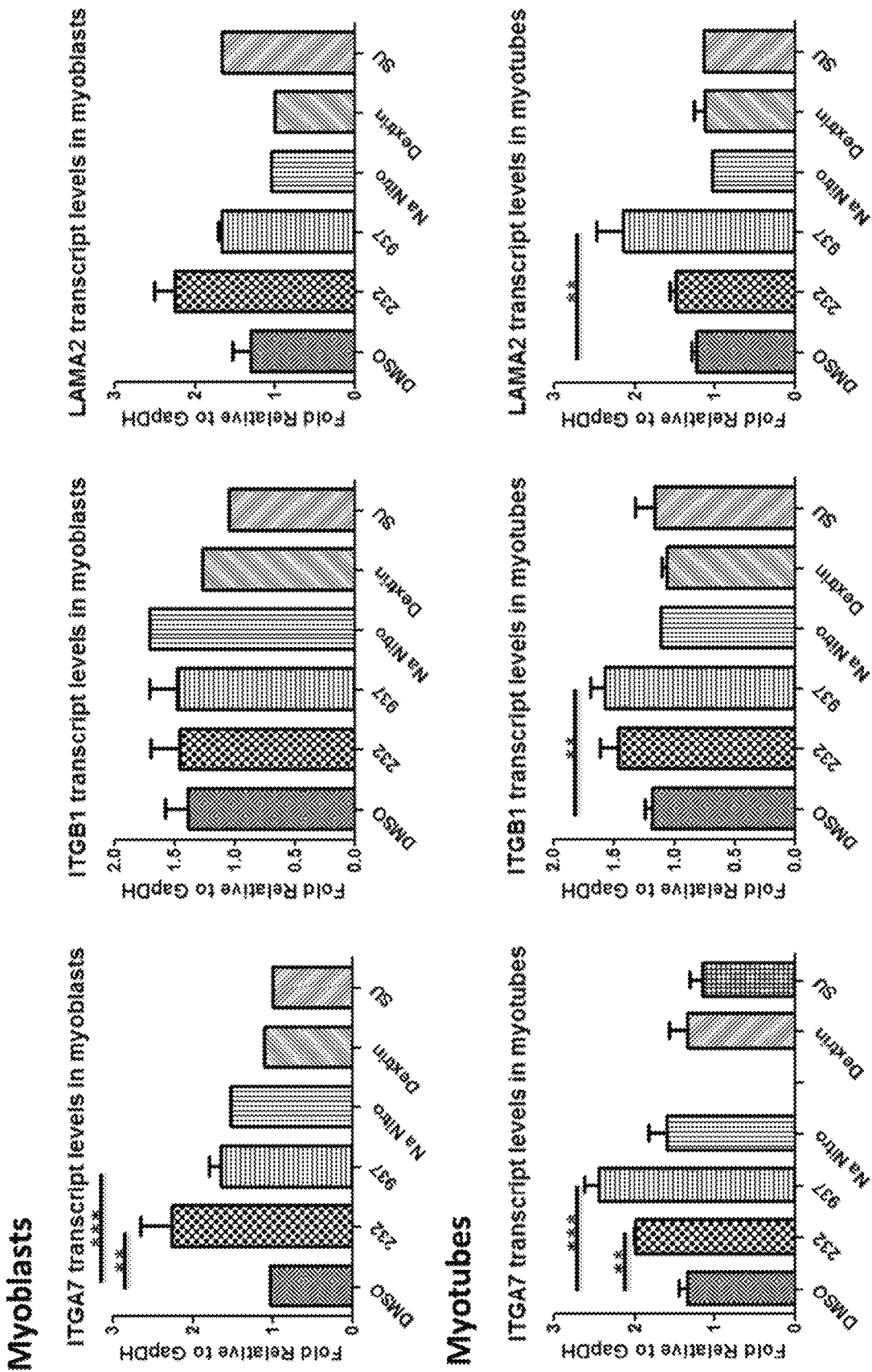
FIG. 1 is a digital image illustrating the results of quantitative real-time PCR used to assess Itga7, Itgb1, and Lama2 transcript levels in C2C12 myoblasts and myotubes treated for 24 hours with DMSO control, 10 μM MLS000683232-01 (IED-232), 10 μM MLS001165937-01 (IED-937). Hydroxylpropyl-Beta-Cyclodextrin (HPBCD) control, or 12 μM SU9516 in HPBCD. * denotes a significant difference in relative transcript levels with  p-value<0.01 and * p<0.001.

Disclosed herein are α7β1 integrin expression modulatory agents and methods of using such to treat a condition associated with impaired α7 integrin expression, such as muscular dystrophy.

In one embodiment, a method for treating a subject with muscular dystrophy is disclosed. The method includes administering an effective amount of an α7β1 integrin modulatory agent to the subject with muscular dystrophy, wherein the α7β1 integrin modulatory agent is a compound encompassed by any one of Formulas 1-16, or provided by any one of Tables 1-16 and 18, or a combination thereof, wherein the α7β1 integrin modulatory agent increases α7β1 integrin expression or activity as compared to α7β1 integrin expression or activity prior to treatment, thereby treating the subject with muscular dystrophy.

In some embodiments, a method for treating a subject with muscular dystrophy, comprises administering an effective amount of an α7β1 integrin modulatory agent to the subject with muscular dystrophy, wherein the α7β1 integrin modulatory agent comprises a compound having a formula selected from any one of the following

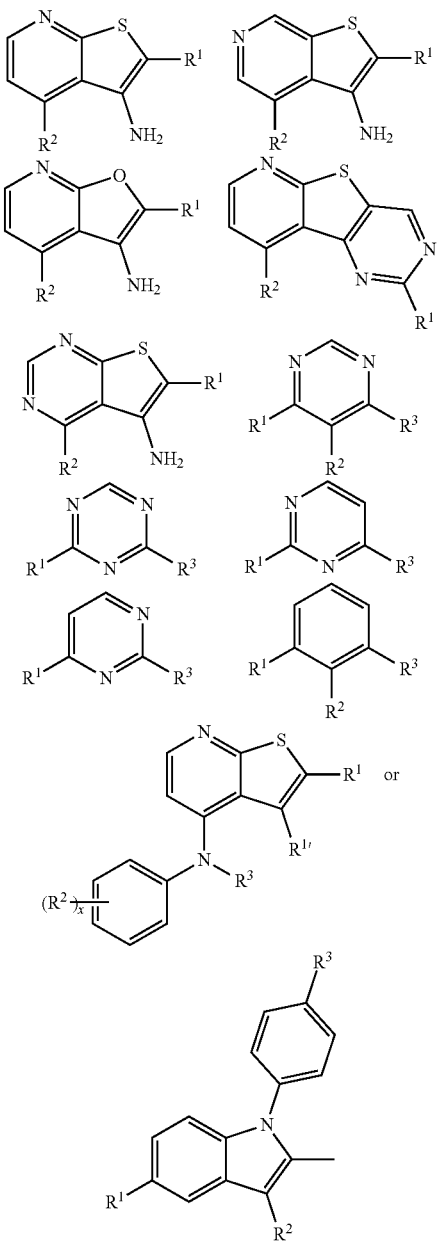

wherein R¹, R², R, and R³ each independently is as specified in Table 3, Table 4, Table 5, and/or Table 6. In some embodiments, a combination of any of these compounds, or any other α7β1 integrin modulatory agents disclosed herein may be used. The α7β1 integrin modulatory agent increases α7β1 integrin expression or activity as compared to α7β1 integrin expression or activity prior to treatment, thereby treating the subject with muscular dystrophy. In some embodiments, the compound may be selected from any of those provided in any one of Tables 1-16 and 18.

In some embodiments, the muscular dystrophy is merosin deficient congenital muscular dystrophy Type 1A (MDC1A), merosin deficient congenital muscular dystrophy Type 1D (MDC1D), limb-girdle muscular dystrophy (LGMD), Duchenne muscular dystrophy (DMD), Fukuyama congenital muscular dystrophy (FCMD) or Facioscapulohumeral muscular dystrophy (FHMD).

In some particular embodiments, the muscular dystrophy is DMD, MDC1A or FCMD.

In one particular embodiment, the muscular dystrophy is DMD.

In some embodiments, the α7β1 integrin modulatory agent is administered with an additional therapeutic agent.

In some embodiments, the additional therapeutic agent is a costameric protein, a growth factor, satellite cells, stem cells, myocytes or an additional α7β1 integrin modulatory agent.

In some embodiments, the additional α7β1 integrin modulatory agent is laminin-111, a laminin-111 fragment, valproic acid, or a valproic acid analog.

In some embodiments, the method further includes selecting a subject with muscular dystrophy.

In some embodiments, the selecting a subject with muscular dystrophy includes diagnosing the subject with muscular dystrophy prior to administering an effective amount of the α7β1 integrin modulatory agent to the subject.

In other embodiments, a method of enhancing muscle regeneration, repair, or maintenance in a subject is disclosed.

In some embodiments, the method includes administering an effective amount of an α7β1 integrin modulatory agent to the subject with muscular dystrophy, wherein the α7β1 integrin modulatory agent comprises a compound encompassed by any one of Formulas 1-16, or provided by any one of Tables 1-16 and 18, or a combination thereof, wherein the α7β1 integrin modulatory agent increases α7β1 integrin expression or activity as compared to α7β1 integrin expression or activity prior to treatment, thereby enhancing muscle regeneration, repair or maintenance in a subject.

In some embodiments, the method includes administering the α7β1 modulatory agent prior to the subject experiencing muscle damage or disease.

In some embodiments, the method is a method of enhancing muscle maintenance in a subject.

In some embodiments, the α7β1 integrin modulatory agent is administered to the subject prior to the subject exercising.

In some embodiments, the α7β1 integrin modulatory agent is administered to a subject at risk of acquiring a muscle disease or damage, such as an elderly subject.

In some embodiments, the method also includes selecting a subject in need of enhancing muscle regeneration, repair, or maintenance.

In some embodiments, selecting a subject in need of enhancing muscle regeneration, repair, or maintenance includes diagnosing the subject with a condition characterized by impaired muscle regeneration prior to administering an effective amount of the α7β1 integrin modulatory agent to the subject.

In some embodiments, selecting a subject in need of enhancing muscle regeneration, repair, or maintenance comprises diagnosing the subject with a condition characterized by impaired production of a component of α7β1 integrin prior to administering an effective amount of the α7β1 integrin modulatory agent to the subject.

In some embodiments, the α7β1 integrin modulatory agent is administered with an additional therapeutic agent.

In some embodiments, the additional therapeutic agent is a costameric protein, a growth factor, satellite cells, stem cells, myocytes or an additional α7β1 integrin modulatory agent.

In some embodiments, the additional α7β1 integrin modulatory agent is laminin-111, a laminin-111 fragment, valproic acid, or a valproic acid analog.

In further embodiments, a method of prospectively preventing or reducing muscle injury or damage in a subject is disclosed.

In some embodiments, the method includes administering an effective amount of an α7β1 integrin modulatory agent to the subject wherein the α7β1 integrin modulatory agent includes a compound encompassed by any one of Formulas 1-16, or provided by any one of Tables 1-16 and 18, or a combination thereof, wherein the α7β1 integrin modulatory agent increases α7β1 integrin expression or activity as compared to α7β1 integrin expression or activity prior to treatment, thereby prospectively preventing or reducing muscle injury or damage in the subject.

In some embodiments, the subject is at risk of developing a muscle injury or damage.

In some embodiments, the α7β1 integrin modulatory agent is administered with an additional therapeutic agent.

In some embodiments, the additional therapeutic agent is a costameric protein, a growth factor, satellite cells, stem cells, myocytes or an additional α7β1 integrin modulatory agent.

In some embodiments, the additional α7β1 integrin modulatory agent is laminin-111, a laminin-111 fragment, valproic acid, or a valproic acid analog.

In even further embodiments, a method of enhancing α7β1 integrin expression is provided.

In some embodiments, the method includes contacting a cell with an effective amount of an α7β1 integrin modulatory agent, wherein the α7β1 integrin modulatory agent includes a compound encompassed by any one of Formulas 1-16, or provided by any one of Tables 1-16 and 18, or a combination thereof and increases α7β1 integrin expression in the treated cell relative α7β1 integrin expression in an untreated cell, thereby enhancing α7β1 integrin expression.

In some embodiments, the cell is a muscle cell.

In some embodiments, the muscle cell is present in a mammal, and wherein contacting the cell with an agent comprises administering the agent to the mammal.

II. Terms

The following explanations of terms and methods are provided to better describe the present disclosure and to guide those of ordinary skill in the art in the practice of the present disclosure. The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless indicated otherwise, the nomenclature of substituents that are not explicitly defined herein are arrived at by naming the terminal portion of the functionality followed by the adjacent functionality toward the point of attachment.

A person of ordinary skill in the art would recognize that the above definitions are not intended to include impermissible substitution patterns (e.g., methyl substituted with 5 different groups, pentavalent carbon, and the like). Such impermissible substitution patterns are easily recognized by a person of ordinary skill in the art.

All publications, patent applications, patents, and other references mentioned herein are incorporated by reference in their entirety. All sequences provided in the disclosed Genbank Accession numbers are incorporated herein by reference as available on Aug. 11, 2011. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Administration: To provide or give a subject one or more agents, such as an agent that increases α7β1 expression and/or treats one or more symptoms associated with muscular dystrophy, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Agent: Any protein, nucleic acid molecule (including chemically modified nucleic acids), compound, antibody, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject, including treating a subject with a muscular dystrophy).

In some examples, an agent can act directly or indirectly to alter the expression and/or activity of α7β1. In a particular example, a therapeutic agent significantly increases the expression and/or activity of α7β1 (which is a muscular dystrophy associated molecule) thereby treating one or more signs or symptoms associated with muscular dystrophy. An example of a therapeutic agent is one that can increase the expression and/or activity of the α7β1 gene or gene product, for example as measured by a clinical response (such as a decrease in one or more signs or symptoms associated with the muscular dystrophy, an improvement in muscular health, regeneration, repair or maintenance of a muscle cell or tissue). "Improving muscular health" refers to an improvement in muscular health compared with a preexisting state or compared with a state which would occur in the absence of treatment. For example, improving muscular health may include enhancing muscle regeneration, maintenance, or repair. Improving muscular health may also include prospectively treating a subject to prevent or reduce muscular damage or injury. "Regeneration" refers to the repair of cells or tissue, such as muscle cells or tissue (or organs) which includes muscle cells, following injury or damage to at least partially restore the muscle or tissue to a condition similar to which the cells or tissue existed before the injury or damage occurred. Regeneration also refers to facilitating repair of cells or tissue in a subject having a disease affecting such cells or tissue to eliminate or ameliorate the effects of the disease. In more specific examples, regeneration places the cells or tissue in the same condition or an improved physiological condition as before the injury or damage occurred or the condition which would exist in the absence of disease. "Maintenance" of cells or tissue, such as muscle cells or tissue organs) which includes muscle cells, refers to maintaining the cells or tissue in at least substantially the same physiological condition, such as maintaining such condition even in the presence of stimulus which would normally cause damage, injury, or disease. "Repair" of cells or tissue, such as muscle cells or tissue (or organs) which includes muscle cells, refers to the physiological process of healing damage to the cells or tissue following damage or other trauma.

A "pharmaceutical agent" is a chemical compound or composition capable of inducing a desired therapeutic or prophylactic effect when administered to a subject, alone or in combination with another therapeutic agent(s) or pharmaceutically acceptable carriers. In a particular example, a pharmaceutical agent significantly increases the expression and/or activity of α7β1 thereby treating a condition or disease associated with decreased α7β1 expression/activity, such as muscular dystrophy.

Acyl: H—C(O)—, alkyl-C(O)—, substituted alkyl-C(O)—, cycloalkyl-C(O)—, substituted cycloalkyl-C(O)—, substituted aryl-C(O)—, heteroaryl-C(O)—, substituted heteroaryl-C(O)—, heterocyclyl-C(O)—, and substituted heterocyclyl-C(O)—.

Acylamino: —$NR^aC(O)$alkyl, —$NR^aC(O)$substituted alkyl. —$NR^aC(O)$cycloalkyl, —$NR^aC(O)$substituted cycloalkyl —$NR^aC(O)$cycloalkenyl, —$NR^aC(O)$substituted cycloalkenyl, —$NR^aC(O)$alkenyl, —$NR^aC(O)$substituted alkenyl, —$NR^aC(O)$alkynyl, —$NR^aC(O)$substituted alkynyl, —$NR^aC(O)$aryl, —$NR^aC(O)$substituted aryl, —$NR^aC(O)$heteroaryl, —$NR^aC(O)$substituted heteroaryl, —$NR^aC(O)$heterocyclyl, and —$NR^aC(O)$substituted heterocyclyl, wherein $R^a$ is selected from hydrogen, alkyl, aryl, and cycloalkyl.

Acyloxy: alkyl-C(O)O—, substituted alkyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclyl-C(O)O—, and substituted heterocyclyl-C(O)O—.

Acylalkyloxy: alkyl-C(O)alkylO—, substituted alkyl-C(O)alkylO—, aryl-C(O)alkylO—, substituted aryl-C(O)alkylO—, cycloalkyl-C(O)alkylO—, substituted cycloalkyl-C(O)alkylO—, heteroaryl-C(O)alkylO—, substituted heteroaryl-C(O)alkylO—, heterocyclyl-C(O)alkylO—, and substituted heterocyclyl-C(O)alkylO—.

Alkyl: A saturated or unsaturated monovalent hydrocarbon having a number of carbon atoms ranging from one to ten (e.g., $C_{1-10}$alkyl), which is derived from removing one hydrogen atom from one carbon atom of a parent compound (e.g., alkane, alkene, alkyne). An alkyl group may be branched or straight-chain.

Alkenyl: A unsaturated monovalent hydrocarbon having a number of carbon atoms ranging from one to ten (e.g., $C_{2-10}$alkenyl), which has at least one carbon-carbon double bond and is derived from removing one hydrogen atom from one carbon atom of a parent alkene. An alkenyl group may be branched, straight-chain, cyclic, cis, or trans (e.g., E or Z).

Alkynyl: A unsaturated monovalent hydrocarbon having a number of carbon atoms ranging from one to ten (e.g., $C_{2-10}$alkynyl), which has at least one carbon-carbon triple bond and is derived from removing one hydrogen atom from one carbon atom of a parent alkyne. An alkynyl group may be branched, straight-chain, or cyclic.

Alkoxy: —O-alkyl (e.g., methoxy, ethoxy, n-propoxy, isopropoxy, n-butoxy, t-butoxy, sec-butoxy, n-pentoxy).

Alkylthio: —S-alkyl, wherein alkyl is as defined herein. This term also encompasses oxidized forms of sulfur, such as —S(O)-alkyl, or —S(O)$_2$-alkyl.

Amino: —$NH_2$.

Aminocarbonyl: —$C(O)N(R^b)_2$, wherein each $R^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each $R^b$ may optionally be joined together with the nitrogen bound thereto to form a heterocyclyl or substituted heterocyclyl group, provided that both $R^b$ are not both hydrogen.

Aminocarbonylalkyl: -alkylC(O)N($R^b$)$_2$, wherein each $R^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each $R^b$ may optionally be joined together with the nitrogen bound thereto to form a heterocyclyl or substituted heterocyclyl group, provided that both $R^b$ are not both hydrogen.

Aminocarbonylamino: —$NR^aC(O)N(R^b)_2$, wherein $R^a$ and each $R^b$ are as defined herein.

Aminodicarbonylamino: —$NR^aC(O)C(O)N(R^b)_2$, wherein $R^a$ and each $R^b$ are as defined herein.

Aminocarbonyloxy: —O—$C(O)N(R^b)_2$, wherein each $R^b$ independently is as defined herein.

Aminosulfonyl: —$SO_2N(R^b)_2$, wherein each $R^b$ independently is as defined herein.

Analog or Derivative: A compound which is sufficiently homologous to a compound such that it has a similar functional activity for a desired purpose as the original compound. Analogs or derivatives refers to a form of a substance, such as cholestan, which has at least one functional group altered, added, or removed, compared with the parent compound. In some examples, examples of an analog are provided in Tables 1-6, for example. "Functional group" refers to a radical, other than a hydrocarbon radical, that adds a physical or chemical property to a substance.

Aryl: a monovalent aromatic carbocyclic group of from 6 to 15 carbon atoms having a single ring (e.g., phenyl) or multiple condensed rings (e.g., naphthyl), which condensed rings may or may not be aromatic provided that the point of attachment is through an atom of the aromatic aryl group.

Aryloxy —O-aryl.

Arylthio —S-aryl, wherein aryl is as defined herein. This term also encompasses oxidized forms of sulfur, such as —S(O)-aryl, or —S(O)$_2$-aryl.

Biological activity: The beneficial or adverse effects of an agent on living matter. When the agent is a complex chemical mixture, this activity is exerted by the substance's active ingredient or pharmacophore, but can be modified by the other constituents. Activity is generally dosage-dependent and it is not uncommon to have effects ranging from beneficial to adverse for one substance when going from low to high doses. In one example, the agent significantly increases the biological activity of α7β1 which reduces one or more signs or symptoms associated with the muscular dystrophy.

Contacting: Placement in direct physical association, including both a solid and liquid form. Contacting an agent with a cell can occur in vitro by adding the agent to isolated cells or in vivo by administering the agent to a subject.

Control: A sample or standard used for comparison with a test sample, such as a biological sample obtained from a patient (or plurality of patients) without a particular disease or condition, such as a muscular dystrophy. In some embodiments, the control is a sample obtained from a healthy patient (or plurality of patients) (also referred to herein as a "normal" control), such as a normal biological sample. In some embodiments, the control is a historical control or standard value (e.g., a previously tested control sample or group of samples that represent baseline or normal values (e.g., expression values), such as baseline or normal values of a particular gene such as a α7β1 gene, gene product in a subject without a muscular dystrophy). In some examples, the control is a standard value representing the average value (or average range of values) obtained from a plurality of patient samples (such as an average value or range of values of the gene or gene products, such as the α7β1 gene or gene products, in the subjects without a muscular dystrophy).

Carboxyl: —COOH or salts thereof.

Carboxyester: —C(O)O-alkyl, —C(O)O— substituted alkyl, —C(O)O-aryl, —C(O)O-substituted —C(O)O-cycloalkyl, —C(O)O-substituted cycloalkyl, —C(O)O-heteroaryl, —C(O)O-substituted heteroaryl, —C(O)O-heterocyclyl, and —C(O)O-substituted heterocyclyl.

(Carboxyester)amino: —NR$^a$—C(O)O-alkyl, —NR$^a$—C(O)O— substituted alkyl, —NR$^a$—C(O)O-aryl, —NR$^a$—C(O)O-substituted aryl, —NR$^a$—C(O)O-cycloalkyl, —NR$^a$—C(O)O-substituted cycloalkyl, —NR$^a$—C(O)O-heteroaryl, —NR$^a$—C(O)O-substituted heteroaryl, —NR$^a$—C(O)O-heterocyclyl, and —NR$^a$—C(O)O-substituted heterocyclyl, wherein R$^a$ is as recited herein.

(Carboxyester)oxy: —O—C(O)O-alkyl, —O—C(O)O— substituted alkyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclyl, and —O—C(O)O-substituted heterocyclyl.

Cyano: —CN.

Cycloalkyl: cyclic alkyl (or alkenyl, or alkynyl) groups of from 3 to 10 carbon atoms having single or multiple cyclic rings including fused, bridged, and spiro ring systems (e.g., cyclopropyl, cyclobutyl, etc.)

(Cycloalkyl)oxy: —O-cycloalkyl.

(Cycloalkyl)thio: —S-cycloalkyl. This term also encompasses oxidized forms of sulfur, such as —S(O)-cycloalkyl, or —S(O)$_2$-cycloalkyl.

Decrease: To reduce the quality, amount, or strength of something. In one example, a therapy decreases one or more symptoms associated with the muscular dystrophy, for example as compared to the response in the absence of the therapy.

Diagnosis: The process of identifying a disease, such as muscular dystrophy, by its signs, symptoms and results of various tests. The conclusion reached through that process is also called "a diagnosis." Forms of testing commonly performed include blood tests, medical imaging, urinalysis, and biopsy.

Effective amount: An amount of agent that is sufficient to generate a desired response, such as reducing or inhibiting one or more signs or symptoms associated with a condition or disease. When administered to a subject, a dosage will generally be used that will achieve target tissue/cell concentrations. In some examples, an "effective amount" is one that treats one or more symptoms and/or underlying causes of any of a disorder or disease. In some examples, an "effective amount" is a therapeutically effective amount in which the agent alone with an additional therapeutic agent(s) (for example anti-pathogenic agents), induces the desired response such as treatment of a muscular dystrophy, such as DMD, FCMD or MDC1A.

In particular examples, it is an amount of an agent capable of increasing α7β1 gene expression or activity by least 20%, at least 50%, at least 60%, at least 70%, at least 80%, at least 90%, at least 95%, at least 98%, or even at least 100% (elimination of the disease to a point beyond detection).

In some examples, an effective amount is an amount of a pharmaceutical preparation that alone, or together with a pharmaceutically acceptable carrier or one or more additional therapeutic agents, induces the desired response.

In one example, a desired response is to increase the subject's survival time by slowing the progression of the disease, such as slowing the progression of muscular dystrophy. The disease does not need to be completely inhibited for the pharmaceutical preparation to be effective. For example, a pharmaceutical preparation can decrease the progression of the disease by a desired amount, for example by at least 20%, at least 50%, at least 60%, at least 70%, at least 80%, at least 90%, at least 95%, at least 98%, or even at least 100%, as compared to the progression typical in the absence of the pharmaceutical preparation.

In another or additional example, it is an amount sufficient to partially or completely alleviate symptoms of the muscular dystrophy within the subject. Treatment can involve only slowing the progression of the disease temporarily, but can also include halting or reversing the progression of the disease permanently.

Effective amounts of the agents described herein can be determined in many different ways, such as assaying for a reduction in of one or more signs or symptoms associated with the muscular dystrophy in the subject or measuring the expression level of one or more molecules known to be associated with the muscular dystrophy. Effective amounts also can be determined through various in vitro, in vivo or in situ assays, including the assays described herein.

The disclosed therapeutic agents can be administered in a single dose, or in several doses, for example daily, during a course of treatment. However, the effective amount can be dependent on the source applied (for example a nucleic acid molecule isolated from a cellular extract versus a chemically synthesized and purified nucleic acid), the subject being treated, the severity and type of the condition being treated, and the manner of administration.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation. RNA transport and processing, degradation of intermediary molecules such as mRNA, or through activation, inactivation, compartmentalization or degradation of specific protein molecules after they are produced. In an example, expression, such as expression of α7β1, can be regulated to treat one or more signs or symptoms associated with muscular dystrophy.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it nominally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have muscular dystrophy, such as DMD, FCMD or MDC1A) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

Extracellular matrix: An extracellular structure of a tissue or a layer thereof, including the arrangement, composition, and forms of one or more matrix components, such as proteins, including structural proteins such as collagen and elastin, proteins such as fibronectin and laminins, and proteoglycans. The matrix may comprise fibrillic collagen, having a network of fibers. In some examples, the extracellular matrix is connected to cells through the costameric protein network.

Halogen or Halo: fluoro, chloro, bromo, and iodo.

Heteroaryl: an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl or furyl) or multiple condensed rings (e.g., indolizinyl or benzothienyl), wherein the condensed rings may or may not be aromatic and/or contain a heteroatom, provided that the point of attachment is through an atom of the aromatic heteroaryl group. In one embodiment, the nitrogen and/or sulfur ring atom(s) of the heteroaryl group are optionally oxidized to provide for the N-oxide (N→O), sulfinyl, or sulfonyl moieties.

Heteroaryloxy: —O-heteroaryl.

Heteroarylthio: —S-heteroaryl. This term also encompasses oxidized forms of sulfur, such as —S(O)-heteroaryl, or —S(O)$_2$-heteroaryl.

Heterocyclyl: a saturated, unsaturated group, or combinations thereof, having a single ring or multiple condensed rings, including fused bridged and Spiro ring systems, and having from 3 to 15 ring atoms, including 1 to 4 heteroatoms, selected from nitrogen, sulfur, or oxygen. These groups may be substituted with one or more of the substituents disclosed herein for substituted aryl and/or substituted alkyl. These groups encompass, for example, a saturated heterocyclyl fused with one or more aromatic hydrocarbons or heteroaryl groups.

Heterocyclyloxy: —O-heterocycyl.

Heterocyclylthio: —S-heterocycyl. This term also encompasses oxidized forms of sulfur, such as —S(O)-heterocyclyl, or —S(O)$_2$-heterocyclyl.

Hydroxyl or Hydroxy: —OH.

Imino: —N=R$^c$ wherein R$^c$ may be selected from hydrogen, aminocarbonylalkyloxy, substituted aminocarbonylalkyloxy, aminocarbonylalkylamino, and substituted aminocarbonylalkylamino.

Increase: To enhance the quality, amount, or strength of something. In one example, an agent increases the activity or expression of α7β1, for example relative to an absence of the agent. In a particular example, an agent increases the activity or expression of α7β1 by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. Such increases can be measured using the methods disclosed herein.

In a particular example, a therapy increases (also known as up-regulates) the expression of α7β1, such as an increase of at least 10%, at least 20%, at least 50%, or even at least 90% in α7β1 expression, thereby treating/alleviating one or more signs or symptoms associated with muscular dystrophy. In some examples, an increase in expression refers to an increase in a α7β1 gene product. An α7β1 gene product can be RNA (such as mRNA, rRNA, tRNA, and structural RNA) or protein.

Gene upregulation includes any detectable increase in the production of a α7β1 gene product. In certain examples, production of a α7β1 gene product increases by at least 2-fold, for example at least 3-fold or at least 4-fold, as compared to a control (such an amount of gene expression in a normal cell). In one example, a control is a relative amount of α7 gene expression or protein expression in a biological sample taken from a subject who does not have muscular dystrophy, such as DMD, FCMD or MDC1A. Such increases can be measured using the methods disclosed herein. For example, "detecting or measuring expression of α7β1" includes quantifying the amount of the gene, gene product or modulator thereof present in a sample. Quantification can be either numerical or relative. Detecting expression of the gene, gene product or modulators thereof can be achieved using any method known in the art or described herein, such as by measuring nucleic acids by PCR (such as RT-PCR) and proteins by ELISA. In primary embodiments, the change detected is an increase or decrease in expression as compared to a control, such as a reference value or a healthy control subject. In some examples, the detected increase or decrease is an increase or decrease of at least two-fold compared with the control or standard. Controls or standards for comparison to a sample, for the determination of differential expression, include samples believed to be normal (in that they are not altered for the desired characteristic, for example a sample from a subject who does not have muscular dystrophy, such as DMD, FCMD or MDC1A) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

In other embodiments of the methods, the increase or decrease is of a diagnostically significant amount, which refers to a change of a sufficient magnitude to provide a statistical probability of the diagnosis.

The level of expression in either a qualitative or quantitative manner can detect nucleic acid or protein. Exemplary methods include microarray analysis, RT-PCR, Northern blot, Western blot, and mass spectrometry.

Inhibiting a disease or condition: A phrase referring to reducing the development of a disease or condition, for example, in a subject who is at risk for a disease or who has a particular disease. Particular methods of the present disclosure provide methods for inhibiting muscular dystrophy.

Integrin: A cell surface transmembrane glycoprotein receptor. Integrins are involved in many biological processes such as wound healing, blood clot formation, gene regulation, and immune responses. Integrins can regulate tissue specific cell adhesion molecules. Integrins are heterodimeric non-covalently associated glycoproteins composed of two subunits. The subunits, which are designated α and beta, have approximate molecular weights of 150-180 kilodaltons and 90-110 kilodaltons, respectively.

The α7β1 integrin is a major laminin receptor expressed in skeletal muscle. The α7β1 integrin plays a role in the development of neuromuscular and myotendinous junctions. In the adult, the α7β1 integrin is concentrated at junctional sites and found in extrajunctional regions where it mediates the adhesion of the muscle fibers to the extracellular matrix. Mice that lack the α7 chain develop muscular dystrophy that affects the myotendinous junctions. The absence of α7 integrin results in defective matrix deposition at the myotendinous junction. Loss of the α7 integrin in γ-sarcoglycan mice results in severe muscle pathology. Absence of the α7 integrin in mdx mice also results in severe muscular dystrophy, confirming that the α7β1 integrin serves as a major genetic modifier for Duchenne and other muscular dystrophies.

Mutations in the α7 gene are responsible for muscular dystrophy in humans. A screen of 117 muscle biopsies from patients with undefined muscle disease revealed 3 which lacked the α7 integrin chain and had reduced levels of β1D integrin chain. These patients exhibited delayed developmental milestones and impaired mobility consistent with the role for the α7β1 integrin in neuromuscular and myotendinous junction development and function.

Several lines of evidence suggest the α7 integrin may be important for muscle regeneration. For example, during embryonic development, the α7β1 integrin regulates myoblast migration to regions of myofiber formation. It has been found that MyoD (myogenic determination protein) transactivates α7 integrin gene expression in vitro, which would increase α7 integrin levels in activated satellite cells. Human, mouse and rat myoblast cell lines derived from satellite cells express high levels of α7 integrin. Elevated α7 integrin mRNA and protein are detected in the skeletal muscle of 5 week old mdx mice, which correlates with the period of maximum muscle degeneration and regeneration. In addition, the α7β1 integrin associates with muscle specific β1-integrin binding protein (MIBP), which regulates laminin deposition in C2C12 myoblasts. Laminin provides an environment that supports myoblast migration and proliferation. Finally, enhanced expression of the α7 integrin in dystrophic skeletal muscle results in increased numbers of satellite cells.

The sequences for α7β1 integrin subunits are publicly available on GenBank, see, for example Gene Accession No. NM_001144116 (human) and NM_008398.2 (mouse) for α7 integrin, and Gene Accession No. NM_002211 for β1 integrin (also known as CD29), each of which is herein incorporated by reference as available on Sep. 8, 2011. Exemplary α7β1 integrin modulatory agents are disclosed herein, such as a compound encompassed by any one of Formulas 1-16, or provided by any one of Tables 1-16 and 18.

A α7β1 integrin-associated condition is a condition associated with altered α7β1 integrin expression or activity, including muscular dystrophy, such as DMD, FCMD, LGMD, FHMD, Beckers muscular dystrophy and/or MDC1A.

Laminin: Any of the family of glycoproteins that are typically involved in the formation and maintenance of extracellular matrices. Laminin is a heterotrimers formed from an α chain, a β chain, and a γ chain. The various chains of a particular laminin can affect the properties of the molecule. In some aspects of the present disclosure, fragments, derivatives, or analogs of various laminins can be used, such as laminins having at least a portion at least substantially homologous to the laminin α1 chain. A "fragment of laminin," as used herein, refers to a portion of a substance, such as laminin. A fragment may be, in some examples, a particular domain or chain of a protein. For example, particular embodiments of the present disclosure involve administering a fragment of laminin-1 corresponding to at least a portion of (or all of) the laminin al chain. Fragments may be synthetic or may be derived from larger parent substances.

In some aspects, laminins may be administered as a mixture of laminins, including fragments, analogs, and derivatives thereof. Suitable methods for preparing analogs of laminin domains are disclosed in U.S. Pat. No. 6,933,280, incorporated by reference herein to the extent not inconsistent with this disclosure.

The laminin materials or compositions of the present disclosure may be delivered as discrete molecules or may be complexed with, or conjugated to, another substance. For example, the laminin may be combined with a carrier, such as to aid in delivery of the laminin to a site of interest or to increase physiological uptake or incorporation of the laminin.

In specific examples, the laminin administered includes or consists of laminin-1 (LAM-111), which includes the chains α1β1γ1. In further examples, the laminin administered includes or consists of laminin-2, which includes the chains α2β1γ1. In yet further examples, the laminin administered includes or consists of laminin-4, which includes the chains α2β2γ1.

Laminins may be obtained from any suitable source. For example, laminin-1 may be obtained from placental tissue or from Engelbreth-Holm-Swarm murine sarcoma. Suitable methods of isolating various laminins are disclosed in U.S.

Pat. No. 5,444,158, incorporated by reference herein to the extent not inconsistent with the present disclosure.

Muscle: Any myoblast, myocyte, myofiber, myotube or other structure composed of muscle cells. Muscles or myocytes can be skeletal, smooth, or cardiac. Muscle may also refer to, in particular implementations of the present disclosure, cells or other materials capable of forming myocytes, such as stem cells and satellite cells.

Muscular dystrophy: A term used to refer to a group of genetic disorders that lead to progressive muscle weakness. Muscular dystrophy can result in skeletal muscle weakness and defects in skeletal muscle proteins, leading to a variety of impaired physiological functions. No satisfactory treatment of muscular dystrophy exists. Existing treatments typically focus on ameliorating the effects of the disease and improving the patient's quality of life, such as through physical therapy or through the provision of orthopedic devices.

Mutated genes associated with muscular dystrophy are responsible for encoding a number of proteins associated with the costameric protein network. Such proteins include laminin-2, collagen, dystroglycan, integrins, caveolin-3, ankyrin, dystrophin, α-dystrobrevin, vinculin, plectin, BPAG1b, muscle LIM protein, desmin, actinin-associated LIM protein, α-actin, titin, telethonin, cypher, myotilin, and the sarcoglycan/sarcospan complex.

The most common form of muscular dystrophy is DMD, affecting 1 in 3,500 live male births. DMD is an X-linked recessive disorder characterized by a mutation in the gene that codes for dystrophin. Dystrophin is a cytoskeletal protein about 430 kDa in size. This protein works to connect the cell's cytoskeleton and extracellular matrix. The loss of dystrophin in DMD patients leads to a loss of muscle fiber attachment at the extracellular matrix during contraction, which ultimately leads to progressive fiber damage, membrane leakage and a loss of muscle function. Most patients die before they reach the age of 30 due to respiratory or cardiac failure.

Beckers muscular dystrophy (also known as Benign pseudohypertrophic muscular dystrophy) is related to DMD in that both result from a mutation in the dystrophin gene, but in DMD no functional dystrophin is produced making DMD much more severe than BMD. BMD is an X-linked recessive inherited disorder characterized by slowly progressive muscle weakness of the legs and pelvis. BMD is a type of dystrophinopathy, which includes a spectrum of muscle diseases in which there is insufficient dystrophin produced in the muscle cells, results in instability in the structure of muscle cell membrane. This is caused by mutations in the dystrophin gene, which encodes the protein dystrophin. The pattern of symptom development of BMD is similar to DMD, but with a later, and much slower rate of progression.

Congenital muscular dystrophies are caused by gene mutations, FCMD and MDC1A are examples of congenital muscular dystrophies. MDC1A is a congenital muscular dystrophy due to a genetic mutation in the LAMA2 gene which results in lack of or complete loss of laminin-α2 protein. This loss of laminin-α2 leads to an absence of laminins-211/221. Laminins-211/221 are major components of the extracellular matrix and play a key role in muscle cell development. During muscle cell differentiation laminin binds to the α7β1 integrin. Without laminin-α2, muscle fibers are unable to adhere to the basement membrane and myotubes undergo apotosis. Muscle regeneration also fails, leading to a loss of muscle repair and an increase in muscle fibrosis and inflammation. This chronic tissue injury is a major cause of morbidity and mortality in MDC1A.

Congenital Muscular Dystrophies (CMD) and Limb-Girdle muscular dystrophy (LGMD) are common forms of highly heterogeneous muscular dystrophies which can be distinguished by their age at onset. In CMD, onset of symptoms is at birth or within the first 6 months of life; in LGMD onset of symptoms is in late childhood, adolescence or even adult life. Inheritance in LGMD can be autosomal dominant (LGMD type 1) or autosomal recessive (LGMD type 2), CMD is recessively inherited. CMD and LGMD can overlap both clinically and genetically MDC1A is a progressive muscle wasting disease that results in children being confirmed to a wheelchair, requiring ventilator assistance to breathe and premature death. Symptoms are detected at birth with poor muscle tone and "floppy" baby syndrome. DMD, BMD and LGMD are progressive muscle degenerative diseases usually diagnosed at 3-5 years of age when children show developmental delay including ability to walk and climb stairs. The disease is progressive and children are usually confined to a wheelchair in their teens and require ventilator assistance.

Fukuyama congenital muscular dystrophy (FCMD) is an inherited condition that predominantly affects the muscles, brain, and eyes. Congenital muscular dystrophies are a group of genetic conditions that cause muscle weakness and wasting (atrophy) beginning very early in life. Fukuyama congenital muscular dystrophy affects the skeletal muscles, which are muscles the body uses for movement. The first signs of the disorder appear in early infancy and include a weak cry, poor feeding, and weak muscle tone (hypotonia). Weakness of the facial muscles often leads to a distinctive facial appearance including droopy eyelids (ptosis) and an open mouth. In childhood, muscle weakness and joint deformities (contractures) restrict movement and interfere with the development of motor skills such as sitting, standing, and walking. Fukuyama congenital muscular dystrophy also impairs brain development. People with this condition have a brain abnormality called cobblestone lissencephaly, in which the surface of the brain develops a bumpy, irregular appearance (like that of cobblestones). These changes in the structure of the brain lead to significantly delayed development of speech and motor skills and moderate to severe intellectual disability. Social skills are less severely impaired. Most children with Fukuyama congenital muscular dystrophy are never able to stand or walk, although some can sit without support and slide across the floor in a seated position. More than half of all affected children also experience seizures. Other signs and symptoms of Fukuyama congenital muscular dystrophy include impaired vision, other eye abnormalities, and slowly progressive heart problems after age 10. As the disease progresses, affected people may develop swallowing difficulties that can lead to a bacterial lung infection called aspiration pneumonia. Because of the serious medical problems associated with Fukuyama congenital muscular dystrophy, most people with the disorder live only into late childhood or adolescence.

Fukuyama congenital muscular dystrophy is seen almost exclusively in Japan, where it is the second most common form of childhood muscular dystrophy (after Duchenne muscular dystrophy). Fukuyama congenital muscular dystrophy has an estimated incidence of 2 to 4 per 100,000 Japanese infants.

Fukuyama congenital muscular dystrophy is caused by mutations in the FKTN gene which encodes fukutin. The most common mutation in the FKTN gene reduces the amount of fukutin produced within cells. A shortage of fukutin likely prevents the normal modification of α-dystroglycan, which disrupts that protein's normal function. Without functional α-dystroglycan to stabilize muscle cells, muscle fibers become damaged as they repeatedly contract and relax with use. The damaged fibers weaken and die over time, leading to progressive weakness and atrophy of the skeletal muscles.

Defective α-dystroglycan also affects the migration of neurons during the early development of the brain. Instead of stopping when they reach their intended destinations, some neurons migrate past the surface of the brain into the fluid-filled space that surrounds it. Because Fukuyama congenital muscular dystrophy involves a malfunction of α-dystroglycan, this condition is described as a dystroglycanopathy.

Facioscapulohumeral muscular dystrophy (FHMD) is a form of muscular dystrophy associated with progressive muscle weakness and loss of muscle tissue. Unlike DMD and BMD which mainly affect the lower body, FSHD affects the upper body mainly the face, shoulder and upper arm muscles. However, it can affect muscles around the pelvis, hips, and lower leg. Symptoms for FSHD often do not appear until age 10-26, but it is not uncommon for symptoms to appear much later. In some cases, symptoms never develop. Symptoms are usually mild and very slowly become worse. Facial muscle weakness is common, and may include eyelid drooping, inability to whistle, decreased facial expression, depressed or angry facial expression, difficulty pronouncing words, shoulder muscle weakness (leading to deformities such as pronounced shoulder blades (scapular winging) and sloping shoulders), weakness of the lower, hearing loss and possible heart conditions.

Oxo: (=O).

Pharmaceutically acceptable carriers: The pharmaceutically acceptable carriers (vehicles) useful in this disclosure are conventional. Remington's Pharmaceutical Sciences, by E. W. Martin, Mack Publishing Co., Easton, Pa., 19th Edition (1995), describes compositions and formulations suitable for pharmaceutical delivery of one or more agents, such as one or more 001 modulatory agents.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical agents to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Sample (or biological sample): A biological specimen containing genomic DNA, RNA (including mRNA), protein, or combinations thereof, obtained from a subject. Examples include, but are not limited to, peripheral blood, urine, saliva, tissue biopsy, surgical specimen, and autopsy material. In one example, a sample includes muscle biopsy, such as from a subject with DMD, FCMD, or MDC1A.

Signs or symptoms: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for detecting muscular dystrophy, including measuring creatine kinase levels, electromyography (to determine if weakness is caused by destruction of muscle tissue rather than by damage to nerves) or immunohistochemistry/immunoblotting/immunoassay (e.g., ELISA) to measure muscular dystrophy-associated molecules, such as α7β1 integrin. In one example, reducing or inhibiting one or more symptoms or signs associated with muscular dystrophy, includes increasing the activity or expression of α7β1 integrin by a desired amount, for example by at least 20%, at least 50%, at least 60%, at least 70%, at least 80%, at least 90%, at least 95%, at least 98%, or even at least 100%, as compared to the activity and/or expression in the absence of the treatment. Symptoms of muscular dystrophy include, but are not limited to, muscle weakness and loss, difficulty running, difficulty hopping, difficulty jumping, difficulty walking, difficulty breathing, fatigue, skeletal deformities, muscle deformities (contractions of heels; pseudohypertrophy of calf muscles), heart disease (such as dilated cardiomyopathy), elevated creatine phosphokinase (CK) levels in blood or combinations thereof.

Subject: Living multi-cellular vertebrate organisms, a category that includes human and non-human mammals.

Substituted Alkyl: an alkyl (or alkenyl, or alkynyl) group having from 1 to 5 hydrogen atoms replaced with substituents selected alkoxy, substituted alkoxy, acyl, acylamino, acyloxy, acylalkyloxy, amino, substituted amino, aminocarbonyl, aminocarbonylamnino, aminocarbonyloxy, aminodicarbonylamino, aminocarbonylalkyl, aminosulfonyl, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, aminodiacylamino, cycloalkyloxy, substituted cycloalkyloxy, cycloalkylthio, substituted cycloalkylthio, halo, hydroxy, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, imino, oxo, sulfonylamino, nitro, $SO_3H$, sulfonyl, thiol, imino, substituted imino, alkylthio, and substituted alkylthio. The alkyl may be substituted with 1 to 2, 1 to 3, or 1 to 4 of these groups, which are defined herein.

Substituted Alkoxy: —O-(substituted alkyl).

Substituted Alkylthio: —S-(substituted alkyl). This term also encompasses oxidized forms of sulfur, such as —S(O)-substituted alkyl, or —S(O)$_2$-substituted alkyl.

Substituted Amino: —N($R^b$)$_2$, wherein each $R^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each $R^b$ may optionally be joined together with the nitrogen bound thereto to form a heterocyclyl or substituted heterocyclyl group, provided that both $R^b$ are not both hydrogen.

Substituted Aryl: aryl groups having 1 to 5 hydrogens replaced with substituents independently selected from alkoxy, substituted alkoxy, acyl, acylamino, acyloxy, amino, substituted amino, aminocarbonyl, aminocarbonylamino, aminocarbonyloxy, aminosulfonyl, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, halo, hydroxy, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, SO₃H, sulfonyl, thiol, alkylthio, and substituted alkylthio. The amyl group may be substituted with 1 to 2, 1 to 3, or 1 to 4 of these groups, which are defined herein.

Substituted Aryloxy: —O-(substituted aryl).

Substituted Arylthio: —S-(substituted aryl), wherein substituted aryl is as defined herein. This term also encompasses oxidized forms of sulfur, such as —S(O)-substituted aryl, or —S(O)₂-substituted aryl.

Substituted Cycloalkyl: cycloalkyl, cycloalkenyl, or cycloalkynyl group having from 1 to 5 substituents selected from the group consisting of oxo, alkoxy, substituted alkoxy, acyl, acylamino, acyloxy, amino, substituted amino, aminocarbonyl, aminocarbonylamino, aminocarbonyloxy, aminosulfonyl, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, halo, hydroxy, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, SO₃H, sulfonyl, thiol, alkylthio, and substituted alkylthio. The aryl group may be substituted with 1 to 2, 1 to 3, or 1 to 4 of these groups, which are defined herein. In some embodiments, the cycloalkyl group may have multiple condensed rings (e.g. tetrahydronaphthyl or tetrahydroanthacenyl), provided that the point of attachment is through an atom of the nonaromatic ring.

Substituted (Cycloalkyl)oxy: —O-(substituted cycloalkyl).

Substituted (Cycloalkyl)thio: refers to —S-(substituted cycloalkyl). This term also encompasses oxidized forms of sulfur, such as —S(O)-substituted cycloalkyl, or —S(O)₂-substituted cycloalkyl.

Substituted Heteroaryl: heteroaryl groups that are substituted with from 1 to 5 substituents selected from the group consisting of the same group of substituents defined for substituted aryl.

Substituted Heteroaryloxy: —O-(substituted heteroaryl).

Substituted Heteroarylthio: —S-(substituted heteroaryl). This term also encompasses oxidized forms of sulfur, such as —S(O)-substituted heteroaryl, or —S(O)₂-substituted heteoaryl.

Substituted Heterocycyloxy: —O-(substituted heterocyclyl) wherein the heterocyclyl group is substituted with one or more of the substituents recited for substituted alkyl.

Substituted Heterocylthio: —S-(substituted heterocycyl). This term also encompasses oxidized forms of sulfur, such as —S(O)-substituted heterocyclyl, or —S(O)₂-substituted heterocyclyl.

Sulfonyl: —SO₂-alkyl, —SO₂-substituted alkyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclyl, and —SO₂-substituted heterocyclyl.

Sulfonylamino: —NR¹SO₂alkyl, —NR¹SO₂substituted alkyl, —NR¹SO₂cycloalkyl, —NR¹SO₂substituted cycloalkyl, —NR¹SO₂aryl, —NR¹SO₂substituted aryl, —NR¹SO₂heteroaryl, —NR¹SO₂substituted heteroaryl, —NR¹SO₂heterocyclyl, —NR¹SO₂substituted heterocyclyl, wherein each $R^a$ independently is as defined herein.

Thiol: —SH.

Thiocarbonyl: (=S)

Tissue: An aggregate of cells, usually of a particular kind, together with their intercellular substance that form one of the structural materials of an animal and that in animals include connective tissue, epithelium, muscle tissue, and nerve tissue.

Treating a disease: A therapeutic intervention that ameliorates a sign or symptom of a disease or pathological condition related to a muscular dystrophy, such as a sign or symptom of muscular dystrophy. Treatment can induce remission or cure of a condition or slow progression, for example, in some instances can include inhibiting the fill development of a disease, for example preventing development of a muscular dystrophy. Prevention of a disease does not require a total absence of disease. For example, a decrease of at least 50% can be sufficient.

Treating a disease can be a reduction in severity of some or all clinical symptoms of the disease or condition, a reduction in the number of relapses of the disease or condition, an improvement in the overall health or well-being of the subject, by other parameters well known in the art that are specific to the particular disease or condition, and combinations of such factors.

Under conditions sufficient for: A phrase that is used to describe any environment that permits the desired activity. In one example, includes administering a disclosed agent to a subject sufficient to allow the desired activity. In particular examples, the desired activity is increasing the expression or activity of α7β1.

III. Compounds for Treating Muscular Dystrophy

Disclosed herein are compounds that may be used as α7β1 integrin modulatory agents in methods disclosed herein. In particular disclosed embodiments, the compound is effective in treating muscular dystrophy. The compound is a small-molecule therapeutic. In particular disclosed embodiments, the small-molecule therapeutic is a cyclic compound comprising a heteroatom-containing skeleton. In other disclosed embodiments, the small-molecule therapeutic is a cyclic compound comprising an all-carbon skeleton. In certain disclosed embodiments, the cyclic compound comprising a heteroatom-containing skeleton has a formula illustrated below:

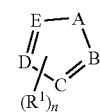

Formula 1 wherein each $R^1$ independently is selected from $C_{1-10}$alkyl, substituted $C_{1-10}$alkyl, $C_{1-10}$alkoxy, substituted $C_{1-10}$alkoxy, acyl, acylamino, acyloxy, acyl$C_{1-10}$alkyloxy, amino, substituted amino, aminoacyl, aminocarbonyl$C_{1-10}$alkyl, aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester) amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, halo, hydroxyl, $C_{3-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, and substituted $C_{1-10}$alkythio, thiocarbonyl; or two $R^1$ substituents, together with the atom to which each is bound, may form ring selected from a $C_{6-15}$aryl, substituted $C_{6-15}$aryl, $C_{3-8}$cycloalkyl, substituted $C_{3-8}$cycloalkyl, $C_{1-10}$heteroaryl, substituted $C_{1-10}$heteroaryl, $C_{2-10}$substituted heterocyclyl, and $C_{2-10}$heterocyclyloxy, substituted;

each of A, B, C, D, and E independently may be selected from carbon, nitrogen, oxygen, and sulfur; and n may be zero, 1, 2, 3, 4, or 5.

In other embodiments, the cyclic compound comprising a heteroatom-containing moiety has a formula illustrated below:

Formula 2

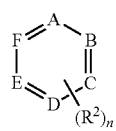

wherein each $R^2$ independently is selected from $C_{1-10}$alkyl, substituted $C_{1-10}$alkyl, $C_{1-10}$alkoxy, substituted $C_{1-10}$alkoxy, acyl, acylamino, acyloxy, acyl$C_{1-10}$alkyloxy, amino, substituted amino, aminoacyl, aminocarbonyl$C_{1-10}$alkyl, aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester) amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, halo, hydroxyl, $C_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, and substituted $C_{1-10}$alkythio, thiocarbonyl; or two $R^2$ substituents, together with the atom to which each is bound, may form ring selected from a $C_{6-15}$aryl, substituted $C_{6-15}$aryl, $C_{3-8}$cycloalkyl, substituted $C_{3-8}$cycloalkyl, $C_{1-10}$heteroaryl, substituted $C_{1-10}$heteroaryl, $C_{2-10}$substituted heterocyclyl, and $C_{2-10}$heterocyclyloxy, substituted;

each of A, B, C, D, E, and F independently may be selected from carbon, nitrogen, oxygen, and sulfur; and n may be zero, 1, 2, 3, 4, or 5.

In particular disclosed embodiments, the cyclic compound comprising an all-carbon skeleton may have a general formula provided below:

Formula 3

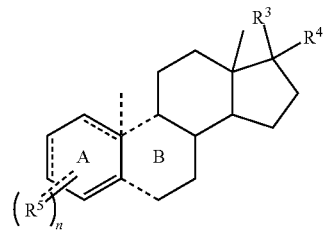

wherein $R^3$ and $R^4$ independently may be selected from hydroxyl, hydrogen, $C_{1-10}$alkyl, substituted $C_{1-10}$alkyl, carboxyl, acyl, aminoacyl, acylamino, amino, substituted amino, $C_{6-15}$aryl, substituted $C_{6-15}$aryl, and $C_{1-10}$alkoxy; $R^5$ is selected from amino, substituted amino, oxo, hydroxyl, $C_{1-10}$alkoxy, and imino; and n may be zero, 1, 2, 3, 4, or 5. A person of ordinary skill in the art will recognize that the dashed lines indicate optional bonds which may be present in certain compounds and not present in others.

In particular disclosed embodiments, rings A and B are connected via the optional bonds to form a steroid-based skeleton. In embodiments wherein rings A and B are connected, $R^5$ may be bound to ring A via a double bond or a single bond, a feature that is indicated with the optional dashed bond in Formula 13. For example, if $R^5$ is amino, hydroxyl, substituted amino, or $C_{1-10}$alkoxy, then $R^5$ is attached to ring A via a single bond, whereas if $R^5$ is oxo or imino, then $R_5$ is attached to ring A via a double bond.

In particular disclosed embodiments. $C_{6-15}$aryl may be selected from phenyl, biphenyl, naphthalene, anthracene, and the like; substituted $C_{6-15}$aryl may be selected from phenyl, biphenyl, naphthalene, and anthracene substituted with one or more substituents as defined herein; $C_{1-10}$alkyl may be selected from $C_{1-10}$alkane, $C_{2-10}$alkene, and $C_{2-10}$alkyne; more typically from methyl, ethyl, propyl, butyl, pentyl, hexyl, and the like; ethylene, propylene, butylene, and the like; and ethyne, propyne, butyne, and the like; substituted $C_{1-10}$alkyl may be selected from $C_{1-10}$alkane, $C_{2-10}$alkene, and $C_{2-10}$alkyne substituted with one or of the substituents as provided herein.

Exemplary embodiments concerning heterocyclyl and heteroaryl substitutents include, but are not limited to, epoxy, pyrrolyl, imidazole, pyrazole, pyridinyl, pyrazine, pyrimidine, oxanyl, thianyl, dioxanyl, dithianyl, coumarin, pyridazine, indolizine, isoindole, indolyl, indolinyl (or dihydroindole), indazole, purine, isoquinoline, quinoline, benzo[d]pyridazine, naphthyridine, quinoxaline, quinazoline, benzopyridazine, pteridine, carbazole, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl, piperidinyl, pyrrolidinyl, piperazinyl, oxazolidinyl, oxazolyl, thiophenyl, isooxazolidinyl, and tetrahydrofuranyl.

Exemplary substituents wherein at least two $R^1$ groups have been joined together include the following:

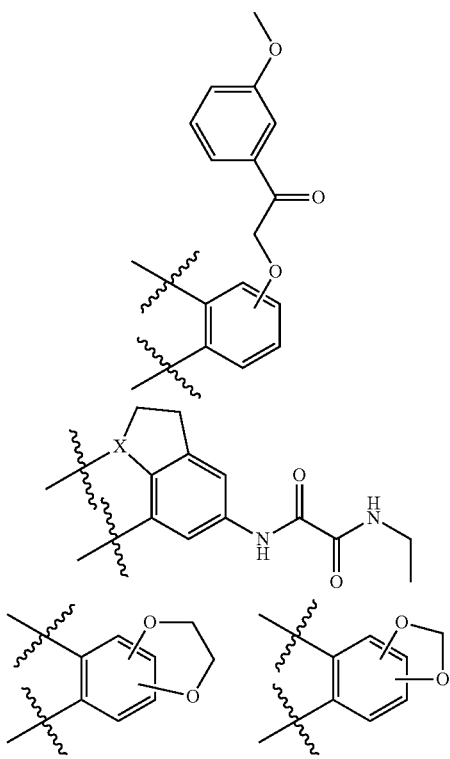

Particular disclosed embodiments concern cyclic compounds comprising a five-membered heteroatom-containing skeleton having a formula selected from those provided below.

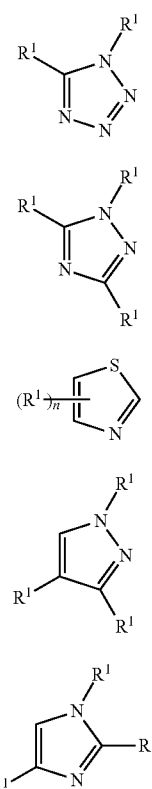

With reference to Formulas 4-6, $R^1$ and n are as recited herein, and each X independently may be selected from carbon, oxygen, nitrogen, and sulfur.

In yet other embodiments, the cyclic compound comprising a five-membered heteroatom-containing skeleton may have any one of the following formulas wherein $R^1$ is as recited herein.

Exemplary compounds are provided below.

TABLE 1

Exemplary Compounds

TABLE 1-continued
Exemplary Compounds
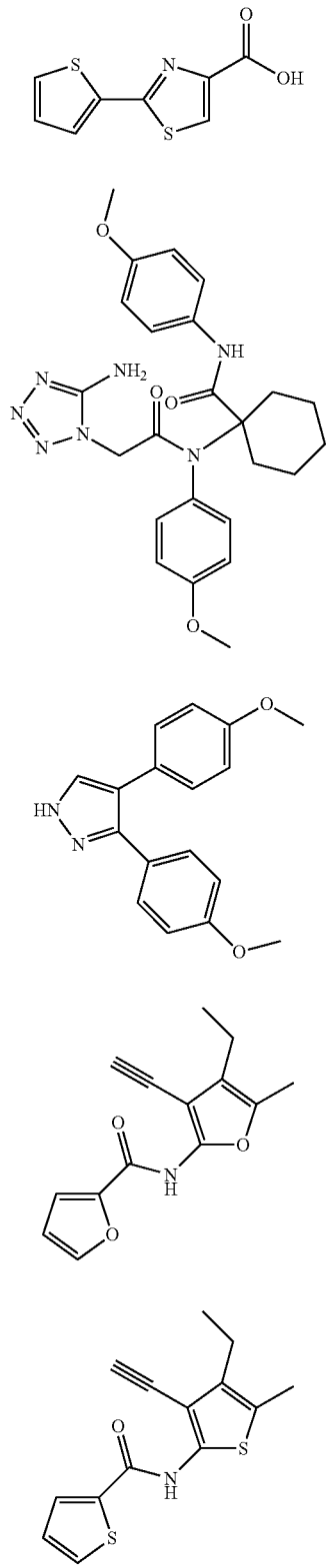
TABLE 1-continued
Exemplary Compounds
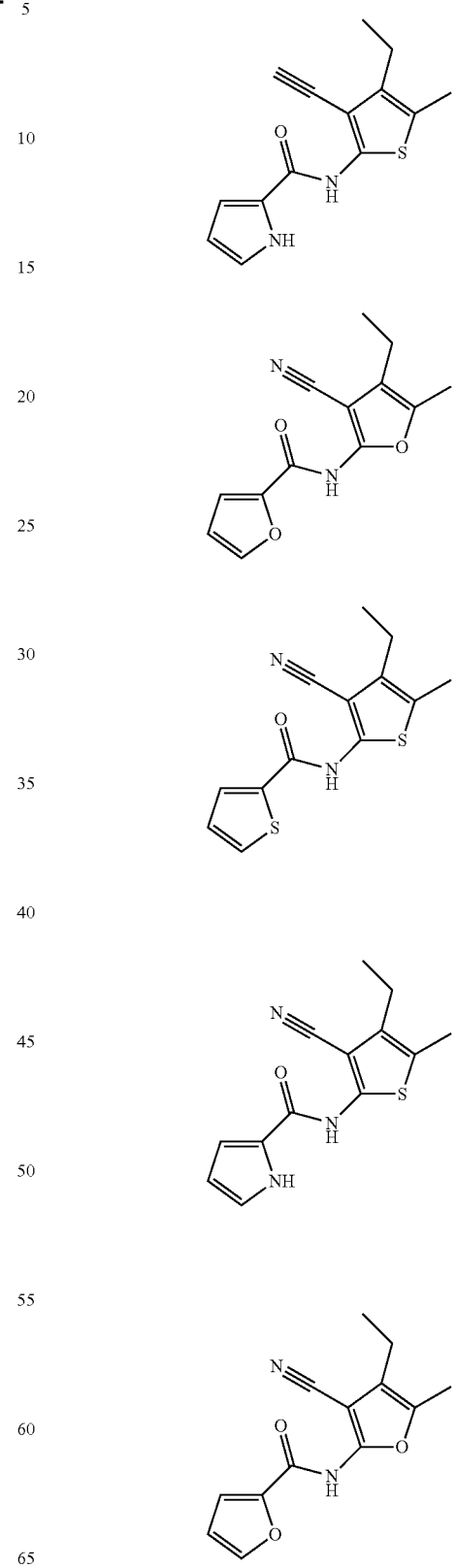

TABLE 1-continued
Exemplary Compounds
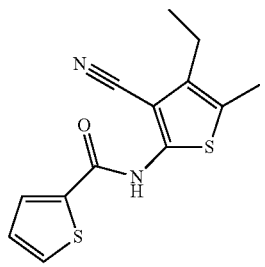 [SMILES: CCc1c(C)sc(NC(=O)c2cccs2)c1C#N]
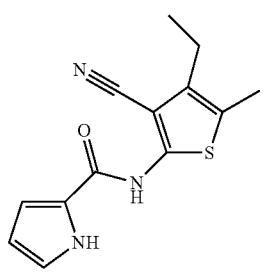
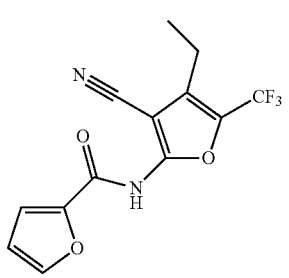 [SMILES: CCc1c(C(F)(F)F)oc(NC(=O)c2ccco2)c1C#N]
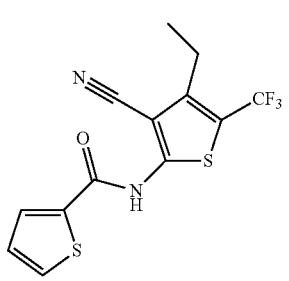 [SMILES: CCc1c(C(F)(F)F)sc(NC(=O)c2cccs2)c1C#N]
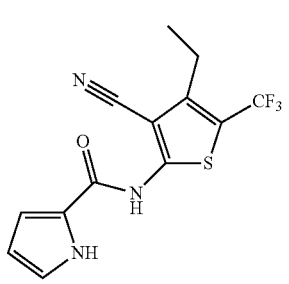 [SMILES: CCc1c(C(F)(F)F)sc(NC(=O)c2ccc[nH]2)c1C#N]
TABLE 1-continued
Exemplary Compounds
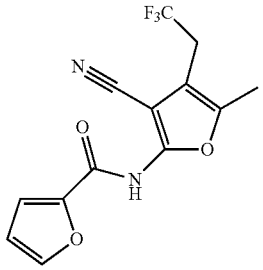 [SMILES: Cc1oc(NC(=O)c2ccco2)c(C#N)c1CC(F)(F)F]
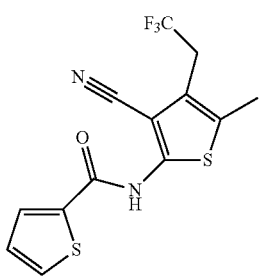 [SMILES: Cc1sc(NC(=O)c2cccs2)c(C#N)c1CC(F)(F)F]
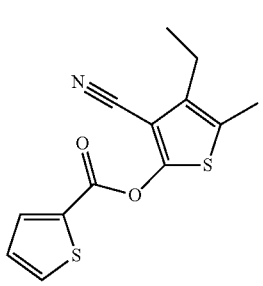 [SMILES: CCc1c(C)sc(OC(=O)c2cccs2)c1C#N]
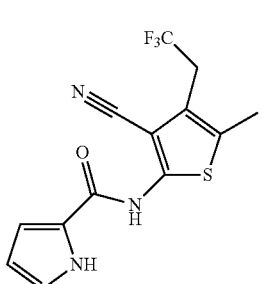
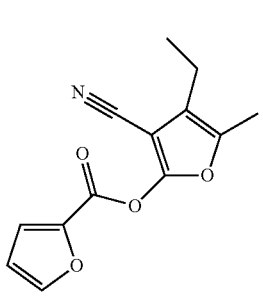 [SMILES: CCc1c(C)oc(OC(=O)c2ccco2)c1C#N]

TABLE 1-continued

Exemplary Compounds

TABLE 1-continued

Exemplary Compounds

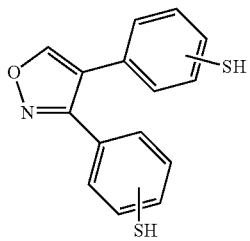

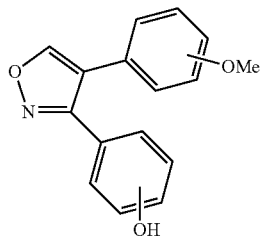

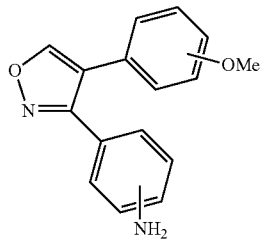

Particular embodiments concern cyclic compounds comprising a six-membered heteroatom-containing skeleton having any one of the formulas provided below:

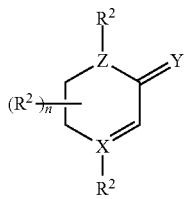

Formula 12

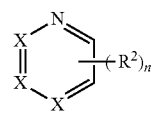

Formula 13

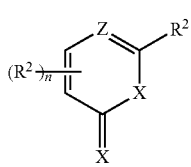

Formula 14 wherein $R^2$ and n are as recited herein, Z may be selected from carbon and nitrogen, Y may be selected from nitrogen and oxygen, and each X independently may be selected from nitrogen and carbon. A person of ordinary skill in the art will recognize that the dashed lines indicate variable bonds which may or may not be present, depending on the valency of the atom to which each variable bond is attached. For example, if the variable bond indicated in Formula 11 is present, X typically is carbon, as a carbon atom can accommodate four bonds. X may be nitrogen in such a compound; however, a person of ordinary skill in the art would recognize that the nitrogen atom would be positively charged due to the fact that its lone pairs are used to accommodate a fourth bond.

Exemplary compounds are provided below solely as illustrative examples.

TABLE 2

Exemplary Compounds

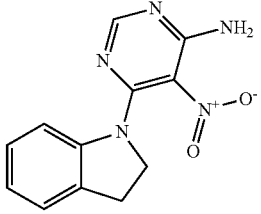 [SMILES: Nc1ncnc(N2CCc3ccccc32)c1[N+](=O)[O-]]

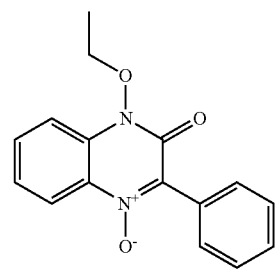 [SMILES: CCOn1c(=O)c(-c2ccccc2)[n+]([O-])c2ccccc21]

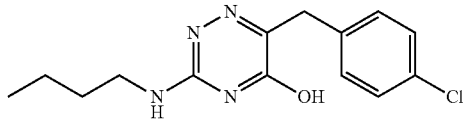 [SMILES: CCCCNc1nnc(Cc2ccc(Cl)cc2)c(O)n1]

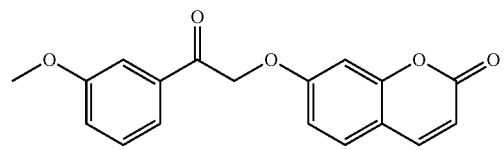 [SMILES: COc1cccc(C(=O)COc2ccc3ccc(=O)oc3c2)c1]

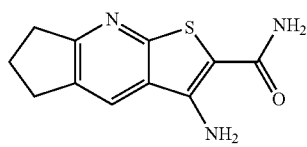 [SMILES: NC(=O)c1sc2nc3c(cc2c1N)CCC3]

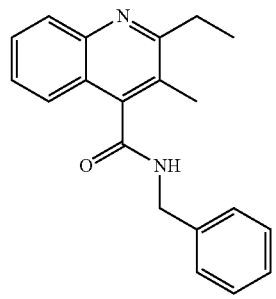 [SMILES: CCc1nc2ccccc2c(C(=O)NCc2ccccc2)c1C]

TABLE 2-continued
Exemplary Compounds
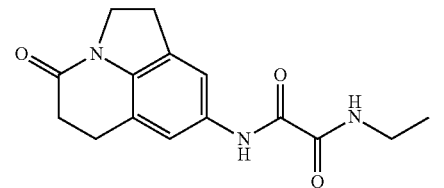 [SMILES: CCNC(=O)C(=O)Nc1cc2c3c(c1)CCN3C(=O)CC2]
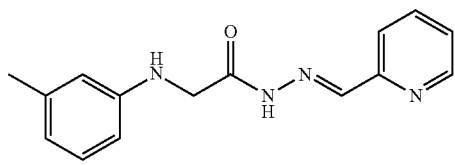 [SMILES: Cc1cccc(NCC(=O)N/N=C/c2ccccn2)c1]
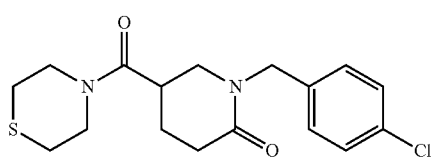 [SMILES: O=C1CCC(C(=O)N2CCSCC2)CN1Cc1ccc(Cl)cc1]
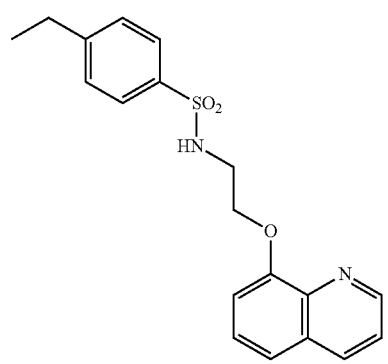 [SMILES: CCc1ccc(S(=O)(=O)NCCOc2cccc3cccnc23)cc1]
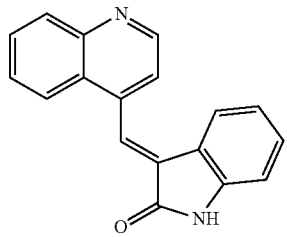 [SMILES: O=C1Nc2ccccc2/C1=C\c1ccnc2ccccc12]
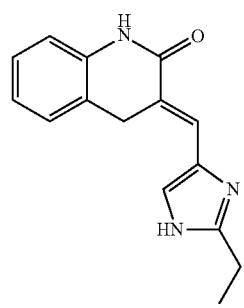 [SMILES: CCc1nc(/C=C2\Cc3ccccc3NC2=O)c[nH]1]
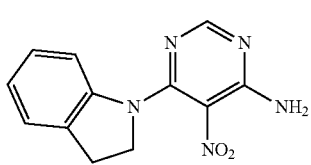 [SMILES: Nc1ncnc(N2CCc3ccccc32)c1[N+](=O)[O-]]
TABLE 2-continued
Exemplary Compounds
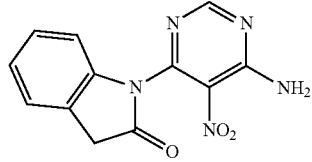 [SMILES: Nc1ncnc(N2C(=O)Cc3ccccc32)c1[N+](=O)[O-]]
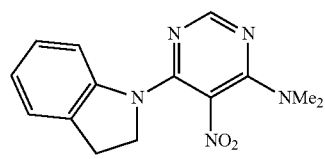 [SMILES: CN(C)c1ncnc(N2CCc3ccccc32)c1[N+](=O)[O-]]
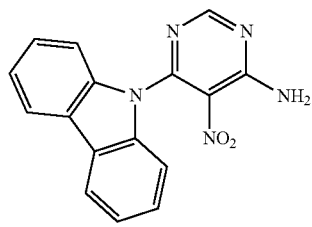 [SMILES: Nc1ncnc(-n2c3ccccc3c3ccccc32)c1[N+](=O)[O-]]
Particular embodiments concern compounds comprising an all-carbon, steroidal skeleton having a formula as illustrated below.
Formula 15
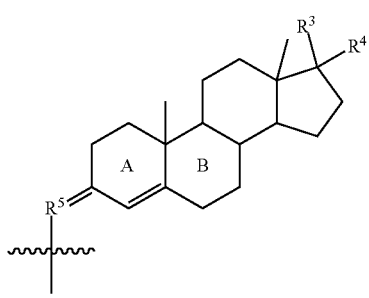

An exemplary compound is provided below.

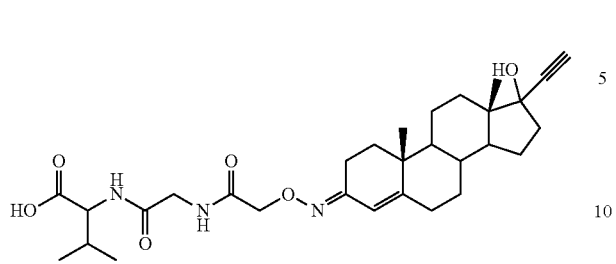

In other disclosed embodiments of the compound comprising an all-carbon skeleton, ring A is not connected with ring B and exists as an aryl compound having a formula illustrated below.

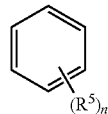

Formula 16

Exemplary compounds are illustrated below.

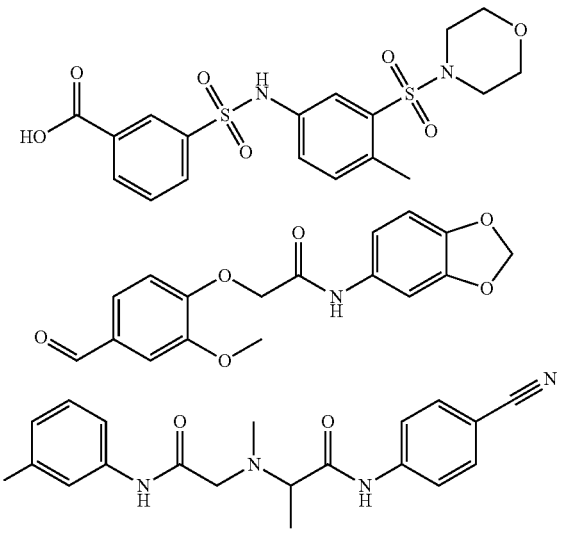

Other compounds suitable for use in the methods disclosed herein are provided below in Tables 3, 4, 5, and 6. Any of the compounds provided in Tables 3-6, and any other compounds disclosed herein, can be made using synthetic methods well known in the art of chemical synthesis.

TABLE 3

| $R^1$ | $R^{1'}$ | $R^2$ | $R^3$ |
|---|---|---|---|
| $C(O)NH_2$ | $NHR_3$, or $N[(CH_2)_{0-5}CH_3]_2$ | Halo | H or $-(CH_2)_{0-5}CH_3$ |
| $C(O)N[(CH_2)_{0-5}CH_3]_2$ | $NHR_3$, or $N[(CH_2)_{0-5}CH_3]_2$ | Halo | H or $-(CH_2)_{0-5}CH_3$ |
| $C(O)NH$-Ph | $NHR_3$, or $N[(CH_2)_{0-5}CH_3]_2$ | Halo | H or $-(CH_2)_{0-5}CH_3$ |
| $C(O)NH$-2,4-fluorophenyl | $NHR_3$, or $N[(CH_2)_{0-5}CH_3]_2$ | Halo | H or $-(CH_2)_{0-5}CH_3$ |
| $C(O)NH$-4-fluorophenyl | $NHR_3$, or $N[(CH_2)_{0-5}CH_3]_2$ | Halo | H or $-(CH_2)_{0-5}CH_3$ |
| $C(O)NH$-3-fluorophenyl | $NHR_3$, or $N[(CH_2)_{0-5}CH_3]_2$ | Halo | H or $-(CH_2)_{0-5}CH_3$ |
| $C(O)NH$-4-morpholinylphenyl | $NHR_3$, or $N[(CH_2)_{0-5}CH_3]_2$ | Halo | H or $-(CH_2)_{0-5}CH_3$ |
| $C(O)NH$-4-piperazinyllphenyl | $NHR_3$, or $N[(CH_2)_{0-5}CH_3]_2$ | Halo | H or $-(CH_2)_{0-5}CH_3$ |
| $C(O)NH$-3-thiomethylphenyl | $NHR_3$, or $N[(CH_2)_{0-5}CH_3]_2$ | Halo | H or $-(CH_2)_{0-5}CH_3$ |
| H | $NHR_3$, or $N[(CH_2)_{0-5}CH_3]_2$ | Halo | H or $-(CH_2)_{0-5}CH_3$ |
| $C(O)O(CH_2)_{0-5}CH_3$ | $NHR_3$, or $N[(CH_2)_{0-5}CH_3]_2$ | Halo | H or $-(CH_2)_{0-5}CH_3$ |
| $C(O)OH$ | $NHR_3$, or $N[(CH_2)_{0-5}CH_3]_2$ | Halo | H or $-(CH_2)_{0-5}CH_3$ |
| $C(O)NH_2$ | $NHR_3$, or $N[(CH_2)_{0-5}CH_3]_2$ | OH | H or $-(CH_2)_{0-5}CH_3$ |
| $C(O)NR[(CH_2)_{0-5}CH_3]_2$ | $NHR_3$, or $N[(CH_2)_{0-5}CH_3]_2$ | OH | H or $-(CH_2)_{0-5}CH_3$ |
| $C(O)NHPh$ | $NHR_3$, or $N[(CH_2)_{0-5}CH_3]_2$ | OH | H or $-(CH_2)_{0-5}CH_3$ |
| $C(O)NH$-2,4-fluorophenyl | $NHR_3$, or $N[(CH_2)_{0-5}CH_3]_2$ | OH | H or $-(CH_2)_{0-5}CH_3$ |
| $C(O)NH$-4-fluorophenyl | $NHR_3$, or $N[(CH_2)_{0-5}CH_3]_2$ | OH | H or $-(CH_2)_{0-5}CH_3$ |
| $C(O)NH$-3-fluorophenyl | $NHR_3$, or $N[(CH_2)_{0-5}CH_3]_2$ | OH | H or $-(CH_2)_{0-5}CH_3$ |
| $C(O)NH$-4-morpholinylphenyl | $NHR_3$, or $N[(CH_2)_{0-5}CH_3]_2$ | OH | H or $-(CH_2)_{0-5}CH_3$ |
| $C(O)NH$-4-piperazinyllphenyl | $NHR_3$, or $N[(CH_2)_{0-5}CH_3]_2$ | OH | H or $-(CH_2)_{0-5}CH_3$ |
| $C(O)NH$-3-thiomethylphenyl | $NHR_3$, or $N[(CH_2)_{0-5}CH_3]_2$ | OH | H or $-(CH_2)_{0-5}CH_3$ |
| H | $NHR_3$, or $N[(CH_2)_{0-5}CH_3]_2$ | OH | H or $-(CH_2)_{0-5}CH_3$ |
| $C(O)O(CH_2)_{0-5}CH_3$ | $NHR_3$, or $N[(CH_2)_{0-5}CH_3]_2$ | OH | H or $-(CH_2)_{0-5}CH_3$ |
| $C(O)OH$ | $NHR_3$, or $N[(CH_2)_{0-5}CH_3]_2$ | OH | H or $-(CH_2)_{0-5}CH_3$ |
| $C(O)NH_2$ | $NHR_3$, or $N[(CH_2)_{0-5}CH_3]_2$ | $-O(CH_2)_{0-5}CH_3$ | H or $-(CH_2)_{0-5}CH_3$ |
| $C(O)N[(CH_2)_{0-5}CH_3]_2$ | $NHR_3$, or $N[(CH_2)_{0-5}CH_3]_2$ | $-O(CH_2)_{0-5}CH_3$ | H or $-(CH_2)_{0-5}CH_3$ |
| $C(O)NHPh$ | $NHR_3$, or $N[(CH_2)_{0-5}CH_3]_2$ | $-O(CH_2)_{0-5}CH_3$ | H or $-(CH_2)_{0-5}CH_3$ |
| $C(O)NH$-2,4-fluorophenyl | $NHR_3$, or $N[(CH_2)_{0-5}CH_3]_2$ | $-O(CH_2)_{0-5}CH_3$ | H or $-(CH_2)_{0-5}CH_3$ |
| $C(O)NH$-4-fluorophenyl | $NHR_3$, or $N[(CH_2)_{0-5}CH_3]_2$ | $-O(CH_2)_{0-5}CH_3$ | H or $-(CH_2)_{0-5}CH_3$ |
| $C(O)NH$-3-fluorophenyl | $NHR_3$, or $N[(CH_2)_{0-5}CH_3]_2$ | $-O(CH_2)_{0-5}CH_3$ | H or $-(CH_2)_{0-5}CH_3$ |
| $C(O)NH$-4-morpholinylphenyl | $NHR_3$, or $N[(CH_2)_{0-5}CH_3]_2$ | $-O(CH_2)_{0-5}CH_3$ | H or $-(CH_2)_{0-5}CH_3$ |

TABLE 3-continued

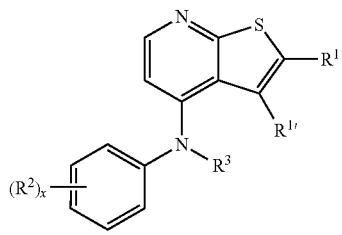

| R¹ | R¹' | R² | R³ |
|---|---|---|---|
| C(O)NH-4-piperazinyllphenyl | $NHR_3$, or $N[(CH_2)_{0-5}CH_3]_2$ | —O$(CH_2)_{0-5}CH_3$ | H or —$(CH_2)_{0-5}CH_3$ |
| C(O)NH-3-thiomethylphenyl | $NHR_3$, or $N[(CH_2)_{0-5}CH_3]_2$ | —O$(CH_2)_{0-5}CH_3$ | H or —$(CH_2)_{0-5}CH_3$ |
| C(O)$NH_2$ | $NHR_3$, or $N[(CH_2)_{0-5}CH_3]_2$ | $NH_2$ | H or —$(CH_2)_{0-5}CH_3$ |
| C(O)N$[(CH_2)_{0-5}CH_3]_2$ | $NHR_3$, or $N[(CH_2)_{0-5}CH_3]_2$ | $NH_2$ | H or —$(CH_2)_{0-5}CH_3$ |
| C(O)NHPh | $NHR_3$, or $N[(CH_2)_{0-5}CH_3]_2$ | $NH_2$ | H or —$(CH_2)_{0-5}CH_3$ |
| C(O)NH-2,4-fluorophenyl | $NHR_3$, or $N[(CH_2)_{0-5}CH_3]_2$ | $NH_2$ | H or —$(CH_2)_{0-5}CH_3$ |
| C(O)NH-4-fluorophenyl | $NHR_3$, or $N[(CH_2)_{0-5}CH_3]_2$ | $NH_2$ | H or —$(CH_2)_{0-5}CH_3$ |
| C(O)NH-3-fluorophenyl | $NHR_3$, or $N[(CH_2)_{0-5}CH_3]_2$ | $NH_2$ | H or —$(CH_2)_{0-5}CH_3$ |
| C(O)NH-4-morpholinylphenyl | $NHR_3$, or $N[(CH_2)_{0-5}CH_3]_2$ | $NH_2$ | H or —$(CH_2)_{0-5}CH_3$ |
| C(O)NH-4-piperazinyllphenyl | $NHR_3$, or $N[(CH_2)_{0-5}CH_3]_2$ | $NH_2$ | H or —$(CH_2)_{0-5}CH_3$ |
| C(O)NH-3-thiomethylphenyl | $NHR_3$, or $N[(CH_2)_{0-5}CH_3]_2$ | $NH_2$ | H or —$(CH_2)_{0-5}CH_3$ |
| C(O)$NH_2$ | $NHR_3$, or $N[(CH_2)_{0-5}CH_3]_2$ | $N[(CH_2)_{0-5}CH_3]_2$ | H or —$(CH_2)_{0-5}CH_3$ |
| C(O)N$[(CH_2)_{0-5}CH_3]_2$ | $NHR_3$, or $N[(CH_2)_{0-5}CH_3]_2$ | $N[(CH_2)_{0-5}CH_3]_2$ | H or —$(CH_2)_{0-5}CH_3$ |
| C(O)NHPh | $NHR_3$, or $N[(CH_2)_{0-5}CH_3]_2$ | $N[(CH_2)_{0-5}CH_3]_2$ | H or —$(CH_2)_{0-5}CH_3$ |
| C(O)NH-2,4-fluorophenyl | $NHR_3$, or $N[(CH_2)_{0-5}CH_3]_2$ | $N[(CH_2)_{0-5}CH_3]_2$ | H or —$(CH_2)_{0-5}CH_3$ |
| C(O)NH-4-fluorophenyl | $NHR_3$, or $N[(CH_2)_{0-5}CH_3]_2$ | $N[(CH_2)_{0-5}CH_3]_2$ | H or —$(CH_2)_{0-5}CH_3$ |
| C(O)NH-3-fluorophenyl | $NHR_3$, or $N[(CH_2)_{0-5}CH_3]_2$ | $N[(CH_2)_{0-5}CH_3]_2$ | H or —$(CH_2)_{0-5}CH_3$ |
| C(O)NH-4-morpholinylphenyl | $NHR_3$, or $N[(CH_2)_{0-5}CH_3]_2$ | $N[(CH_2)_{0-5}CH_3]_2$ | H or —$(CH_2)_{0-5}CH_3$ |
| C(O)NR-4-piperazinyllphenyl | $NHR_3$, or $N[(CH_2)_{0-5}CH_3]_2$ | $N[(CH_2)_{0-5}CH_3]_2$ | H or —$(CH_2)_{0-5}CH_3$ |
| C(O)NH-3-thiomethylphenyl | $NHR_3$, or $N[(CH_2)_{0-5}CH_3]_2$ | $N[(CH_2)_{0-5}CH_3]_2$ | H or —$(CH_2)_{0-5}CH_3$ |
| C(O)$NH_2$ | $NHR_3$, or $N[(CH_2)_{0-5}CH_3]_2$ | —$(CH_2)_{0-5}CH_3$ | H or —$(CH_2)_{0-5}CH_3$ |
| C(O)N$[(CH_2)_{0-5}CH_3]_2$ | $NHR_3$, or $N[(CH_2)_{0-5}CH_3]_2$ | —$(CH_2)_{0-5}CH_3$ | H or —$(CH_2)_{0-5}CH_3$ |
| C(O)NHPh | $NHR_3$, or $N[(CH_2)_{0-5}CH_3]_2$ | —$(CH_2)_{0-5}CH_3$ | H or —$(CH_2)_{0-5}CH_3$ |
| C(O)NH-2,4-fluorophenyl | $NHR_3$, or $N[(CH_2)_{0-5}CH_3]_2$ | —$(CH_2)_{0-5}CH_3$ | H or —$(CH_2)_{0-5}CH_3$ |
| C(O)NH-4-fluorophenyl | $NHR_3$, or $N[(CH_2)_{0-5}CH_3]_2$ | —$(CH_2)_{0-5}CH_3$ | H or —$(CH_2)_{0-5}CH_3$ |
| C(O)NH-3-fluorophenyl | $NHR_3$, or $N[(CH_2)_{0-5}CH_3]_2$ | —$(CH_2)_{0-5}CH_3$ | H or —$(CH_2)_{0-5}CH_3$ |
| C(O)NH-4-morpholinylphenyl | $NHR_3$, or $N[(CH_2)_{0-5}CH_3]_2$ | —$(CH_2)_{0-5}CH_3$ | H or —$(CH_2)_{0-5}CH_3$ |
| C(O)NH-4-piperazinyllphenyl | $NHR_3$, or $N[(CH_2)_{0-5}CH_3]_2$ | —$(CH_2)_{0-5}CH_3$ | H or —$(CH_2)_{0-5}CH_3$ |
| C(O)NH-3-thiomethylphenyl | $NHR_3$, or $N[(CH_2)_{0-5}CH_3]_2$ | —$(CH_2)_{0-5}CH_3$ | H or —$(CH_2)_{0-5}CH_3$ |
| C(O)$NH_2$ | $NHR_3$, or $N[(CH_2)_{0-5}CH_3]_2$ | $S[(CH_2)_{0-5}CH_3]_2$ | H or —$(CH_2)_{0-5}CH_3$ |
| C(O)N$[(CH_2)_{0-5}CH_3]_2$ | $NHR_3$, or $N[(CH_2)_{0-5}CH_3]_2$ | $S[(CH_2)_{0-5}CH_3]_2$ | H or —$(CH_2)_{0-5}CH_3$ |
| C(O)NHPh | $NHR_3$, or $N[(CH_2)_{0-5}CH_3]_2$ | $S[(CH_2)_{0-5}CH_3]_2$ | H or —$(CH_2)_{0-5}CH_3$ |
| C(O)NH-2,4-fluorophenyl | $NHR_3$, or $N[(CH_2)_{0-5}CH_3]_2$ | $S[(CH_2)_{0-5}CH_3]_2$ | H or —$(CH_2)_{0-5}CH_3$ |
| C(O)NH-4-fluorophenyl | $NHR_3$, or $N[(CH_2)_{0-5}CH_3]_2$ | $S[(CH_2)_{0-5}CH_3]_2$ | H or —$(CH_2)_{0-5}CH_3$ |
| C(O)NH-3-fluorophenyl | $NHR_3$, or $N[(CH_2)_{0-5}CH_3]_2$ | $S[(CH_2)_{0-5}CH_3]_2$ | H or —$(CH_2)_{0-5}CH_3$ |
| C(O)NH-4-morpholinylphenyl | $NHR_3$, or $N[(CH_2)_{0-5}CH_3]_2$ | $S[(CH_2)_{0-5}CH_3]_2$ | H or —$(CH_2)_{0-5}CH_3$ |
| C(O)NH-4-piperazinyllphenyl | $NHR_3$, or $N[(CH_2)_{0-5}CH_3]_2$ | $S[(CH_2)_{0-5}CH_3]_2$ | H or —$(CH_2)_{0-5}CH_3$ |
| C(O)NH-3-thiomethylphenyl | $NHR_3$, or $N[(CH_2)_{0-5}CH_3]_2$ | $S[(CH_2)_{0-5}CH_3]_2$ | H or —$(CH_2)_{0-5}CH_3$ |
| C(O)$NH_2$ | $NHR_3$, or $N[(CH_2)_{0-5}CH_3]_2$ | $NO_2$ | H or —$(CH_2)_{0-5}CH_3$ |
| C(O)N$[(CH_2)_{0-5}CH_3]_2$ | $NHR_3$, or $N[(CH_2)_{0-5}CH_3]_2$ | $NO_2$ | H or —$(CH_2)_{0-5}CH_3$ |
| C(O)NHPh | $NHR_3$, or $N[(CH_2)_{0-5}CH_3]_2$ | $NO_2$ | H or —$(CH_2)_{0-5}CH_3$ |
| C(O)NH-2,4-fluorophenyl | $NHR_3$, or $N[(CH_2)_{0-5}CH_3]_2$ | $NO_2$ | H or —$(CH_2)_{0-5}CH_3$ |
| C(O)NH-4-fluorophenyl | $NHR_3$, or $N[(CH_2)_{0-5}CH_3]_2$ | $NO_2$ | H or —$(CH_2)_{0-5}CH_3$ |
| C(O)NH-3-fluorophenyl | $NHR_3$, or $N[(CH_2)_{0-5}CH_3]_2$ | $NO_2$ | H or —$(CH_2)_{0-5}CH_3$ |
| C(O)NH-4-morpholinylphenyl | $NHR_3$, or $N[(CH_2)_{0-5}CH_3]_2$ | $NO_2$ | H or —$(CH_2)_{0-5}CH_3$ |
| C(O)NH4-piperazinyllphenyl | $NHR_3$, or $N[(CH_2)_{0-5}CH_3]_2$ | $NO_2$ | H or —$(CH_2)_{0-5}CH_3$ |
| C(O)NH-3-thiomethylphenyl | $NHR_3$, or $N[(CH_2)_{0-5}CH_3]_2$ | $NO_2$ | H or —$(CH_2)_{0-5}CH_3$ |
| C(O)$NH_2$ | $NHR_3$, or $N[(CH_2)_{0-5}CH_3]_2$ | $CF_3$ | H or —$(CH_2)_{0-5}CH_3$ |
| C(O)N$[(CH_2)_{0-5}CH_3]_2$ | $NHR_3$, or $N[(CH_2)_{0-5}CH_3]_2$ | $CF_3$ | H or —$(CH_2)_{0-5}CH_3$ |
| C(O)NHPh | $NHR_3$, or $N[(CH_2)_{0-5}CH_3]_2$ | $CF_3$ | H or —$(CH_2)_{0-5}CH_3$ |
| C(O)NH-2,4-fluorophenyl | $NHR_3$, or $N[(CH_2)_{0-5}CH_3]_2$ | $CF_3$ | H or —$(CH_2)_{0-5}CH_3$ |
| C(O)NH-4-fluorophenyl | $NHR_3$, or $N[(CH_2)_{0-5}CH_3]_2$ | $CF_3$ | H or —$(CH_2)_{0-5}CH_3$ |
| C(O)NH-3-fluorophenyl | $NHR_3$, or $N[(CH_2)_{0-5}CH_3]_2$ | $CF_3$ | H or —$(CH_2)_{0-5}CH_3$ |
| C(O)NH-4-morpholinylphenyl | $NHR_3$, or $N[(CH_2)_{0-5}CH_3]_2$ | $CF_3$ | H or —$(CH_2)_{0-5}CH_3$ |
| C(O)NH-4-piperazinyllphenyl | $NHR_3$, or $N[(CH_2)_{0-5}CH_3]_2$ | $CF_3$ | H or —$(CH_2)_{0-5}CH_3$ |
| C(O)NH-3-thiomethylphenyl | $NHR_3$, or $N[(CH_2)_{0-5}CH_3]_2$ | $CF_3$ | H or —$(CH_2)_{0-5}CH_3$ |
| C(O)$NH_2$ | $NHR_3$, or $N[(CH_2)_{0-5}CH_3]_2$ | H | H or —$(CH_2)_{0-5}CH_3$ |
| C(O)N$[(CH_2)_{0-5}CH_3]_2$ | $NHR_3$, or $N[(CH_2)_{0-5}CH_3]_2$ | H | H or —$(CH_2)_{0-5}CH_3$ |
| C(O)NHPh | $NHR_3$, or $N[(CH_2)_{0-5}CH_3]_2$ | H | H or —$(CH_2)_{0-5}CH_3$ |
| C(O)NH-2,4-fluorophenyl | $NHR_3$, or $N[(CH_2)_{0-5}CH_3]_2$ | H | H or —$(CH_2)_{0-5}CH_3$ |
| C(O)NH-4-fluorophenyl | $NHR_3$, or $N[(CH_2)_{0-5}CH_3]_2$ | H | H or —$(CH_2)_{0-5}CH_3$ |
| C(O)NH-3-fluorophenyl | $NHR_3$, or $N[(CH_2)_{0-5}CH_3]_2$ | H | H or —$(CH_2)_{0-5}CH_3$ |
| C(O)NH-4-morpholinylphenyl | $NHR_3$, or $N[(CH_2)_{0-5}CH_3]_2$ | H | H or —$(CH_2)_{0-5}CH_3$ |
| C(O)NH-4-piperazinyllphenyl | $NHR_3$, or $N[(CH_2)_{0-5}CH_3]_2$ | H | H or —$(CH_2)_{0-5}CH_3$ |
| C(O)NH-3-thiomethylphenyl | $NHR_3$, or $N[(CH_2)_{0-5}CH_3]_2$ | H | H or —$(CH_2)_{0-5}CH_3$ |

TABLE 4

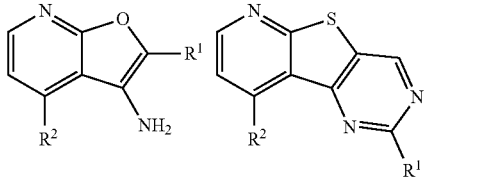

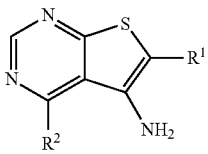

| R¹ | R² |
|---|---|
| C(O)NH$_2$ | —Ph-Halo |
| C(O)N[(CH$_2$)$_{0-5}$CH$_3$]$_2$ | —Ph-Halo |
| C(O)NHPh | —Ph-Halo |
| C(O)NH-2,4-fluorophenyl | —Ph-Halo |
| C(O)NH-4-fluorophenyl | —Ph-Halo |
| C(O)NH-3-fluorophenyl | —Ph-Halo |
| C(O)NH-4-morpholinylphenyl | —Ph-Halo |
| C(O)NH-4-piperazinylphenyl | —Ph-Halo |
| C(O)NH-3-thiomethylphenyl | —Ph-Halo |
| H | —Ph-Halo |
| C(O)O(CH$_2$)$_{0-5}$CH$_3$ | —Ph-Halo |
| C(O)OH | —Ph-Halo |
| Ph—OH | —Ph-Halo |
| Ph—NH$_2$ | —Ph-Halo |
| Ph-Halo | —Ph-Halo |
| Ph—O(CH$_2$)$_{0-5}$CH$_3$ | —Ph-Halo |
| Ph—N[(CH$_2$)$_{0-5}$CH$_3$]$_2$ | —Ph-Halo |
| C(O)NH$_2$ | —Ph—OH |
| C(O)N[(CH$_2$)$_{0-5}$CH$_3$]$_2$ | —Ph—OH |
| C(O)NHPh | —Ph—OH |
| C(O)NH-2,4-fluorophenyl | —Ph—OH |
| C(O)NH-4-fluorophenyl | —Ph—OH |
| C(O)NH-3-fluorophenyl | —Ph—OH |
| C(O)NH-4-morpholinylphenyl | —Ph—OH |
| C(O)NH-4-piperazinylphenyl | —Ph—OH |
| C(O)NH-3-thiomethylphenyl | —Ph—OH |
| H | —Ph—OH |
| C(O)O(CH$_2$)$_{0-5}$CH$_3$ | —Ph—OH |
| C(O)OH | —Ph—OH |
| Ph—OH | —Ph—OH |
| Ph—NH$_2$ | —Ph—OH |
| Ph-Halo | —Ph—OH |
| Ph—O(CH$_2$)$_{0-5}$CH$_3$ | —Ph—OH |
| Ph—N[(CH$_2$)$_{0-5}$CH$_3$]$_2$ | —Ph—OH |
| C(O)NH$_2$ | —Ph—O(CH$_2$)$_{0-5}$CH$_3$ |
| C(O)N[(CH$_2$)$_{0-5}$CH$_3$]$_2$ | —Ph—O(CH$_2$)$_{0-5}$CH$_3$ |
| C(O)NHPh | —Ph—O(CH$_2$)$_{0-5}$CH$_3$ |
| C(O)NH-2,4-fluorophenyl | —Ph—O(CH$_2$)$_{0-5}$CH$_3$ |
| C(O)NH-4-fluorophenyl | —Ph—O(CH$_2$)$_{0-5}$CH$_3$ |
| C(O)NH-3-fluorophenyl | —Ph—O(CH$_2$)$_{0-5}$CH$_3$ |
| C(O)NH-4-morpholinylphenyl | —Ph—O(CH$_2$)$_{0-5}$CH$_3$ |
| C(O)NH-4-piperazinylphenyl | —Ph—O(CH$_2$)$_{0-5}$CH$_3$ |
| C(O)NH-3-thiomethylphenyl | —Ph—O(CH$_2$)$_{0-5}$CH$_3$ |
| H | —Ph—O(CH$_2$)$_{0-5}$CH$_3$ |
| C(O)O(CH$_2$)$_{0-5}$CH$_3$ | —Ph—O(CH$_2$)$_{0-5}$CH$_3$ |
| C(O)OH | —Ph—O(CH$_2$)$_{0-5}$CH$_3$ |
| Ph—OH | —Ph—O(CH$_2$)$_{0-5}$CH$_3$ |
| Ph—NH$_2$ | —Ph—O(CH$_2$)$_{0-5}$CH$_3$ |
| Ph-Halo | —Ph—O(CH$_2$)$_{0-5}$CH$_3$ |
| Ph—O(CH$_2$)$_{0-5}$CH$_3$ | —Ph—O(CH$_2$)$_{0-5}$CH$_3$ |
| Ph—N[(CH$_2$)$_{0-5}$CH$_3$]$_2$ | —Ph—O(CH$_2$)$_{0-5}$CH$_3$ |
| C(O)NH$_2$ | —Ph—NH$_2$ |
| C(O)N[(CH$_2$)$_{0-5}$CH$_3$]$_2$ | —Ph—NH$_2$ |
| C(O)NHPh | —Ph—NH$_2$ |
| C(O)NH-2,4-fluorophenyl | —Ph—NH$_2$ |
| C(O)NH-4-fluorophenyl | —Ph—NH$_2$ |
| C(O)NH-3-fluorophenyl | —Ph—NH$_2$ |
| C(O)NH-4-morpholinylphenyl | —Ph—NH$_2$ |
| C(O)NH-4-piperazinylphenyl | —Ph—NH$_2$ |
| C(O)NH-3-thiomethylphenyl | —Ph—NH$_2$ |
| H | —Ph—NH$_2$ |
| C(O)O(CH$_2$)$_{0-5}$CH$_3$ | —Ph—NH$_2$ |
| C(O)OH | —Ph—NH$_2$ |
| Ph—OH | —Ph—NH$_2$ |
| Ph—NH$_2$ | —Ph—NH$_2$ |
| Ph-Halo | —Ph—NH$_2$ |
| Ph—O(CH$_2$)$_{0-5}$CH$_3$ | —Ph—NH$_2$ |
| Ph—N[(CH$_2$)$_{0-5}$CH$_3$]$_2$ | —Ph—NH$_2$ |
| C(O)NH$_2$ | —Ph—N[(CH$_2$)$_{0-5}$CH$_3$]$_2$ |
| C(O)N[(CH$_2$)$_{0-5}$CH$_3$]$_2$ | —Ph—N[(CH$_2$)$_{0-5}$CH$_3$]$_2$ |
| C(O)NHPh | —Ph—N[(CH$_2$)$_{0-5}$CH$_3$]$_2$ |
| C(O)NH-2,4-fluorophenyl | —Ph—N[(CH$_2$)$_{0-5}$CH$_3$]$_2$ |
| C(O)NH-4-fluorophenyl | —Ph—N[(CH$_2$)$_{0-5}$CH$_3$]$_2$ |
| C(O)NH-3-fluorophenyl | —Ph—N[(CH$_2$)$_{0-5}$CH$_3$]$_2$ |
| C(O)NH-4-morpholinylphenyl | —Ph—N[(CH$_2$)$_{0-5}$CH$_3$]$_2$ |
| C(O)NH-4-piperazinylphenyl | —Ph—N[(CH$_2$)$_{0-5}$CH$_3$]$_2$ |
| C(O)NH-3-thiomethylphenyl | —Ph—N[(CH$_2$)$_{0-5}$CH$_3$]$_2$ |
| H | —Ph—N[(CH$_2$)$_{0-5}$CH$_3$]$_2$ |
| C(O)O(CH$_2$)$_{0-5}$CH$_3$ | —Ph—N[(CH$_2$)$_{0-5}$CH$_3$]$_2$ |
| C(O)OH | —Ph—N[(CH$_2$)$_{0-5}$CH$_3$]$_2$ |
| Ph—OH | —Ph—N[(CH$_2$)$_{0-5}$CH$_3$]$_2$ |
| Ph—NH$_2$ | —Ph—N[(CH$_2$)$_{0-5}$CH$_3$]$_2$ |
| Ph-Halo | —Ph—N[(CH$_2$)$_{0-5}$CH$_3$]$_2$ |
| Ph-O(CH$_2$)$_{0-5}$CH$_3$ | —Ph—N[(CH$_2$)$_{0-5}$CH$_3$]$_2$ |
| Ph—N[(CH$_2$)$_{0-5}$CH$_3$]$_2$ | —Ph—N[(CH$_2$)$_{0-5}$CH$_3$]$_2$ |
| C(O)NH$_2$ | —Ph—(CH$_2$)$_{0-5}$CH$_3$ |
| C(O)N[(CH$_2$)$_{0-5}$CH$_3$]$_2$ | —Ph—(CH$_2$)$_{0-5}$CH$_3$ |
| C(O)NHPh | —Ph—(CH$_2$)$_{0-5}$CH$_3$ |
| C(O)NH-2,4-fluorophenyl | —Ph—(CH$_2$)$_{0-5}$CH$_3$ |

TABLE 4-continued

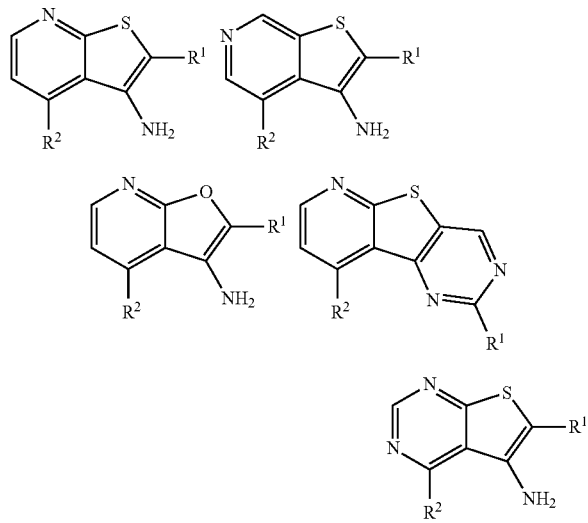
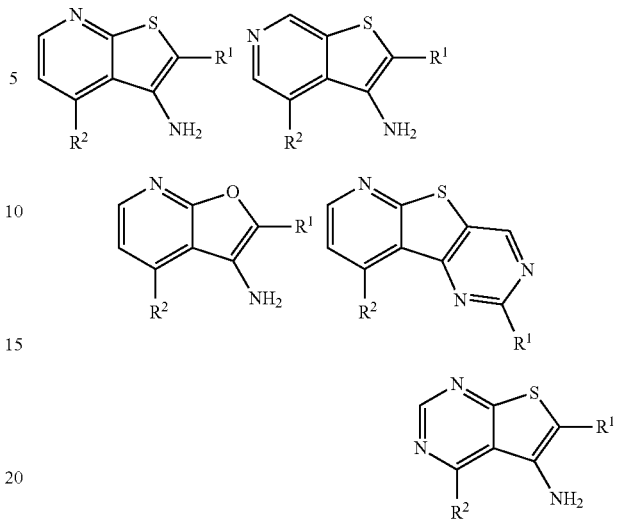

| R¹ | R² |
|---|---|
| C(O)NH-4-fluorophenyl | —Ph—(CH$_2$)$_{0-5}$CH$_3$ |
| C(O)NH-3-fluorophenyl | —Ph—(CH$_2$)$_{0-5}$CH$_3$ |
| C(O)NH-4-morpholinylphenyl | —Ph—(CH$_2$)$_{0-5}$CH$_3$ |
| C(O)NH-4-piperazinyllphenyl | —Ph—(CH$_2$)$_{0-5}$CH$_3$ |
| C(O)NH-3-thiomethylphenyl | —Ph—(CH$_2$)$_{0-5}$CH$_3$ |
| H | —Ph—(CH$_2$)$_{0-5}$CH$_3$ |
| C(O)O(CH$_2$)$_{0-5}$CH$_3$ | —Ph—(CH$_2$)$_{0-5}$CH$_3$ |
| C(O)OH | —Ph—(CH$_2$)$_{0-5}$CH$_3$ |
| Ph—OH | —Ph—(CH$_2$)$_{0-5}$CH$_3$ |
| Ph—NH$_2$ | —Ph—(CH$_2$)$_{0-5}$CH$_3$ |
| Ph-Halo | —Ph—(CH$_2$)$_{0-5}$CH$_3$ |
| Ph—O(CH$_2$)$_{0-5}$CH$_3$ | —Ph—(CH$_2$)$_{0-5}$CH$_3$ |
| Ph—N[(CH$_2$)$_{0-5}$CH$_3$]$_2$ | —Ph—(CH$_2$)$_{0-5}$CH$_3$ |
| C(O)NH$_2$ | —Ph—S[(CH$_2$)$_{0-5}$CH$_3$]$_2$ |
| C(O)N[(CH$_2$)$_{0-5}$CH$_3$]$_2$ | —Ph—S[(CH$_2$)$_{0-5}$CH$_3$]$_2$ |
| C(O)NHPh | —Ph—S[(CH$_2$)$_{0-5}$CH$_3$]$_2$ |
| C(O)NH-2,4-fluorophenyl | —Ph—S[(CH$_2$)$_{0-5}$CH$_3$]$_2$ |
| C(O)NH-4-fluorophenyl | —Ph—S[(CH$_2$)$_{0-5}$CH$_3$]$_2$ |
| C(O)NH-3-fluorophenyl | —Ph—S[(CH$_2$)$_{0-5}$CH$_3$]$_2$ |
| C(O)NH-4-morpholinylphenyl | —Ph—S[(CH$_2$)$_{0-5}$CH$_3$]$_2$ |
| C(O)NH-4-piperazinyllphenyl | —Ph—S[(CH$_2$)$_{0-5}$CH$_3$]$_2$ |
| C(O)NH-3-thiomethylphenyl | —Ph—S[(CH$_2$)$_{0-5}$CH$_3$]$_2$ |
| H | —Ph—S[(CH$_2$)$_{0-5}$CH$_3$]$_2$ |
| C(O)O(CH$_2$)$_{0-5}$CH$_3$ | —Ph—S[(CH$_2$)$_{0-5}$CH$_3$]$_2$ |
| C(O)OH | —Ph—S[(CH$_2$)$_{0-5}$CH$_3$]$_2$ |
| Ph—OH | —Ph—S[(CH$_2$)$_{0-5}$CH$_3$]$_2$ |
| Ph—NH$_2$ | —Ph—S[(CH$_2$)$_{0-5}$CH$_3$]$_2$ |
| Ph-Halo | —Ph—S[(CH$_2$)$_{0-5}$CH$_3$]$_2$ |
| Ph—O(CH$_2$)$_{0-5}$CH$_3$ | —Ph—S[(CH$_2$)$_{0-5}$CH$_3$]$_2$ |
| Ph—N[(CH$_2$)$_{0-5}$CH$_3$]$_2$ | —Ph—S[(CH$_2$)$_{0-5}$CH$_3$]$_2$ |
| C(O)NH$_2$ | —Ph—NO$_2$ |
| C(O)N[(CH$_2$)$_{0-5}$CH$_3$]$_2$ | —Ph—NO$_2$ |
| C(O)NHPh | —Ph—NO$_2$ |
| C(O)NH-2,4-fluorophenyl | —Ph—NO$_2$ |
| C(O)NH-4-fluorophenyl | —Ph—NO$_2$ |
| C(O)NH-3-fluorophenyl | —Ph—NO$_2$ |
| C(O)NH-4-morpholinylphenyl | —Ph—NO$_2$ |
| C(O)NH-4-piperazinyllphenyl | —Ph—NO$_2$ |
| C(O)NH-3-thiomethylphenyl | —Ph—NO$_2$ |
| H | —Ph—NO$_2$ |
| C(O)O(CH$_2$)$_{0-5}$CH$_3$ | —Ph—NO$_2$ |
| C(O)OH | —Ph—NO$_2$ |
| Ph—OH | —Ph—NO$_2$ |
| Ph—NH$_2$ | —Ph—NO$_2$ |
| Ph-Halo | —Ph—NO$_2$ |
| Ph—O(CH$_2$)$_{0-5}$CH$_3$ | —Ph—NO$_2$ |
| Ph—N[(CH$_2$)$_{0-5}$CH$_3$]$_2$ | —Ph—NO$_2$ |
| C(O)NH$_2$ | —Ph—CF$_3$ |
| C(O)N[(CH$_2$)$_{0-5}$CH$_3$]$_2$ | —Ph—CF$_3$ |
| C(O)NHPh | —Ph—CF$_3$ |
| C(O)NH-2,4-fluorophenyl | —Ph—CF$_3$ |
| C(O)NH-4-fluorophenyl | —Ph—CF$_3$ |
| C(O)NH-3-fluorophenyl | —Ph—CF$_3$ |
| C(O)NH-4-morpholinylphenyl | —Ph—CF$_3$ |
| C(O)NH-4-piperazinyllphenyl | —Ph—CF$_3$ |
| C(O)NH-3-thiomethylphenyl | —Ph—CF$_3$ |
| H | —Ph—CF$_3$ |
| C(O)O(CH$_2$)$_{0-5}$CH$_3$ | —Ph—CF$_3$ |
| C(O)OH | —Ph—CF$_3$ |
| Ph—OH | —Ph—CF$_3$ |
| Ph—NH$_2$ | —Ph—CF$_3$ |
| Ph-Halo | —Ph—CF$_3$ |
| Ph—O(CH$_2$)$_{0-5}$CH$_3$ | —Ph—CF$_3$ |
| Ph—N[(CH$_2$)$_{0-5}$CH$_3$]$_2$ | —Ph—CF$_3$ |
| C(O)NH$_2$ | NH$_2$, NH(CH$_2$)$_{0-5}$CH$_3$, or N[(CH$_2$)$_{0-5}$CH$_3$]$_2$ |
| C(O)N[(CH$_2$)$_{0-5}$CH$_3$]$_2$ | NH$_2$, NH(CH$_2$)$_{0-5}$CH$_3$, or N[(CH$_2$)$_{0-5}$CH$_3$]$_2$ |
| C(O)NHPh | NH$_2$, NH(CH$_2$)$_{0-5}$CH$_3$, or N[(CH$_2$)$_{0-5}$CH$_3$]$_2$ |
| C(O)NH-2,4-fluorophenyl | NH$_2$, NH(CH$_2$)$_{0-5}$CH$_3$, or N[(CH$_2$)$_{0-5}$CH$_3$]$_2$ |
| C(O)NH-4-fluorophenyl | NH$_2$, NH(CH$_2$)$_{0-5}$CH$_3$, or N[(CH$_2$)$_{0-5}$CH$_3$]$_2$ |
| C(O)NH-3-fluorophenyl | NH$_2$, NH(CH$_2$)$_{0-5}$CH$_3$, or N[(CH$_2$)$_{0-5}$CH$_3$]$_2$ |
| C(O)NH-4-morpholinylphenyl | NH$_2$, NH(CH$_2$)$_{0-5}$CH$_3$, or N[(CH$_2$)$_{0-5}$CH$_3$]$_2$ |
| C(O)NH-4-piperazinyllphenyl | NH$_2$, NH(CH$_2$)$_{0-5}$CH$_3$, or N[(CH$_2$)$_{0-5}$CH$_3$]$_2$ |
| C(O)NH-3-thiomethylphenyl | NH$_2$, NH(CH$_2$)$_{0-5}$CH$_3$, or N[(CH$_2$)$_{0-5}$CH$_3$]$_2$ |
| H | NH$_2$, NH(CH$_2$)$_{0-5}$CH$_3$, or N[(CH$_2$)$_{0-5}$CH$_3$]$_2$ |
| C(O)O(CH$_2$)$_{0-5}$CH$_3$ | NH$_2$, NH(CH$_2$)$_{0-5}$CH$_3$, or N[(CH$_2$)$_{0-5}$CH$_3$]$_2$ |
| C(O)OH | NH$_2$, NH(CH$_2$)$_{0-5}$CH$_3$ or N[(CH$_2$)$_{0-5}$CH$_3$]$_2$ |
| Ph—OH | NH$_2$, NH(CH$_2$)$_{0-5}$CH$_3$, or N[(CH$_2$)$_{0-5}$CH$_3$]$_2$ |
| Ph—NH$_2$ | NH$_2$, NH(CH$_2$)$_{0-5}$CH$_3$, or N[(CH$_2$)$_{0-5}$CH$_3$]$_2$ |

TABLE 4-continued

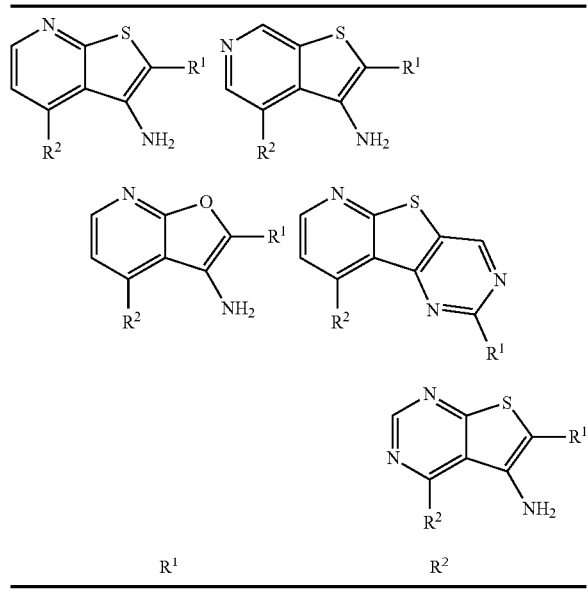
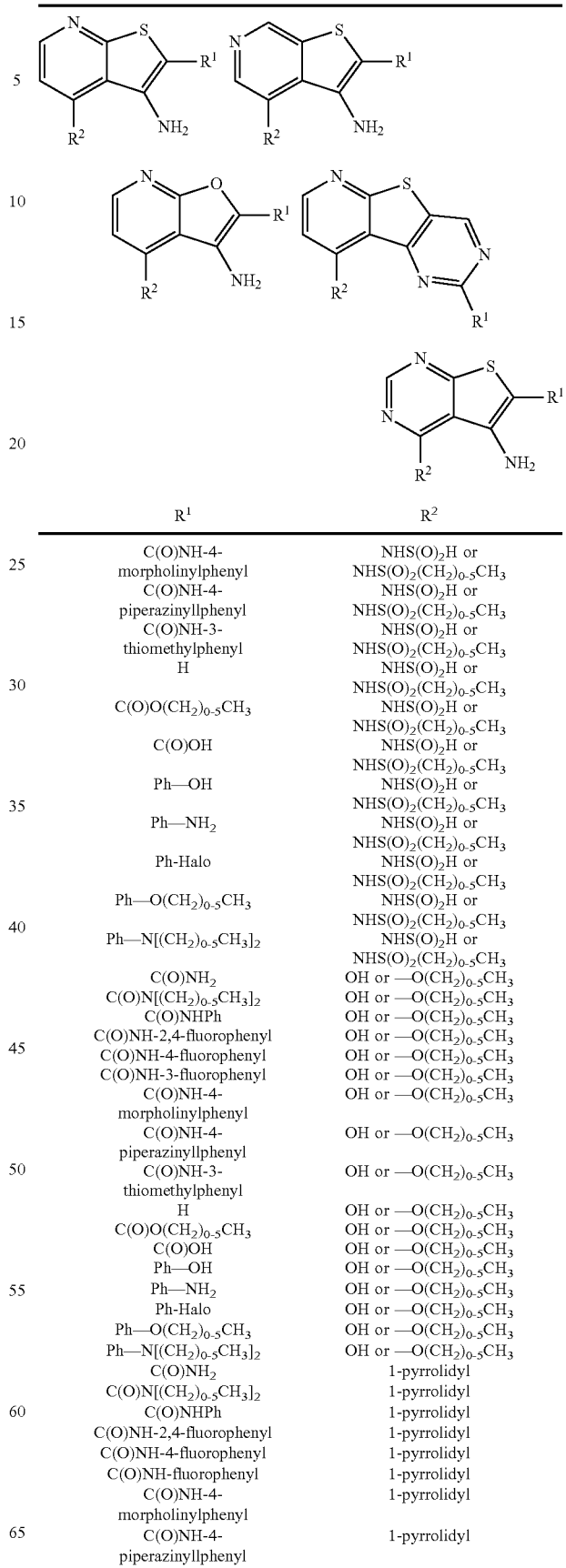

| R¹ | R² |
|---|---|
| Ph-Halo | NH₂, NH(CH₂)₀₋₅CH₃, or N[(CH₂)₀₋₅CH₃]₂ |
| Ph—O(CH₂)₀₋₅CH₃ | NH₂, NH(CH₂)₀₋₅CH₃, or N[(CH₂)₀₋₅CH₃]₂ |
| Ph—N[(CH₂)₀₋₅CH₃]₂ | NH₂, NH(CH₂)₀₋₅CH₃ or N[(CH₂)₀₋₅CH₃]₂ |
| C(O)NH₂ | NHC(O)H or NHC(O)(CH₂)₀₋₅CH₃ |
| C(O)N[(CH₂)₀₋₅CH₃]₂ | NHC(O)H or NHC(O)(CH₂)₀₋₅CH₃ |
| C(O)NHPh | NHC(O)H or NHC(O)(CH₂)₀₋₅CH₃ |
| C(O)NH-2,4-fluorophenyl | NHC(O)H or NHC(O)(CH₂)₀₋₅CH₃ |
| C(O)NH-4-fluorophenyl | NHC(O)H or NHC(O)(CH₂)₀₋₅CH₃ |
| C(O)NH-3-fluorophenyl | NHC(O)H or NHC(O)(CH₂)₀₋₅CH₃ |
| C(O)NH-4-morpholinylphenyl | NHC(O)H or NHC(O)(CH₂)₀₋₅CH₃ |
| C(O)NH-4-piperazinyllphenyl | NHC(O)H or NHC(O)(CH₂)₀₋₅CH₃ |
| C(O)NH-3-thiomethylphenyl | NHC(O)H or NHC(O)(CH₂)₀₋₅CH₃ |
| H | NHC(O)H or NHC(O)(CH₂)₀₋₅CH₃ |
| C(O)O(CH₂)₀₋₅CH₃ | NHC(O)H or NHC(O)(CH₂)₀₋₅CH₃ |
| C(O)OH | NHC(O)H or NHC(O)(CH₂)₀₋₅CH₃ |
| Ph—OH | NHC(O)H or NHC(O)(CH₂)₀₋₅CH₃ |
| Ph—NH₂ | NHC(O)H or NHC(O)(CH₂)₀₋₅CH₃ |
| Ph-Halo | NHC(O)H or NHC(O)(CH₂)₀₋₅CH₃ |
| Ph—O(CH₂)₀₋₅CH₃ | NHC(O)H or NHC(O)(CH₂)₀₋₅CH₃ |
| Ph—N[(CH₂)₀₋₅CH₃]₂ | NHC(O)H or NHC(O)(CH₂)₀₋₅CH₃ |
| C(O)NH₂ | NHS(O)₂H or NHS(O)₂(CH₂)₀₋₅CH₃ |
| C(O)N[(CH₂)₀₋₅CH₃]₂ | NHS(O)₂H or NHS(O)₂(CH₂)₀₋₅CH₃ |
| C(O)NHPh | NHS(O)₂H or NHS(O)₂(CH₂)₀₋₅CH₃ |
| C(O)NH-2,4-fluorophenyl | NHS(O)₂H or NHS(O)₂(CH₂)₀₋₅CH₃ |
| C(O)NH-4-fluorophenyl | NHS(O)₂H or NHS(O)₂(CH₂)₀₋₅CH₃ |
| C(O)NH-3-fluorophenyl | NHS(O)₂H or NHS(O)₂(CH₂)₀₋₅CH₃ |
| C(O)NH-4-morpholinylphenyl | NHS(O)₂H or NHS(O)₂(CH₂)₀₋₅CH₃ |
| C(O)NH-4-piperazinyllphenyl | NHS(O)₂H or NHS(O)₂(CH₂)₀₋₅CH₃ |
| C(O)NH-3-thiomethylphenyl | NHS(O)₂H or NHS(O)₂(CH₂)₀₋₅CH₃ |
| H | NHS(O)₂H or NHS(O)₂(CH₂)₀₋₅CH₃ |
| C(O)O(CH₂)₀₋₅CH₃ | NHS(O)₂H or NHS(O)₂(CH₂)₀₋₅CH₃ |
| C(O)OH | NHS(O)₂H or NHS(O)₂(CH₂)₀₋₅CH₃ |
| Ph—OH | NHS(O)₂H or NHS(O)₂(CH₂)₀₋₅CH₃ |
| Ph—NH₂ | NHS(O)₂H or NHS(O)₂(CH₂)₀₋₅CH₃ |
| Ph-Halo | NHS(O)₂H or NHS(O)₂(CH₂)₀₋₅CH₃ |
| Ph—O(CH₂)₀₋₅CH₃ | NHS(O)₂H or NHS(O)₂(CH₂)₀₋₅CH₃ |
| Ph—N[(CH₂)₀₋₅CH₃]₂ | NHS(O)₂H or NHS(O)₂(CH₂)₀₋₅CH₃ |
| C(O)NH₂ | OH or —O(CH₂)₀₋₅CH₃ |
| C(O)N[(CH₂)₀₋₅CH₃]₂ | OH or —O(CH₂)₀₋₅CH₃ |
| C(O)NHPh | OH or —O(CH₂)₀₋₅CH₃ |
| C(O)NH-2,4-fluorophenyl | OH or —O(CH₂)₀₋₅CH₃ |
| C(O)NH-4-fluorophenyl | OH or —O(CH₂)₀₋₅CH₃ |
| C(O)NH-3-fluorophenyl | OH or —O(CH₂)₀₋₅CH₃ |
| C(O)NH-4-morpholinylphenyl | OH or —O(CH₂)₀₋₅CH₃ |
| C(O)NH-4-piperazinyllphenyl | OH or —O(CH₂)₀₋₅CH₃ |
| C(O)NH-3-thiomethylphenyl | OH or —O(CH₂)₀₋₅CH₃ |
| H | OH or —O(CH₂)₀₋₅CH₃ |
| C(O)O(CH₂)₀₋₅CH₃ | OH or —O(CH₂)₀₋₅CH₃ |
| C(O)OH | OH or —O(CH₂)₀₋₅CH₃ |
| Ph—OH | OH or —O(CH₂)₀₋₅CH₃ |
| Ph—NH₂ | OH or —O(CH₂)₀₋₅CH₃ |
| Ph-Halo | OH or —O(CH₂)₀₋₅CH₃ |
| Ph—O(CH₂)₀₋₅CH₃ | OH or —O(CH₂)₀₋₅CH₃ |
| Ph—N[(CH₂)₀₋₅CH₃]₂ | OH or —O(CH₂)₀₋₅CH₃ |
| C(O)NH₂ | 1-pyrrolidyl |
| C(O)N[(CH₂)₀₋₅CH₃]₂ | 1-pyrrolidyl |
| C(O)NHPh | 1-pyrrolidyl |
| C(O)NH-2,4-fluorophenyl | 1-pyrrolidyl |
| C(O)NH-4-fluorophenyl | 1-pyrrolidyl |
| C(O)NH-fluorophenyl | 1-pyrrolidyl |
| C(O)NH-4-morpholinylphenyl | 1-pyrrolidyl |
| C(O)NH-4-piperazinyllphenyl | 1-pyrrolidyl |

TABLE 4-continued

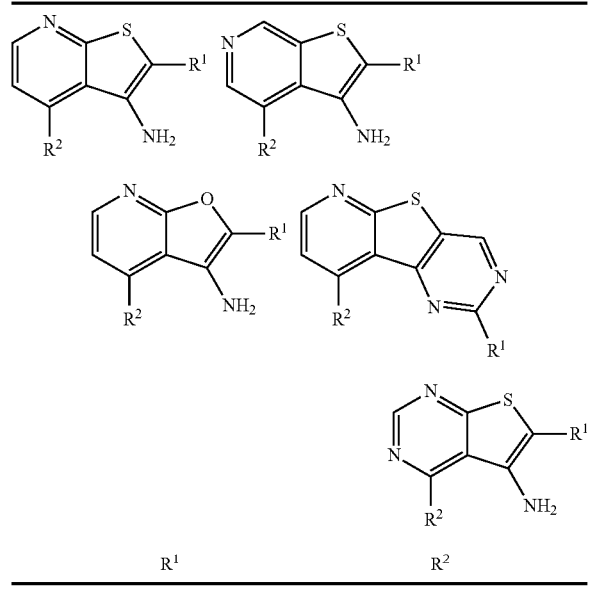

| R¹ | R² |
|---|---|
| C(O)NH-3-thiomethylphenyl | 1-pyrrolidyl |
| H | 1-pyrrolidyl |
| C(O)O(CH$_2$)$_{0-5}$CH$_3$ | 1-pyrrolidyl |
| C(O)OH | 1-pyrrolidyl |
| Ph—OH | 1-pyrrolidyl |
| Ph—NH$_2$ | 1-pyrrolidyl |
| Ph-Halo | 1-pyrrolidyl |
| Ph—O(CH$_2$)$_{0-5}$CH$_3$ | 1-pyrrolidyl |
| Ph—N[(CH$_2$)$_{0-5}$CH$_3$]$_2$ | 1-pyrrolidyl |
| C(O)NH$_2$ | 1-piperidinyl |
| C(O)N[(CH$_2$)$_{0-5}$CH$_3$]$_2$ | 1-piperidinyl |
| C(O)NHPh | 1-piperidinyl |
| C(O)NH-2,4-fluorophenyl | 1-piperidinyl |
| C(O)NH-4-fluorophenyl | 1-piperidinyl |
| C(O)NH-3-fluorophenyl | 1-piperidinyl |
| C(O)NH-4-morpholinylphenyl | 1-piperidinyl |
| C(O)NH-4-piperazinyllphenyl | 1-piperidinyl |
| C(O)NH-3-thiomethylphenyl | 1-piperidinyl |
| H | 1-piperidinyl |
| C(O)O(CH$_2$)$_{0-5}$CH$_3$ | 1-piperidinyl |
| C(O)OH | 1-piperidinyl |
| Ph—OH | 1-piperidinyl |
| Ph—NH$_2$ | 1-piperidinyl |
| Ph-Halo | 1-piperidinyl |
| Ph—O(CH$_2$)$_{0-5}$CH$_3$ | 1-piperidinyl |
| Ph—N—[(CH$_2$)$_{0-5}$CH$_3$]$_2$ | 1-piperidinyl |
| C(O)NH$_2$ | 4-morpholinyl |
| C(O)N[(CH$_2$)$_{0-5}$CH$_3$]$_2$ | 4-morpholinyl |
| C(O)NHPh | 4-morpholinyl |
| C(O)NH-2,4-fluorophenyl | 4-morpholinyl |
| C(O)NH-4-fluorophenyl | 4-morpholinyl |
| C(O)NH-3-fluorophenyl | 4-morpholinyl |
| C(O)NH-4-morpholinylphenyl | 4-morpholinyl |
| C(O)NH-4-piperazinyllphenyl | 4-morpholinyl |
| C(O)NH-3-thiomethylphenyl | 4-morphylinyl |
| H | 4-morpholinyl |
| C(O)O(CH$_2$)$_{0-5}$CH$_3$ | 4-morpholinyl |
| C(O)OH | 4-morpholinyl |
| Ph—OH | 4-morpholinyl |
| Ph—NH$_2$ | 4-morpholinyl |
| Ph-Halo | 4-morpholinyl |
| Ph—O(CH$_2$)$_{0-5}$CH$_3$ | 4-morpholinyl |
| Ph—N[(CH$_2$)$_{0-5}$CH$_3$]$_2$ | 4-morpholinyl |
| C(O)NH$_2$ | —(CH$_2$)$_{0-5}$CH$_3$ |
| C(O)N[(CH$_2$)$_{0-5}$CH$_3$]$_2$ | —(CH$_2$)$_{0-5}$CH$_3$ |

TABLE 4-continued

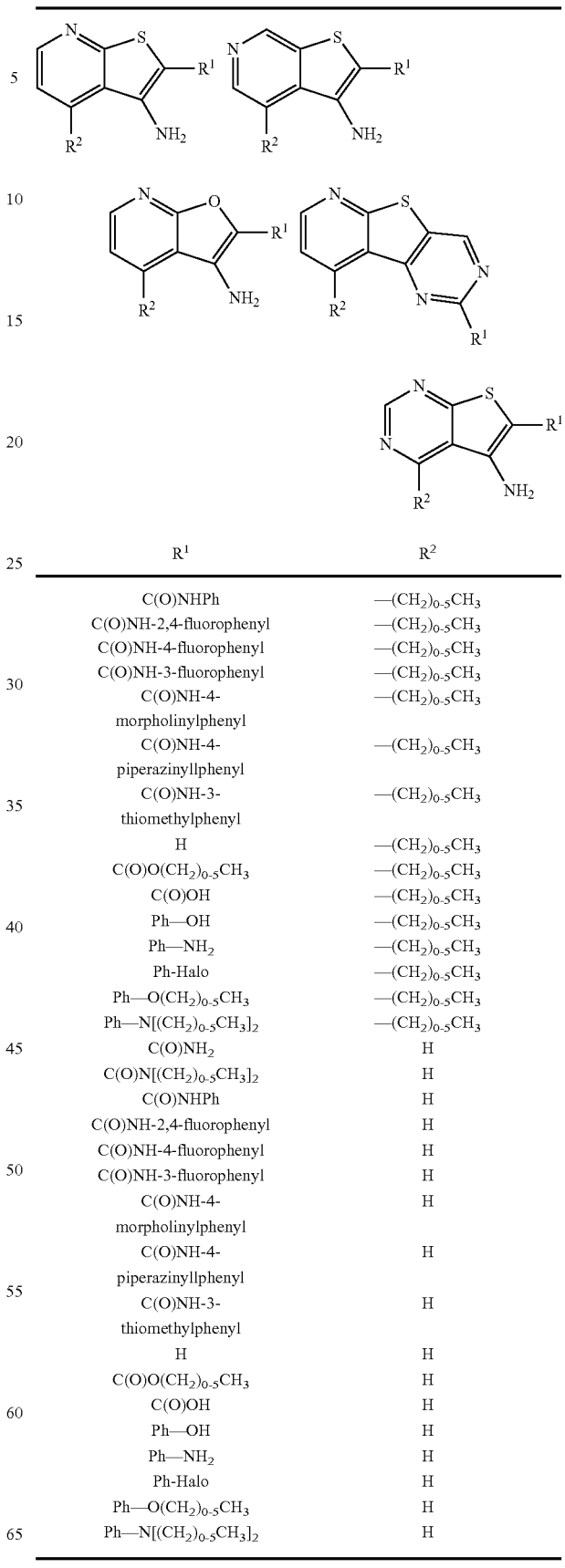

| R¹ | R² |
|---|---|
| C(O)NHPh | —(CH$_2$)$_{0-5}$CH$_3$ |
| C(O)NH-2,4-fluorophenyl | —(CH$_2$)$_{0-5}$CH$_3$ |
| C(O)NH-4-fluorophenyl | —(CH$_2$)$_{0-5}$CH$_3$ |
| C(O)NH-3-fluorophenyl | —(CH$_2$)$_{0-5}$CH$_3$ |
| C(O)NH-4-morpholinylphenyl | —(CH$_2$)$_{0-5}$CH$_3$ |
| C(O)NH-4-piperazinyllphenyl | —(CH$_2$)$_{0-5}$CH$_3$ |
| C(O)NH-3-thiomethylphenyl | —(CH$_2$)$_{0-5}$CH$_3$ |
| H | —(CH$_2$)$_{0-5}$CH$_3$ |
| C(O)O(CH$_2$)$_{0-5}$CH$_3$ | —(CH$_2$)$_{0-5}$CH$_3$ |
| C(O)OH | —(CH$_2$)$_{0-5}$CH$_3$ |
| Ph—OH | —(CH$_2$)$_{0-5}$CH$_3$ |
| Ph—NH$_2$ | —(CH$_2$)$_{0-5}$CH$_3$ |
| Ph-Halo | —(CH$_2$)$_{0-5}$CH$_3$ |
| Ph—O(CH$_2$)$_{0-5}$CH$_3$ | —(CH$_2$)$_{0-5}$CH$_3$ |
| Ph—N[(CH$_2$)$_{0-5}$CH$_3$]$_2$ | —(CH$_2$)$_{0-5}$CH$_3$ |
| C(O)NH$_2$ | H |
| C(O)N[(CH$_2$)$_{0-5}$CH$_3$]$_2$ | H |
| C(O)NHPh | H |
| C(O)NH-2,4-fluorophenyl | H |
| C(O)NH-4-fluorophenyl | H |
| C(O)NH-3-fluorophenyl | H |
| C(O)NH-4-morpholinylphenyl | H |
| C(O)NH-4-piperazinyllphenyl | H |
| C(O)NH-3-thiomethylphenyl | H |
| H | H |
| C(O)O(CH$_2$)$_{0-5}$CH$_3$ | H |
| C(O)OH | H |
| Ph—OH | H |
| Ph—NH$_2$ | H |
| Ph-Halo | H |
| Ph—O(CH$_2$)$_{0-5}$CH$_3$ | H |
| Ph—N[(CH$_2$)$_{0-5}$CH$_3$]$_2$ | H |

TABLE 5

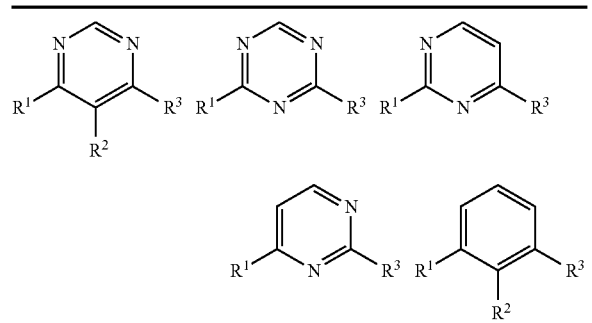
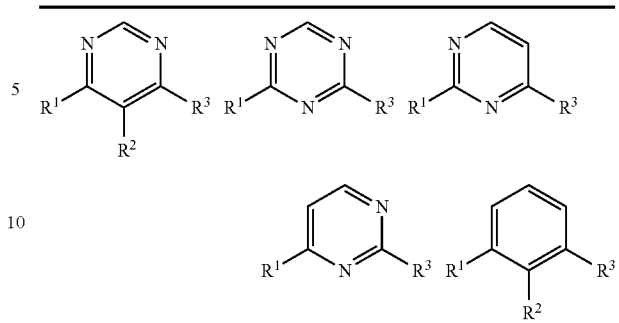

| R¹ | R² | R³ |
|---|---|---|
| pyrrolidinyl | H, NO₂, CN, or SO₂CF₃ | NH₂, NH(CH₂)₀₋₅CH₃, or N[(CH₂)₀₋₅CH₃]₂ |
| piperidinyl | H, NO₂, CN, or SO₂CF₃ | NH₂, NH(CH₂)₀₋₅CH₃, or N[(CH₂)₀₋₅CH₃]₂ |
| indole | H, NO₂, CN, or SO₂CF₃ | NH₂, NH(CH₂)₀₋₅CH₃, or N[(CH₂)₀₋₅CH₃]₂ |
| NH₂ | H, NO₂, CN, or SO₂CF₃ | NH₂, NH(CH₂)₀₋₅CH₃, or N[(CH₂)₀₋₅CH₃]₂ |
| —NHPh | H, NO₂, CN, or SO₂CF₃ | NH₂, NH(CH₂)₀₋₅CH₃, or N[(CH₂)₀₋₅CH₃]₂ |
| Ph | H, NO₂, CN, or SO₂CF₃ | NH₂, NH(CH₂)₀₋₅CH₃, or N[(CH₂)₀₋₅CH₃]₂ |
| OPh | H, NO₂, CN, or SO₂CF₃ | NH₂, NH(CH₂)₀₋₅CH₃, or N[(CH₂)₀₋₅CH₃]₂ |
| pyrrolidinyl | H, NO₂, CN, or SO₂CF₃ | NHC(O)H or NHC(O)(CH₂)₀₋₅CH₃ |
| piperidinyl | H, NO₂, CN, or SO₂CF₃ | NHC(O)H or NHC(O)(CH₂)₀₋₅CH₃ |
| indole | H, NO₂, CN, or SO₂CF₃ | NHC(O)H or NHC(O)(CH₂)₀₋₅CH₃ |
| NH₂ | H, NO₂, CN, or SO₂CF₃ | NHC(O)H or NHC(O)(CH₂)₀₋₅CH₃ |
| —NHPh | H, NO₂, CN, or SO₂CF₃ | NHC(O)H or NHC(O)(CH₂)₀₋₅CH₃ |
| Ph | H, NO₂, CN, or SO₂CF₃ | NHC(O)H or NHC(O)(CH₂)₀₋₅CH₃ |
| OPh | H, NO₂, CN, or SO₂CF₃ | NHC(O)H or NHC(O)(CH₂)₀₋₅CH₃ |
| pyrrolidinyl | H, NO₂, CN, or SO₂CH₃ | NHS(O)₂H or NHS(O)₂(CH₂)₀₋₅CH₃ |
| piperidinyl | H, NO₂, CN, or SO₂CF₃ | NHS(O)₂H or NHS(O)₂(CH₂)₀₋₅CH₃ |
| indole | H, NO₂, CN, or SO₂CF₃ | NHS(O)₂H or NHS(O)₂(CH₂)₀₋₅CH₃ |
| NH₂ | H, NO₂, CN, or SO₂CF₃ | NHS(O)₂H or NHS(O)₂(CH₂)₀₋₅CH₃ |
| —NHPh | H, NO₂, CN, or SO₂CF₃ | NHS(O)₂H or NHS(O)₂(CH₂)₀₋₅CH₃ |
| Ph | H, NO₂, CN, or SO₂CF₃ | NHS(O)₂H or NHS(O)₂(CH₂)₀₋₅CH₃ |
| OPh | H, NO₂, CN, or SO₂CF₃ | NHS(O)₂H or NHS(O)₂(CH₂)₀₋₅CH₃ |
| pyrrolidinyl | H, NO₂, CN, or SO₂CF₃ | H |
| piperidinyl | H, NO₂, CN, or SO₂CF₃ | H |
| indole | H, NO₂, CN, or SO₂CF₃ | H |
| NH₂ | H, NO₂, CN, or SO₂CF₃ | H |
| —NHPh | H, NO₂, CN, or SO₂CF₃ | H |
| Ph | H, NO₂, CN, or SO₂CF₃ | H |
| OPh | H, NO₂, CN, or SO₂CF₃ | H |
| pyrrolidinyl | H, NO₂, CN, or SO₂CF₃ | —NHPh |
| piperidinyl | H, NO₂, CN, or SO₂CF₃ | —NHPh |
| indole | H, NO₂, CN, or SO₂CF₃ | —NHPh |
| NH₂ | H, NO₂, CN, or SO₂CF₃ | —NHPh |
| —NHPh | H, NO₂, CN, or SO₂CF₃ | —NHPh |
| Ph | H, NO₂, CN, or SO₂CF₃ | —NHPh |
| OPh | H, NO₂, CN, or SO₂CF₃ | —NHPh |
| pyrrolidinyl | H, NO₂, CN, or SO₂CF₃ | OH |
| piperidinyl | H, NO₂, CN, or SO₂CF₃ | OH |
| indole | H, NO₂, CN, or SO₂CF₃ | OH |
| NH₂ | H, NO₂, CN, or SO₂CF₃ | OH |
| —NHPh | H, NO₂, CN, or SO₂CF₃ | OH |
| Ph | H, NO₂, CN, or SO₂CF₃ | OH |
| OPh | H, NO₂, CN, or SO₂CF₃ | OH |
| pyrrolidinyl | H, NO₂, CN or, SO₂CF₃ | 1-pyrrolidyl |
| piperidinyl | H, NO₂, CN, or SO₂CF₃ | 1-pyrrolidyl |
| indole | H, NO₂, CN, or SO₂CF₃ | 1-pyrrolidyl |
| NH₂ | H, NO₂, CN, or SO₂CF₃ | 1-pyrrolidyl |
| —NHPh | H, NO₂, CN, or SO₂CF₃ | 1-pyrrolidyl |
| Ph | H, NO₂, CN, or SO₂CF₃ | 1-pyrrolidyl |
| OPh | H, NO₂, CN, or SO₂CF₃ | 1-pyrrolidyl |
| pyrrolidinyl | H, NO₂, CN, or SO₂CF₃ | 1-piperidinyl |
| piperidinyl | H, NO₂, CN or SO₂CF₃ | 1-piperidinyl |
| indole | H, NO₂, CN , or SO₂CF₃ | 1-piperidinyl |
| NH₂ | H, NO₂, CN, or SO₂CF₃ | 1-piperidinyl |
| —NHPh | H, NO₂, CN, or SO₂CF₃ | 1-piperidinyl |
| Ph | H, NO₂, CN, or SO₂CF₃ | 1-piperidinyl |
| OPh | H, NO₂, CN, or SO₂CF₃ | 1-piperidinyl |
| pyrrolidinyl | H, NO₂, CN, or SO₂CF₃ | Ph |
| piperidinyl | H, NO₂, CN, or SO₂CF₃ | Ph |
| indole | H, NO₂, CN, or SO₂CF₃ | Ph |
| NH₂ | H, NO₂, CN, or SO₂CF₃ | Ph |
| —NHPh | H, NO₂, CN, or SO₂CF₃ | Ph |
| Ph | H, NO₂, CN, or SO₂CF₃ | Ph |

TABLE 5-continued

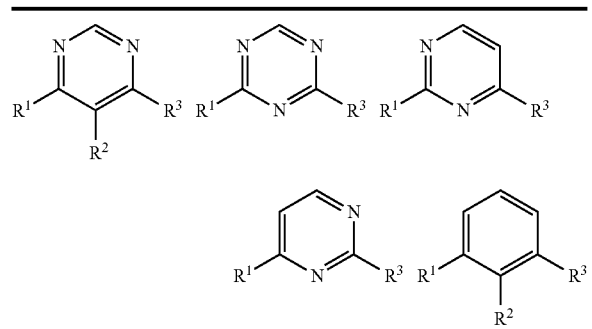

| R$^1$ | R$^2$ | R$^3$ |
|---|---|---|
| OPh | H, NO$_2$, CN, or SO$_2$CF$_3$ | Ph |
| pyrrolidinyl | H, NO$_2$, CN, or SO$_2$CF$_3$ | —Ph-Halo |
| piperidinyl | H, NO, CN, or SO$_2$CF$_3$ | —Ph-Halo |
| indole | H, NO$_2$, CN, or SO$_2$CF$_3$ | —Ph-Halo |

TABLE 5-continued

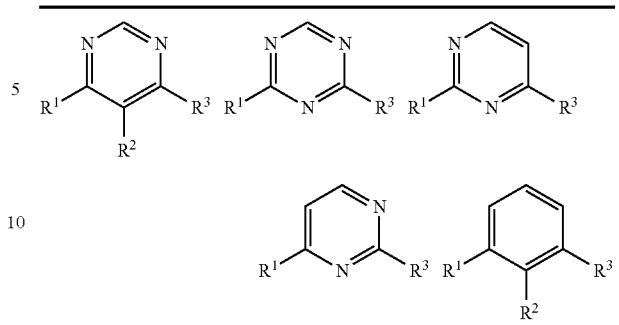

| R$^1$ | R$^2$ | R$^3$ |
|---|---|---|
| NH$_2$ | H, NO$_2$, CN, or SO$_2$CF$_3$ | —Ph-Halo |
| —NHPh | H, NO$_2$, CN, or SO$_2$CF$_3$ | —Ph-Halo |
| Ph | H, NO$_2$, CN, or SO$_2$CF$_3$ | —Ph-Halo |
| OPh | H, NO$_2$, CN, or SO$_2$CF$_3$ | —Ph-Halo |

TABLE 6

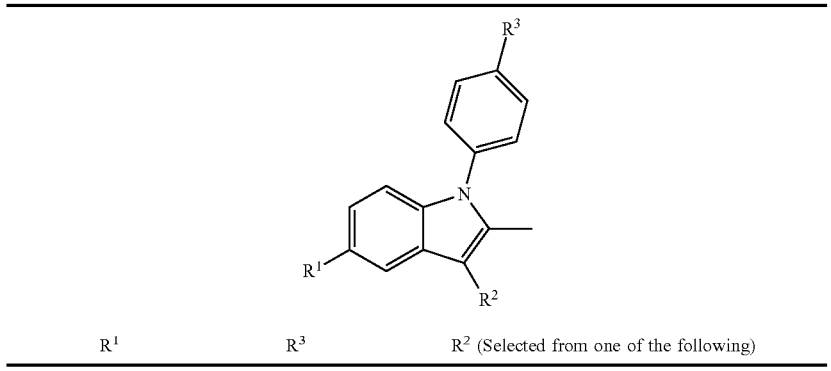

| R$^1$ | R$^3$ | R$^2$ (Selected from one of the following) | | | |
|---|---|---|---|---|---|
| OC(O)NH$_2$ | Halo | C(O)NH$_2$ | C(O)N[(CH$_2$)$_{0-5}$CH$_3$]$_2$ | | C(O)O(CH$_2$)$_{0-5}$CH$_3$ |
| OC(O)N[(CH$_2$)$_{0-5}$CH$_3$]$_2$ | Halo | C(O)NH$_2$ | C(O)N[(CH$_2$)$_{0-5}$CH$_3$]$_2$ | | C(O)O(CH$_2$)$_{0-5}$CH$_3$ |
| OC(O)OH | Halo | C(O)NH$_2$ | C(O)N[(CH$_2$)$_{0-5}$CH$_3$]$_2$ | | C(O)O(CH$_2$)$_{0-5}$CH$_3$ |
| OC(O)OP(O)(OH)$_2$ | Halo | C(O)NH$_{22}$ | C(O)N[(CH$_2$)$_{0-5}$CH$_3$]$_2$ | | C(O)O(CH$_2$)$_{0-5}$CH$_3$ |
| OC(O)OC(O)C(CH$_3$)$_3$ | Halo | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)NMe$_2$ | Halo | C(O)NH$_2$ | C(O)N[(CH$_2$)$_{0-5}$CH$_3$]$_2$ | | C(O)O(CH$_2$)$_{0-5}$CH$_3$ |
| OC(O)O(CH$_2$)$_{0-5}$CH$_3$ | Halo | C(O)NH$_2$ | C(O)N[(CH$_2$)$_{0-5}$CH$_3$]$_2$ | | C(O)O(CH$_2$)$_{0-5}$CH$_3$ |
| OC(O)(CH$_2$)$_{0-5}$CH$_3$ | Halo | C(O)NH$_2$ | C(O)N[(CH$_2$)$_{0-5}$CH$_3$]$_2$ | | C(O)O(CH$_2$)$_{0-5}$CH$_3$ |
| OC(O)NH$_2$ | OH | C(O)NH$_2$ | C(O)N[(CH$_2$)$_{0-5}$CH$_3$]$_2$ | | C(O)O(CH$_2$)$_{0-5}$CH$_3$ |
| OC(O)N[(CH$_2$)$_{0-5}$CH$_3$]$_2$ | OH | C(O)NH$_2$ | C(O)N[(CH$_2$)$_{0-5}$CH$_3$]$_2$ | | C(O)O(CH$_2$)$_{0-5}$CH$_3$ |
| OC(O)OH | OH | C(O)NH$_2$ | C(O)N[(CH$_2$)$_{0-5}$CH$_3$]$_2$ | | C(O)O(CH$_2$)$_{0-5}$CH$_3$ |
| OC(O)OP(O)(OH)$_2$ | OH | C(O)NH$_{22}$ | C(O)N[(CH$_2$)$_{0-5}$CH$_3$]$_2$ | | C(O)O(CH$_2$)$_{0-5}$CH$_3$ |
| OC(O)OC(O)C(CH$_3$)$_3$ | OH | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)NMe$_2$ | OH | C(O)NH$_2$ | C(O)N[(CH$_2$)$_{0-5}$CH$_3$]$_2$ | | C(O)O(CH$_2$)$_{0-5}$CH$_3$ |
| OC(O)O(CH$_2$)$_{0-5}$CH$_3$ | OH | C(O)NH$_2$ | C(O)N[(CH$_2$)$_{0-5}$CH$_3$]$_2$ | | C(O)O(CH$_2$)$_{0-5}$CH$_3$ |
| OC(O)(CH$_2$)$_{0-5}$CH$_3$ | OH | C(O)NH$_2$ | C(O)N[(CH$_2$)$_{0-5}$CH$_3$]$_2$ | | C(O)O(CH$_2$)$_{0-5}$CH$_3$ |
| OC(O)NH$_2$ | —O(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)N[(CH$_2$)$_{0-5}$CH$_3$]$_2$ | —O(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OH | —O(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OP(O)(OH)$_2$ | —O(CH$_2$)$_{0-5}$CH$_3$ | C(O)NH$_{22}$ | C(O)N[(CH$_2$)$_{0-5}$CH$_3$]$_2$ | | C(O)O(CH$_2$)$_{0-5}$CH$_3$ |
| OC(O)OC(O)(CH$_3$)$_3$ | —O(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)NMe$_2$ | —O(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)O(CH$_2$)$_{0-5}$CH$_3$ | —O(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)(CH$_2$)$_{0-5}$CH$_3$ | —O(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)NH$_2$ | NH$_2$ | C(O)NH$_{22}$ | C(O)N[(CH$_2$)$_{0-5}$CH$_3$]$_2$ | | C(O)O(CH$_2$)$_{0-5}$CH$_3$ |
| OC(O)N[(CH$_2$)$_{0-5}$CH$_3$]$_2$ | NH$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OH | NH$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OP(O)(OH)$_2$ | NH$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)C(CH$_3$)$_3$ | NH$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)NMe$_2$ | NH$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)O(CH$_2$)$_{0-5}$CH$_3$ | NH$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)(CH$_2$)$_{0-5}$CH$_3$ | NH$_2$ | C(O)NH$_2$ | C(O)N[(CH$_2$)$_{0-5}$CH$_3$]$_2$ | | C(O)O(CH$_2$)$_{0-5}$CH$_3$ |

TABLE 6-continued

| R¹ | R³ | R² (Selected from one of the following) | | | |
|---|---|---|---|---|---|
| OC(O)NH$_2$ | N[(CH$_2$)$_{0-5}$CH$_3$]$_2$ | C(O)NH$_{22}$ | C(O)NH$_2$ | C(O)N[(CH$_2$)$_{0-5}$CH$_3$]$_2$ | C(O)O(CH$_2$)$_{0-5}$CH$_3$ |
| OC(O)N[(CH$_2$)$_{0-5}$CH$_3$]$_2$ | N[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OH | N[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OP(O)(OH)$_2$ | N[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)C(CH$_3$)$_3$ | N[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)NMe$_2$ | N[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)O(CH$_2$)$_{0-5}$CH$_3$ | N[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)(CH$_2$)$_{0-5}$CH$_3$ | N[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)NH$_2$ | —(CH$_2$)$_{0-5}$CH$_3$ | C(O)NH$_{22}$ | C(O)NH$_2$ | C(O)N[(CH$_2$)$_{0-5}$CH$_3$]$_2$ | C(O)O(CH$_2$)$_{0-5}$CH$_3$ |
| OC(O)N[(CH$_2$)$_{0-5}$CH$_3$]$_2$ | —(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OH | —(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OP(O)(OH)$_2$ | —(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)C(CH$_3$)$_3$ | —(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)NMe$_2$ | —(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)O(CH$_2$)$_{0-5}$CH$_3$ | —(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)(CH$_2$)$_{0-5}$CH$_3$ | —(CH$_2$)$_{0-5}$CH$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)NH$_2$ | S[(CH$_2$)$_{0-5}$CH$_3$]$_2$ | C(O)NH$_{22}$ | C(O)NH$_2$ | C(O)N[(CH$_2$)$_{0-5}$CH$_3$]$_2$ | C(O)O(CH$_2$)$_{0-5}$CH$_3$ |
| OC(O)N[(CH$_2$)$_{0-5}$CH$_3$]$_2$ | S[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OH | S[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OP(O)(OH)$_2$ | S[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)C(CH$_3$)$_3$ | S[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)NMe$_2$ | S[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)O(CH$_2$)$_{0-5}$CH$_3$ | S[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)(CH$_2$)$_{0-5}$CH$_3$ | S[(CH$_2$)$_{0-5}$CH$_3$]$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)NH$_2$ | NO$_2$ | C(O)NH$_{22}$ | C(O)NH$_2$ | C(O)N[(CH$_2$)$_{0-5}$CH$_3$]$_2$ | C(O)O(CH$_2$)$_{0-5}$CH$_3$ |
| OC(O)N[(CH$_2$)$_{0-5}$CH$_3$]$_2$ | NO$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OH | NO$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OP(O)(OH)$_2$ | NO$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)C(CH$_3$)$_3$ | NO$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)NMe$_2$ | NO$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)O(CH$_2$)$_{0-5}$CH$_3$ | NO$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)(CH$_2$)$_{0-5}$CH$_3$ | NO$_2$ | C(O)NH$_2$ | C(O)N[(CH$_2$)$_{0-5}$CH$_3$]$_2$ | | C(O)O(CH$_2$)$_{0-5}$CH$_3$ |
| OC(O)NH$_2$ | CF$_3$ | C(O)NH$_{22}$ | C(O)NH$_2$ | C(O)N[(CH$_2$)$_{0-5}$CH$_3$]$_2$ | C(O)O(CH$_2$)$_{0-5}$CH$_3$ |
| OC(O)N[(CH$_2$)$_{0-5}$CH$_3$]$_2$ | CF$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OH | CF$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OP(O)(OH)$_2$ | CF$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)C(CH$_3$)$_3$ | CF$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)OC(O)NMe$_2$ | CF$_3$ | C(O)NH$_2$ | C(O)N[(CH$_2$)$_{0-5}$CH$_3$]$_2$ | | C(O)O(CH$_2$)$_{0-5}$CH$_3$ |
| O(CO)O(CH$_2$)$_{0-5}$CH$_3$ | CF$_3$ | C(O)NH$_2$ | C(O)N[(CH$_2$)$_{0-5}$CH$_3$]$_2$ | | C(O)O(CH$_2$)$_{0-5}$CH$_3$ |
| OC(O)(CH$_2$)$_{0-5}$CH$_3$ | CF | C(O)NH$_2$ | C(O)N[(CH$_2$)$_{0-5}$CH$_3$]$_2$ | | C(O)O(CH$_2$)$_{0-5}$CH$_3$ |

Certain embodiments can use any one or more of the following compounds:

MLS001212998-01

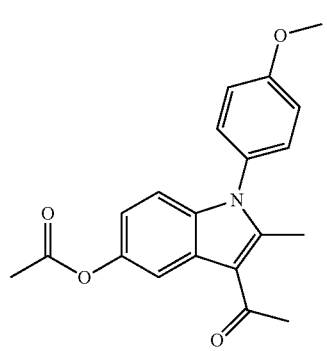

MLS001223482-01

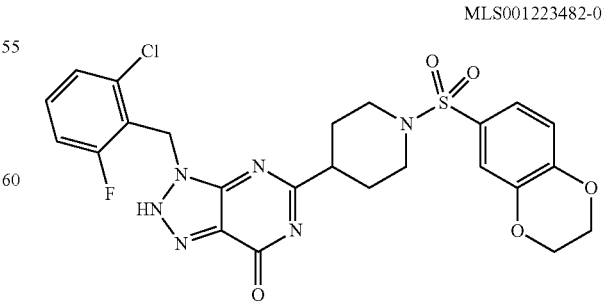

MLS000047918-01
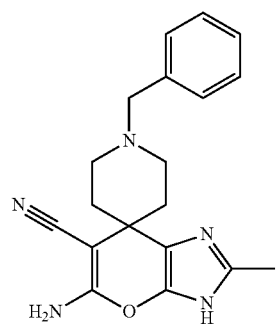
MLS000763405-01
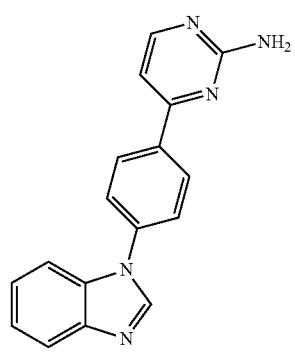
MLS000695955-01
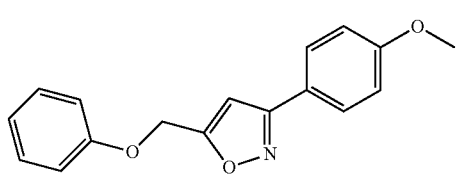
MLS001125488-01
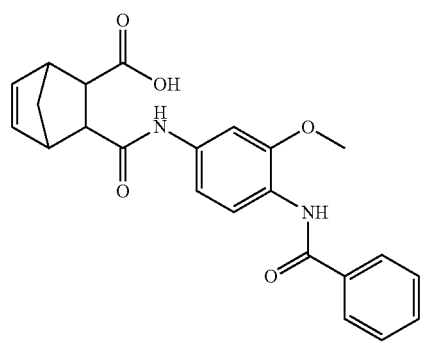
MLS000525404-01
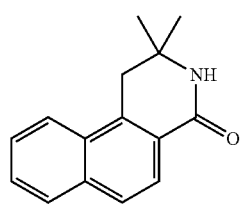
MLS000772430-01
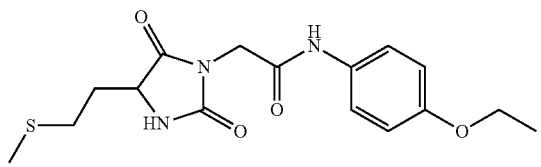
MLS000693370-01
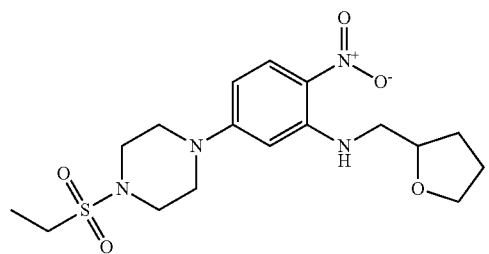
MLS001124046-01
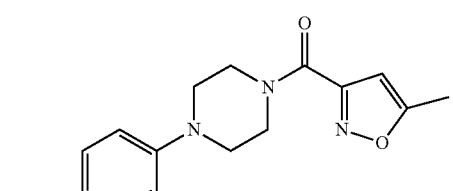
MLS001216714-01
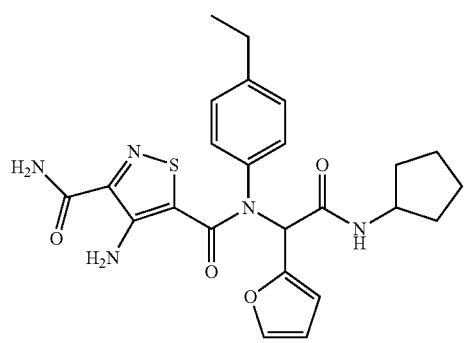
MLS001077207-01
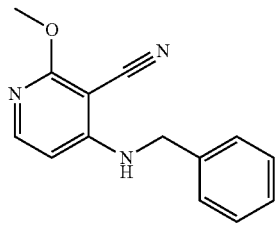

57
-continued
MLS000585616-01
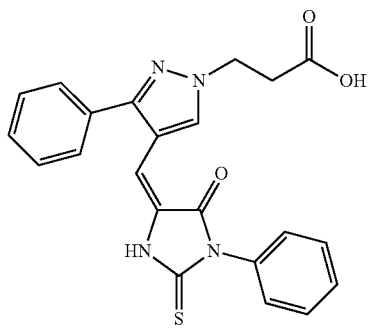
MLS001096269-01
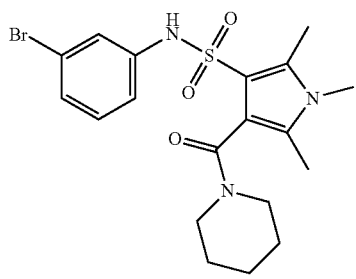
MLS001196422-01
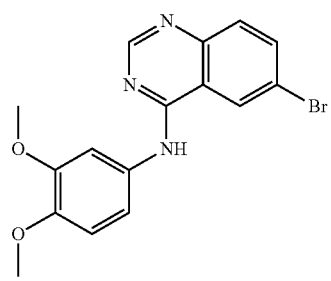
MLS001223425-01
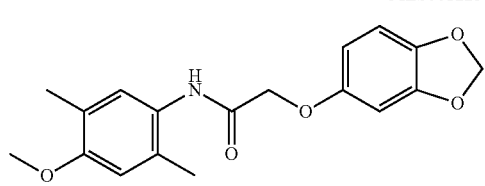
MLS001117140-01
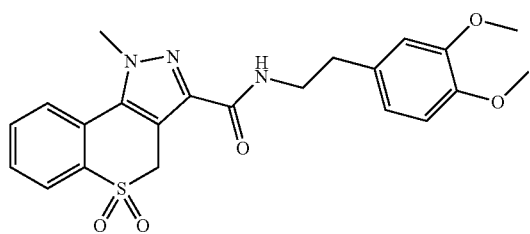
58
-continued
MLS002164687-01
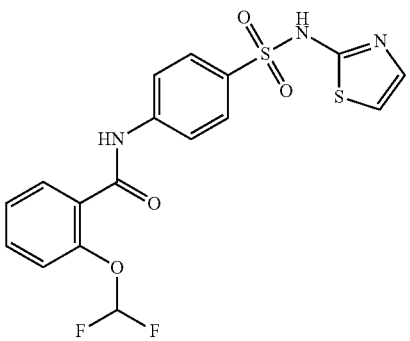
MLS001212498-01
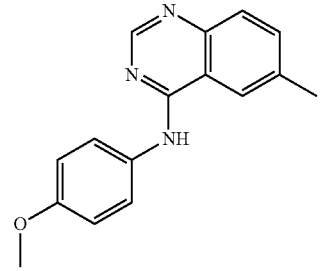
MLS002158881-01
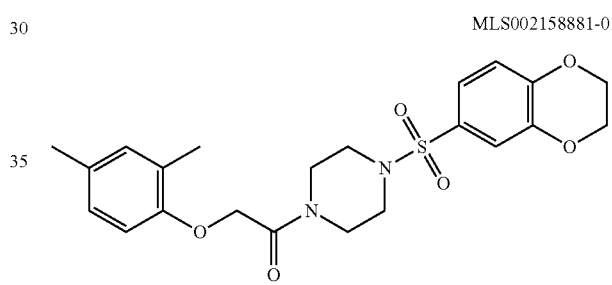
MLS000419555-01
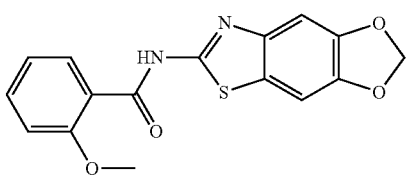
MLS000579238-01
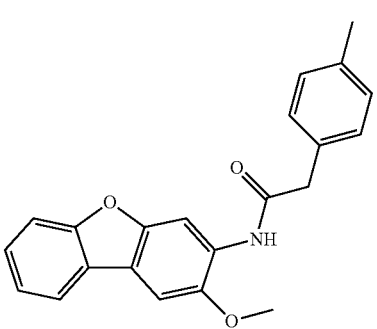

MLS001214704-01
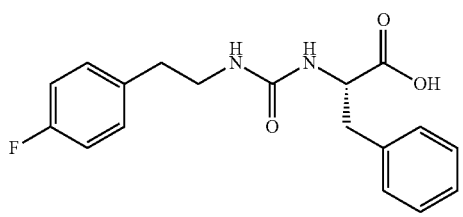
MLS000850824-01
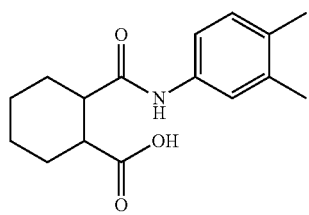
MLS000879190-01
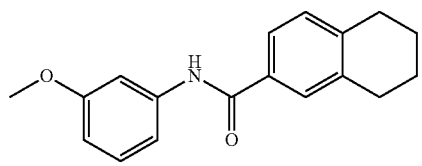
MLS000086970-01
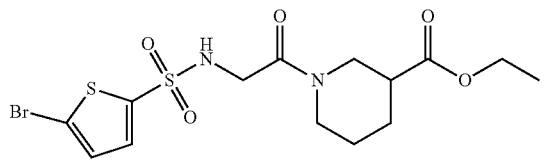
MLS001204005-01
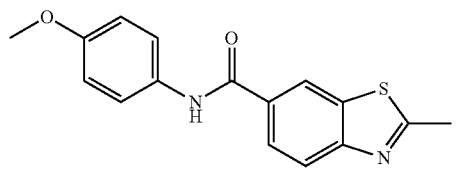
MLS000334464-01
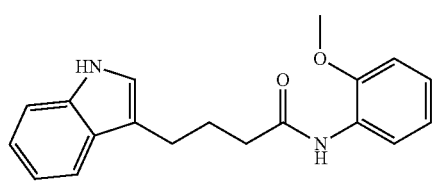
MLS001141113-01
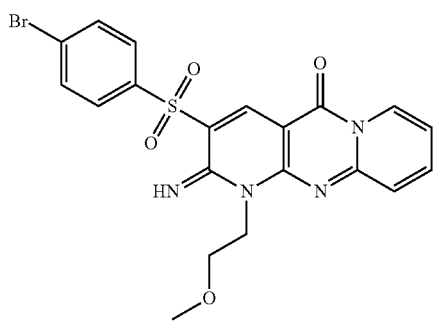
MLS000765108-01
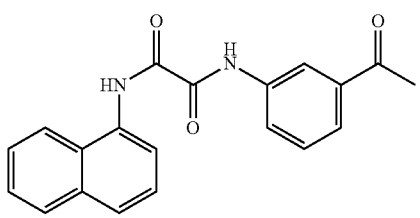
MLS001217697-01
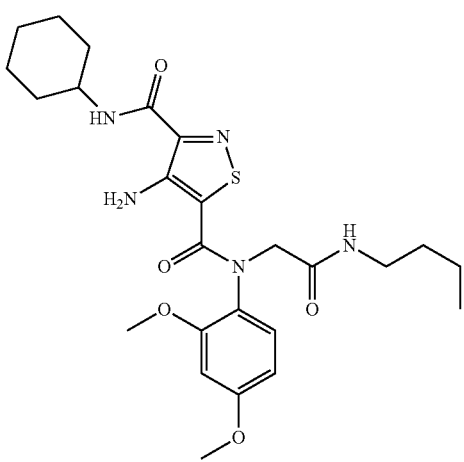
MLS001202634-01
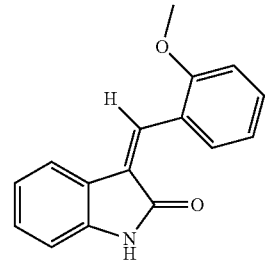
MLS000834755-01
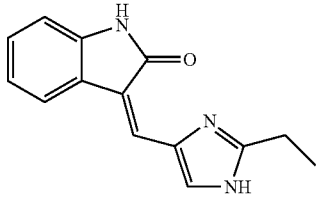
MLS000327715-01
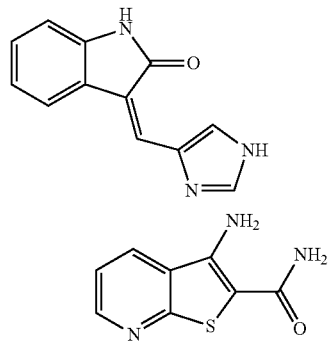

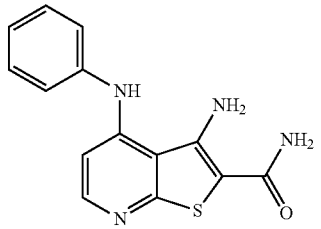
MLS000061149-01
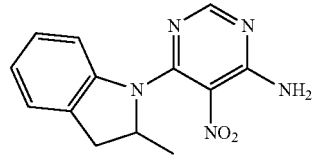
MLS000665974-01
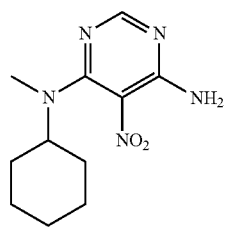
MLS001167337-01
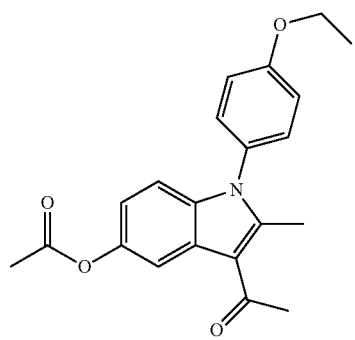
MLS001207978-01
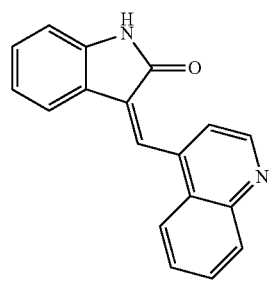
MLS001182278-01
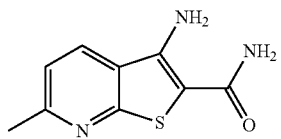
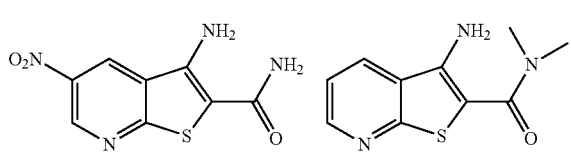
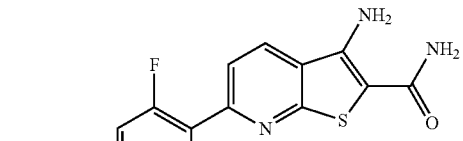
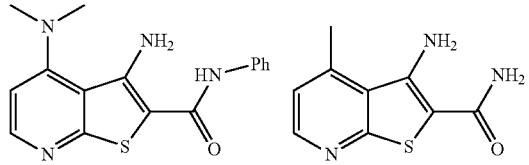
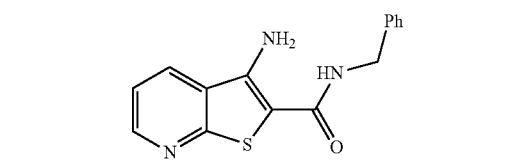
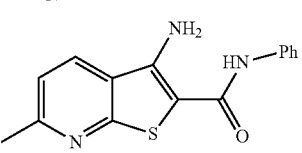
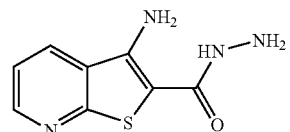
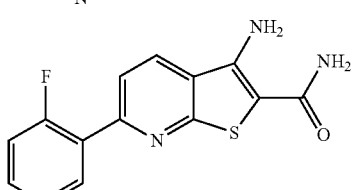
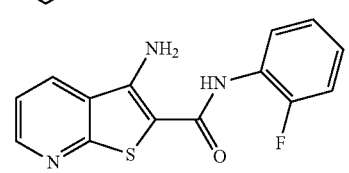
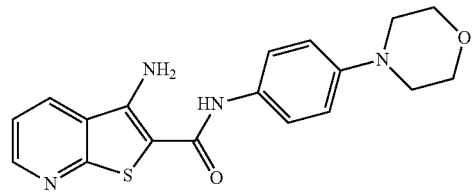
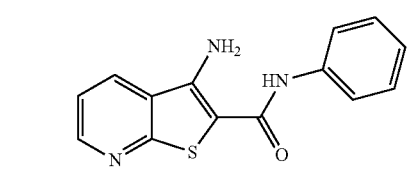
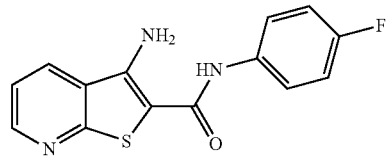

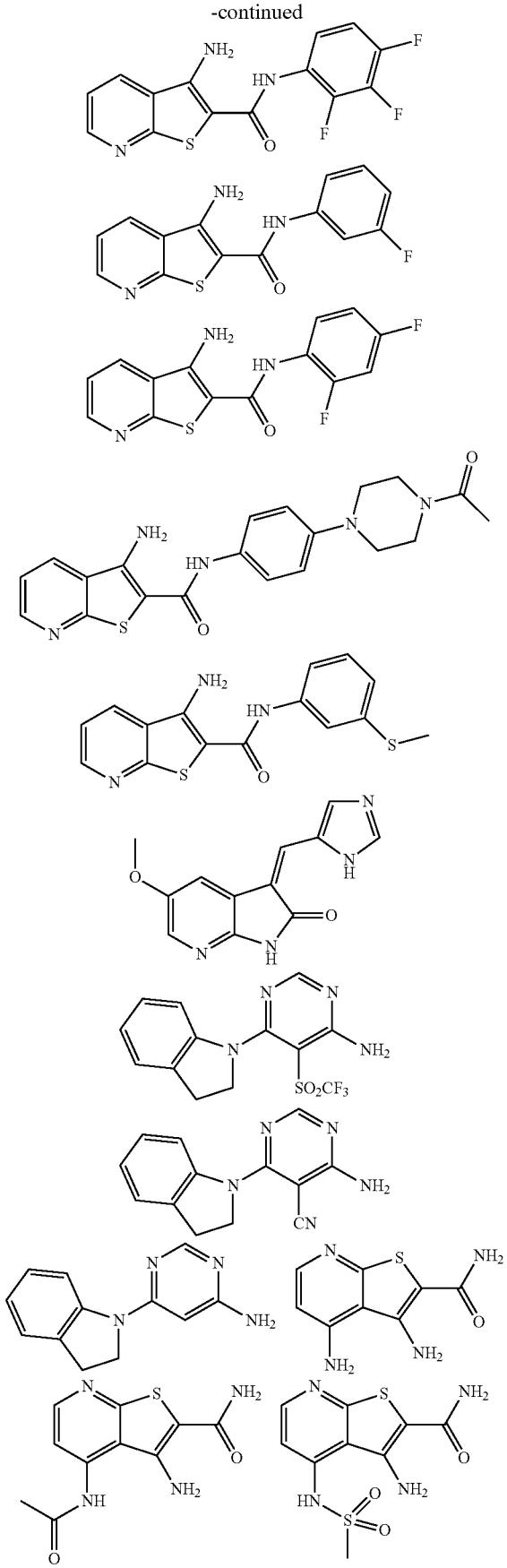
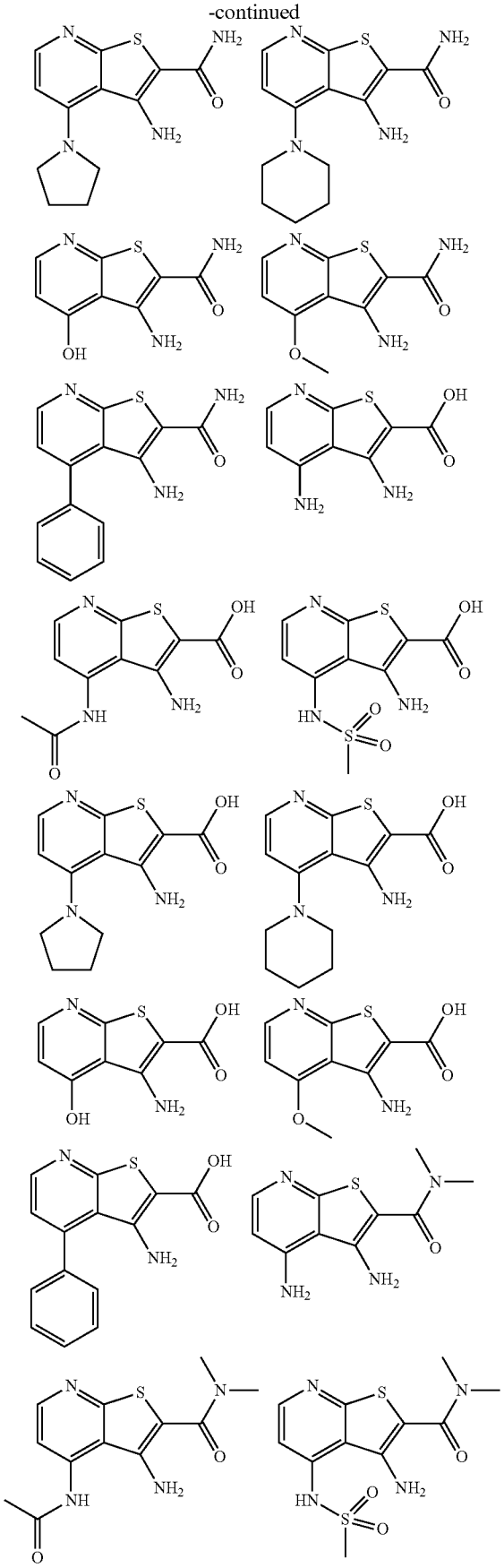

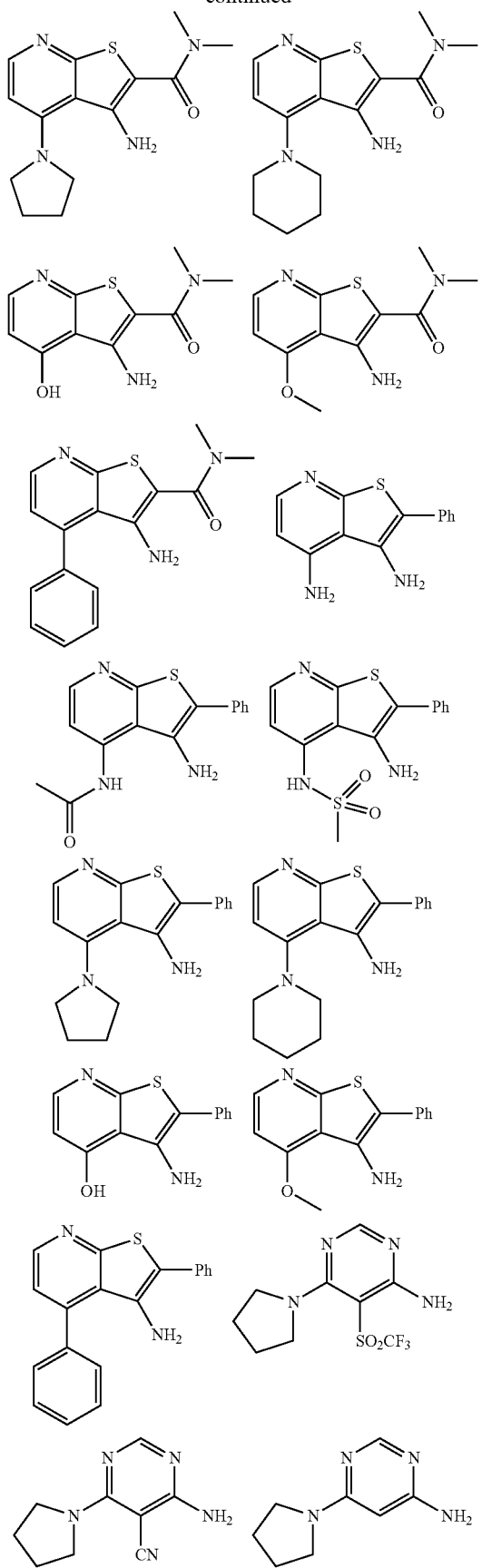
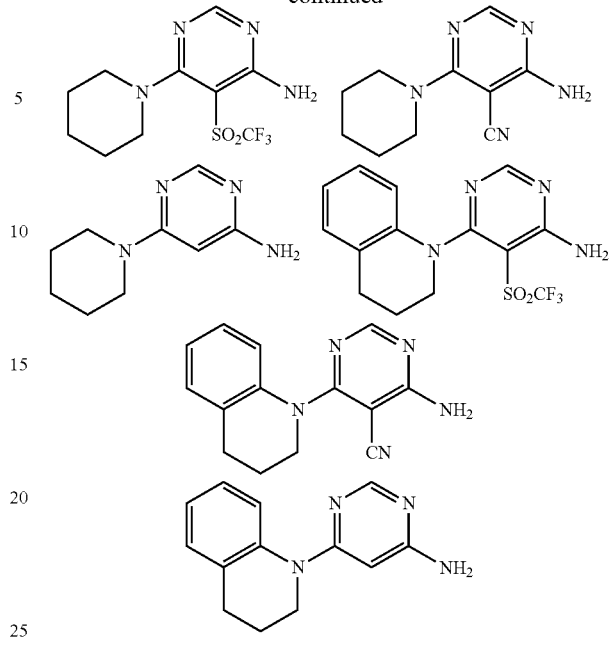

III. Methods of Use i. Methods of Treating Muscular Dystrophy

The α7β1 integrin has been shown to be a major modifier of disease progression in patients with muscular dystrophy. Increased expression of the α7 integrin in muscle can alleviate muscle disease in mouse models of muscular dystrophy. By use of a muscle cell-based assay, the inventors identified molecules that up-regulate α7β1 integrin expression in muscle: laminin-111; valproic acid; ciclopirox ethanolamine; deferoxamine; 2,2-dipyridyl; 5α-cholestan-3β-ol-6-one; Compound ID #1001; Compound ID #1002; Compound ID #1003; and analogs of cholestan. Based on these observations, methods of treatment of muscular dystrophy by increasing the expression or activity of α7β1 integrin with additional suitable compounds are disclosed.

In particular, methods are disclosed herein for treating muscular dystrophy, such as DMD, FCMD, LGMD, FHMD, BMD, MDC1A or MDC1D. In one example, the method includes administering an effective amount of a α7β1 integrin modulatory agent to a subject with muscular dystrophy or suspected of having or developing muscular dystrophy, in which the agent increases the biological activity or expression of α7β1 integrin and thereby, treating the muscular dystrophy in the subject. In some example, the method of treatment inhibits or reduces one or more signs or symptoms associated with muscular dystrophy in the subject.

In some examples, the α7β1 integrin modulatory agent includes one or more of the following molecules: a compound encompassed by any one of Formulas 1-16, or provided by any one of Tables 1-16 and 18. In some examples, an analog is synthesized according to the synthesis pathway shown in the Schemes below. In further examples, the α7β1 integrin modulatory agent is an analog/derivative of any of the disclosed α7β1 integrin modulatory agents which may be designed and synthesized according to the chemical principles known to one of ordinary skill in the art and identified as a α7β1 integrin modulatory agent by methods known to those of ordinary skill in the art, including the muscle cell based assay described Example 1, For examples, in some examples, the α7β1 integrin modulatory agent includes one or more molecules provided by any one of Formulas 1-16, or provided by any one of Tables 1-16 and 18.

The disclosed α7β1 integrin modulatory agents can alter the expression of nucleic acid sequences (such as DNA, cDNA, or mRNAs) and proteins of α7β1 integrin. An increase in the expression or activity does not need to be 100% for the agent to be effective. For example, an agent can increase the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing α7β1 integrin expression and activity are known to those of ordinary skill in the art, including those described in the Examples below (e.g., Western blot and ELISA assay with commercially available antibodies).

In a particular example, the subject is a human.

In additional aspects, the method involves selecting a subject with muscular dystrophy. In some example, a subject is selected for treatment following diagnosing the subject with muscular dystrophy. For example, the method can include diagnosing the subject as suffering from muscular dystrophy, such as DMD, MDC1A, MDC1D, LGMD, DMD, FCMD or FHMD.

Methods of diagnosing a subject with muscular dystrophy are known to those of skill in the art and include, but are not limited to, muscle biopsies and measuring serum creatine kinase levels. Additionally, alterations in biomarker known to be associated with muscular dystrophy may be detected by measuring such levels in serum or urine sample.

In a further implementation, the method involves diagnosing the subject as suffering from a disease, disorder, or condition characterized by a mutation in the gene encoding α7 integrin. In another implementation, the method involves diagnosing the subject as suffering from a disease, disorder, or condition characterized by a decreased level of α7 integrin expression.

Alterations in the expression can be measured at the nucleic acid level (such as by real time quantitative polymerase chain reaction or microarray analysis) or at the protein level (such as by Western blot analysis or ELISA). These methods are known to those of skill in the art.

In some examples, following the measurement of the expression levels of α7 integrin expression or serum creatine kinase levels, the assay results, findings, diagnoses, predictions and/or treatment recommendations are recorded and communicated to technicians, physicians and/or patients, for example. In certain embodiments, computers are used to communicate such information to interested parties, such as, patients and/or the attending physicians. The therapy selected for administered is then based upon these results.

In one embodiment, the results and/or related information is communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a subject as having muscular dystrophy, such as DMD, LGMD, FHMD, BMD, FCMD, MDC1D or MDC1A, results in the physician treating the subject, such as prescribing one or more disclosed α7β1 agents for inhibiting or delaying one or more signs and symptoms associated with muscular dystrophy. In additional embodiments, the dose or dosing regimen is modified based on the information obtained using the methods disclosed herein.

ii. Methods of Enhancing Muscle Regeneration, Repair, or Maintenance

Also disclosed are methods of enhancing muscle regeneration, repair or maintenance in a subject. In some examples, the method includes administering an effective amount of an α7β1 integrin modulatory agent to a subject in need of muscle regeneration, repair or maintenance, wherein the α7β1 integrin modulatory agent includes a compound encompassed by any one of Formulas 1-16, or provided by any one of Tables 1-16 and 18, or a combination thereof, wherein the α7β1 integrin modulatory agent increases α7β1 integrin expression or activity as compared to α7β1 integrin expression or activity prior to treatment, thereby enhancing muscle regeneration, repair or maintenance in a subject.

In some examples, the α7β1 integrin modulatory agent includes one or more of the following molecules: a compound encompassed by any one of Formulas 1-16, or provided by any one of Tables 1-16 and 18. In some examples, an analog is synthesized according to the synthesis pathway provided in the Examples below. In further examples, the α7β1 integrin modulatory agent is an analog/derivative of any of the disclosed α7β1 integrin modulatory agents which may be designed and synthesized according to the chemical principles known to one of ordinary skill in the art and identified as a α7β1 integrin modulatory agent by methods known to those of ordinary skill in the art, including the muscle cell based assay described Example 1. For examples, in some examples, the α7β1 integrin modulatory agent includes one or more molecules provided in a compound encompassed by any one of Formulas 1-16, or provided by any one of Tables 1-16 and 18.

The disclosed α7β1 integrin modulatory agents can increase the expression of nucleic acid sequences (such as DNA, cDNA, or mRNAs) and proteins of α7β1 integrin. An increase in the expression or activity does not need to be 100% for the agent to be effective. For example, an agent can increase the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing α7β1 integrin expression and activity are known to those of ordinary skill in the art, including those described in the Examples below (e.g., Western blot and ELISA assay with commercially available antibodies).

Muscle regeneration may benefit, for example, geriatric or other patient populations with reduced muscle repair capability, or simply speed the muscle repair process for otherwise physiologically unimpaired patients. In particular implementations, administration of a α7β1 integrin modulatory agent can aid muscle repair, or reduction of muscle damage, in athletes or others having activity-induced muscle injury or damage. In yet further implementations, muscle repair in patients suffering from muscle damage, such as through accident or injury, can be augmented by administration of a α7β1 integrin modulatory agent.

In some examples, α7β1 modulatory agent is administered prior to the subject experiencing muscle damage or disease. In some examples, the α7β1 integrin modulatory agent is administered to the subject prior to the subject exercising.

In some examples, the method further includes selecting a subject in need of enhancing muscle regeneration, repair, or maintenance. For example, in some instances, selecting a subject in need of enhancing muscle regeneration, repair, or maintenance comprises diagnosing the subject with a condition characterized by impaired muscle regeneration prior to administering an effective amount of the α7β1 integrin modulatory agent to the subject. Methods for diagnosing and selecting a subject in need of muscle regeneration, repair or maintenance are known to those of ordinary skill in the art and include those provided described herein (including those in the Methods of Treatment of Muscular Dystrophy). As stated above, subjects may be selected based upon their life style (e.g., engaged in moderate to intense exercise or physical activities), age (e.g., elderly population at more risk of experiencing muscle degeneration or injury) or predisposition to muscle degeneration or injury (e.g., aenetics or previous muscle injury).

iii. Methods of Prospectively Preventing or Reducing Muscle Injury or Damage

Also disclosed are methods prospectively preventing or reducing muscle injury or damage in a subject. In some embodiments, the method includes administering an effective amount of an α7β1 integrin modulatory agent to the subject wherein the α7β1 integrin modulatory agent comprises a compound encompassed by any one of Formulas 1-16, or provided by any one of Tables 1-16 and 18, or a combination thereof, wherein the α7β1 integrin modulatory agent increases α7β1 integrin expression or activity as compared to α7β1 integrin expression or activity prior to treatment, thereby prospectively preventing or reducing muscle injury or damage in the subject.

In some examples, the α7β1 integrin modulatory agent includes one or more of the following molecules: a compound encompassed by any one of Formulas 1-16, or provided by any one of Tables 1-16 and 18. In further examples, the α7β1 integrin modulatory agent is an analog/derivative of any of the disclosed α7β1 integrin modulatory agents which may be designed and synthesized according to the chemical principles known to one of ordinary skill in the art and identified as a α7β1 integrin modulatory agent by methods known to those of ordinary skill in the art, including the muscle cell based assay described Example 1. For examples, in some examples, the α7β1 integrin modulatory agent includes one or more molecules provided by any one of Formulas 1-16, or provided by any one of Tables 1-16 and 18. An exemplary synthetic scheme for making certain α7β1 integrin modulatory agent disclosed herein is provided in Schemes 1 and 2 as illustrated in FIG. 12. A person of ordinary skill in the art would recognize that derivatives of such compounds can be obtained using methods known in the art, such as functionalizing the core structure using suitable reagents and conditions. Exemplary groups that can be modified to produce various analogs are indicated in the Schemes shown in FIG. 12; and in some embodiments, the core of the molecule can be modified to include one or more additional heteroatoms and/or to replace an existing heteroatom with a different suitable heteroatom.

The disclosed α7β1 integrin modulatory agents can increase the expression of nucleic acid sequences (such as DNA, cDNA, or mRNAs) and proteins of α7β1 integrin. An increase in the expression or activity does not need to be 100% for the agent to be effective. For example, an agent can increase the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing α7β1 integrin expression and activity are known to those of ordinary skill in the art, including those described in the Examples below (e.g., Western blot and ELISA assay with commercially available antibodies).

In some examples, the method further includes selecting a subject at risk for developing a muscle injury or damage. In some examples, the α7β1 integrin modulatory agent is administered to a subject prior to the subject exercising.

In some examples, the method further includes selecting a subject at risk for developing a muscle injury or damage. Methods for selecting such s subject are known to those of ordinary skill in the art and include those provided described herein. As stated above, subjects may be selected based upon their life style (e.g., engaged in moderate to intense exercise or physical activities), age (elderly population at more risk of experiencing muscle degeneration or injury) or predisposition to muscle degeneration or injury (e.g., genetics or previous muscle injury).

iv. Methods of Enhancing α7β1 Integrin Expression

Also disclosed herein are methods of enhancing α7β1 integrin expression. In some examples, these methods include contacting a cell with an effective amount of an α7β1 integrin modulatory agent, wherein the α7β1 integrin modulatory agent comprises a compound encompassed by any one of Formulas 1-16, or provided by any one of Tables 1-16 and 18, or a combination thereof and increases α7β1 integrin expression in the treated cell relative to α7β1 integrin expression in an untreated cell, thereby enhancing α7β1 integrin expression. In some examples, the cell is a muscle cell, such as a skeletal muscle cell. In some examples, the muscle cell is present in a mammal, and wherein contacting the cell with an agent comprises administering the agent to the mammal.

In some examples, the α7β1 integrin modulatory agent includes one or more of the following molecules: a compound encompassed by any one of Formulas 1-16, or provided by any one of Tables 1-16 and 18. In further examples, the α7β1 integrin modulatory agent is an analog/derivative of any of the disclosed α7β1 integrin modulatory agents which may be designed and synthesized according to the chemical principles known to one of ordinary skill in the art and identified as a α7β1 integrin modulatory agent by methods known to those of ordinary skill in the art, including the muscle cell based assay described Example 1. In some examples, the α7β1 integrin modulatory agent includes one or more molecules encompassed by any one of Formulas 1-16, or provided by any one of Tables 1-16 and 18.

In some examples, the disclosed α7β1 integrin modulatory agents can increase the expression of nucleic acid sequences (such as DNA, cDNA, or mRNAs) and proteins of α7β1 integrin. An increase in the expression or activity does not need to be 100% for the agent to be effective. For example, an agent can increase the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing α7β1 integrin expression and activity are known to those of ordinary skill in the art, including those described in the Examples below (e.g., Western blot and ELISA assay with commercially available antibodies).

Administration of an Effective Amount of an α7β1 Integrin Modulatory Agent

For any of the disclosed methods, an effective amount of α7β1 integrin modulatory agent is one when administered by a particular route and concentration induces the desired response (e.g., treatment of muscular dystrophy, enhancing muscle regeneration, repair or maintenance, preventing or reducing muscle injury or damage, or enhancing α7β1 integrin expression).

i. Administration Routes, Formulations and Concentrations

Methods of administration of the disclosed α7β1 integrin modulatory agents are routine, and can be determined by a skilled clinician. The disclosed α7β1 integrin modulatory agents or other therapeutic substance are in general administered topically, nasally, intravenously, orally, intracranially, intramuscularly, parenterally or as implants, but even rectal or vaginal use is possible in principle. The disclosed α7β1 integrin modulatory agents also may be administered to a subject using a combination of these techniques.

Suitable solid or liquid pharmaceutical preparation forms are, for example, aerosols, (micro)capsules, creams, drops, drops or injectable solution in ampoule form, emulsions, granules, powders, suppositories, suspensions, syrups, tablets, coated tablets, and also preparations with protracted release of active compounds, in whose preparation excipients and additives and/or auxiliaries such as binders, coating agents, disintegrants, flavorings, lubricants, solubilizers, sweeteners, or swelling agents are customarily used as described above. The pharmaceutical agents are suitable for use in a variety of drug delivery systems. For a brief review of various methods for drug delivery, see Langer, "New Methods of Drug Delivery," *Science* 249:1527-1533 (1990), incorporated by reference herein to the extent not inconsistent with the present disclosure.

The disclosed α7β1 integrin modulatory agents or other therapeutic agents of the present disclosure can be formulated into therapeutically-active pharmaceutical agents that can be administered to a subject parenterally or orally.

Parenteral administration routes include, but are not limited to, epidermal, intraarterial, intramuscular (IM and depot IM), intraperitoneal (IP), intravenous (IV), intrasternal injection or infusion techniques, intranasal (inhalation), intrathecal, injection into the stomach, subcutaneous injections (subcutaneous (SQ and depot SQ), transdermal, topical, and ophthalmic.

The disclosed α7β1 integrin modulatory agents or other therapeutic agents can be mixed or combined with a suitable pharmaceutically acceptable excipients to prepare pharmaceutical agents. Pharmaceutically acceptable excipients include, but are not limited to, alumina, aluminum stearate, buffers (such as phosphates), glycine, ion exchangers (such as to help control release of charged substances), lecithin, partial glyceride mixtures of saturated vegetable fatty acids, potassium sorbate, serum proteins (such as human serum albumin), sorbic acid, water, salts or electrolytes such as cellulose-based substances, colloidal silica, disodium hydrogen phosphate, magnesium trisilicate, polyacrylates, polyalkylene glycols, such as polyethylene glycol, polyethylene-polyoxypropylene-block polymers, polyvinyl pyrrolidone, potassium hydrogen phosphate, protamine sulfate, group 1 halide salts such as sodium chloride, sodium carboxymethylcellulose, waxes, wool fat, and zinc salts, for example, Liposomal suspensions may also be suitable as pharmaceutically acceptable carriers.

Upon mixing or addition of one or more disclosed α7β1 integrin modulatory agents and/or or other therapeutic agents, the resulting mixture may be a solid, solution, suspension, emulsion, or the like. These may be prepared according to methods known to those of ordinary skill in the art. The form of the resulting mixture depends upon a number of factors, including the intended mode of administration and the solubility of the agent in the selected carrier. Pharmaceutical carriers suitable for administration of the disclosed α7β1 integrin modulatory agents or other therapeutic agents include any such carriers known to b suitable for the particular mode of administration. In addition, the disclosed α7β1 integrin modulatory agents or other therapeutic substance can also be mixed with other inactive or active materials that do not impair the desired action, or with materials that supplement the desired action, or have another action.

Methods for solubilizing may be used where the agents exhibit insufficient solubility in a carrier. Such methods are known and include, but are not limited to, dissolution in aqueous sodium bicarbonate, using cosolvents such as dimethylsulfoxide (DMSO), and using surfactants such as TWEEN® (ICI Americas, Inc., Wilmington, Del.).

The disclosed α7β1 integrin modulatory agents or other therapeutic agents can be prepared with carriers that protect them against rapid elimination from the body, such as coatings or time-release formulations. Such carriers include controlled release formulations, such as, but not limited to, microencapsulated delivery systems. A disclosed α7β1 integrin modulatory agents or other therapeutic agent is included in the pharmaceutically acceptable carrier in an amount sufficient to exert a therapeutically useful effect, typically in an amount to avoid undesired side effects, on the treated subject. The therapeutically effective concentration may be determined empirically by testing the compounds in known in vitro and in vivo model systems for the treated condition. For example, mouse models of muscular dystrophy may be used to determine effective amounts or concentrations that can then be translated to other subjects, such as humans, as known in the art.

Injectable solutions or suspensions can be formulated, using suitable non-toxic, parenterally-acceptable diluents or solvents, such as 1,3-butanediol, isotonic sodium chloride solution, mannitol, Ringer's solution, saline solution, or water; or suitable dispersing or wetting and suspending agents, such as sterile, bland, fixed oils, including synthetic mono- or diglycerides, and fatty acids, including oleic acid; a naturally occurring vegetable oil such as coconut oil, cottonseed oil, peanut oil, sesame oil, and the like; glycerine; polyethylene glycol; propylene glycol; or other synthetic solvent; antimicrobial agents such as benzyl alcohol and methyl parabens; antioxidants such as ascorbic acid and sodium bisulfite; buffers such as acetates, citrates, and phosphates, chelating agents such as ethylenediaminetetraacetic acid (EDTA); agents for the adjustment of tonicity such as sodium chloride and dextrose; and combinations thereof. Parenteral preparations can be enclosed in ampoules, disposable syringes, or multiple dose vials made of glass, plastic, or other suitable material. Buffers, preservatives, antioxidants, and the like can be incorporated as required. Where administered intravenously, suitable carriers include physiological saline, phosphate-buffered saline (PBS), and solutions containing thickening and solubilizing agents such as glucose, polyethylene glycol, polypropyleneglycol, and mixtures thereof. Liposomal suspensions, including tissue-targeted liposomes, may also be suitable as pharmaceutically acceptable carriers.

For topical application, one or more disclosed α7β1 integrin modulatory agents, or other therapeutic agent may be made up into a cream, lotion, ointment, solution, or suspension in a suitable aqueous or non-aqueous carrier. Topical application can also be accomplished by transdermal patches or bandages which include the therapeutic substance. Additives can also be included, e.g., buffers such as sodium metabisulphite or disodium edetate; preservatives such as bactericidal and fungicidal agents, including phenyl mercuric acetate or nitrate, benzalkonium chloride, or chlorhexidine; and thickening agents, such as hypromellose.

If the disclosed α7β1 integrin modulatory agent, or other therapeutic agent is administered orally as a suspension, the pharmaceutical agents can be prepared according to techniques well known in the art of pharmaceutical formulation and may contain a suspending agent, such as alginic acid or sodium alginate, bulking agent, such as microcrystalline cellulose, a viscosity enhancer, such as methylcellulose, and sweeteners/flavoring agents. Oral liquid preparations can contain conventional additives such as suspending agents, gelatin, glucose syrup, hydrogenated edible fats, methyl cellulose, sorbitol, and syrup; emulsifying agents, e.g., acacia, lecithin, or sorbitan monooleate; non-aqueous carriers (including edible oils), e.g., almond oil, fractionated coconut oil, oily esters such as glycerine, propylene glycol, or ethyl alcohol; preservatives such as methyl or propyl p-hydroxybenzoate or sorbic acid; and, if desired, conventional flavoring or coloring agents. When formulated as immediate release tablets, these agents can contain dicalcium phosphate, lactose, magnesium stearate, microcrystalline cellulose, and starch and/or other binders, diluents, disintegrants, excipients, extenders, and lubricants.

If oral administration is desired, one or more disclosed α7β1 integrin modulatory agents, or other therapeutic substances can be provided in a composition that protects it from the acidic environment of the stomach. For example, he disclosed α7β1 integrin modulatory agents or other therapeutic agents can be formulated with an enteric coating that maintains its integrity in the stomach and releases the active compound in the intestine. The disclosed α7β1 integrin modulatory agents, or other therapeutic agent can also be formulated in combination with an antacid or other such ingredient.

Oral compositions generally include an inert diluent or an edible carrier and can be compressed into tablets or enclosed in gelatin capsules. For the purpose of oral therapeutic administration, one or more of the disclosed α7β1 integrin modulatory agents, or other therapeutic substances can be incorporated with excipients and used in the form of capsules, tablets, or troches. Pharmaceutically compatible adjuvant materials or binding agents can be included as part of the composition.

The capsules, pills, tablets, troches, and the like can contain any of the following ingredients or compounds of a similar nature: a binder such as, but not limited to, acacia, corn starch, gelatin, gum tragacanth, polyvinylpyrrolidone, or sorbitol; a filler such as calcium phosphate, glycine, lactose, microcrystalline cellulose, or starch; a disintegrating agent such as, but not limited to, alginic acid and corn starch; a lubricant such as, but not limited to, magnesium stearate, polyethylene glycol, silica, or talc; a gildant, such as, but not limited to, colloidal silicon dioxide; a sweetening agent such as sucrose or saccharin; disintegrants such as potato starch; dispersing or wetting agents such as sodium lauryl sulfate; and a flavoring agent such as peppermint, methyl salicylate, or fruit flavoring.

When the dosage unit form is a capsule, it can contain, in addition to material of the above type, a liquid carrier, such as a fatty oil. In addition, dosage unit forms can contain various other materials that modify the physical form of the dosage unit, for example, coatings of sugar and other enteric agents. One or more of the disclosed α7β1 integrin modulatory agents, or other therapeutic agent can also be administered as a component of an elixir, suspension, syrup, wafer, tea, chewing gum, or the like. A syrup may contain, in addition to the active compounds, sucrose or glycerin as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, they can be of the sustained release type so that the compounds need to be administered less frequently.

In some examples, one or more of the disclosed α7β1 integrin modulatory agents and/or a therapeutic agent is injected into the stomach of a subject is incorporated systemically in the subject, such as in diverse muscle groups. Examples of methods and compositions for administering therapeutic substances which include proteins include those discussed in Banga, *Therapeutic Peptides and Proteins: Formulation, Processing, and Delivery Systems* 2ed. (2005); Mahato, *Biomaterials for Delivery and Targeting of Proteins and Nucleic Acids* (2004); McNally, *Protein Formulation and Delivery*, 2ed. (2007); and Kumar et al., "Novel Delivery Technologies for Protein and Peptide Therapeutics," *Current Pharm. Biotech.*, 7:261-276 (2006); each of which is incorporated by reference herein to the extent not inconsistent with the present disclosure.

In some implementations, the effective amount of one or more of the disclosed α7β1 integrin modulatory agents is administered as a single dose per time period, such as every three or four months, month, week, or day, or it can be divided into at least two unit dosages for administration over a period. Treatment may be continued as long as necessary to achieve the desired results. For instance, treatment may continue for about 3 or 4 weeks up to about 12-24 months or longer, including ongoing treatment. The compound can also be administered in several doses intermittently, such as every few days (for example, at least about every two, three, four, five, or ten days) or every few weeks (for example at least about every two, three, four, five, or ten weeks).

Particular dosage regimens can be tailored to a particular subject, condition to be treated, or desired result. For example, when the methods of the present disclosure are used to treat muscular dystrophy or similar conditions, an initial treatment regimen can be applied to arrest the condition. Such initial treatment regimen may include administering a higher dosage of one or more of the disclosed α7β1 integrin modulatory agents, or administering such material more frequently, such as daily. After a desired therapeutic result has been obtained, such as a desired level of muscle regeneration, a second treatment regimen may be applied, such as administering a lower dosage of one or more of the disclosed α7β1 integrin modulatory agents or administering such material less frequently, such as monthly, bi-monthly, quarterly, or semi-annually. In such cases, the second regimen may serve as a "booster" to restore or maintain a desired level of muscle regeneration. Similar treatment regimens may be used for other subjects with reduced or impaired muscle regeneration capabilities, such as geriatric subjects.

When particular methods of the present disclosure are used to prevent or mitigate muscle damage, such as damage caused by exertion or injury, the subject is typically treated a sufficient period of time before the exertion or injury in order to provide therapeutic effect. For example, the subject may be treated at least about 24 hours before the expected activity or potential injury, such as at least about 48 hours, about 72 hours, about 1 week, about 2 weeks, about three weeks, or about 4 weeks or more prior.

When embodiments of the method of the present disclosure are used to prevent or treat a muscle injury, one or more of the disclosed α7β1 integrin modulatory agents or other therapeutic substance can be applied directly to, or proximately to, the area to be treated. For example, the substance can be injected into or near the area. In further examples, the substance can be applied topically to the area to be treated. Treatment is typically initiated prior to the injury to several weeks following the injury. In more specific implementations, the treatment is initiated between about 12 and about 72 hours following injury, such as between about 24 and about 48 hours following injury. In some cases, a single administration of the substance is effective to provide the desired therapeutic effect. In further examples, additional administrations are provided in order to achieve the desired therapeutic effect.

Amounts effective for various therapeutic treatments of the present disclosure may, of course, depend on the severity of the disease and the weight and general state of the subject, as well as the absorption, inactivation, and excretion rates of the therapeutically-active compound or component, the dosage schedule, and amount administered, as well as other factors known to those of ordinary skill in the art. It also should be apparent to one of ordinary skill in the art that the exact dosage and frequency of administration will depend on the particular α7β1 integrin modulatory agent, or other therapeutic substance being administered, the particular condition being treated, the severity of the condition being treated, the age, weight, general physical condition of the particular subject, and other medication the subject may be taking. Typically, dosages used in vitro may provide useful guidance in the amounts useful for in vivo administration of the pharmaceutical composition, and animal models may be used to determine effective dosages for treatment of particular disorders. For example, mouse models of muscular dystrophy may be used to determine effective dosages that can then be translated to dosage amount for other subjects, such as humans, as known in the art. Various considerations in dosage determination are described, e.g., in Gilman et al., eds., *Goodman And Gilman's: The Pharmacological Bases of Therapeutics,* 8th ed., Pergamon Press (1990); and *Remington's Pharmaceutical Sciences,* 17th ed., Mack Publishing Co., Easton, Pa. (1990), each of which is herein incorporated by reference to the extent not inconsistent with the present disclosure.

In specific examples, the one or more disclosed α7β1 integrin modulatory agents is administered to a subject in an amount sufficient to provide a dose of the agent of between about 10 fmol/g and about 500 nmol/g, such as between about 2 nmol/g and about 20 nmol/g or between about 2 nmol/g and about 10 mmol/g. In additional examples, the α7β1 integrin modulatory agent is administered to a subject in an amount sufficient to provide a dose of between about 0.01 μg/kg and about 1000 mg/kg or between about 0.1 mg/kg and about 1000 mg/kg, in particular examples this amount is provided per day or per week. In another example, the disclosed α7β1 integrin modulatory agent is administered to a subject in an amount sufficient to provide a dose of agent of between about 0.2 mg/kg and about 2 mg/kg. In further examples, the α7β1 integrin modulatory agent is administered to a subject in an amount sufficient to provide a concentration of α7β1 integrin modulatory agent in the administrated material of between about 5 nM and about 500 nM, such as between about 50 nM and about 200 nm, or about 100 nM. In other examples, the α7β1 integrin modulatory agent is administered to a subject between about 500 μg/ml and about 1 μg/ml, such as about 300 μg/ml and about 3 μg/ml, about 200 μg/ml and about 20 μg/ml, including 500 μg/ml, 400 μg/ml, 300 μg/ml, 250 μg/ml, 200 μg/ml, 150 μg/ml, 100 μg/ml, 50 μg/ml, 25 μg/ml, 12.5 μg/ml, 6.25 μg/ml, 3.125 μg/ml, 2.5 μg/ml and 1.25 μg/ml.

ii. Desired Response

One or more disclosed α7β1 integrin modulatory agents and/or additional therapeutic agents are administered by a specific route and/or concentration to generate a desired response. In some examples, a desired response refers to an amount effective for lessening, ameliorating, eliminating, preventing, or inhibiting at least one symptom of a disease, disorder, or condition treated and may be empirically determined. In various embodiments of the present disclosure, a desired response is muscle regeneration, reductions or prevention of muscle degeneration, promotion of muscle maintenance, reduction or prevention of muscle injury or damage, reduction or prevention in one more signs or symptoms associated with muscular dystrophy.

In particular, indicators of muscular health, such as muscle cell regeneration, maintenance, or repair, can be assessed through various means, including monitoring markers of muscle regeneration, such as transcription factors such as Pax7, Pax3, MyoD, MRF4, and myogenin. For example, increased expression of such markers can indicate that muscle regeneration is occurring or has recently occurred. Markers of muscle regeneration, such as expression of embryonic myosin heavy chain (eMyHC), can also be used to gauge the extent of muscle regeneration, maintenance, or repair. For example, the presence of eMyHC can indicate that muscle regeneration has recently occurred in a subject.

Muscle cell regeneration, maintenance, or repair can also be monitored by determining the girth, or mean cross sectional area, of muscle cells or density of muscle fibers. Additional indicators of muscle condition include muscle weight and muscle protein content. Mitotic index (such as by measuring BrdU incorporation) and myogenesis can also be used to evaluate the extent of muscle regeneration.

In particular examples, the improvement in muscle condition, such as regeneration, compared with control is at least about 10%, such as at least about 30%, or at least about 50% or more, including an at least 15%, at least 20%, at least 25%, at least 30%, at least 40%, at least 45%, at least 50%, at least 60%, at least 70%, at least 80%, at least 90%, including a 10% to 90% decrease, 20% to 80% increase, 30% to 70% increase or a 40% to 60% increase (e a 10%, 20%, 30%, 40%, 50%, 60%, 70%, 80%, 90%, 95%, 100%, 200% or more increase)

iii. Additional Treatments or Therapeutic Agents

In particular examples, prior to, during, or following administration of an effective amount of an agent that reduces or inhibits one or more signs or symptoms associated with muscular dystrophy, the subject can receive one or more other therapies. In one example, the subject receives one or more treatments prior to administration of a disclosed α7β1 modulatory agent. Examples of such therapies include, but are not limited to, laminin-111 protein therapy, which works to stabilize the sarcolemma and reduce muscle degeneration. In some examples, a source of muscle cells can be added to aid in muscle regeneration and repair. In some aspects of the present disclosure, satellite cells are administered to a subject in combination with laminin therapy. U.S. Patent Publication 2006/0014287, incorporated by reference herein to the extent not inconsistent with the present disclosure, provides methods of enriching a collection of cells in myogenic cells and administering those cells to a subject. In further aspects, stem cells, such as adipose-derived stem cells, are administered to the subject. Suitable methods of preparing and administering adipose-derived stem cells are disclosed in U.S. Patent Publication 2007/0025972, incorporated by reference herein to the extent not inconsistent with the present disclosure. Additional cellular materials, such as fibroblasts, can also be administered, in some examples.

Additional therapeutic agents include agents which enhance the effect of the disclosed α7β1 modulatory agents, such as a component of the extracellular matrix, such as an integrin, dystrophin, dystroglycan, utrophin, or a growth factor. In some examples, the additional therapeutic agent reduces or enhances expression of a substance that enhances the formation or maintenance of the extracellular matrix. In some examples, the additional substance can include aggrecan, angiostatin, cadherins, collagens (including collagen I, collagen III, or collagen IV), decorin, elastin, enactin, endostatin, fibrin, fibronectin, osteopontin, tenascin, thrombospondin, vitronectin, and combinations thereof. Biglycans, glycosaminoglycans (such as heparin), glycoproteins (such as dystroglycan), proteoglycans (such as heparan sulfate), and combinations thereof can also be administered.

In some examples, growth stimulants such as cytokines, polypeptides, and growth factors such as brain-derived neurotrophic factor (BDNF), CNF (ciliary neurotrophic factor), EGF (epidermal growth factor), FGF (fibroblast growth factor), glial growth factor (GGF), glial maturation factor (GMF) glial-derived neurotrophic factor (GDNF), hepatocyte growth factor (HGF), insulin, insulin-like growth factors, kerotinocyte growth factor (KGF), nerve growth factor (NGF), neurotropin-3 and -4, PDGF (platelet-derived growth factor), vascular endothelial growth factor (VEGF), and combinations thereof may be administered with one of the disclosed methods.

IV. Clinical Trials

To obtain regulatory approval for the use of one or more of the disclosed α7β1 modulatory agents to treat a muscular disorder, clinical trials are performed. As is known in the art, clinical trials progress through phases of testing, which are identified as Phases I, II, III, and IV.

Initially the disclosed α7β1 modulatory agent is evaluated in a Phase I trial. Typically Phase I trials are used to determine the best mode of administration (for example, by pill or by injection), the frequency of administration, and the toxicity for the compounds. Phase I studies frequently include laboratory tests, such as blood tests and biopsies, to evaluate the effects of the potential therapeutic in the body of the patient. For a Phase I trial, a small group of patients with a muscular disorder are treated with a specific dose of a disclosed α7β1 modulatory agent. During the trial, the dose is typically increased group by group in order to determine the maximum tolerated dose (MTD) and the dose-limiting toxicities (DLT) associated with the compound. This process determines an appropriate dose to use in a subsequent Phase II trial.

A Phase II trial can be conducted to further evaluate the effectiveness and safety of the disclosed α7β1 modulatory agent. In Phase H trials, a disclosed α7β1 modulatory agent is administered to groups of patients with a muscular disorder using the dosage found to be effective in Phase I trials.

Phase III trials focus on determining how a disclosed α7β1 modulatory agent compares to the standard, or most widely accepted, treatment. In Phase III trials, patients are randomly assigned to one of two or more "arms". In a trial with two arms, for example, one arm will receive the standard treatment (control group) and the other arm will receive a disclosed α7β1 modulatory agent treatment (investigational group).

Phase IV trials are used to further evaluate the long-term safety and effectiveness of a disclosed α7β1 modulatory agent. Phase IV trials are less common than Phase I, II and III trials and take place after a disclosed α7β1 modulatory agent has been approved for standard use.

Eligibility of Patients for Clinical Trials

Participant eligibility criteria can range from general (for example, age, sex, type of disease) to specific (for example, type and number of prior treatments, disease characteristics, blood cell counts, organ function). In one embodiment, eligible patients have been diagnosed with a muscular disorder. Eligibility criteria may also vary with trial phase. Patients eligible for clinical trials can also be chosen based on objective measurement of a muscular disorder and failure to respond to other muscular disorder treatments. For example, in Phase I and II trials, the criteria often exclude patients who may be at risk from the investigational treatment because of abnormal organ function or other factors. In Phase II and III trials additional criteria are often included regarding disease type and stage, and number and type of prior treatments.

Phase I trials usually include 15 to 30 participants for whom other treatment options have not been effective. Phase II trials typically include up to 100 participants who have already received drug therapy, but whom the treatment has not been effective.

Participation in Phase III trials is often restricted based on the previous treatment received. Phase III trials usually include hundreds to thousands of participants. This large number of participants is necessary in order to determine whether there are true differences between the effectiveness of a disclosed α7β1 modulatory agent and the standard treatment. Phase III can include patients ranging from those newly diagnosed with a muscular disorder to those with re-occurring signs and/or symptoms associated with a muscular disorder or a muscular disorder that did not respond to prior treatment.

One skilled in the art will appreciate that clinical trials should be designed to be as inclusive as possible without making the study population too diverse to determine whether the treatment might be as effective on a more narrowly defined population. The more diverse the population included in the trial, the more applicable the results could be to the general population, particularly in Phase III trials. Selection of appropriate participants in each phase of clinical trial is considered to be within the ordinary skills of a worker in the art.

Assessment of Patients Prior to Treatment

Prior to commencement of the study, several measures known in the art can be used to first classify the patients. Patients can first be assessed, for example by determining serum creatine kinase (CK) levels or other indicators of a muscle disorder, such as increased levels of muscle inflammation, apoptosis, muscle loss, myotube hypertrophy, and/or decreased myofibers stability and cell survival.

Administration of a Disclosed α7β1 Modulatory Agent in Clinical Trials

A disclosed α7β1 modulatory agent is typically administered to the trial participants orally. A range of doses of the agent can be tested. Provided with information from pre-clinical testing, a skilled practitioner can readily determine appropriate dosages of agent for use in clinical trials. In one embodiment, a dose range is from about 100 μg/kg and about 5000 mg/kg of the subject's weight, such as 1 mg/kg and about 2000 mg/kg of the subject's weight, about 100 mg/kg and about 1500 mg/kg of the subject's weight, about 100 μg/kg and about 2000 mg/kg of the subject's weight, about 200 mg/kg and about 1000 mg/kg of the subject's weight, about 200 mg/kg and about 750 mg/kg of the subject's weight, about 250 mg/kg and about 500 mg/kg of the subject's weight, about 100 μm and about 500 mM. In some embodiments, subjects are given a disclosed α7β1 modulatory agent orally at 10 to 60 mg/kg of body weight per day. For example, 10-15 mg/kg of a disclosed α7β1 modulatory agent is administered for two weeks and if well tolerated the dose is increased by 5-10 mg/kg/week to achieve optimal clinical response. In some examples, the daily dose does not exceed 60 mg/kg of body weight and is given for a minimum of 6 months with liver function monitored every two weeks to monthly.

Pharmacokinetic Monitoring

To fulfill Phase I criteria, distribution of the disclosed α7β1 modulatory agent is monitored, for example, by chemical analysis of samples, such as blood, collected at regular intervals. For example, samples can be taken at regular intervals up until about 72 hours after the start of treatment.

If analysis is not conducted immediately, the samples can be placed on dry ice after collection and subsequently transported to a freezer to be stored at −70° C. until analysis can be conducted. Samples can be prepared for analysis using standard techniques known in the art and the amount of the disclosed α7β1 modulatory agent present can be determined, for example, by high-performance liquid chromatography (HPLC). Pharmacokinetic data can be generated and analyzed in collaboration with an expert clinical pharmacologist and used to determine, for example, clearance, half-life and maximum plasma concentration, Monitoring of Patient Outcome The endpoint of a clinical trial is a measurable outcome that indicates the effectiveness of a compound under evaluation. The endpoint is established prior to the commencement of the trial and will vary depending on the type and phase of the clinical trial. Examples of endpoints include, for example, decline in serum CK levels, inflammation, apoptosis, and muscle loss. For example, at least a 10% reduction in serum CK levels indicates the patient is responsive to the treatment.

The following examples are provided to illustrate certain particular features and/or embodiments. These examples should not be construed to limit the invention to the particular features or embodiments described.

EXAMPLES

Example 1

Figure 2:
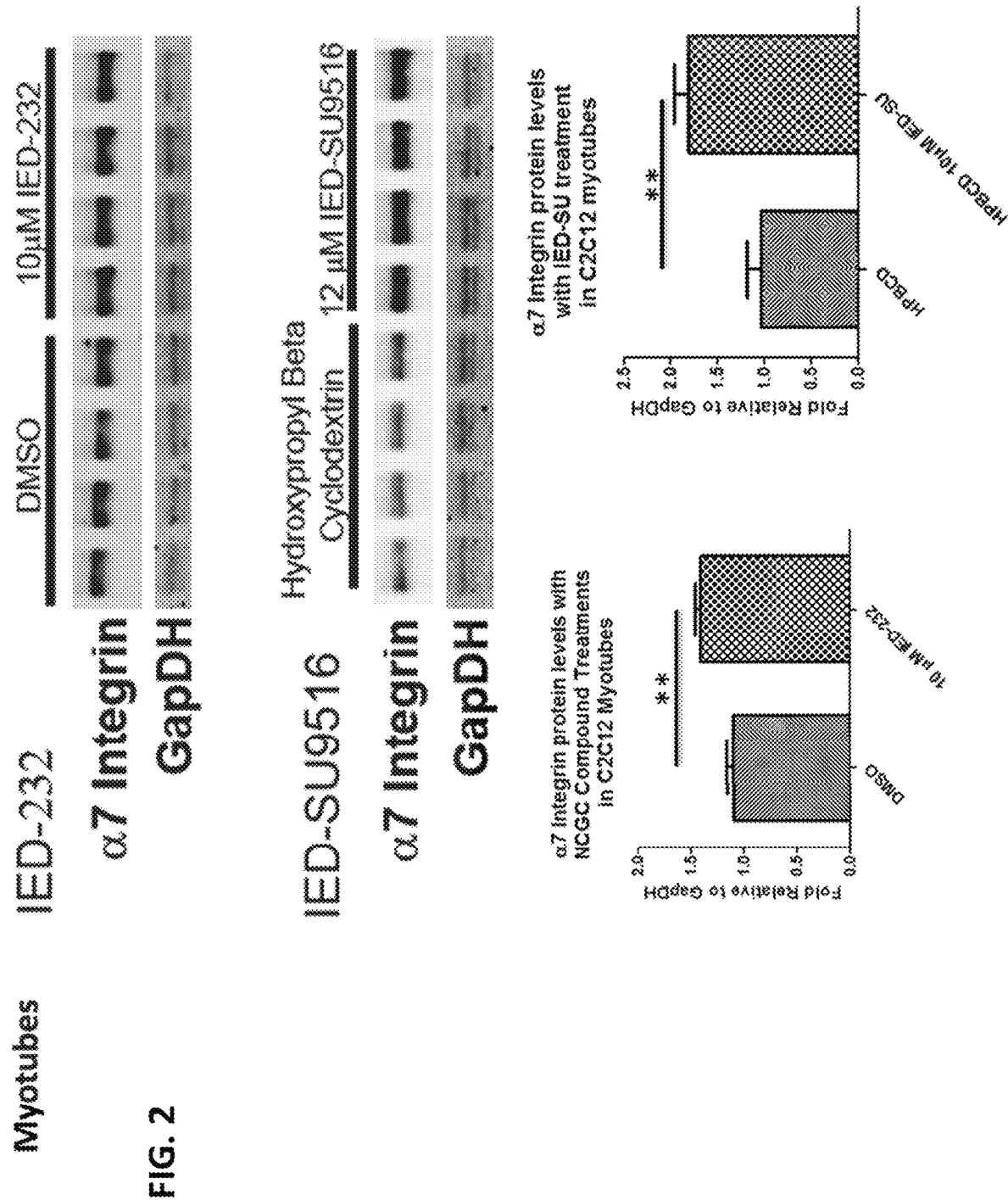
FIG. 2 is a digital image of Western Blots and quantitative analysis of α7 Integrin and GAPDH protein levels in C2C12 myotubes treated for 48 hours with DMSO control, 10 μM MLS000683232-01 (IED-232), Hydroxylpropyl-Beta-Cyclodextrin (HPBCD) control, or 12 μM SU9516 in HPBCD. Bands were quantified using Image J software and then graphed as α7 Integrin protein levels relative to GAPDH protein levels. * denotes a significant difference in relative protein levels with ** p<0.01.
Figure 3:
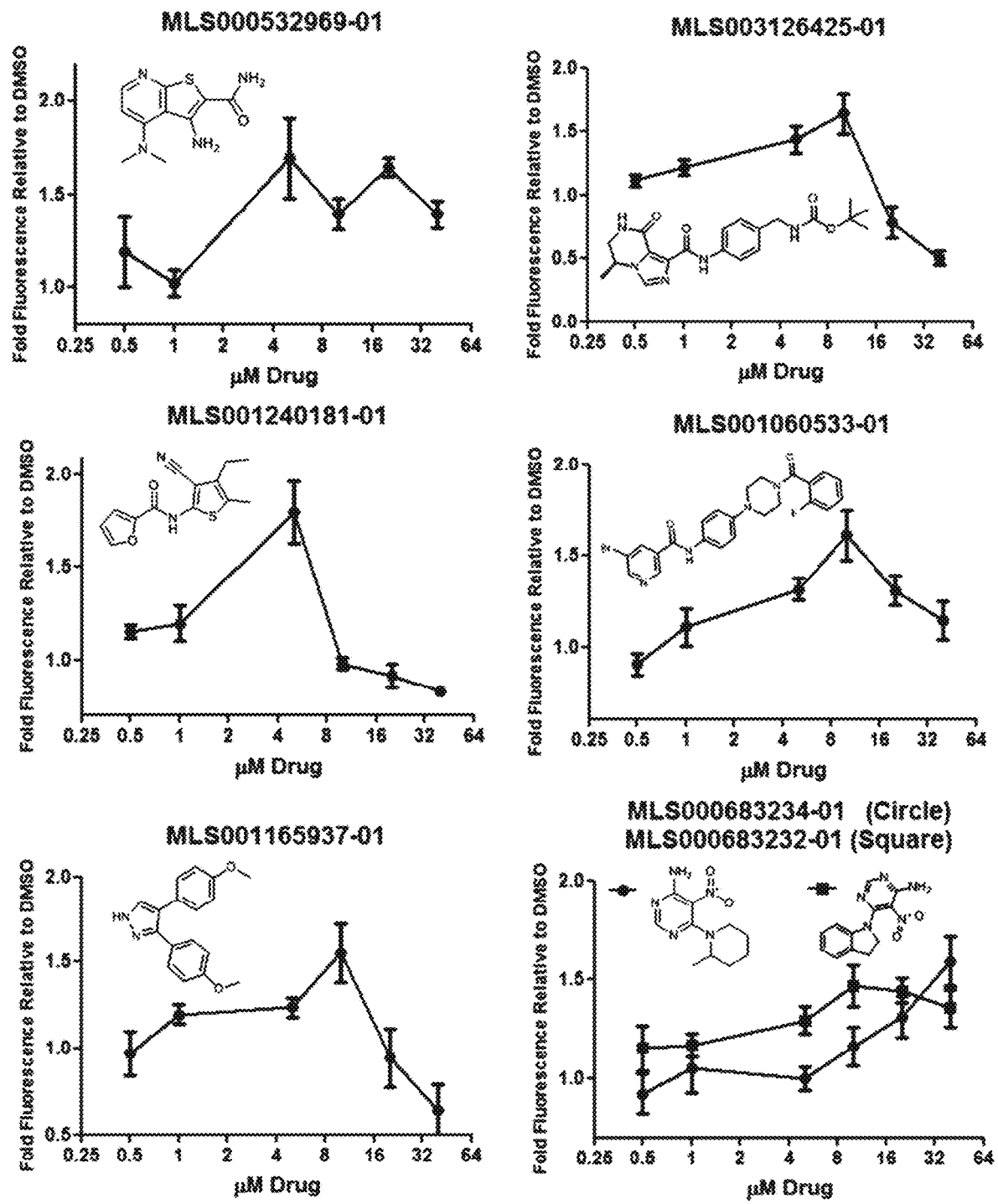
FIG. 3 is an image of results (fluorescence relative to DMSO at various concentrations of the agent) from a screen using particular embodiments of the disclosed α7β1 integrin modulatory agents.

This example demonstrates the results of quantitative real-time PCR used to assess Itga7, Itgb1, and Lama2 transcript levels in C2C12 myoblasts and myotubes treated for 24 hours with DMSO control, 10 μM MLS000683232-01 (IED-232), 10 μM MLS001165937-01 (IED-937), Hydroxylpropyl-Beta-Cyclodextrin (HPBCD) control, or 12 μM SU9516 in HPBCD (FIG. 1). FIG. 2 is a digital image of Western Blots and quantitative analysis of α7 Integrin and GAPDH protein levels in C2C12 myotubes treated for 48 hours with DMSO control, 10 μM MLS000683232-01 (IED-232), Hydroxylpropyl-Beta-Cyclodextrin (HPBCD) control, or 12 μM SU9516 in HPBCD. Bands were quantified using Image J software and then graphed as α7 Integrin protein levels relative to GAPDH protein levels. * denotes a significant difference in relative protein levels with ** p<0.01.

Example 2

The additional structures provided below provide additional compounds that may be used in the methods disclosed herein increasing α7 integrin expression in muscle (see Table 7). In some examples, the analogs were made in 5 mg quantities, salt form (e.g., hydrochloride salt), as a dry powder, at an at least 90% purity as measured by HPLC. In some embodiments, physical properties (kinetic, solubility, PAMPA permeability, clog P) and metabolic stability (plasma and microsomal stability, metabolite identification) of all synthesized molecules, as well as measure pharmacokinetics properties, compound levels and distribution of selected compounds are determined. Besides systematic substitution for exploring selected chemotypes, classical medicinal chemistry parameters (MW, number of hydrogen donors and acceptors, tPSA, c log P, flexibility of the molecule) as well as in house-measured physical and metabolic properties of analog molecules are used to guide the selection of potent, efficacious and non-toxic compounds having suitable pharmacokinetic properties for use in the disclosed methods.

TABLE 7

Exemplary Compounds

Compound 1

Potency: 1.122
Efficacy: 198.146

Compound 2

Potency: 3.5481
Efficacy: 228.085

Compound 3

Potency: 2.2387
Efficacy: 193.433

Compound 4

Potency: 2.8184
Efficacy: 129.298

Compound 5

TABLE 7-continued
Exemplary Compounds
Potency: 1.122
Efficacy: 92.4838
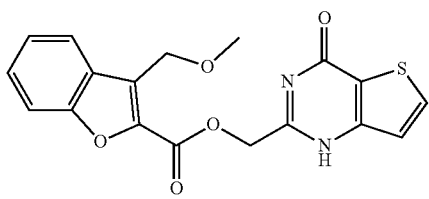 [SMILES: COCc1c(C(=O)OCc2nc(=O)c3sccc3[nH]2)oc2ccccc12]
Compound 6
Potency: 1.122
Efficacy: 128.12
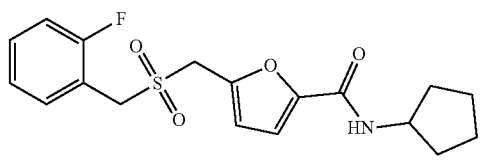 [SMILES: O=C(NC1CCCC1)c1ccc(CS(=O)(=O)Cc2ccccc2F)o1]
Compound 7
Potency: 4.4668
Efficacy: 94.9208
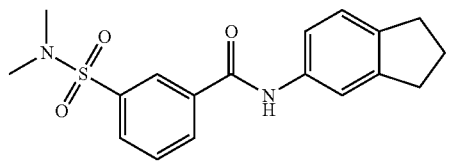 [SMILES: CN(C)S(=O)(=O)c1cccc(C(=O)Nc2ccc3c(c2)CCC3)c1]
Compound 8
Potency: 2.8184
Efficacy: 111.685
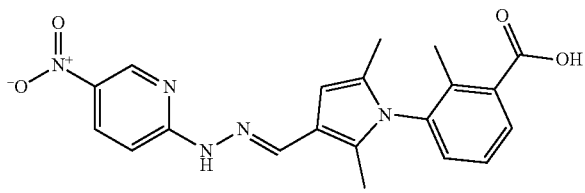
Compound 9
Potency: 2.8184
Efficacy: 122.703
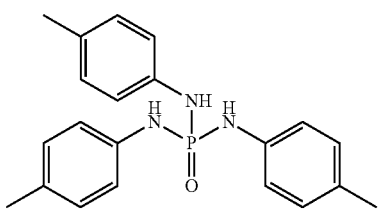
Compound 10
Potency: 3.1623
Efficacy: 102.022
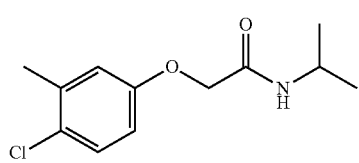 [SMILES: Cc1cc(OCC(=O)NC(C)C)ccc1Cl]
Compound 11
Potency: 3.9811
Efficacy: 101.893

TABLE 7-continued
Exemplary Compounds
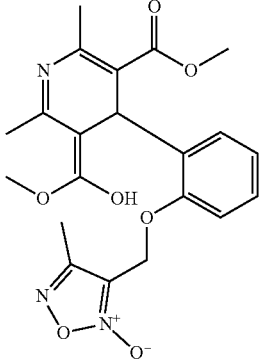 [SMILES: COC(=O)C1=C(C)N=C(C)/C(=C(/O)OC)C1c1ccccc1OCc1c(C)no[n+]1[O-]]
Compound 12
Potency: 2.8184
Efficacy: 92.9057
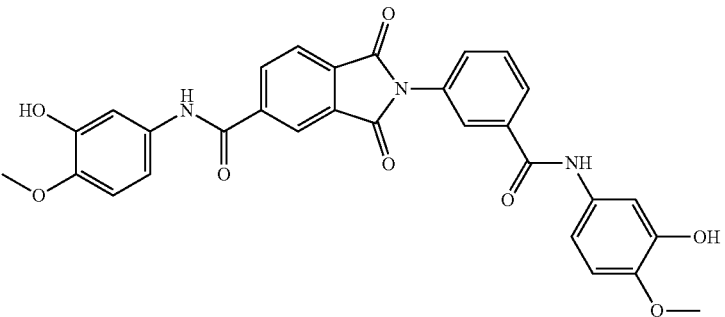 [SMILES: COc1ccc(NC(=O)c2cccc(N3C(=O)c4ccc(C(=O)Nc5ccc(OC)c(O)c5)cc4C3=O)c2)cc1O]
Compound 13
Potency: 4.4668
Efficacy: 121.996
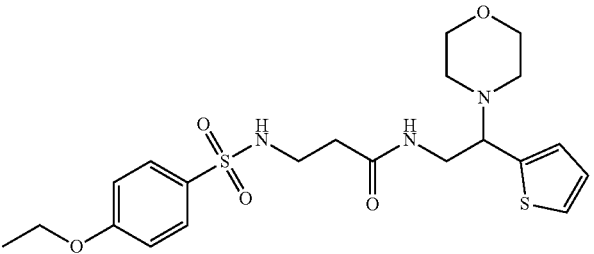 [SMILES: CCOc1ccc(S(=O)(=O)NCCC(=O)NCC(c2cccs2)N2CCOCC2)cc1]
Compound 14
Potency: 2.2387
Efficacy: 84.7736
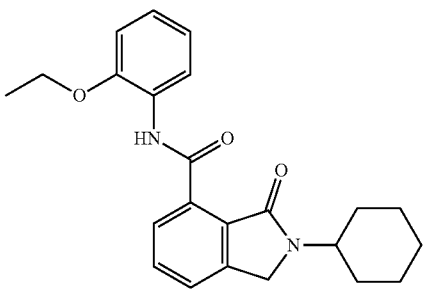 [SMILES: CCOc1ccccc1NC(=O)c1cccc2c1C(=O)N(C1CCCCC1)C2]
Compound 15
Potency: 3.1623
Efficacy: 91.3808

TABLE 7-continued
Exemplary Compounds
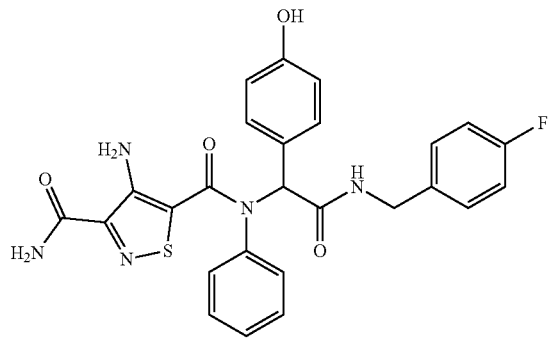 [SMILES: NC(=O)c1nsc(C(=O)N(c2ccccc2)C(C(=O)NCc2ccc(F)cc2)c2ccc(O)cc2)c1N]
Compound 16
Potency: 2.2387
Efficacy: 115.349
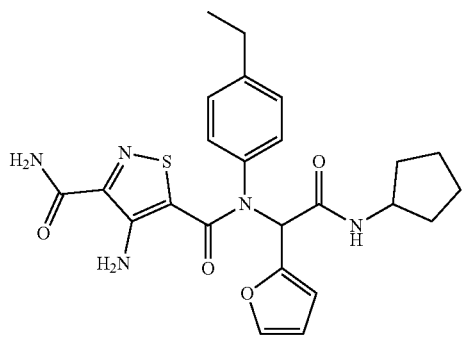 [SMILES: CCc1ccc(N(C(=O)c2snc(C(N)=O)c2N)C(C(=O)NC2CCCC2)c2ccco2)cc1]
Compound 17
Potency: 2.5119
Efficacy: 96.1948
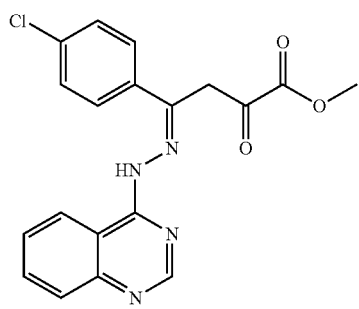 [SMILES: COC(=O)C(=O)C/C(=N/Nc1ncnc2ccccc12)c1ccc(Cl)cc1]
Compound 18
Potency: 10
Efficacy: 1751.56
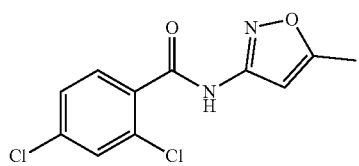 [SMILES: Cc1cc(NC(=O)c2ccc(Cl)cc2Cl)no1]
Compound 19
Potency: 1.4125
Efficacy: 81.6138

TABLE 7-continued
Exemplary Compounds
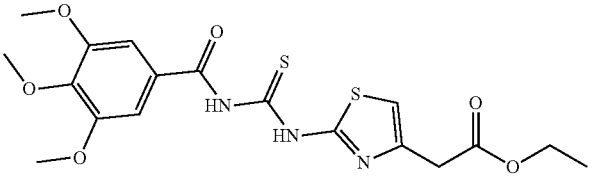 [SMILES: CCOC(=O)Cc1csc(NC(=S)NC(=O)c2cc(OC)c(OC)c(OC)c2)n1]
Compound 20
Potency: 3.5481
Efficacy: 101.579
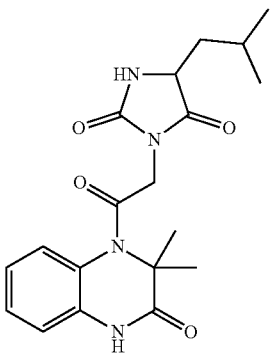 [SMILES: CC(C)CC1NC(=O)N(CC(=O)N2c3ccccc3NC(=O)C2(C)C)C1=O]
Compound 21
Potency: 5.6234
Efficacy: 92.2825
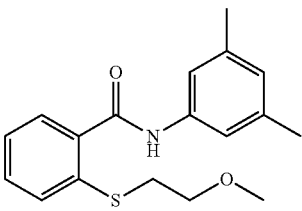 [SMILES: COCCSc1ccccc1C(=O)Nc1cc(C)cc(C)c1]
Compound 22
Potency: 4.4668
Efficacy: 83.4252
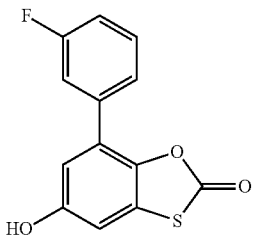 [SMILES: O=c1oc2c(-c3cccc(F)c3)cc(O)cc2s1]
Compound 23
Potency: 3.9811
Efficacy: 85.1623
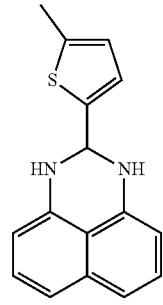 [SMILES: Cc1ccc(C2Nc3cccc4cccc(c34)N2)s1]
Compound 24
Potency: 3.1623
Efficacy: 76.9771

TABLE 7-continued
Exemplary Compounds
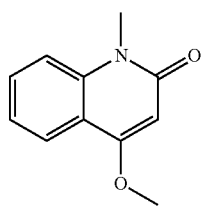
Potency: 2.2387
Efficacy: 82.8995
Compound 25
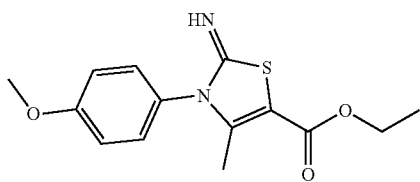 [SMILES: CCOC(=O)c1sc(=N)n(-c2ccc(OC)cc2)c1C]
Potency: 1.9953
Efficacy: 95.7363
Compound 26
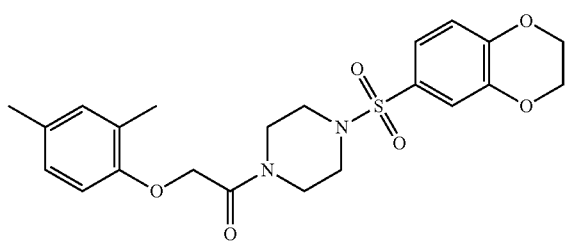 [SMILES: Cc1ccc(OCC(=O)N2CCN(S(=O)(=O)c3ccc4c(c3)OCCO4)CC2)c(C)c1]
Potency: 1.9953
Efficacy: 81.8506
Compound 27
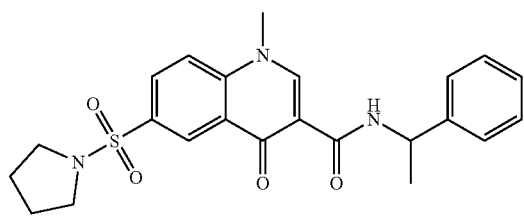 [SMILES: CC(NC(=O)c1cn(C)c2ccc(S(=O)(=O)N3CCCC3)cc2c1=O)c1ccccc1]
Potency: 2.8184
Efficacy: 92.0171
Compound 28
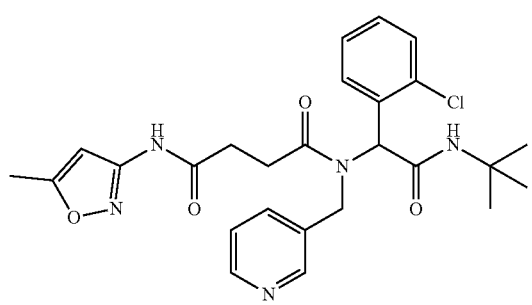 [SMILES: Cc1cc(NC(=O)CCC(=O)N(Cc2cccnc2)C(C(=O)NC(C)(C)C)c2ccccc2Cl)no1]
Potency: 3.9811
Efficacy: 81.1658
Compound 29

TABLE 7-continued

| Exemplary Compounds | |
|---|---|
| [structure] | Compound 30 |
| Potency: 3.9811 Efficacy: 92.7977 | |
| [structure] | Compound 31 |
| Potency: 2.5119 Efficacy: 86.4354 | |
| [structure] | Compound 32 |
| Potency: 2.8184 Efficacy: 88.796 | |
| [structure] | Compound 33 |
| Potency: 1.9953 Efficacy: 83.3258 | |
| [structure] | Compound 34 |
| Potency: 1.4125 Efficacy: 70.4537 | |
| [structure] | Compound 35 |
| Potency: 2.5119 Efficacy: 72.7515 | |

TABLE 7-continued
Exemplary Compounds
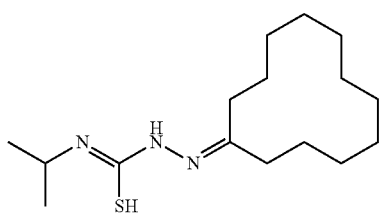 [SMILES: CC(C)/N=C(\S)NN=C1CCCCCCCCCCC1]
Compound 36
Potency: 3.1623
Efficacy: 75.7047
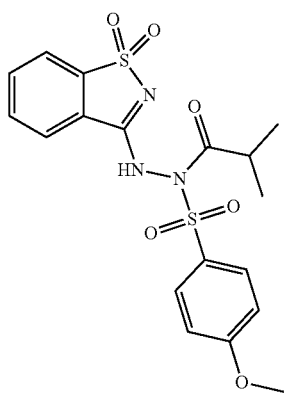 [SMILES: COc1ccc(S(=O)(=O)N(NC2=NS(=O)(=O)c3ccccc32)C(=O)C(C)C)cc1]
Compound 37
Potency: 2.5119
Efficacy: 77.0458
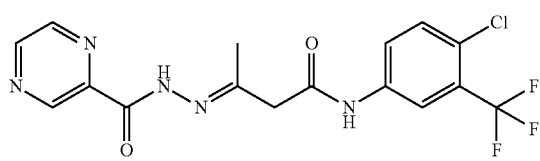 [SMILES: C/C(CC(=O)Nc1ccc(Cl)c(C(F)(F)F)c1)=N\NC(=O)c1cnccn1]
Compound 38
Potency: 4.4668
Efficacy: 75.5605
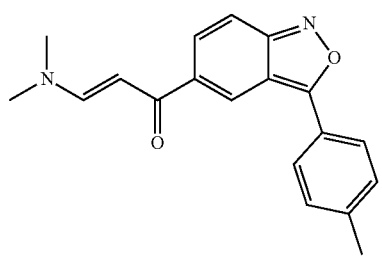 [SMILES: Cc1ccc(-c2onc3ccc(C(=O)/C=C/N(C)C)cc23)cc1]
Compound 39
Potency: 3.5481
Efficacy: 78.5404
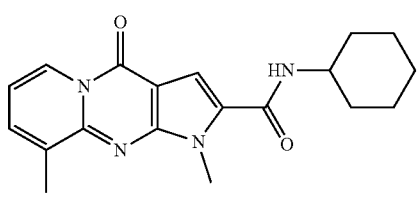 [SMILES: Cc1cccn2c(=O)c3cc(C(=O)NC4CCCCC4)n(C)c3nc12]
Compound 40
Potency: 14.1254
Efficacy: 436.691

TABLE 7-continued
Exemplary Compounds
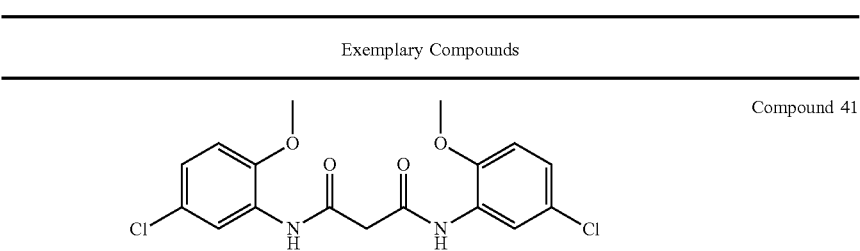
Compound 41
Potency: 14.1254
Efficacy: 447.862
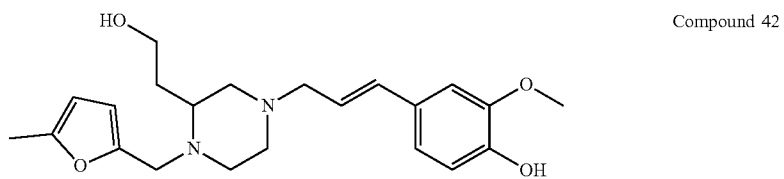
Compound 42
Potency: 14.1254
Efficacy: 475.262
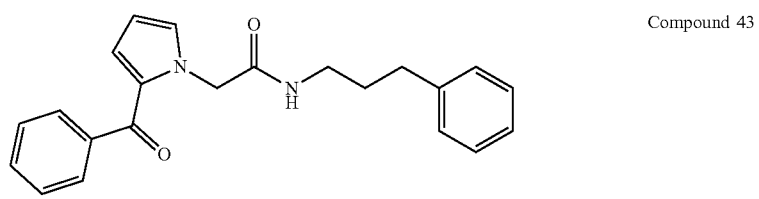
Compound 43
Potency: 3.9811
Efficacy: 148.01
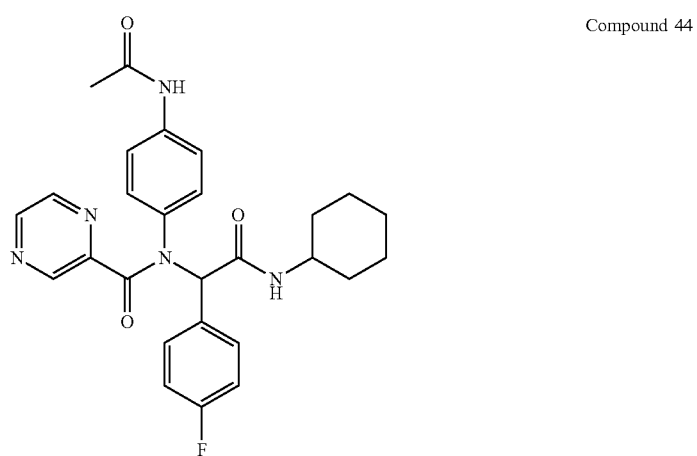
Compound 44
Potency: 11.2202
Efficacy: 328.277

TABLE 7-continued

Exemplary Compounds

Compound 45

Potency: 14.1254
Efficacy: 426.535

Compound 46

Potency: 7.9433
Efficacy: 231.415

Compound 47

Potency: 5.6234
Efficacy: 141.317

Compound 48

Potency: 7.0795
Efficacy: 214.145

Compound 49

Potency: 5.6234
Efficacy: 150.998

TABLE 7-continued
Exemplary Compounds
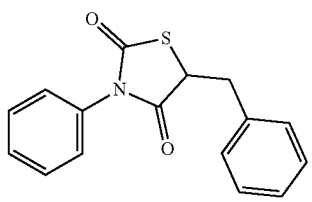 [SMILES: O=C1SC(Cc2ccccc2)C(=O)N1c1ccccc1]
Compound 50
Potency: 7.9433
Efficacy: 181.323
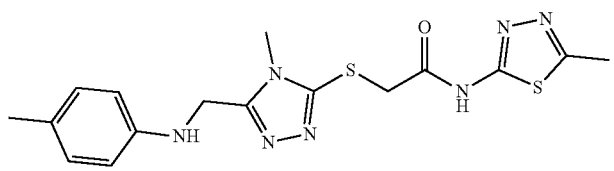
Compound 51
Potency: 10
Efficacy: 273.425
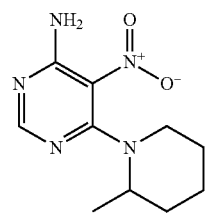 [SMILES: CC1CCCCN1c1ncnc(N)c1[N+](=O)[O-]]
Compound 52
Potency: 4.4668
Efficacy: 165.293
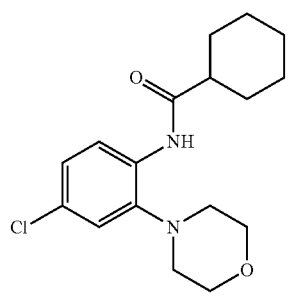 [SMILES: O=C(Nc1ccc(Cl)cc1N1CCOCC1)C1CCCCC1]
Compound 53
Potency: 7.0795
Efficacy: 163.55
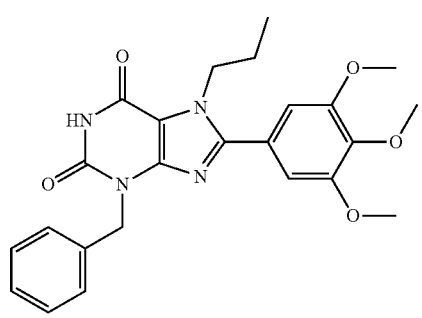 [SMILES: CCCn1c(-c2cc(OC)c(OC)c(OC)c2)nc2c1c(=O)[nH]c(=O)n2Cc1ccccc1]
Compound 54
Potency: 12.5893
Efficacy: 222.708

TABLE 7-continued

Exemplary Compounds

Compound 55

Potency: 12.5893
Efficacy: 271.246

Compound 56

Potency: 3.9811
Efficacy: 88.764

Compound 57

Potency: 4.4668
Efficacy: 115.732

Compound 58

Potency: 3.5481
Efficacy: 137.991

Compound 59

Potency: 10
Efficacy: 188.981

TABLE 7-continued
Exemplary Compounds
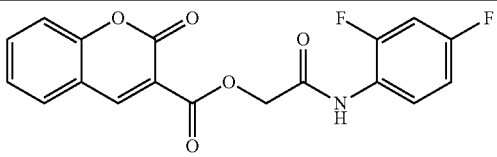
Potency: 4.4668
Efficacy: 128.904
Compound 60
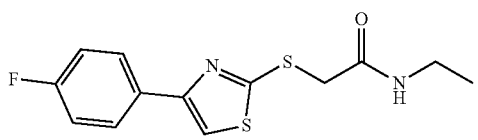 [SMILES: CCNC(=O)CSc1nc(-c2ccc(F)cc2)cs1]
Potency: 5.0119
Efficacy: 140.322
Compound 61
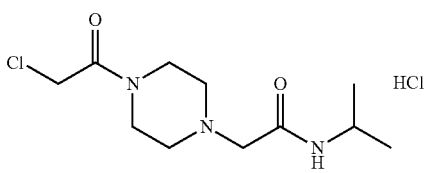 [SMILES: CC(C)NC(=O)CN1CCN(C(=O)CCl)CC1 ; Cl]
Potency: 7.0795
Efficacy: 186.257
Compound 62
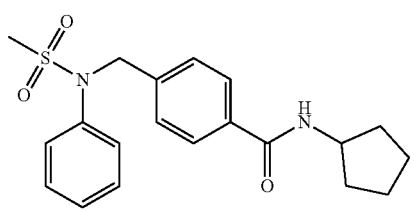 [SMILES: CS(=O)(=O)N(Cc1ccc(C(=O)NC2CCCC2)cc1)c1ccccc1]
Potency: 10
Efficacy: 200.43
Compound 63
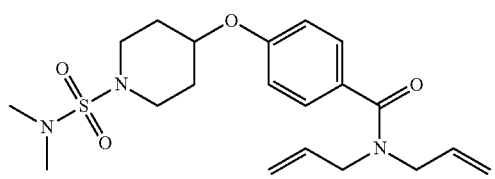 [SMILES: C=CCN(CC=C)C(=O)c1ccc(OC2CCN(S(=O)(=O)N(C)C)CC2)cc1]
Potency: 5.0119
Efficacy: 134.919
Compound 64
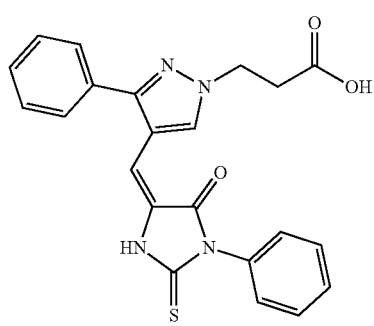 [SMILES: O=C(O)CCn1cc(/C=C2/NC(=S)N(c3ccccc3)C2=O)c(-c2ccccc2)n1]
Potency: 19.9526
Efficacy: 491.985
Compound 65

TABLE 7-continued
Exemplary Compounds
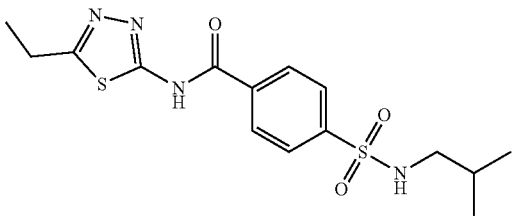 [SMILES: CCc1nnc(NC(=O)c2ccc(S(=O)(=O)NCC(C)C)cc2)s1]
Compound 66
Potency: 12.5893
Efficacy: 215.25
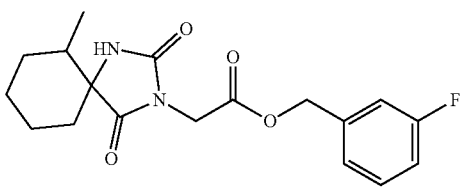 [SMILES: CC1CCCCC12NC(=O)N(CC(=O)OCc1cccc(F)c1)C2=O]
Compound 67
Potency: 10
Efficacy: 157.616
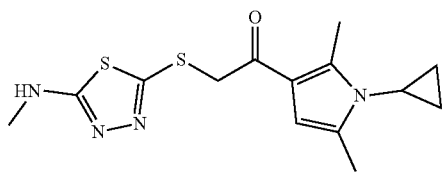 [SMILES: CNc1nnc(SCC(=O)c2cc(C)n(C3CC3)c2C)s1]
Compound 68
Potency: 12.5893
Efficacy: 239.617
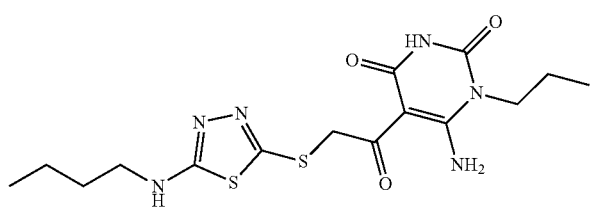 [SMILES: CCCCNc1nnc(SCC(=O)c2c(N)n(CCC)c(=O)[nH]c2=O)s1]
Compound 69
Potency: 3.9811
Efficacy: 90.5081
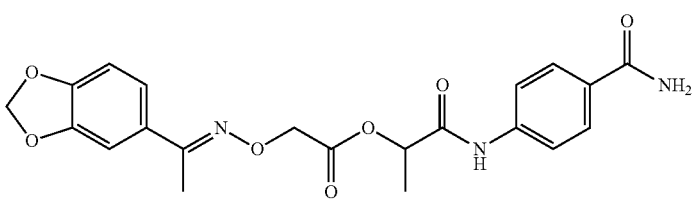 [SMILES: C/C(=N\OCC(=O)OC(C)C(=O)Nc1ccc(C(N)=O)cc1)c1ccc2c(c1)OCO2]
Compound 70
Potency: 4.4668
Efficacy: 115.234

TABLE 7-continued
Exemplary Compounds
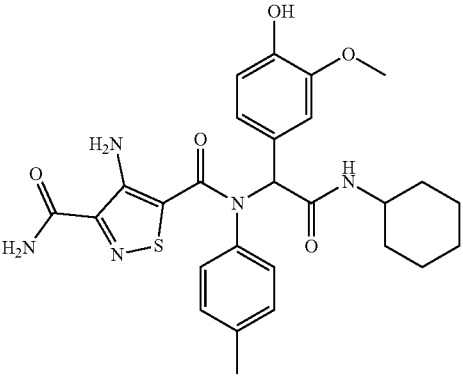 [SMILES: COc1cc(C(C(=O)NC2CCCCC2)N(C(=O)c2snc(C(N)=O)c2N)c2ccc(C)cc2)ccc1O]
Compound 71
Potency: 7.9433
Efficacy: 124.512
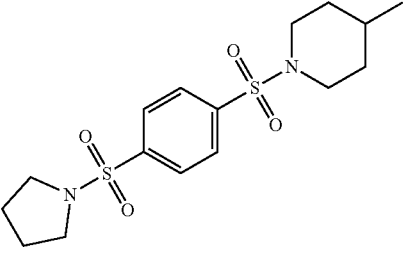 [SMILES: CC1CCN(S(=O)(=O)c2ccc(S(=O)(=O)N3CCCC3)cc2)CC1]
Compound 72
Potency: 8.9125
Efficacy: 138.663
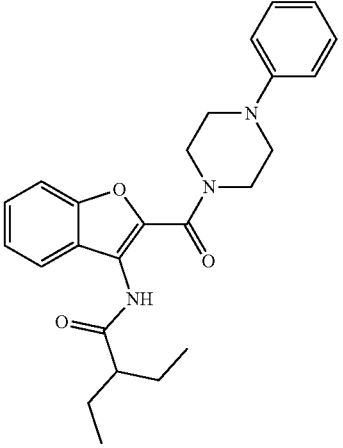 [SMILES: CCC(CC)C(=O)Nc1c(C(=O)N2CCN(c3ccccc3)CC2)oc2ccccc12]
Compound 73
Potency: 12.5893
Efficacy: 170.328
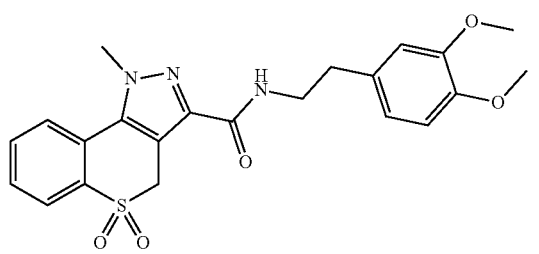 [SMILES: COc1ccc(CCNC(=O)c2nn(C)c3c2CS(=O)(=O)c2ccccc2-3)cc1OC]
Compound 74
Potency: 4.4668
Efficacy: 109.274

TABLE 7-continued
| Exemplary Compounds | |
|---|---|
| 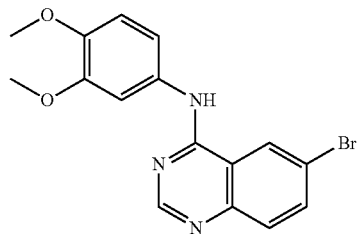 [SMILES: COc1ccc(Nc2ncnc3ccc(Br)cc23)cc1OC]<br>Potency: 3.9811<br>Efficacy: 71.4431 | Compound 75 |
| 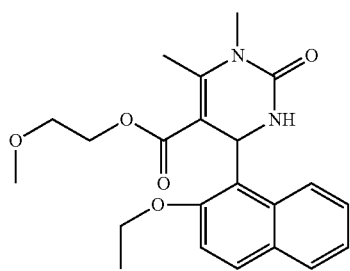 [SMILES: CCOc1ccc2ccccc2c1C1NC(=O)N(C)C(C)=C1C(=O)OCCOC]<br>Potency: 6.3096<br>Efficacy: 114.425 | Compound 76 |
| 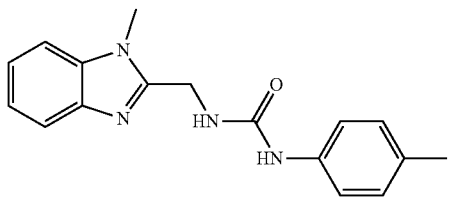 [SMILES: Cc1ccc(NC(=O)NCc2nc3ccccc3n2C)cc1]<br>Potency: 4.4668<br>Efficacy: 121.35 | Compound 77 |
| 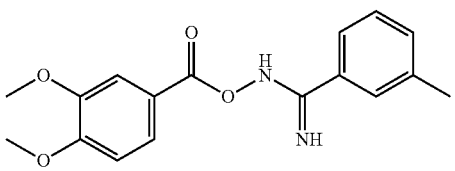<br>Potency: 10<br>Efficacy: 152.941 | Compound 78 |
| 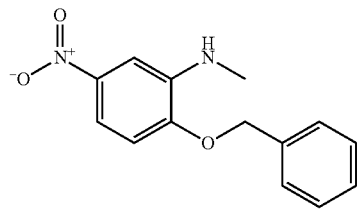<br>Potency: 4.4668<br>Efficacy: 85.208 | Compound 79 |

TABLE 7-continued

Exemplary Compounds

Compound 80

Potency: 10
Efficacy: 175.516

Compound 81

Potency: 12.5893
Efficacy: 213.226

Compound 82

Potency: 3.1623
Efficacy: 96.4736

Compound 83

Potency: 11.2202
Efficacy: 175.054

Compound 84

Potency: 6.3096
Efficacy: 122.242

Compound 85

Potency: 5.0119
Efficacy: 99.705

TABLE 7-continued
Exemplary Compounds
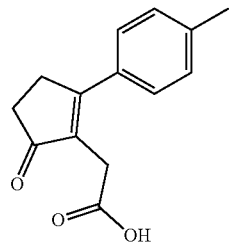 [SMILES: Cc1ccc(C2=C(CC(=O)O)C(=O)CC2)cc1]
Compound 86
Potency: 4.4668
Efficacy: 94.2018
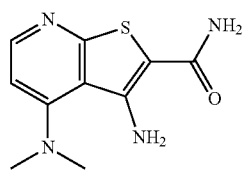 [SMILES: CN(C)c1ccnc2sc(C(N)=O)c(N)c12]
Compound 87
Potency: 5.0119
Efficacy: 66.4058
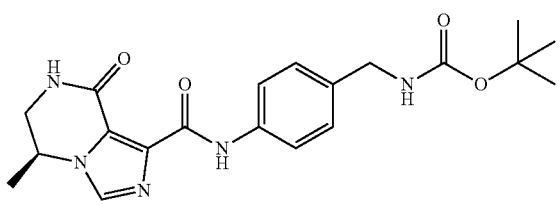 [SMILES: C[C@H]1CNC(=O)c2c(C(=O)Nc3ccc(CNC(=O)OC(C)(C)C)cc3)ncn21]
Compound 88
Potency: 8.9125
Efficacy: 88.9864
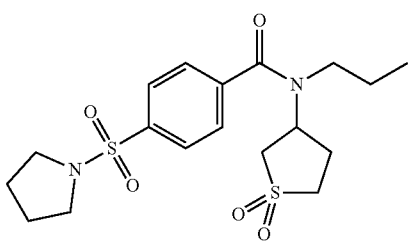 [SMILES: CCCN(C(=O)c1ccc(S(=O)(=O)N2CCCC2)cc1)C1CCS(=O)(=O)C1]
Compound 89
Potency: 5.0119
Efficacy: 86.1979
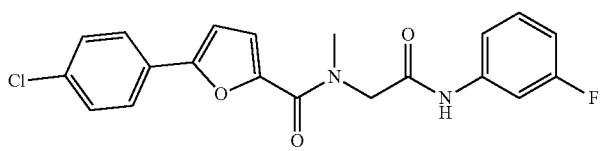 [SMILES: CN(CC(=O)Nc1cccc(F)c1)C(=O)c1ccc(-c2ccc(Cl)cc2)o1]
Compound 90
Potency: 11.2202
Efficacy: 140.713

TABLE 7-continued
Exemplary Compounds
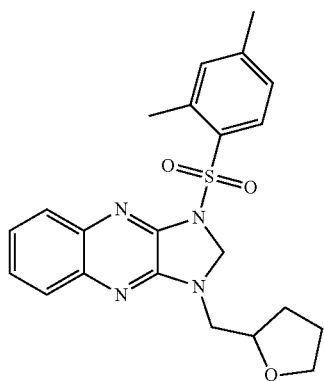 [SMILES: Cc1ccc(S(=O)(=O)N2CN(CC3CCCO3)c3nc4ccccc4nc32)c(C)c1]
Compound 91
Potency: 11.2202
Efficacy: 139.097
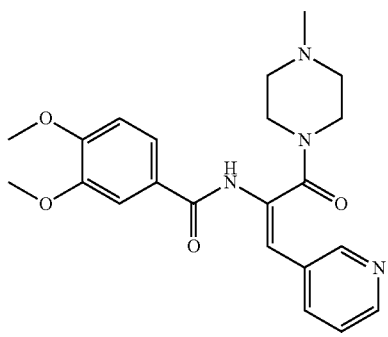 [SMILES: COc1ccc(C(=O)N/C(=C/c2cccnc2)C(=O)N2CCN(C)CC2)cc1OC]
Compound 92
Potency: 4.4668
Efficacy: 75.211
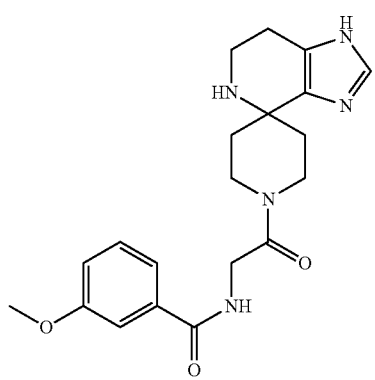 [SMILES: COc1cccc(C(=O)NCC(=O)N2CCC3(CC2)NCCc2[nH]cnc23)c1]
Compound 93
Potency: 11.2202
Efficacy: 117.921

TABLE 7-continued
Exemplary Compounds
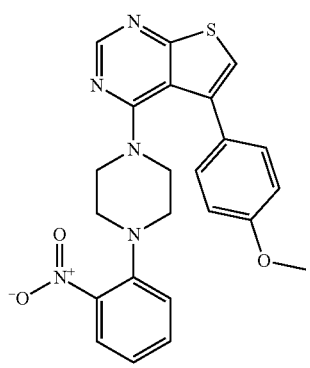
Compound 94
Potency: 10
Efficacy: 128.349
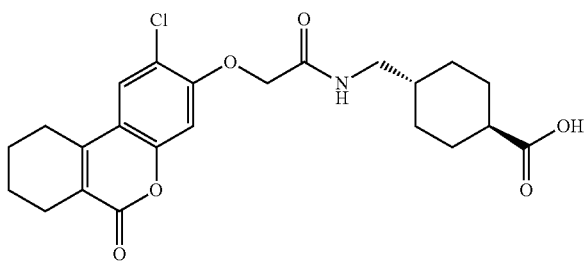 [SMILES: O=C(COc1cc2oc(=O)c3c(c2cc1Cl)CCCC3)NC[C@H]1CC[C@H](C(=O)O)CC1]
Compound 95
Potency: 7.0795
Efficacy: 98.2729
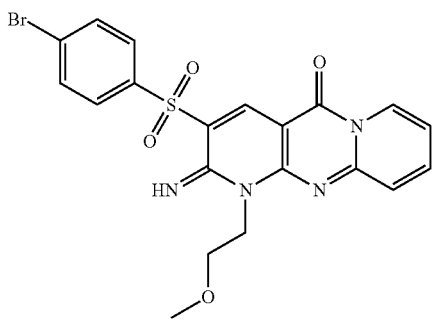 [SMILES: COCCn1c(=N)c(S(=O)(=O)c2ccc(Br)cc2)cc2c(=O)n3ccccc3nc21]
Compound 96
Potency: 4.4668
Efficacy: 83.068
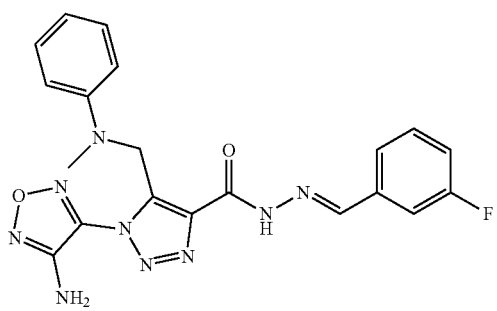 [SMILES: CN(Cc1c(C(=O)N/N=C/c2cccc(F)c2)nnn1-c1nonc1N)c1ccccc1]
Compound 97
Potency: 5.6234
Efficacy: 78.6154

TABLE 7-continued
Exemplary Compounds
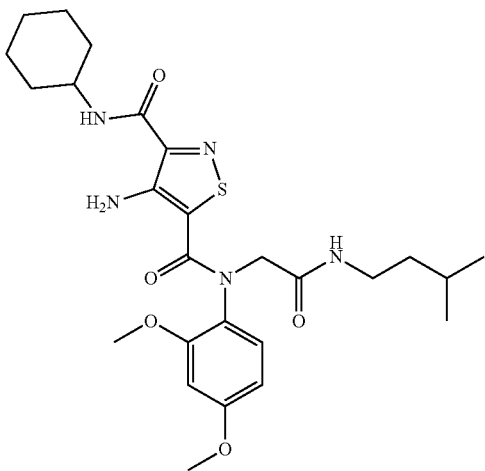 [SMILES: COc1ccc(N(CC(=O)NCCC(C)C)C(=O)c2snc(C(=O)NC3CCCCC3)c2N)c(OC)c1]
Compound 98
Potency: 10
Efficacy: 125.681
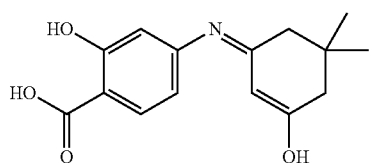 [SMILES: CC1(C)CC(O)=C/C(=N\c2ccc(C(=O)O)c(O)c2)C1]
Compound 99
Potency: 10
Efficacy: 121.073
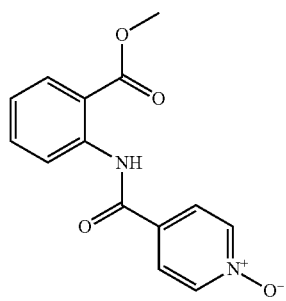 [SMILES: COC(=O)c1ccccc1NC(=O)c1cc[n+]([O-])cc1]
Compound 100
Potency: 3.9811
Efficacy: 95.5318
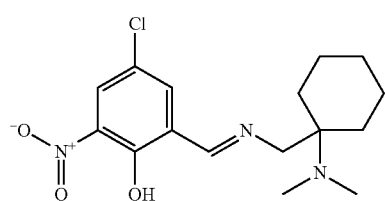
Compound 101
Potency: 8.9125
Efficacy: 131.53

TABLE 7-continued
Exemplary Compounds
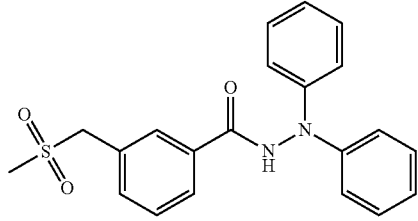 [SMILES: CS(=O)(=O)Cc1cccc(C(=O)NN(c2ccccc2)c2ccccc2)c1]
Compound 102
Potency: 12.5893
Efficacy: 149.767
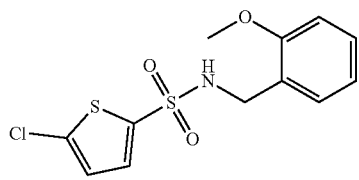 [SMILES: COc1ccccc1CNS(=O)(=O)c1ccc(Cl)s1]
Compound 103
Potency: 6.3096
Efficacy: 119.897
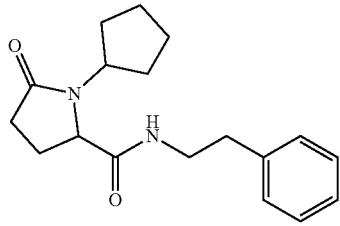 [SMILES: O=C(NCCc1ccccc1)C1CCC(=O)N1C1CCCC1]
Compound 104
Potency: 10
Efficacy: 137.595
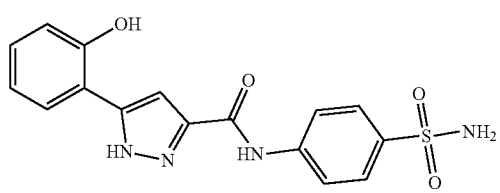 [SMILES: NS(=O)(=O)c1ccc(NC(=O)c2cc(-c3ccccc3O)[nH]n2)cc1]
Compound 105
Potency: 10
Efficacy: 96.3714
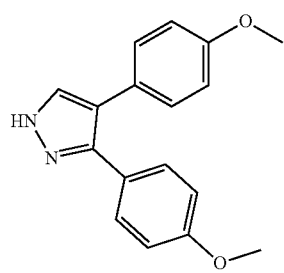 [SMILES: COc1ccc(-c2c[nH]nc2-c2ccc(OC)cc2)cc1]
Compound 106
Potency: 7.0795
Efficacy: 81.3792

TABLE 7-continued
Exemplary Compounds
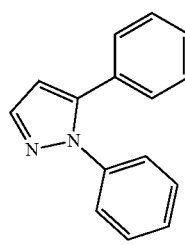
Compound 107
Potency: 4.4668
Efficacy: 95.5906
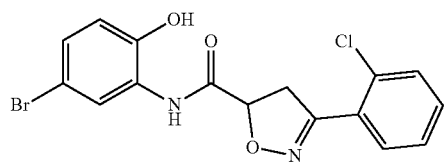 [SMILES: O=C(Nc1cc(Br)ccc1O)C1CC(c2ccccc2Cl)=NO1]
Compound 108
Potency: 12.5893
Efficacy: 139.967
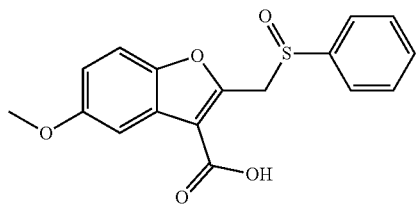 [SMILES: COc1ccc2oc(CS(=O)c3ccccc3)c(C(=O)O)c2c1]
Compound 109
Potency: 12.5893
Efficacy: 166.495
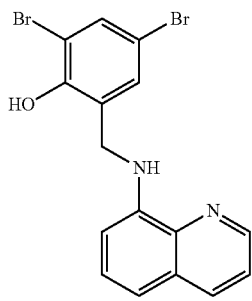 [SMILES: Oc1c(Br)cc(Br)cc1CNc1cccc2cccnc12]
Compound 110
Potency: 12.5893
Efficacy: 180.783
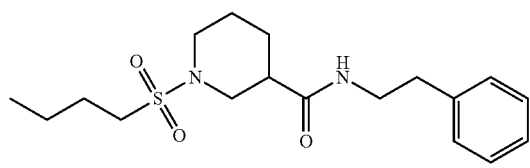 [SMILES: CCCCS(=O)(=O)N1CCCC(C(=O)NCCc2ccccc2)C1]
Compound 111
Potency: 7.0795
Efficacy: 99.2205

TABLE 7-continued
Exemplary Compounds
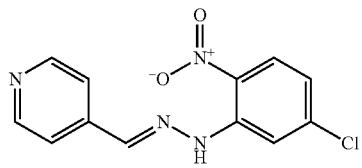
Potency: 5.6234
Efficacy: 73.9187
Compound 112
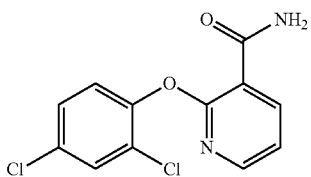 [SMILES: NC(=O)c1cccnc1Oc1ccc(Cl)cc1Cl]
Potency: 10
Efficacy: 111.758
Compound 113
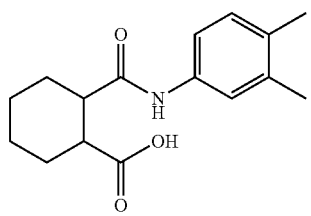 [SMILES: Cc1ccc(NC(=O)C2CCCCC2C(=O)O)cc1C]
Potency: 11.2202
Efficacy: 138.65
Compound 114
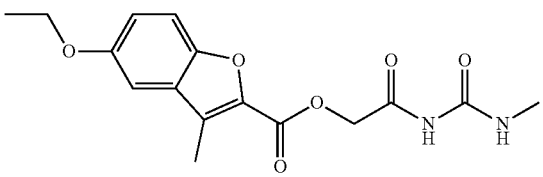 [SMILES: CCOc1ccc2oc(C(=O)OCC(=O)NC(=O)NC)c(C)c2c1]
Potency: 7.0795
Efficacy: 85.5436
Compound 115
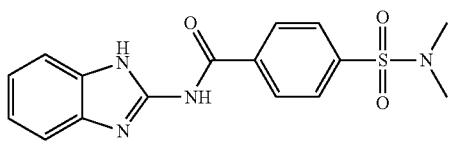 [SMILES: CN(C)S(=O)(=O)c1ccc(C(=O)Nc2nc3ccccc3[nH]2)cc1]
Potency: 8.9125
Efficacy: 104.576
Compound 116
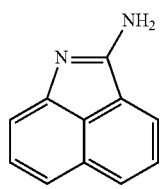 [SMILES: NC1=Nc2cccc3cccc1c23]
Potency: 7.9433
Efficacy: 88.998
Compound 117

TABLE 7-continued
Exemplary Compounds
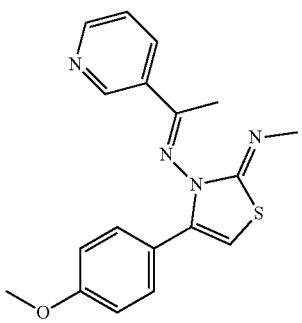
Compound 118
Potency: 5.0119
Efficacy: 82.7908
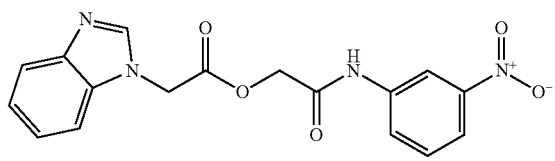 [SMILES: O=C(COC(=O)Cn1cnc2ccccc21)Nc1cccc([N+](=O)[O-])c1]
Compound 119
Potency: 11.2202
Efficacy: 127.904
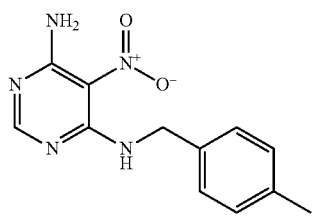 [SMILES: Cc1ccc(CNc2ncnc(N)c2[N+](=O)[O-])cc1]
Compound 120
Potency: 10
Efficacy: 114.827
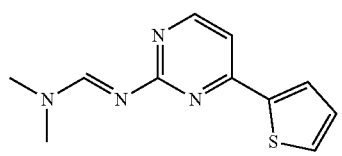 [SMILES: CN(C)/C=N/c1nccc(-c2cccs2)n1]
Compound 121
Potency: 8.9125
Efficacy: 92.062
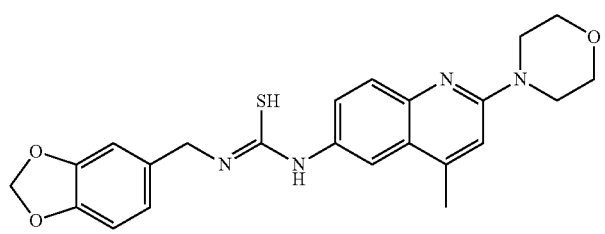 [SMILES: Cc1cc(N2CCOCC2)nc2ccc(N/C(S)=N/Cc3ccc4c(c3)OCO4)cc12]
Compound 122
Potency: 10
Efficacy: 127.132

TABLE 7-continued

Exemplary Compounds

Compound 123

Potency: 8.9125
Efficacy: 92.918

Compound 124

Potency: 8.9125
Efficacy: 123.416

Compound 125

Potency: 11.2202
Efficacy: 136.36

Compound 126

Potency: 8.9125
Efficacy: 124.439

Compound 127

Potency: 12.5893
Efficacy: 171.242

133
134
TABLE 7-continued
Exemplary Compounds
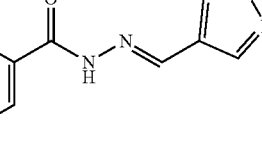
Compound 128
Potency: 14.1254
Efficacy: 138.869
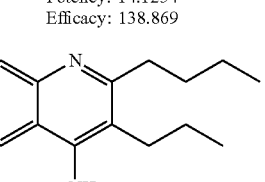
Compound 129
Potency: 11.2202
Efficacy: 145.936
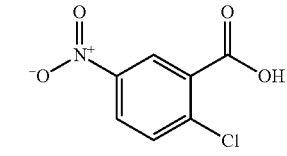
Compound 130
Potency: 11.2202
Efficacy: 119.808
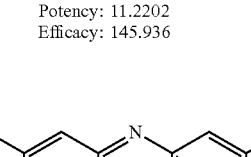
Compound 131
Potency: 14.1254
Efficacy: 175.002
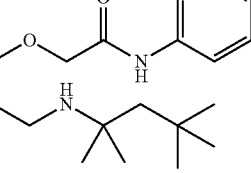
Compound 132
Potency: 12.5893
Efficacy: 120.609

TABLE 7-continued
Exemplary Compounds
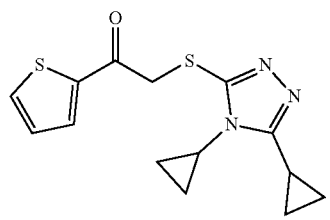 [SMILES: O=C(CSc1nnc(C2CC2)n1C1CC1)c1cccs1]
Potency: 10
Efficacy: 100.712
Compound 133
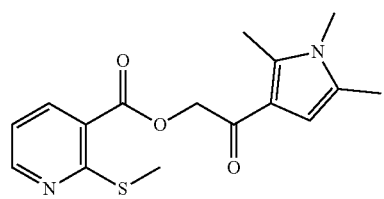 [SMILES: CSc1ncccc1C(=O)OCC(=O)c1cc(C)n(C)c1C]
Potency: 10
Efficacy: 95.4818
Compound 134
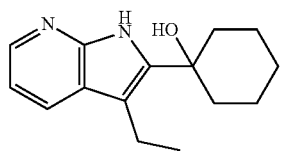 [SMILES: CCc1c(C2(O)CCCCC2)[nH]c2ncccc12]
Potency: 10
Efficacy: 91.1222
Compound 135
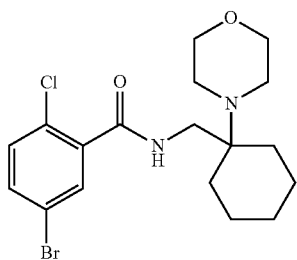 [SMILES: O=C(NCC1(N2CCOCC2)CCCCC1)c1cc(Br)ccc1Cl]
Potency: 8.9125
Efficacy: 89.1179
Compound 136
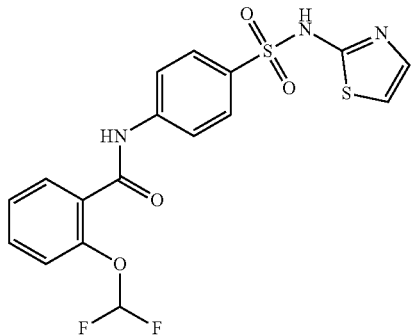 [SMILES: O=C(Nc1ccc(S(=O)(=O)Nc2nccs2)cc1)c1ccccc1OC(F)F]
Potency: 10
Efficacy: 81.023
Compound 137

TABLE 7-continued
Exemplary Compounds
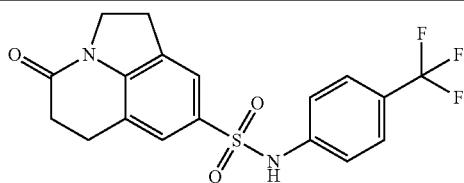
Compound 138
Potency: 11.2202
Efficacy: 135.363
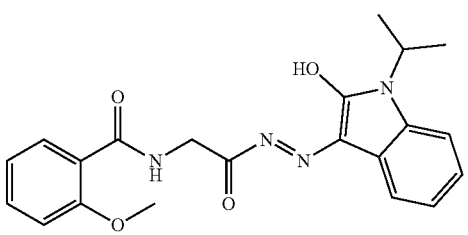 [SMILES: COc1ccccc1C(=O)NCC(=O)/N=N/c1c(O)n(C(C)C)c2ccccc12]
Compound 139
Potency: 11.2202
Efficacy: 67.3145
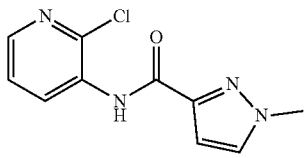 [SMILES: Cn1ccc(C(=O)Nc2cccnc2Cl)n1]
Compound 140
Potency: 10
Efficacy: 81.9056
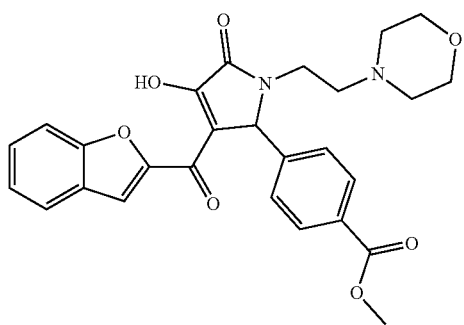 [SMILES: COC(=O)c1ccc(C2C(C(=O)c3cc4ccccc4o3)=C(O)C(=O)N2CCN2CCOCC2)cc1]
Compound 141
Potency: 10
Efficacy: 100.669
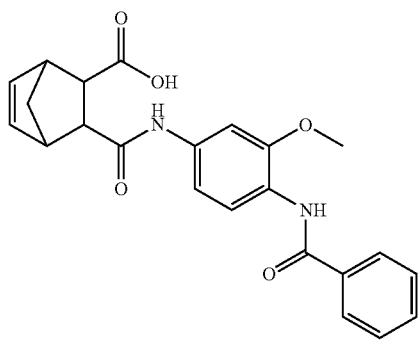 [SMILES: COc1cc(NC(=O)C2C3C=CC(C3)C2C(=O)O)ccc1NC(=O)c1ccccc1]
Compound 142
Potency: 8.9125
Efficacy: 89.9548

TABLE 7-continued
Exemplary Compounds
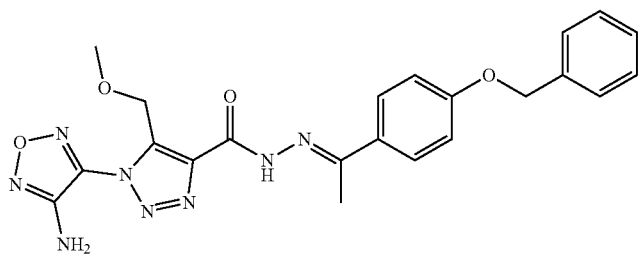 [SMILES: COCc1c(C(=O)N/N=C(\C)c2ccc(OCc3ccccc3)cc2)nnn1-c1nonc1N]
Compound 143
Potency: 10
Efficacy: 76.5877
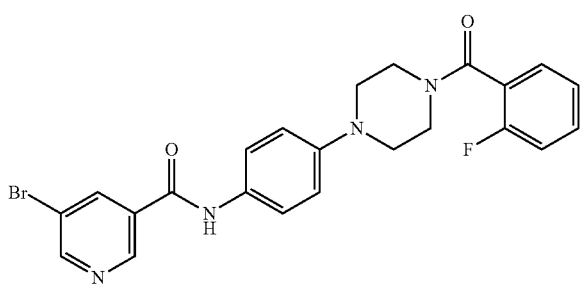 [SMILES: O=C(Nc1ccc(N2CCN(C(=O)c3ccccc3F)CC2)cc1)c1cncc(Br)c1]
Compound 144
Potency: 12.5893
Efficacy: 94.0383
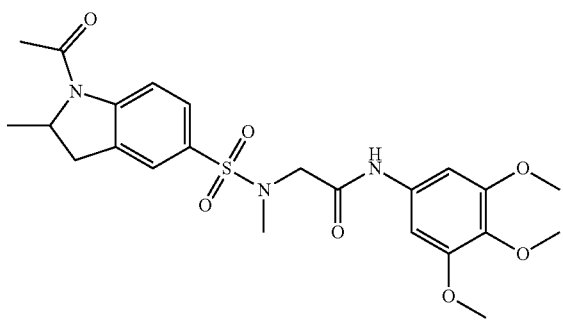
Compound 145
Potency: 10
Efficacy: 69.9943
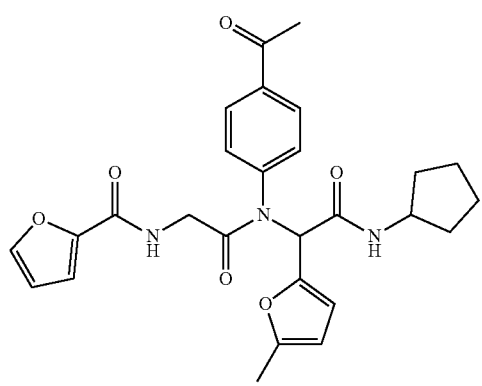 [SMILES: CC(=O)c1ccc(N(C(=O)CNC(=O)c2ccco2)C(C(=O)NC2CCCC2)c2ccc(C)o2)cc1]
Compound 146
Potency: 10
Efficacy: 96.4095

TABLE 7-continued
Exemplary Compounds
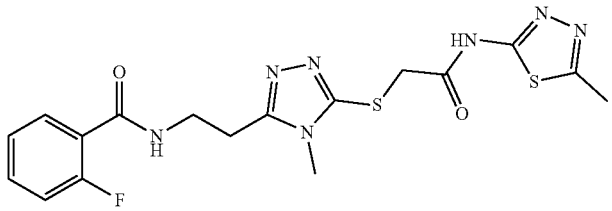 [SMILES: Cc1nnc(NC(=O)CSc2nnc(CCNC(=O)c3ccccc3F)n2C)s1]
Compound 147
Potency: 11.2202
Efficacy: 90.1504
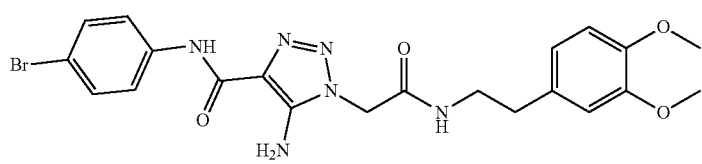 [SMILES: COc1ccc(CCNC(=O)Cn2nnc(C(=O)Nc3ccc(Br)cc3)c2N)cc1OC]
Compound 148
Potency: 11.2202
Efficacy: 138.741
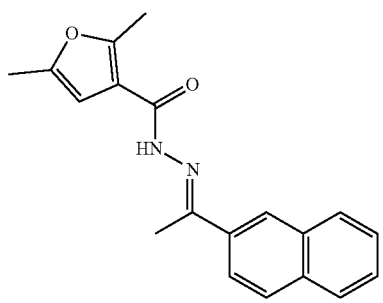 [SMILES: C/C(=N\NC(=O)c1cc(C)oc1C)c1ccc2ccccc2c1]
Compound 149
Potency: 8.9125
Efficacy: 84.3701
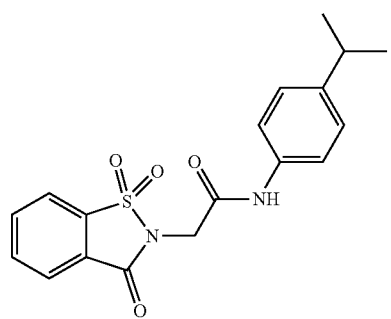 [SMILES: CC(C)c1ccc(NC(=O)CN2C(=O)c3ccccc3S2(=O)=O)cc1]
Compound 150
Potency: 10
Efficacy: 67.6116

TABLE 7-continued
Exemplary Compounds
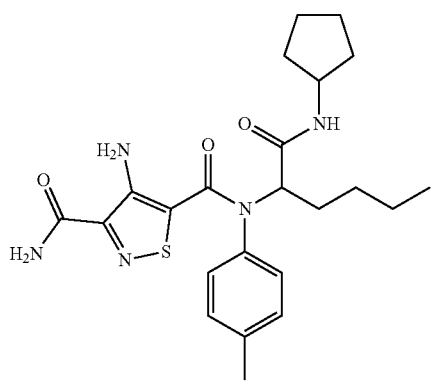 [SMILES: CCCCC(C(=O)NC1CCCC1)N(C(=O)c1snc(C(N)=O)c1N)c1ccc(C)cc1]
Compound 151
Potency: 10
Efficacy: 91.5246
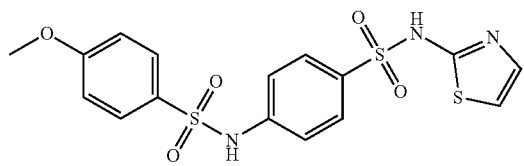 [SMILES: COc1ccc(S(=O)(=O)Nc2ccc(S(=O)(=O)Nc3nccs3)cc2)cc1]
Compound 152
Potency: 12.5893
Efficacy: 97.2406
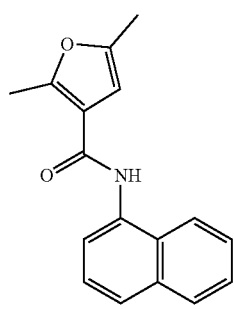 [SMILES: Cc1cc(C(=O)Nc2cccc3ccccc23)c(C)o1]
Compound 153
Potency: 7.9433
Efficacy: 95.7207
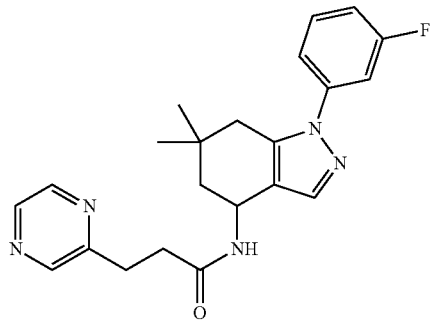 [SMILES: CC1(C)Cc2c(cnn2-c2cccc(F)c2)C(NC(=O)CCc2cnccn2)C1]
Compound 154
Potency: 3.1623
Efficacy: 93.8685

TABLE 7-continued
Exemplary Compounds
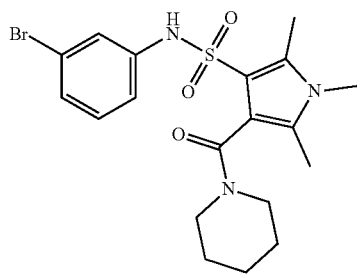 [SMILES: Cc1c(C(=O)N2CCCCC2)c(S(=O)(=O)Nc2cccc(Br)c2)c(C)n1C]
Compound 155
Potency: 10
Efficacy: 93.0585
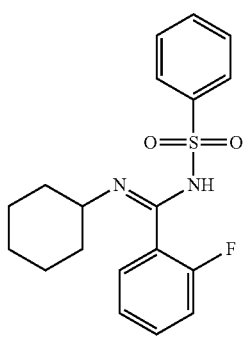 [SMILES: O=S(=O)(N/C(=N/C1CCCCC1)c1ccccc1F)c1ccccc1]
Compound 156
Potency: 10
Efficacy: 67.8359
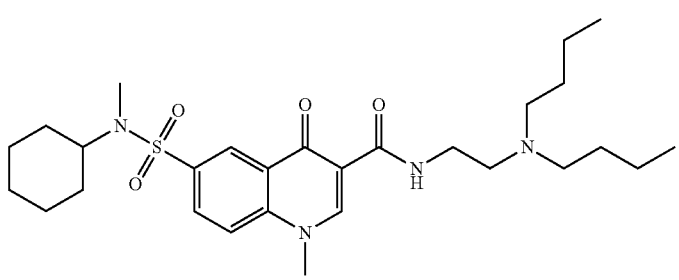 [SMILES: CCCCN(CCCC)CCNC(=O)c1cn(C)c2ccc(S(=O)(=O)N(C)C3CCCCC3)cc2c1=O]
Compound 157
Potency: 10
Efficacy: 70.1776
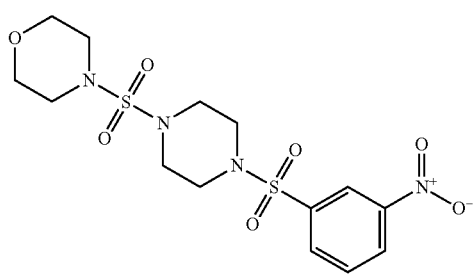 [SMILES: O=[N+]([O-])c1cccc(S(=O)(=O)N2CCN(S(=O)(=O)N3CCOCC3)CC2)c1]
Compound 158
Potency: 10
Efficacy: 71.256

TABLE 7-continued
Exemplary Compounds
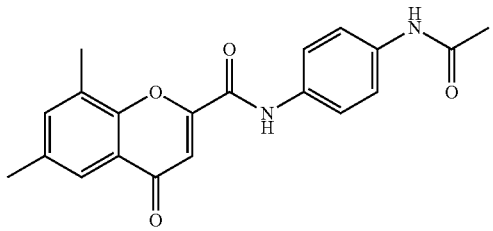 [SMILES: CC(=O)Nc1ccc(NC(=O)c2cc(=O)c3cc(C)cc(C)c3o2)cc1]
Potency: 11.2202
Efficacy: 109.576
Compound 159
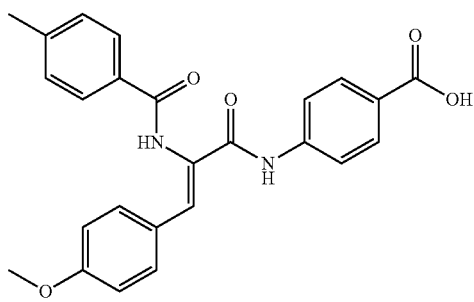 [SMILES: COc1ccc(/C=C(\NC(=O)c2ccc(C)cc2)C(=O)Nc2ccc(C(=O)O)cc2)cc1]
Potency: 11.2202
Efficacy: 103.065
Compound 160
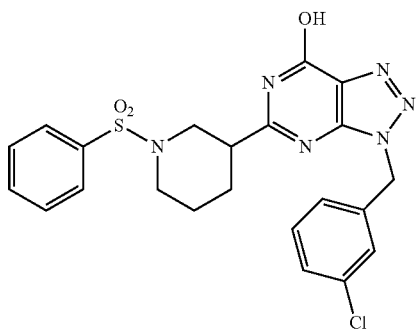 [SMILES: O=S(=O)(c1ccccc1)N1CCCC(c2nc(O)c3nnn(Cc4cccc(Cl)c4)c3n2)C1]
Potency: 3.9811
Efficacy: 97.9916
Compound 161
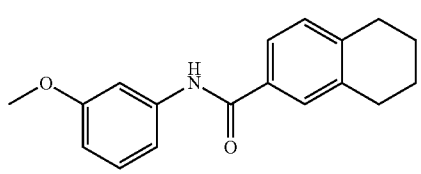 [SMILES: COc1cccc(NC(=O)c2ccc3c(c2)CCCC3)c1]
Potency: 5.6234
Efficacy: 87.0645
Compound 162

TABLE 7-continued
Exemplary Compounds
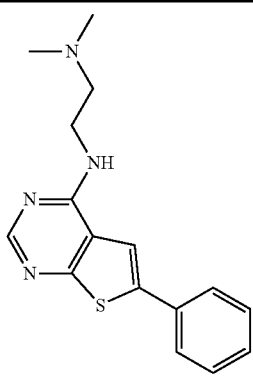
Compound 163
Potency: 10
Efficacy: 79.1483
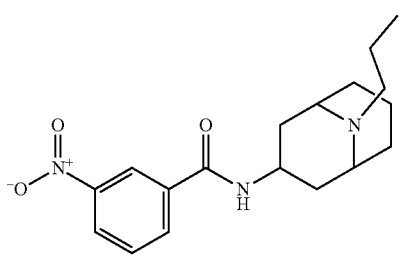
Compound 164
Potency: 10
Efficacy: 90.988
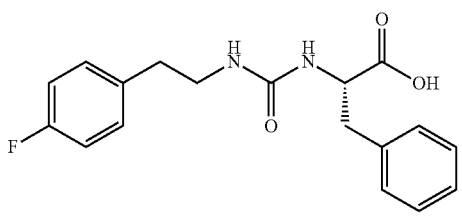 [SMILES: O=C(NCCc1ccc(F)cc1)N[C@@H](Cc1ccccc1)C(=O)O]
Compound 165
Potency: 11.2202
Efficacy: 128.695
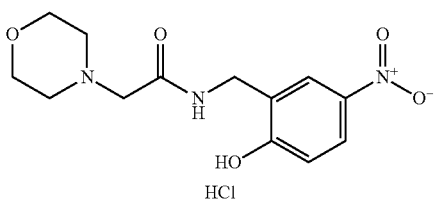 [SMILES: O=C(CN1CCOCC1)NCc1cc([N+](=O)[O-])ccc1O ; Cl]
HCl
Compound 166
Potency: 12.5893
Efficacy: 93.7937
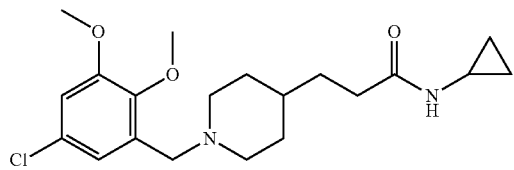 [SMILES: COc1cc(Cl)cc(CN2CCC(CCC(=O)NC3CC3)CC2)c1OC]
Compound 167
Potency: 7.0795
Efficacy: 86.8199

TABLE 7-continued

Exemplary Compounds

Compound 168

Potency: 8.9125
Efficacy: 83.6415

Compound 169

Potency: 10
Efficacy: 84.5587

Compound 170

Potency: 10
Efficacy: 84.3344

Compound 171

Potency: 10
Efficacy: 59.61

Compound 172

Potency: 10
Efficacy: 65.8043

Compound 173

Potency: 11.2202
Efficacy: 85.4536

TABLE 7-continued
Exemplary Compounds
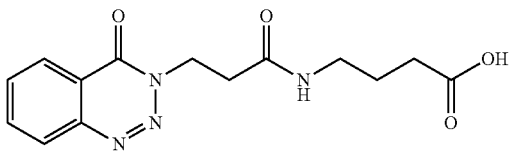 [SMILES: O=C(O)CCCNC(=O)CCn1nnc2ccccc2c1=O]
Potency: 11.2202
Efficacy: 104.045
Compound 174
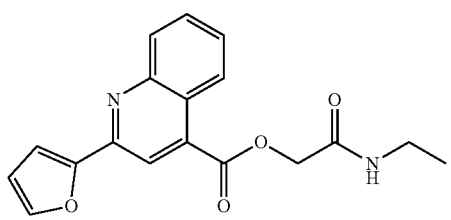 [SMILES: CCNC(=O)COC(=O)c1cc(-c2ccco2)nc2ccccc12]
Potency: 5.6234
Efficacy: 116.69
Compound 175
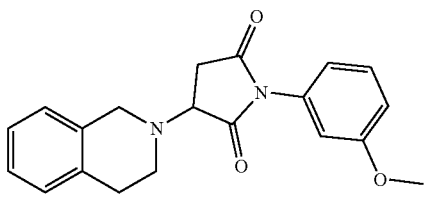 [SMILES: COc1cccc(N2C(=O)CC(N3CCc4ccccc4C3)C2=O)c1]
Potency: 10
Efficacy: 115.567
Compound 176
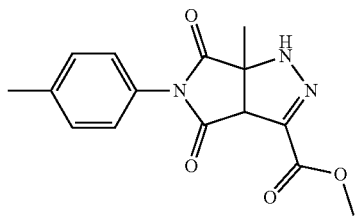
Potency: 10
Efficacy: 70.6131
Compound 177
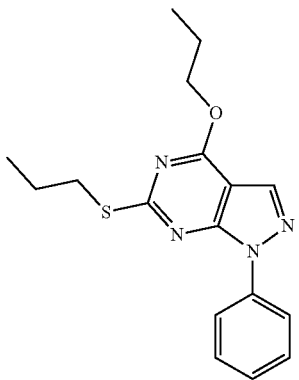 [SMILES: CCCOc1nc(SCCC)nc2c1cnn2-c1ccccc1]
Potency: 11.2202
Efficacy: 107.982
Compound 178

TABLE 7-continued
Exemplary Compounds
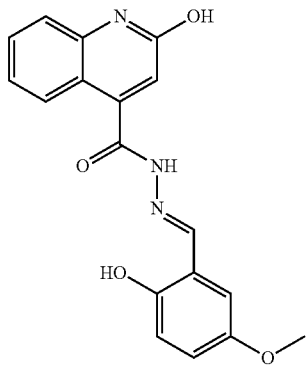 [SMILES: COc1ccc(O)c(/C=N/NC(=O)c2cc(O)nc3ccccc23)c1]
Compound 179
Potency: 5.6234
Efficacy: 84.0774
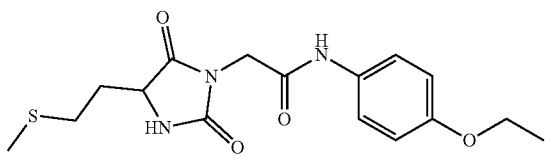 [SMILES: CCOc1ccc(NC(=O)CN2C(=O)NC(CCSC)C2=O)cc1]
Compound 180
Potency: 10
Efficacy: 77.6845
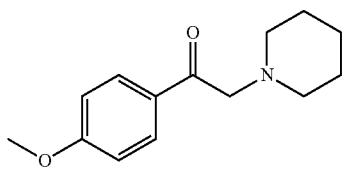
Compound 181
HBr
Potency: 12.5893
Efficacy: 80.5239
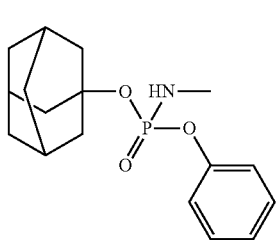 [SMILES: CNP(=O)(Oc1ccccc1)OC12CC3CC(CC(C3)C1)C2]
Compound 182
Potency: 10
Efficacy: 99.1066
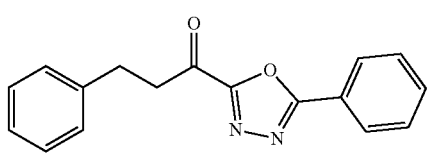 [SMILES: O=C(CCc1ccccc1)c1nnc(-c2ccccc2)o1]
Compound 183
Potency: 10
Efficacy: 98.6809

TABLE 7-continued
Exemplary Compounds
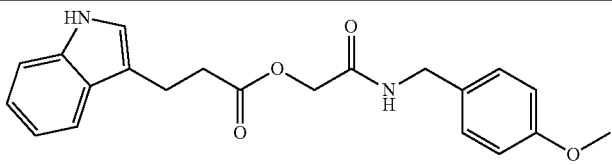
Compound 184
Potency: 10
Efficacy: 86.1315
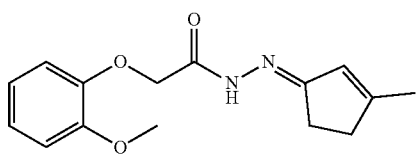 [SMILES: COc1ccccc1OCC(=O)N/N=C1/C=C(C)CC1]
Compound 185
Potency: 10
Efficacy: 117.72
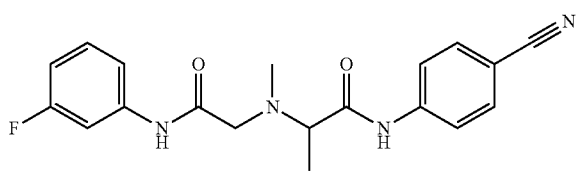 [SMILES: CC(C(=O)Nc1ccc(C#N)cc1)N(C)CC(=O)Nc1cccc(F)c1]
Compound 186
Potency: 3.9811
Efficacy: 93.5129
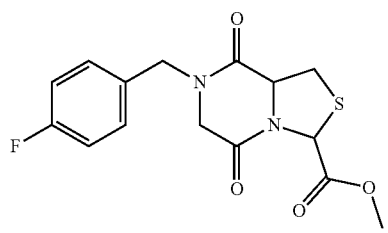 [SMILES: COC(=O)C1SCC2C(=O)N(Cc3ccc(F)cc3)CC(=O)N21]
Compound 187
Potency: 8.9125
Efficacy: 120.104
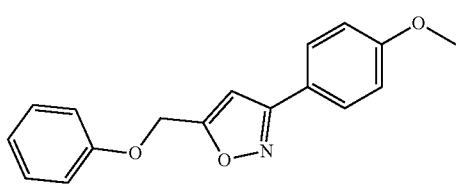 [SMILES: COc1ccc(-c2cc(COc3ccccc3)on2)cc1]
Compound 188
Potency: 10
Efficacy: 88.0312
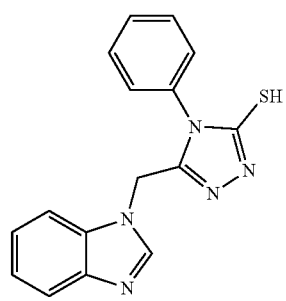 [SMILES: Sc1nnc(Cn2cnc3ccccc32)n1-c1ccccc1]
Compound 189
Potency: 8.9125
Efficacy: 76.0346

TABLE 7-continued
Exemplary Compounds
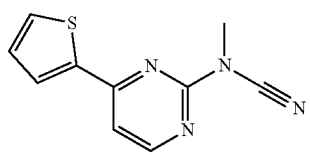
Compound 190
Potency: 11.2202
Efficacy: 116.431
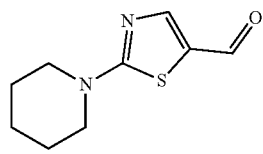 [SMILES: O=Cc1cnc(N2CCCCC2)s1]
Compound 191
Potency: 11.2202
Efficacy: 115.598
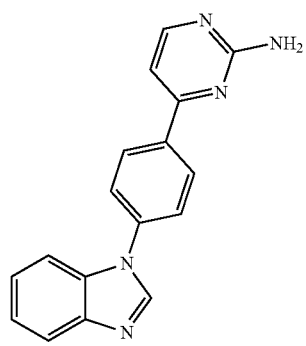 [SMILES: Nc1nccc(-c2ccc(-n3cnc4ccccc43)cc2)n1]
Compound 192
Potency: 11.2202
Efficacy: 74.0117
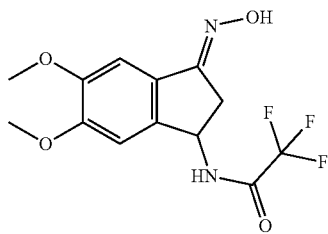 [SMILES: COc1cc2c(cc1OC)C(NC(=O)C(F)(F)F)C/C2=N\O]
Compound 193
Potency: 11.2202
Efficacy: 89.7146
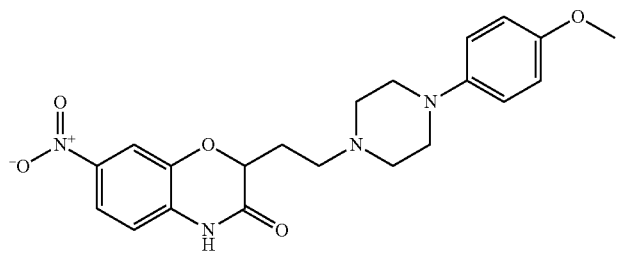
Compound 194
Potency: 8.9125
Efficacy: 76.8665

TABLE 7-continued
Exemplary Compounds
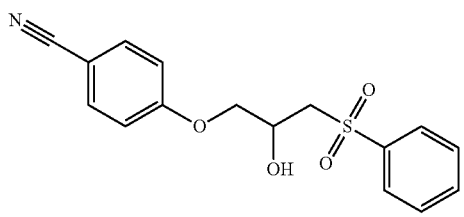 [SMILES: N#Cc1ccc(OCC(O)CS(=O)(=O)c2ccccc2)cc1]
Compound 195
Potency: 10
Efficacy: 99.4569
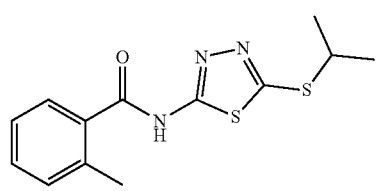 [SMILES: Cc1ccccc1C(=O)Nc1nnc(SC(C)C)s1]
Compound 196
Potency: 10
Efficacy: 67.0912
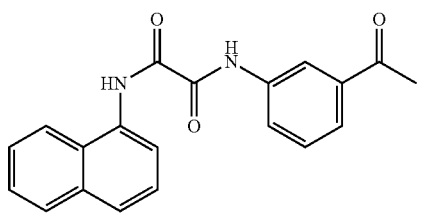 [SMILES: CC(=O)c1cccc(NC(=O)C(=O)Nc2cccc3ccccc23)c1]
Compound 197
Potency: 8.9125
Efficacy: 83.2038
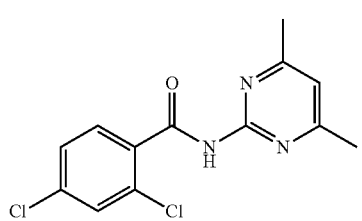 [SMILES: Cc1cc(C)nc(NC(=O)c2ccc(Cl)cc2Cl)n1]
Compound 198
Potency: 10
Efficacy: 78.0861
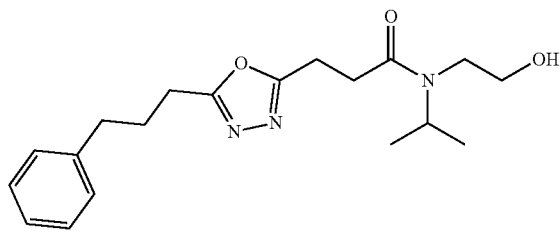 [SMILES: CC(C)N(CCO)C(=O)CCc1nnc(CCCc2ccccc2)o1]
Compound 199
Potency: 12.5893
Efficacy: 96.0151

TABLE 7-continued
Exemplary Compounds
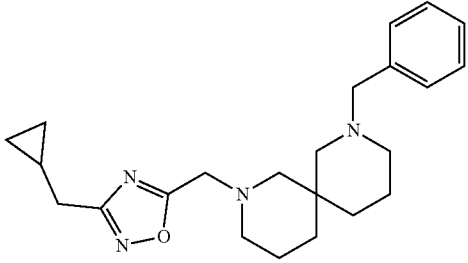 [SMILES: c1ccc(CN2CCCC3(CCCN(Cc4nc(CC5CC5)no4)C3)C2)cc1]
Compound 200
Potency: 8.9125
Efficacy: 98.6316
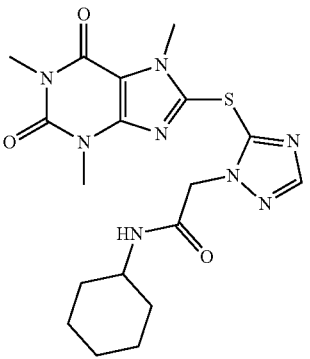 [SMILES: Cn1c(=O)c2c(nc(Sc3ncnn3CC(=O)NC3CCCCC3)n2C)n(C)c1=O]
Compound 201
Potency: 11.2202
Efficacy: 94.7942
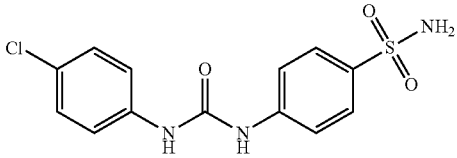 [SMILES: NS(=O)(=O)c1ccc(NC(=O)Nc2ccc(Cl)cc2)cc1]
Compound 202
Potency: 10
Efficacy: 83.9426
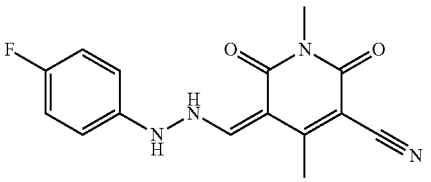 [SMILES: CC1=C(C#N)C(=O)N(C)C(=O)/C1=C\NNc1ccc(F)cc1]
Compound 203
Potency: 7.0795
Efficacy: 106.69
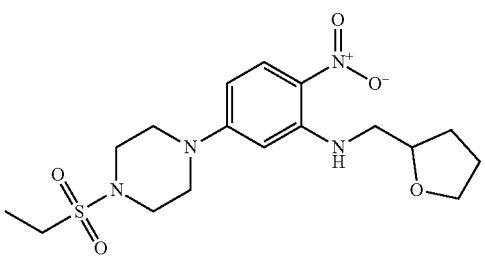 [SMILES: CCS(=O)(=O)N1CCN(c2ccc([N+](=O)[O-])c(NCC3CCCO3)c2)CC1]
Compound 204
Potency: 10
Efficacy: 70.2778

TABLE 7-continued
Exemplary Compounds
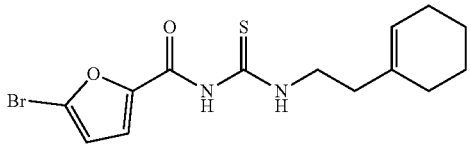 [SMILES: O=C(NC(=S)NCCC1=CCCCC1)c1ccc(Br)o1]
Compound 205
Potency: 7.0795
Efficacy: 98.0553
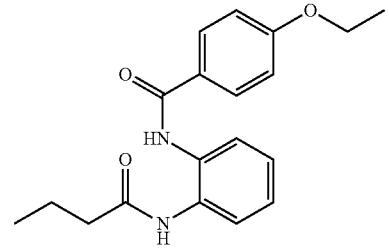 [SMILES: CCCC(=O)Nc1ccccc1NC(=O)c1ccc(OCC)cc1]
Compound 206
Potency: 11.2202
Efficacy: 77.9394
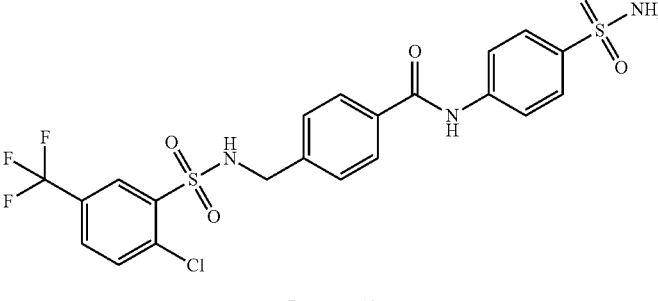
Compound 207
Potency: 10
Efficacy: 75.3009
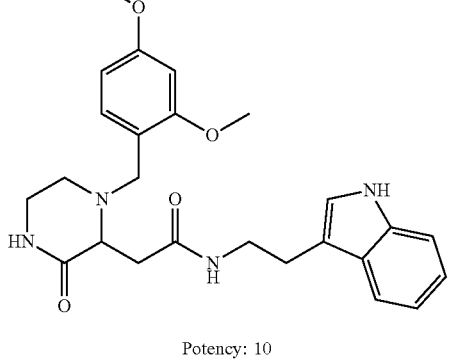
Compound 208
Potency: 10
Efficacy: 83.7154
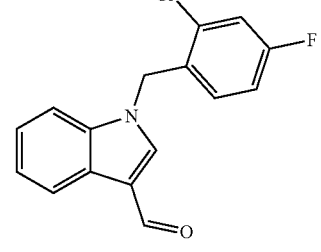
Compound 209
Potency: 15.8489
Efficacy: 130.232

TABLE 7-continued
Exemplary Compounds
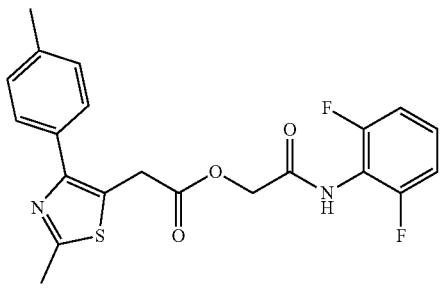 [SMILES: Cc1ccc(-c2nc(C)sc2CC(=O)OCC(=O)Nc2c(F)cccc2F)cc1]
Compound 210
Potency: 12.5893
Efficacy: 101.354
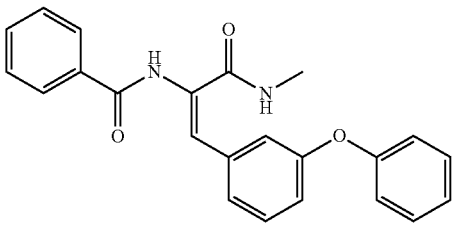 [SMILES: CNC(=O)/C(=C\c1cccc(Oc2ccccc2)c1)NC(=O)c1ccccc1]
Compound 211
Potency: 11.2202
Efficacy: 109.939
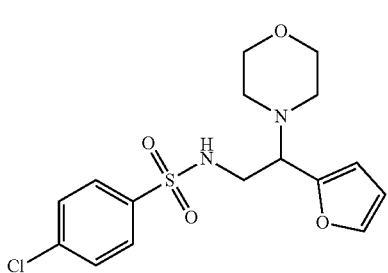 [SMILES: O=S(=O)(NCC(c1ccco1)N1CCOCC1)c1ccc(Cl)cc1]
Compound 212
Potency: 14.1254
Efficacy: 119.538
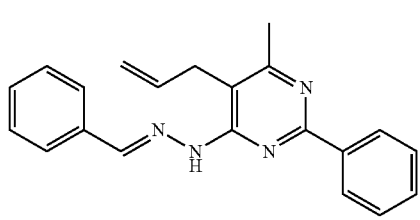 [SMILES: C=CCc1c(C)nc(-c2ccccc2)nc1N/N=C/c1ccccc1]
Compound 213
Potency: 11.2202
Efficacy: 110.24

TABLE 7-continued
Exemplary Compounds
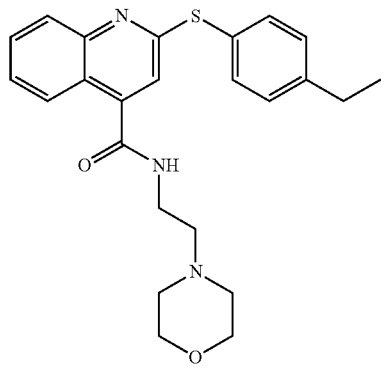 [SMILES: CCc1ccc(Sc2cc(C(=O)NCCN3CCOCC3)c3ccccc3n2)cc1]
Compound 214
Potency: 11.2202
Efficacy: 94.2928
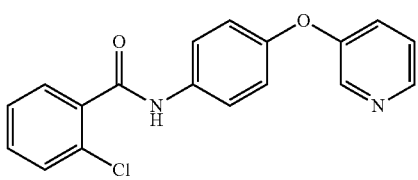 [SMILES: O=C(Nc1ccc(Oc2cccnc2)cc1)c1ccccc1Cl]
Compound 215
Potency: 10
Efficacy: 73.527
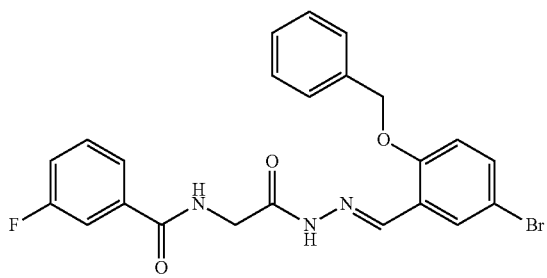 [SMILES: O=C(CNC(=O)c1cccc(F)c1)N/N=C/c1cc(Br)ccc1OCc1ccccc1]
Compound 216
Potency: 10
Efficacy: 90.7389
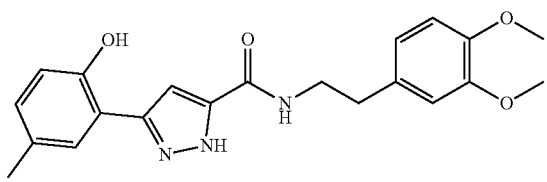
Compound 217
Potency: 10
Efficacy: 56.3855
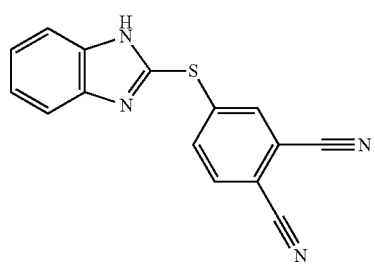 [SMILES: N#Cc1ccc(Sc2nc3ccccc3[nH]2)cc1C#N]
Compound 218
Potency: 10
Efficacy: 58.0835

TABLE 7-continued
Exemplary Compounds
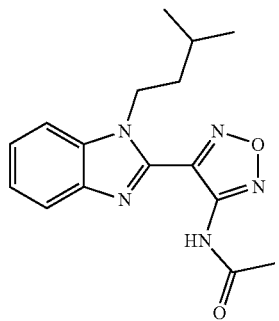 [SMILES: CC(=O)Nc1nonc1-c1nc2ccccc2n1CCC(C)C]
Compound 219
Potency: 11.2202
Efficacy: 83.9475
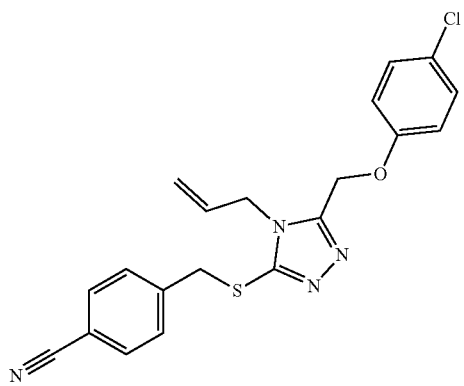 [SMILES: C=CCn1c(COc2ccc(Cl)cc2)nnc1SCc1ccc(C#N)cc1]
Compound 220
Potency: 11.2202
Efficacy: 86.9112
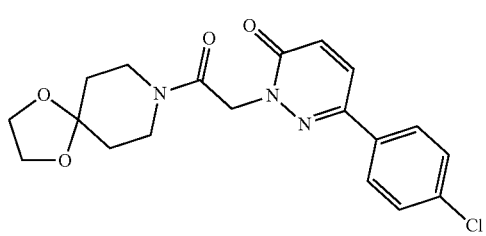 [SMILES: O=C(Cn1nc(-c2ccc(Cl)cc2)ccc1=O)N1CCC2(CC1)OCCO2]
Compound 221
Potency: 11.2202
Efficacy: 59.5046
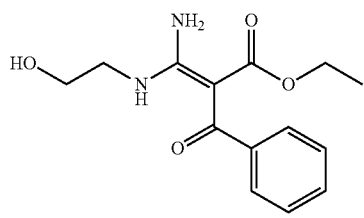 [SMILES: CCOC(=O)/C(C(=O)c1ccccc1)=C(\N)NCCO]
Compound 222
Potency: 12.5893
Efficacy: 56.9925

TABLE 8

| | | | | | | Compound data | | |
|---|---|---|---|---|---|---|---|---|
| No. | Score | Curve Description | Fit LogAC50 | Fit Hill Slope | Fit R2 | Fit Infinite Activity [%] | Fit Zero Activity [%] | Fit Curve Class |
| 1 | 94 | Complete curve; high efficacy | −5.95 | 3.132 | 0.9985 | 195.171 | −2.9752 | 1.1 |
| 2 | 91 | Complete curve; high efficacy | −5.45 | 1.4163 | 0.9999 | 231.285 | 3.1995 | 1.1 |
| 3 | 89 | Complete curve; high efficacy | −5.65 | 3.0654 | 0.9999 | 158.124 | −35.3084 | 1.1 |
| 4 | 87 | Complete curve; high efficacy | −5.55 | 1.8617 | 0.9998 | 136.905 | 7.6069 | 1.1 |
| 5 | 86 | Complete curve; high efficacy | −5.95 | 2.5334 | 0.9999 | 87.4201 | −5.0637 | 1.1 |
| 6 | 85 | Complete curve; high efficacy | −5.95 | 1.3437 | 0.9999 | 69.589 | −58.5311 | 1.1 |
| 7 | 85 | Complete curve; high efficacy | −5.35 | 1.6924 | 0.9999 | 107.421 | 12.5 | 1.1 |
| 8 | 85 | Complete curve; high efficacy | −5.55 | 4.9549 | 0.9996 | 96.0327 | −15.6523 | 1.1 |
| 9 | 85 | Complete curve; high efficacy | −5.55 | 1.3723 | 0.9999 | 92.2022 | −30.5005 | 1.1 |
| 10 | 85 | Complete curve; high efficacy | −5.5 | 2.8473 | 1 | 102.022 | 0 | 1.1 |
| 11 | 85 | Complete curve; high efficacy | −5.4 | 2.5334 | 0.9997 | 101.384 | −0.509 | 1.1 |
| 12 | 85 | Complete curve; high efficacy | −5.55 | 1.4781 | 0.9999 | 102.305 | 9.3996 | 1.1 |
| 13 | 84 | Complete curve; high efficacy | −5.35 | 3.9295 | 0.9991 | 94.7101 | −27.2857 | 1.1 |
| 14 | 84 | Complete curve; high efficacy | −5.65 | 2.3332 | 0.9995 | 62.8391 | −21.9345 | 1.1 |
| 15 | 84 | Complete curve; high efficacy | −5.5 | 1.6259 | 0.9999 | 75.2612 | −16.1195 | 1.1 |
| 16 | 84 | Complete curve; high efficacy | −5.65 | 1.3443 | 0.9999 | 77.492 | −37.8568 | 1.1 |
| 17 | 84 | Complete curve; high efficacy | −5.6 | 1.2475 | 0.9998 | 71.4307 | −24.7641 | 1.1 |
| 18 | 84 | Partial curve; high efficacy | −5 | 4.9549 | 0.9995 | 1760.36 | 8.7984 | 2.1 |
| 19 | 84 | Complete curve; high efficacy | −5.85 | 1.3437 | 0.9992 | 52.7174 | −28.8963 | 1.1 |
| 20 | 84 | Complete curve; high efficacy | −5.45 | 2.3031 | 0.9999 | 83.8587 | −17.7204 | 1.1 |
| 21 | 84 | Complete curve; high efficacy | −5.25 | 4.4495 | 0.9992 | 93.4556 | 1.1731 | 1.1 |
| 22 | 84 | Complete curve; high efficacy | −5.35 | 4.9549 | 0.9999 | 83.1353 | −0.2899 | 1.1 |
| 23 | 84 | Complete curve; high efficacy | −5.4 | 2.9023 | 0.9998 | 98.4745 | 13.3122 | 1.1 |
| 24 | 84 | Complete curve; high efficacy | −5.5 | 2.1211 | 0.9996 | 82.7045 | 5.7274 | 1.1 |

TABLE 8-continued

| | | Compound data | | | | | | |
|---|---|---|---|---|---|---|---|---|
| 25 | 84 | Complete curve; high efficacy | −5.65 | 1.6604 | 0.9995 | 64.1141 | −18.7854 | 1.1 |
| 26 | 84 | Complete curve; high efficacy | −5.7 | 1.1 | 1 | 59.5556 | −36.1807 | 1.1 |
| 27 | 83 | Complete curve; high efficacy | −5.7 | 2.2526 | 0.9994 | 54.9511 | −26.8995 | 1.1 |
| 28 | 83 | Complete curve; high efficacy | −5.55 | 2.5334 | 0.9999 | 55.3257 | −36.6914 | 1.1 |
| 29 | 83 | Complete curve; high efficacy | −5.4 | 1.7885 | 0.9997 | 55.7271 | −25.4387 | 1.1 |
| 30 | 83 | Complete curve; high efficacy | −5.4 | 2.1876 | 0.9999 | 73.6408 | −19.157 | 1.1 |
| 31 | 83 | Complete curve; high efficacy | −5.6 | 1.9673 | 0.9999 | 62.1733 | −24.2621 | 1.1 |
| 32 | 83 | Complete curve; high efficacy | −5.55 | 2.1211 | 1 | 60.2337 | −28.5623 | 1.1 |
| 33 | 82 | Complete curve; high efficacy | −5.7 | 1.1 | 0.9991 | 33.1603 | −50.1655 | 1.1 |
| 34 | 65 | Complete curve; partial efficacy | −5.85 | 1.8851 | 0.9995 | 76.3552 | 5.9015 | 1.2 |
| 35 | 64 | Complete curve; partial efficacy | −5.6 | 3.132 | 0.9995 | 72.5763 | −0.1751 | 1.2 |
| 36 | 64 | Complete curve; partial efficacy | −5.5 | 1.4163 | 0.9997 | 81.2047 | 5.5 | 1.2 |
| 37 | 64 | Complete curve; partial efficacy | −5.6 | 2.4064 | 0.9991 | 74.4523 | −2.5935 | 1.2 |
| 38 | 63 | Complete curve; partial efficacy | −5.35 | 4.9549 | 0.9992 | 73.5449 | −2.0156 | 1.2 |
| 39 | 63 | Complete curve; partial efficacy | −5.45 | 1.7529 | 0.9998 | 69.5378 | −9.0026 | 1.2 |
| 40 | 48 | Partial curve; high efficacy | −4.85 | 4.5045 | 0.9986 | 433.479 | −3.212 | 2.1 |
| 41 | 48 | Partial curve; high efficacy | −4.85 | 4.5045 | 1 | 456.749 | 8.8874 | 2.1 |
| 42 | 48 | Partial curve; high efficacy | −4.85 | 4.9549 | 0.9987 | 484.883 | 9.6207 | 2.1 |
| 43 | 47 | Partial curve; high efficacy | −5.4 | 0.9 | 0.9999 | 148.01 | 0 | 2.1 |
| 44 | 47 | Partial curve; high efficacy | −4.95 | 4.095 | 0.9997 | 310.669 | −17.6073 | 2.1 |
| 45 | 47 | Partial curve; high efficacy | −4.85 | 4.5045 | 0.9989 | 419.509 | −7.0263 | 2.1 |
| 46 | 46 | Partial curve; high efficacy | −5.1 | 1.01 | 0.9992 | 195.813 | −35.6022 | 2.1 |
| 47 | 46 | Partial curve; high efficacy | −5.25 | 1.331 | 0.9993 | 153.844 | 12.5272 | 2.1 |
| 48 | 46 | Partial curve; high efficacy | −5.15 | 1.7137 | 0.9992 | 178.694 | −35.4511 | 2.1 |
| 49 | 46 | Partial curve; high efficacy | −5.25 | 1.9282 | 0.9996 | 153.971 | 2.973 | 2.1 |
| 50 | 46 | Partial curve; high efficacy | −5.1 | 1.8851 | 0.9989 | 186.381 | 5.0579 | 2.1 |

TABLE 8-continued

| | | Compound data | | | | | | |
|---|---|---|---|---|---|---|---|---|
| 51 | 46 | Partial curve; high efficacy | −5 | 4.9549 | 0.9988 | 249.6 | −23.8252 | 2.1 |
| 52 | 46 | Partial curve; high efficacy | −5.35 | 1.4781 | 0.9998 | 137.586 | −27.7073 | 2.1 |
| 53 | 45 | Partial curve; high efficacy | −5.15 | 0.8 | 0.9991 | 152.283 | −11.267 | 2.1 |
| 54 | 45 | Partial curve; high efficacy | −4.9 | 1.1341 | 1 | 262.045 | 39.3368 | 2.1 |
| 55 | 45 | Partial curve; high efficacy | −4.9 | 4.9549 | 0.9985 | 252.825 | −18.4203 | 2.1 |
| 56 | 45 | Partial curve; high efficacy | −5.4 | 1.5095 | 0.9999 | 110.65 | 21.8862 | 2.1 |
| 57 | 45 | Partial curve; high efficacy | −5.35 | 1.7529 | 0.9999 | 115.173 | −0.5596 | 2.1 |
| 58 | 45 | Partial curve; high efficacy | −5.45 | 0.9 | 0.999 | 95.6282 | −42.3624 | 2.1 |
| 59 | 45 | Partial curve; high efficacy | −5 | 3.5722 | 0.9991 | 185.351 | −3.6299 | 2.1 |
| 60 | 45 | Partial curve; high efficacy | −5.35 | 1.7529 | 0.9992 | 116.389 | −12.5146 | 2.1 |
| 61 | 45 | Partial curve; high efficacy | −5.3 | 1.1705 | 0.9991 | 136.382 | −3.94 | 2.1 |
| 62 | 45 | Partial curve; high efficacy | −5.15 | 1.9673 | 0.9992 | 162.393 | −23.864 | 2.1 |
| 63 | 45 | Partial curve; high efficacy | −5 | 3.1925 | 0.9993 | 198.688 | −1.7425 | 2.1 |
| 64 | 45 | Partial curve; high efficacy | −5.3 | 2.4729 | 0.9996 | 129.946 | −4.9734 | 2.1 |
| 65 | 45 | Partial curve; high efficacy | −4.7 | 4.095 | 0.9991 | 501.215 | 9.2299 | 2.1 |
| 66 | 45 | Partial curve; high efficacy | −4.9 | 4.5045 | 0.9991 | 227.168 | 11.9175 | 2.1 |
| 67 | 44 | Partial curve; high efficacy | −5 | 1.4163 | 0.9999 | 162.351 | 4.7344 | 2.1 |
| 68 | 44 | Partial curve; high efficacy | −4.9 | 4.5045 | 0.9986 | 221.625 | −17.9914 | 2.1 |
| 69 | 44 | Partial curve; high efficacy | −5.4 | 1.3987 | 0.9999 | 88.0721 | −2.436 | 2.1 |
| 70 | 44 | Partial curve; high efficacy | −5.35 | 1.2876 | 0.9999 | 96.1281 | −19.1057 | 2.1 |
| 71 | 44 | Partial curve; high efficacy | −5.1 | 1.3443 | 0.9999 | 122.331 | −2.1806 | 2.1 |
| 72 | 44 | Partial curve; high efficacy | −5.05 | 2.3332 | 0.9987 | 136.354 | −2.3089 | 2.1 |
| 73 | 44 | Partial curve; high efficacy | −4.9 | 4.095 | 0.9993 | 186.64 | 16.3113 | 2.1 |
| 74 | 44 | Partial curve; high efficacy | −5.35 | 1.8617 | 1 | 86.169 | −23.105 | 2.1 |
| 75 | 44 | Partial curve; partial efficacy | −5.4 | 1.5579 | 0.9999 | 98.3982 | 26.9551 | 2.2 |
| 76 | 44 | Partial curve; high efficacy | −5.2 | 1.3443 | 0.9997 | 105.907 | −8.518 | 2.1 |

TABLE 8-continued

| | | Compound data | | | | | | |
|---|---|---|---|---|---|---|---|---|
| 77 | 44 | Partial curve; high efficacy | −5.35 | 1.8617 | 1 | 87.1172 | −34.2328 | 2.1 |
| 78 | 44 | Partial curve; high efficacy | −5 | 1.7137 | 0.9999 | 162.598 | 9.6566 | 2.1 |
| 79 | 44 | Partial curve; high efficacy | −5.35 | 1.3437 | 0.9999 | 84.8433 | −0.3646 | 2.1 |
| 80 | 44 | Partial curve; high efficacy | −5 | 1.4163 | 0.9999 | 169.032 | −6.484 | 2.1 |
| 81 | 44 | Partial curve; high efficacy | −4.9 | 4.5045 | 0.9998 | 216.419 | 3.1931 | 2.1 |
| 82 | 44 | Partial curve; high efficacy | −5.5 | 1.1341 | 1 | 89.9991 | −6.4745 | 2.1 |
| 83 | 44 | Partial curve; high efficacy | −4.95 | 2.0937 | 1 | 162.065 | −12.9886 | 2.1 |
| 84 | 44 | Partial curve; high efficacy | −5.2 | 1.2221 | 0.9999 | 114.278 | −7.9639 | 2.1 |
| 85 | 44 | Partial curve; high efficacy | −5.3 | 1.8617 | 0.9999 | 102.938 | 3.2331 | 2.1 |
| 86 | 44 | Partial curve; high efficacy | −5.35 | 0.8 | 0.9999 | 94.6981 | 0.4963 | 2.1 |
| 87 | 44 | Partial curve; partial efficacy | −5.3 | 2.1211 | 0.9997 | 87.756 | 21.3502 | 2.2 |
| 88 | 43 | Partial curve; high efficacy | −5.05 | 1.01 | 0.9999 | 98.4045 | 9.418 | 2.1 |
| 89 | 43 | Partial curve; partial efficacy | −5.3 | 1.6924 | 0.999 | 75.3022 | −10.8957 | 2.2 |
| 90 | 43 | Partial curve; high efficacy | −4.95 | 4.5045 | 0.999 | 146.447 | 5.7331 | 2.1 |
| 91 | 43 | Partial curve; high efficacy | −4.95 | 4.095 | 0.9986 | 122.391 | −16.7058 | 2.1 |
| 92 | 43 | Partial curve; partial efficacy | −5.35 | 1.6259 | 0.9999 | 76.9712 | 1.7602 | 2.2 |
| 93 | 43 | Partial curve; high efficacy | −4.95 | 1.7529 | 1 | 114.284 | −3.6365 | 2.1 |
| 94 | 43 | Partial curve; high efficacy | −5 | 4.9549 | 0.9996 | 138.031 | 9.6823 | 2.1 |
| 95 | 43 | Partial curve; partial efficacy | −5.15 | 1.01 | 0.9993 | 83.3763 | −14.8966 | 2.2 |
| 96 | 43 | Partial curve; partial efficacy | −5.35 | 1.9887 | 0.9998 | 74.9858 | −8.0822 | 2.2 |
| 97 | 43 | Partial curve; partial efficacy | −5.25 | 3.132 | 0.9994 | 79.8262 | 1.2108 | 2.2 |
| 98 | 43 | Partial curve; high efficacy | −5 | 4.5045 | 1 | 125.633 | −0.0479 | 2.1 |
| 99 | 43 | Partial curve; high efficacy | −5 | 2.1211 | 0.9999 | 121.073 | 0 | 2.1 |
| 100 | 43 | Partial curve; high efficacy | −5.4 | 1.01 | 0.9992 | 64.0202 | −31.5116 | 2.1 |
| 101 | 43 | Partial curve; high efficacy | −5.05 | 1.6604 | 0.9989 | 115.659 | −15.8708 | 2.1 |
| 102 | 43 | Partial curve; high efficacy | −4.9 | 4.5045 | 0.9999 | 160.171 | 10.4042 | 2.1 |

TABLE 8-continued

| | | Compound data | | | | | | |
|---|---|---|---|---|---|---|---|---|
| 103 | 43 | Partial curve; high efficacy | −5.2 | 1.8265 | 0.9986 | 96.8922 | −23.0045 | 2.1 |
| 104 | 43 | Partial curve; high efficacy | −5 | 3.6772 | 0.9988 | 128.477 | −9.1182 | 2.1 |
| 105 | 43 | Partial curve; high efficacy | −5 | 3.5117 | 0.9995 | 113.218 | 16.8467 | 2.1 |
| 106 | 43 | Partial curve; partial efficacy | −5.15 | 1.21 | 1 | 79.2242 | −2.155 | 2.2 |
| 107 | 43 | Partial curve; high efficacy | −5.35 | 1.4781 | 0.9998 | 76.3701 | −19.2206 | 2.1 |
| 108 | 43 | Partial curve; high efficacy | −4.9 | 4.5045 | 0.9999 | 142.05 | 2.0834 | 2.1 |
| 109 | 43 | Partial curve; high efficacy | −4.9 | 4.9549 | 0.9994 | 174.079 | 7.5839 | 2.1 |
| 110 | 43 | Partial curve; high efficacy | −4.9 | 4.5045 | 0.9999 | 162.565 | −18.2174 | 2.1 |
| 111 | 43 | Partial curve; high efficacy | −5.15 | 1.21 | 0.9999 | 101.431 | 2.2101 | 2.1 |
| 112 | 43 | Partial curve; partial efficacy | −5.25 | 3.132 | 1 | 74.0416 | 0.1229 | 2.2 |
| 113 | 43 | Partial curve; high efficacy | −5 | 3.9295 | 0.9994 | 105.867 | −5.8907 | 2.1 |
| 114 | 43 | Partial curve; high efficacy | −4.95 | 4.5045 | 0.9989 | 134.828 | −3.8223 | 2.1 |
| 115 | 43 | Partial curve; partial efficacy | −5.15 | 1.8265 | 0.9997 | 80.6607 | −4.8829 | 2.2 |
| 116 | 43 | Partial curve; high efficacy | −5.05 | 1.5579 | 0.9999 | 94.7519 | −9.8246 | 2.1 |
| 117 | 43 | Partial curve; high efficacy | −5.1 | 1.6604 | 0.9998 | 88.7778 | −0.2202 | 2.1 |
| 118 | 43 | Partial curve; partial efficacy | −5.3 | 1.6924 | 0.9992 | 74.8733 | −7.9176 | 2.2 |
| 119 | 43 | Partial curve; high efficacy | −4.95 | 4.9549 | 0.9997 | 111.883 | −16.0213 | 2.1 |
| 120 | 43 | Partial curve; high efficacy | −5 | 0.8 | 0.9996 | 126.76 | 11.933 | 2.1 |
| 121 | 43 | Partial curve; high efficacy | −5.05 | 1.8851 | 0.9997 | 97.7753 | 5.7133 | 2.1 |
| 122 | 43 | Partial curve; high efficacy | −5 | 1.2475 | 0.9999 | 127.656 | 0.5248 | 2.1 |
| 123 | 43 | Partial curve; high efficacy | −5.05 | 1.3443 | 0.9999 | 96.9016 | 3.9836 | 2.1 |
| 124 | 43 | Partial curve; high efficacy | −5.05 | 1.2475 | 0.9999 | 102.977 | −20.4393 | 2.1 |
| 125 | 43 | Partial curve; high efficacy | −4.95 | 1.1705 | 0.9999 | 133.669 | −2.6906 | 2.1 |
| 126 | 43 | Partial curve; high efficacy | −5.05 | 1 | 1 | 125.112 | 0.673 | 2.1 |
| 127 | 43 | Partial curve; high efficacy | −4.9 | 4.5045 | 0.9995 | 152.332 | −18.9102 | 2.1 |
| 128 | 43 | Partial curve; high efficacy | −4.85 | 4.5045 | 0.9991 | 153.542 | 14.6735 | 2.1 |

TABLE 8-continued

| | | Compound data | | | | | | |
|---|---|---|---|---|---|---|---|---|
| 129 | 43 | Partial curve; high efficacy | −4.95 | 4.095 | 0.9985 | 128.069 | −17.8675 | 2.1 |
| 130 | 43 | Partial curve; high efficacy | −4.95 | 4.5045 | 0.9998 | 127.62 | 7.8122 | 2.1 |
| 131 | 43 | Partial curve; high efficacy | −4.85 | 4.9549 | 0.9997 | 183.761 | 8.7591 | 2.1 |
| 132 | 43 | Partial curve; high efficacy | −4.9 | 4.9549 | 0.9996 | 133.42 | 12.8108 | 2.1 |
| 133 | 42 | Partial curve; high efficacy | −5 | 2.7202 | 0.9992 | 73.1459 | −27.5656 | 2.1 |
| 134 | 42 | Partial curve; high efficacy | −5 | 4.4495 | 0.9993 | 72.9186 | −22.5632 | 2.1 |
| 135 | 42 | Partial curve; high efficacy | −5 | 4.9549 | 0.9997 | 61.8199 | −29.3022 | 2.1 |
| 136 | 42 | Partial curve; partial efficacy | −5.05 | 0.8 | 0.9997 | 85.8101 | −3.3079 | 2.2 |
| 137 | 42 | Partial curve; high efficacy | −5 | 4.9549 | 0.9999 | 61.7369 | −19.2861 | 2.1 |
| 138 | 42 | Partial curve; high efficacy | −4.95 | 1.3437 | 1 | 107.998 | −27.3652 | 2.1 |
| 139 | 42 | Partial curve; high efficacy | −4.95 | 4.5045 | 0.9999 | 82.0264 | 14.712 | 2.1 |
| 140 | 42 | Partial curve; partial efficacy | −5 | 2.7868 | 0.9991 | 77.8665 | −4.0391 | 2.2 |
| 141 | 42 | Partial curve; high efficacy | −5 | 4.9549 | 0.9998 | 82.7722 | −17.8968 | 2.1 |
| 142 | 42 | Partial curve; high efficacy | −5.05 | 2.4064 | 0.9988 | 71.1773 | −18.7775 | 2.1 |
| 143 | 42 | Partial curve; high efficacy | −5 | 4.4495 | 0.9999 | 81.2596 | 4.6719 | 2.1 |
| 144 | 42 | Partial curve; high efficacy | −4.9 | 4.095 | 0.9995 | 103.816 | 9.7776 | 2.1 |
| 145 | 42 | Partial curve; partial efficacy | −5 | 4.9549 | 0.9999 | 70.4611 | 0.4668 | 2.2 |
| 146 | 42 | Partial curve; high efficacy | −5 | 4.9549 | 0.9999 | 75.4854 | −20.924 | 2.1 |
| 147 | 42 | Partial curve; high efficacy | −4.95 | 2.0937 | 0.9999 | 91.2034 | 1.0531 | 2.1 |
| 148 | 42 | Partial curve; high efficacy | −4.95 | 2.3531 | 0.9997 | 109.969 | −28.7719 | 2.1 |
| 149 | 42 | Partial curve; partial efficacy | −5.05 | 1.111 | 0.9999 | 82.4023 | −1.9678 | 2.2 |
| 150 | 42 | Partial curve; partial efficacy | −5 | 4.5045 | 0.9999 | 67.4005 | −0.2112 | 2.2 |
| 151 | 42 | Partial curve; high efficacy | −5 | 3.132 | 0.9999 | 65.1432 | −26.3814 | 2.1 |
| 152 | 42 | Partial curve; partial efficacy | −4.9 | 1.1341 | 0.9999 | 88.7605 | −8.4801 | 2.2 |
| 153 | 42 | Partial curve; high efficacy | −5.1 | 1.5095 | 0.9998 | 74.4536 | −21.2671 | 2.1 |
| 154 | 42 | Partial curve; high efficacy | −5.5 | 0.9 | 0.9999 | 47.5155 | −46.353 | 2.1 |

TABLE 8-continued

| | | Compound data | | | | | | |
|---|---|---|---|---|---|---|---|---|
| 155 | 42 | Partial curve; high efficacy | −5 | 3.99 | 0.9998 | 60.936 | −32.1225 | 2.1 |
| 156 | 42 | Partial curve; partial efficacy | −5 | 2.5334 | 0.9999 | 67.8023 | −0.0336 | 2.2 |
| 157 | 42 | Partial curve; partial efficacy | −5 | 3.6272 | 0.9989 | 68.2216 | −1.9559 | 2.2 |
| 158 | 42 | Partial curve; partial efficacy | −5 | 1.9282 | 0.9994 | 70.7327 | −0.5234 | 2.2 |
| 159 | 42 | Partial curve; high efficacy | −4.95 | 4.095 | 0.9995 | 106.672 | −2.9033 | 2.1 |
| 160 | 42 | Partial curve; high efficacy | −4.95 | 4.095 | 0.9998 | 100.584 | −2.4804 | 2.1 |
| 161 | 42 | Partial curve; high efficacy | −5.4 | 1.1 | 0.9998 | 55.0498 | −42.9418 | 2.1 |
| 162 | 42 | Partial curve; high efficacy | −5.25 | 2.2526 | 1 | 55.2524 | −31.8121 | 2.1 |
| 163 | 42 | Partial curve; partial efficacy | −5 | 4.045 | 0.9999 | 78.2931 | −0.8551 | 2.2 |
| 164 | 42 | Partial curve; high efficacy | −5 | 4.5045 | 0.9998 | 91.825 | 0.8371 | 2.1 |
| 165 | 42 | Partial curve; high efficacy | −4.95 | 4.5045 | 0.9999 | 108.575 | −20.12 | 2.1 |
| 166 | 42 | Partial curve; high efficacy | −4.9 | 1.3987 | 0.9998 | 104.163 | 10.3691 | 2.1 |
| 167 | 42 | Partial curve; high efficacy | −5.15 | 1.7885 | 0.9995 | 48.5966 | −38.2233 | 2.1 |
| 168 | 42 | Partial curve; partial efficacy | −5.05 | 1.9673 | 0.9989 | 82.861 | −0.7805 | 2.2 |
| 169 | 42 | Partial curve; high efficacy | −5 | 4.4495 | 0.9987 | 64.8483 | −19.7104 | 2.1 |
| 170 | 42 | Partial curve; high efficacy | −5 | 4.4495 | 0.9988 | 87.8075 | 3.4732 | 2.1 |
| 171 | 42 | Partial curve; partial efficacy | −5 | 3.132 | 0.9999 | 69.5258 | 9.9159 | 2.2 |
| 172 | 42 | Partial curve; partial efficacy | −5 | 2.3332 | 0.9987 | 73.8043 | 8 | 2.2 |
| 173 | 42 | Partial curve; partial efficacy | −4.95 | 0.9 | 0.9987 | 93.0488 | 7.5952 | 2.2 |
| 174 | 42 | Partial curve; high efficacy | −4.95 | 1.8579 | 0.9993 | 83.6585 | −20.386 | 2.1 |
| 175 | 42 | Partial curve; high efficacy | −5.25 | 1.3443 | 0.9985 | 54.0029 | −62.687 | 2.1 |
| 176 | 42 | Partial curve; high efficacy | −5 | 4.9549 | 0.9985 | 96.131 | −19.4361 | 2.1 |
| 177 | 42 | Partial curve; partial efficacy | −5 | 4.9549 | 0.9998 | 71.5284 | 0.9153 | 2.2 |
| 178 | 42 | Partial curve; high efficacy | −4.95 | 1.1341 | 0.9994 | 85.3274 | −22.6542 | 2.1 |
| 179 | 42 | Partial curve; high efficacy | −5.25 | 2.2526 | 0.9998 | 48.386 | −35.6913 | 2.1 |
| 180 | 42 | Partial curve; partial efficacy | −5 | 3.1925 | 0.9991 | 76.0607 | −1.6238 | 2.2 |

TABLE 8-continued

| | | Compound data | | | | | | |
|---|---|---|---|---|---|---|---|---|
| 181 | 42 | Partial curve; high efficacy | −4.9 | 4.9549 | 1 | 93.0239 | 12.5 | 2.1 |
| 182 | 42 | Partial curve; high efficacy | −5 | 2.2481 | 0.9998 | 98.2495 | −0.8571 | 2.1 |
| 183 | 42 | Partial curve; high efficacy | −5 | 4.4495 | 0.9997 | 99.728 | 1.0471 | 2.1 |
| 184 | 42 | Partial curve; high efficacy | −5 | 2.9023 | 0.9998 | 85.5304 | −0.6011 | 2.1 |
| 185 | 42 | Partial curve; high efficacy | −5 | 4.9549 | 0.9994 | 94.2492 | −23.4705 | 2.1 |
| 186 | 42 | Partial curve; high efficacy | −5.4 | 0.9 | 0.9999 | 47.9827 | −45.5302 | 2.1 |
| 187 | 42 | Partial curve; high efficacy | −5.05 | 1.3437 | 0.9992 | 65.7373 | −54.3669 | 2.1 |
| 188 | 42 | Partial curve; high efficacy | −5 | 4.5045 | 0.9999 | 88.2262 | 0.195 | 2.1 |
| 189 | 42 | Partial curve; partial efficacy | −5.05 | 0.8 | 0.9999 | 84.5737 | 8.5392 | 2.2 |
| 190 | 42 | Partial curve; high efficacy | −4.95 | 2.0937 | 0.9991 | 87.524 | −28.9068 | 2.1 |
| 191 | 42 | Partial curve; high efficacy | −4.95 | 4.9549 | 0.9998 | 96.2795 | −19.3188 | 2.1 |
| 192 | 42 | Partial curve; partial efficacy | −4.95 | 4.095 | 0.9992 | 76.4906 | 2.4789 | 2.2 |
| 193 | 42 | Partial curve; high efficacy | −4.95 | 4.095 | 0.9997 | 92.2616 | 2.547 | 2.1 |
| 194 | 42 | Partial curve; partial efficacy | −5.05 | 1.7137 | 0.9999 | 73.9084 | −2.9581 | 2.2 |
| 195 | 42 | Partial curve; high efficacy | −5 | 4.045 | 0.9987 | 89.5777 | −9.8792 | 2.1 |
| 196 | 42 | Partial curve; partial efficacy | −5 | 2.8473 | 0.9999 | 66.5821 | −0.5091 | 2.2 |
| 197 | 42 | Partial curve; partial efficacy | −5.05 | 0.9 | 0.9999 | 84.7038 | 1.5 | 2.2 |
| 198 | 42 | Partial curve; partial efficacy | −5 | 4.9549 | 0.9993 | 79.1775 | 1.0914 | 2.2 |
| 199 | 42 | Partial curve; partial efficacy | −4.9 | 1.2876 | 0.9988 | 96.2012 | 0.1862 | 2.2 |
| 200 | 42 | Partial curve; high efficacy | −5.05 | 1.4781 | 0.9999 | 56.5654 | −42.0662 | 2.1 |
| 201 | 42 | Partial curve; high efficacy | −4.95 | 2.3531 | 0.9987 | 74.9126 | −19.8816 | 2.1 |
| 202 | 42 | Partial curve; partial efficacy | −5 | 1.8617 | 0.9999 | 80.5565 | −3.3861 | 2.2 |
| 203 | 42 | Partial curve; high efficacy | −5.15 | 1.4781 | 0.9998 | 59.3901 | −47.2995 | 2.1 |
| 204 | 42 | Partial curve; partial efficacy | −5 | 3.5722 | 0.9999 | 70.7642 | 0.4864 | 2.2 |
| 205 | 42 | Partial curve; high efficacy | −5.15 | 1.4781 | 0.9999 | 57.7575 | −40.2978 | 2.1 |
| 206 | 42 | Partial curve; high efficacy | −4.95 | 4.095 | 0.9985 | 91.8921 | 13.9528 | 2.1 |

TABLE 8-continued

| | | | | Compound data | | | | |
|---|---|---|---|---|---|---|---|---|
| 207 | 42 | Partial curve; partial efficacy | −5 | 2.5334 | 0.9998 | 75.4708 | 0.1699 | 2.2 |
| 208 | 42 | Partial curve; partial efficacy | −5 | 3.1925 | 0.9988 | 74.5741 | −9.1413 | 2.2 |
| 209 | 42 | Partial curve; high efficacy | −4.8 | 4.095 | 0.9997 | 142.41 | 12.1779 | 2.1 |
| 210 | 42 | Partial curve; high efficacy | −4.9 | 4.9549 | 0.9986 | 113.27 | 11.9156 | 2.1 |
| 211 | 42 | Partial curve; high efficacy | −4.95 | 1.1341 | 0.9991 | 109.674 | −0.265 | 2.1 |
| 212 | 42 | Partial curve; high efficacy | −4.85 | 4.5045 | 0.9993 | 128.55 | 9.0119 | 2.1 |
| 213 | 42 | Partial curve; high efficacy | −4.95 | 1.2876 | 0.9999 | 109.228 | −1.0122 | 2.1 |
| 214 | 42 | Partial curve; high efficacy | −4.95 | 2.0937 | 0.9997 | 108.196 | 13.9034 | 2.1 |
| 215 | 42 | Partial curve; high efficacy | −5 | 2.1211 | 0.9999 | 87.4293 | 13.9023 | 2.1 |
| 216 | 42 | Partial curve; partial efficacy | −5 | 0.8 | 0.9996 | 94.4089 | 3.67 | 2.2 |
| 217 | 42 | Partial curve; partial efficacy | −5 | 3.0654 | 0.9995 | 66.1813 | 9.7958 | 2.2 |
| 218 | 42 | Partial curve; partial efficacy | −5 | 3.6272 | 0.9998 | 71.8402 | 13.7566 | 2.2 |
| 219 | 42 | Partial curve; partial efficacy | −4.95 | 1.5936 | 0.9993 | 76.3682 | −7.5793 | 2.2 |
| 220 | 42 | Partial curve; high efficacy | −4.95 | 3.2975 | 0.9995 | 95.08 | 8.1688 | 2.1 |
| 221 | 41 | Partial curve; partial efficacy | −4.95 | 4.095 | 0.9994 | 66.5046 | 7 | 2.2 |
| 222 | 41 | Partial curve; partial efficacy | −4.9 | 4.095 | 0.9999 | 66.8444 | 9.8519 | 2.2 |

| No. | Excl'd Points | Max Response [%] | Activity at 0.307 uM [%] ** | Activity at 1.530 uM [%] ** | Activity at 7.660 uM [%] ** | Activity at 38.30 uM [%] ** |
|---|---|---|---|---|---|---|
| 1 | 0 0 0 0 | 190.551 | 0 | 142.678 | 198.344 | 190.551 |
| 2 | 0 0 0 0 | 222.818 | 9.5199 | 56.9884 | 175.022 | 222.818 |
| 3 | 0 0 0 0 | 158.59 | −34.2446 | 9.5695 | 153.966 | 158.59 |
| 4 | 0 0 0 0 | 136.632 | 9.8511 | 38.314 | 118.549 | 136.632 |
| 5 | 0 0 0 0 | 87.1241 | −1.7993 | 58.4455 | 87.2456 | 87.1241 |
| 6 | 0 0 0 0 | 68.1048 | −39.7851 | 19.1903 | 60.5602 | 68.1048 |
| 7 | 0 0 0 0 | 104.699 | 13.4132 | 25.2727 | 80.6487 | 104.699 |
| 8 | 0 0 0 0 | 94.3383 | −15.3725 | −10.6082 | 96.4184 | 94.3383 |
| 9 | 0 0 0 0 | 88.6572 | −24.4743 | 6.2893 | 68.0567 | 88.6572 |
| 10 | 0 0 0 0 | 101.819 | 0 | 11.3964 | 94.1328 | 101.819 |
| 11 | 0 0 0 0 | 101.791 | 0 | 7.5981 | 83.8704 | 101.791 |
| 12 | 0 0 0 0 | 100.299 | 12.3078 | 36.4535 | 84.576 | 100.299 |
| 13 | 0 0 0 0 | 95.6495 | −24.7665 | −27.3506 | 80.6874 | 95.6495 |
| 14 | 0 0 0 0 | 61.7295 | −21.6121 | 3.5416 | 59.0823 | 61.7295 |
| 15 | 0 0 0 0 | 73.6236 | −13.6594 | 4.7051 | 58.0277 | 73.6236 |
| 16 | 0 0 0 0 | 75.2018 | −30.2295 | 5.6414 | 58.1985 | 75.2018 |
| 17 | 0 0 0 0 | 67.6004 | −18.3073 | 9.3675 | 52.6808 | 67.6004 |
| 18 | 0 0 0 0 | 1767.43 | 7.745 | 30.584 | 357.845 | 1767.43 |
| 19 | 0 0 0 0 | 52.0677 | −20.1458 | 14.9627 | 43.8719 | 52.0677 |
| 20 | 0 0 0 0 | 82.8998 | −18.1348 | −4.4619 | 69.3278 | 82.8998 |
| 21 | 0 0 0 0 | 93.2691 | 2.856 | 0 | 75.5731 | 93.2691 |
| 22 | 0 0 0 0 | 82.8991 | 0 | 0 | 78.2915 | 82.8991 |
| 23 | 0 0 0 0 | 98.87 | 12.6255 | 18.8414 | 87.3421 | 98.87 |
| 24 | 0 0 0 0 | 81.3384 | 5.8865 | 19.6198 | 73.0848 | 81.3384 |
| 25 | 0 0 0 0 | 63.0097 | −16.5079 | 11.1354 | 54.5336 | 63.0097 |

TABLE 8-continued

Compound data

| | | | | | | |
|---|---|---|---|---|---|---|
| 26 | 0 0 0 0 | 56.0664 | −25.4416 | 4.5885 | 41.9493 | 56.0664 |
| 27 | 0 0 0 0 | 53.7617 | −26.1631 | 3.3138 | 51.6127 | 53.7617 |
| 28 | 0 0 0 0 | 54.6586 | −35.9928 | −20.5758 | 48.8507 | 54.6586 |
| 29 | 0 0 0 0 | 54.9055 | −23.8063 | −13.4709 | 35.9591 | 54.9055 |
| 30 | 0 0 0 0 | 73.4371 | −18.3179 | −9.0684 | 55.4601 | 73.4371 |
| 31 | 0 0 0 0 | 62.3312 | −22.9164 | −0.943 | 53.2493 | 62.3312 |
| 32 | 0 0 0 0 | 59.833 | −28.0565 | −9.4589 | 51.0458 | 59.833 |
| 33 | 0 0 0 0 | 31.0963 | −41.8046 | −14.3237 | 16.9691 | 31.0963 |
| 34 | 0 0 0 0 | 75.3947 | 9.4093 | 43.8029 | 74.3361 | 75.3947 |
| 35 | 0 0 0 0 | 71.7515 | 0 | 12.0467 | 71.5303 | 71.7515 |
| 36 | 0 0 0 0 | 78.5607 | 7.6747 | 25.7129 | 65.0516 | 78.5607 |
| 37 | 0 0 0 0 | 72.867 | −1.7745 | 15.279 | 70.7278 | 72.867 |
| 38 | 0 0 0 0 | 72.6726 | −0.6248 | −2.8833 | 69.1705 | 72.6726 |
| 39 | 0 0 0 0 | 69.0926 | −7.7641 | 5.5069 | 52.9348 | 69.0926 |
| 40 | 0 0 0 0 | 427.494 | −13.7066 | 5.577 | 25.2218 | 427.494 |
| 41 | 0 0 0 0 | 453.124 | 8.7547 | 9.7092 | 34.1487 | 453.124 |
| 42 | 0 0 0 0 | 481.034 | 20.1308 | 0 | 32.0577 | 481.034 |
| 43 | 0 0 0 0 | 131.214 | 13.6807 | 43.9438 | 94.2627 | 131.214 |
| 44 | 0 0 0 0 | 308.204 | −13.4703 | −18.7598 | 38.1168 | 308.204 |
| 45 | 0 0 0 0 | 413.716 | −16.6135 | 0.0514 | 18.6133 | 413.716 |
| 46 | 0 0 0 0 | 156.151 | −29.6685 | 4.4407 | 77.5979 | 156.151 |
| 47 | 0 0 0 0 | 142.448 | 17.1767 | 32.1719 | 97.3497 | 142.448 |
| 48 | 0 0 0 0 | 165.458 | −32.0109 | −23.2923 | 76.5902 | 165.458 |
| 49 | 0 0 0 0 | 150.952 | 2.3042 | 15.4629 | 102.178 | 150.952 |
| 50 | 0 0 0 0 | 176.497 | 7.9011 | 9.4014 | 94.1426 | 176.497 |
| 51 | 0 0 0 0 | 249.102 | −27.9345 | −17.6035 | 31.4284 | 249.102 |
| 52 | 0 0 0 0 | 130.29 | −25.6891 | 1.731 | 86.3564 | 130.29 |
| 53 | 0 0 0 0 | 118.6 | 0 | 28.0603 | 71.9463 | 118.6 |
| 54 | 0 0 0 0 | 213.045 | 42.0153 | 58.6176 | 119.863 | 213.045 |
| 55 | 0 0 0 0 | 252.32 | −24.5803 | −12.1219 | 3.459 | 252.32 |
| 56 | 0 0 0 0 | 107.846 | 23.9844 | 38.0808 | 86.6615 | 107.846 |
| 57 | 0 0 0 0 | 112.914 | 1.0034 | 14.5781 | 82.1622 | 112.914 |
| 58 | 0 0 0 0 | 82.8269 | −29.6769 | 3.3459 | 49.0869 | 82.8269 |
| 59 | 0 0 0 0 | 183.88 | 0 | −6.1928 | 48.4893 | 183.88 |
| 60 | 0 0 0 0 | 115.466 | −10.9556 | 4.4512 | 78.2781 | 115.466 |
| 61 | 0 0 0 0 | 126.28 | −0.1233 | 25.8337 | 82.3962 | 126.28 |
| 62 | 0 0 0 0 | 154.66 | −21.3534 | −18.0137 | 77.9021 | 154.66 |
| 63 | 0 0 0 0 | 195.944 | −3.9508 | 2.2361 | 57.8488 | 195.944 |
| 64 | 0 0 0 0 | 128.914 | −6.3997 | 3.462 | 95.0937 | 128.914 |
| 65 | 0 0 0 0 | 464.087 | 8.214 | 2.5941 | 27.1667 | 464.087 |
| 66 | 0 0 0 0 | 225.365 | 16.1816 | 8.6821 | 32.7652 | 225.365 |
| 67 | 0 0 0 0 | 141.667 | 6.398 | 14.4975 | 69.8045 | 141.667 |
| 68 | 0 0 0 0 | 219.866 | −11.823 | −22.0487 | 4.4563 | 219.866 |
| 69 | 0 0 0 0 | 84.3602 | 0 | 16.1931 | 62.7677 | 84.3602 |
| 70 | 0 0 0 0 | 89.5048 | −15.4839 | 4.1098 | 57.1687 | 89.5048 |
| 71 | 0 0 0 0 | 109.03 | 0 | 9.6296 | 58.7582 | 109.03 |
| 72 | 0 0 0 0 | 132.126 | 0.9098 | −2.4849 | 54.5396 | 132.126 |
| 73 | 0 0 0 0 | 185.158 | 13.4604 | 18.6219 | 35.6621 | 185.158 |
| 74 | 0 0 0 0 | 84.2199 | −22.8223 | −9.7273 | 56.677 | 84.2199 |
| 75 | 0 0 0 0 | 95.9047 | 28.0842 | 39.9836 | 79.7093 | 95.9047 |
| 76 | 0 0 0 0 | 96.9841 | −5.8134 | 5.6525 | 55.1076 | 96.9841 |
| 77 | 0 0 0 0 | 85.0608 | −33.466 | −19.7149 | 54.711 | 85.0608 |
| 78 | 0 0 0 0 | 148.085 | 10.1341 | 15.4808 | 69.8478 | 148.085 |
| 79 | 0 0 0 0 | 80.1706 | 1.5242 | 16.235 | 57.3461 | 80.1706 |
| 80 | 0 0 0 0 | 145.969 | −4.7753 | 4.5639 | 65.9307 | 145.969 |
| 81 | 0 0 0 0 | 214.702 | 1.8272 | 5.1171 | 24.2861 | 214.702 |
| 82 | 0 0 0 0 | 84.7449 | 0 | 23.1094 | 63.7317 | 84.7449 |
| 83 | 0 0 0 0 | 149.231 | −13.5366 | −10.5766 | 41.5268 | 149.231 |
| 84 | 0 0 0 0 | 102.4 | −5.2905 | 11.0012 | 59.7194 | 102.4 |
| 85 | 0 0 0 0 | 100.92 | 3.2508 | 13.2564 | 71.6469 | 100.92 |
| 86 | 0 0 0 0 | 80.4147 | 10.3775 | 28.9147 | 57.3965 | 80.4147 |
| 87 | 0 0 0 0 | 86.5444 | 20.8761 | 26.4772 | 69.1414 | 86.5444 |
| 88 | 0 0 0 0 | 81.7691 | 12.5888 | 21.7607 | 50.5291 | 81.7691 |
| 89 | 0 0 0 0 | 74.1053 | −9.9886 | −0.2967 | 45.5813 | 74.1053 |
| 90 | 0 0 0 0 | 146.154 | 2.8256 | 8.1166 | 27.152 | 146.154 |
| 91 | 0 0 0 0 | 121.42 | −19.1946 | −13.3374 | 6.5712 | 121.42 |
| 92 | 0 0 0 0 | 74.9657 | 2.5679 | 13.3008 | 54.89 | 74.9657 |
| 93 | 0 0 0 0 | 101.857 | −3.4693 | 0 | 36.266 | 101.857 |
| 94 | 0 0 0 0 | 137.756 | 11.4997 | 8.6578 | 36.5266 | 137.756 |
| 95 | 0 0 0 0 | 67.941 | −12.4138 | 3.0575 | 36.2186 | 67.941 |
| 96 | 0 0 0 0 | 73.1974 | −7.8942 | 1.1034 | 54.4732 | 73.1974 |
| 97 | 0 0 0 0 | 79.2643 | 1.9074 | 1.3725 | 59.0705 | 79.2643 |
| 98 | 0 0 0 0 | 125.383 | −0.0399 | 0.1051 | 28.903 | 125.383 |
| 99 | 0 0 0 0 | 114.004 | 0.7442 | 1.7316 | 44.4339 | 114.004 |
| 100 | 0 0 0 0 | 56.3462 | −24.5207 | −4.9865 | 30.1418 | 56.3462 |
| 101 | 0 0 0 0 | 104.197 | −14.2124 | −11.5581 | 43.2955 | 104.197 |
| 102 | 0 0 0 0 | 158.9 | 10.2684 | 11.2981 | 24.3058 | 158.9 |
| 103 | 0 0 0 0 | 91.3206 | −22.0036 | −16.3773 | 50.2037 | 91.3206 |

TABLE 8-continued

| | | | Compound data | | | |
|---|---|---|---|---|---|---|
| 104 | 0 0 0 0 | 127.457 | −6.4868 | −11.6559 | 27.3282 | 127.457 |
| 105 | 0 0 0 0 | 112.32 | 15.3847 | 17.8982 | 44.2423 | 112.32 |
| 106 | 0 0 0 0 | 70.115 | −0.495 | 9.0228 | 40.4026 | 70.115 |
| 107 | 0 0 0 0 | 73.3496 | −17.2197 | −3.2434 | 45.9779 | 73.3496 |
| 108 | 0 0 0 0 | 140.923 | 2.0308 | 3.1422 | 15.3462 | 140.923 |
| 109 | 0 0 0 0 | 173.731 | 5.1999 | 10.0589 | 20.86 | 173.731 |
| 110 | 0 0 0 0 | 161.275 | −18.9356 | −17.8813 | 0 | 161.275 |
| 111 | 0 0 0 0 | 89.9207 | 4.1224 | 15.4494 | 54.5855 | 89.9207 |
| 112 | 0 0 0 0 | 73.7713 | 0 | 1.5319 | 54.0265 | 73.7713 |
| 113 | 0 0 0 0 | 105.027 | −4.9426 | −7.7278 | 23.4771 | 105.027 |
| 114 | 0 0 0 0 | 134.559 | −6.7171 | −1.2468 | 17.1799 | 134.559 |
| 115 | 0 0 0 0 | 77.6085 | −3.9401 | 0 | 40.2449 | 77.6085 |
| 116 | 0 0 0 0 | 84.9032 | −9.1033 | −3.9425 | 36.7288 | 84.9032 |
| 117 | 0 0 0 0 | 82.2017 | 0 | 5.0693 | 43.6203 | 82.2017 |
| 118 | 0 0 0 0 | 73.5555 | −8.1247 | 2.294 | 48.7391 | 73.5555 |
| 119 | 0 0 0 0 | 111.66 | −17.1068 | −14.6664 | 0.6285 | 111.66 |
| 120 | 0 0 0 0 | 97.3577 | 17.804 | 33.8372 | 63.3531 | 97.3577 |
| 121 | 0 0 0 0 | 92.5902 | 6.8559 | 8.4589 | 45.0425 | 92.5902 |
| 122 | 0 0 0 0 | 107.455 | 2.4969 | 11.4724 | 54.0343 | 107.455 |
| 123 | 0 0 0 0 | 85.4512 | 5.1227 | 12.1485 | 45.1238 | 85.4512 |
| 124 | 0 0 0 0 | 85.8569 | −19.2219 | −7.3929 | 35.4594 | 85.8569 |
| 125 | 0 0 0 0 | 107.624 | 0 | 9.2558 | 50.3725 | 107.624 |
| 126 | 0 0 0 0 | 101.717 | 5.1764 | 18.9708 | 58.0571 | 101.717 |
| 127 | 0 0 0 0 | 151.123 | −20.0375 | −16.1406 | −2.9507 | 151.123 |
| 128 | 0 0 0 0 | 152.324 | 17.3412 | 12.5761 | 22.6146 | 152.324 |
| 129 | 0 0 0 0 | 127.052 | −21.7078 | −15.591 | 8.9584 | 127.052 |
| 130 | 0 0 0 0 | 127.365 | 7.1779 | 9.1804 | 26.1033 | 127.365 |
| 131 | 0 0 0 0 | 182.302 | 10.6925 | 7.1202 | 16.169 | 182.302 |
| 132 | 0 0 0 0 | 133.154 | 11.1461 | 13.8268 | 23.024 | 133.154 |
| 133 | 0 0 0 0 | 70.2432 | −25.994 | −28.4428 | 5.985 | 70.2432 |
| 134 | 0 0 0 0 | 72.8618 | −20.9617 | −23.9361 | −0.0686 | 72.8618 |
| 135 | 0 0 0 0 | 62.005 | −28.5367 | −29.3616 | −11.1775 | 62.005 |
| 136 | 0 0 0 0 | 65.1019 | 2.0231 | 14.5105 | 38.0502 | 65.1019 |
| 137 | 0 0 0 0 | 61.7759 | −19.2435 | −19.3578 | −1.6699 | 61.7759 |
| 138 | 0 0 0 0 | 85.8466 | −26.0685 | −19.0518 | 23.5861 | 85.8466 |
| 139 | 0 0 0 0 | 81.696 | 15.171 | 14.5765 | 24.988 | 81.696 |
| 140 | 0 0 0 0 | 75.9628 | −2.7644 | −4.956 | 22.8114 | 75.9628 |
| 141 | 0 0 0 0 | 82.663 | −17.1706 | −18.2787 | 2.6033 | 82.663 |
| 142 | 0 0 0 0 | 68.9039 | −17.1048 | −18.6659 | 16.7527 | 68.9039 |
| 143 | 0 0 0 0 | 80.844 | 4.2822 | 4.8849 | 22.4204 | 80.844 |
| 144 | 0 0 0 0 | 102.992 | 8.5445 | 11.1102 | 20.4218 | 102.992 |
| 145 | 0 0 0 0 | 70.5123 | 0.3023 | 0.1807 | 15.6647 | 70.5123 |
| 146 | 0 0 0 0 | 75.4881 | −20.8468 | −20.9197 | 0 | 75.4881 |
| 147 | 0 0 0 0 | 84.9194 | 0.4502 | 2.7027 | 29.0697 | 84.9194 |
| 148 | 0 0 0 0 | 102.444 | −30.0492 | −26.8413 | 12.5122 | 102.444 |
| 149 | 0 0 0 0 | 68.0415 | −0.1259 | 8.5917 | 37.0328 | 68.0415 |
| 150 | 0 0 0 0 | 67.1116 | 0 | 0.1599 | 15.1419 | 67.1116 |
| 151 | 0 0 0 0 | 63.6617 | −26.5586 | −25.9538 | 2.045 | 63.6617 |
| 152 | 0 0 0 0 | 67.3709 | −6.7254 | 0 | 26.2892 | 67.3709 |
| 153 | 0 0 0 0 | 66.0451 | −20.7719 | −14.2846 | 26.1958 | 66.0451 |
| 154 | 0 0 0 0 | 38.9061 | −36.1249 | −14.4105 | 17.8641 | 38.9061 |
| 155 | 0 0 0 0 | 60.5343 | −32.0766 | −31.7653 | −9.1234 | 60.5343 |
| 156 | 0 0 0 0 | 65.3359 | 0 | 0 | 22.9027 | 65.3359 |
| 157 | 0 0 0 0 | 67.4685 | −0.7059 | −3.266 | 17.7416 | 67.4685 |
| 158 | 0 0 0 0 | 65.8674 | 0.6705 | 0.6338 | 26.3415 | 65.8674 |
| 159 | 0 0 0 0 | 105.826 | −4.2541 | −1.9112 | 17.1057 | 105.826 |
| 160 | 0 0 0 0 | 99.7859 | −2.4977 | −3.3563 | 16.0042 | 99.7859 |
| 161 | 0 0 0 0 | 48.073 | −37.0265 | −17.738 | 22.4249 | 48.073 |
| 162 | 0 0 0 0 | 54.2827 | −31.8337 | −27.5288 | 26.3243 | 54.2827 |
| 163 | 0 0 0 0 | 78.1035 | −0.8037 | −0.3894 | 19.4261 | 78.1035 |
| 164 | 0 0 0 0 | 91.6418 | 1.1551 | 0.0123 | 22.043 | 91.6418 |
| 165 | 0 0 0 0 | 107.713 | −20.5064 | −20.4325 | 0 | 107.713 |
| 166 | 0 0 0 0 | 87.6791 | 10.2974 | 15.5578 | 41.6567 | 87.6791 |
| 167 | 0 0 0 0 | 43.999 | −38.1941 | −33.4689 | 9.5564 | 43.999 |
| 168 | 0 0 0 0 | 77.8049 | | 0 | 35.7996 | 77.8049 |
| 169 | 0 0 0 0 | 64.3252 | −18.1947 | −21.5953 | 0.301 | 64.3252 |
| 170 | 0 0 0 0 | 87.6323 | 2.3641 | 5.3324 | 22.1704 | 87.6323 |
| 171 | 0 0 0 0 | 68.362 | 10.0449 | 10.2067 | 28.1342 | 68.362 |
| 172 | 0 0 0 0 | 71.1503 | 8.9457 | 7.2239 | 31.1775 | 71.1503 |
| 173 | 0 0 0 0 | 72.2674 | 10.3627 | 21.0562 | 42.1173 | 72.2674 |
| 174 | 0 0 0 0 | 74.1998 | −21.7408 | −16.656 | 13.5733 | 74.1998 |
| 175 | 0 0 0 0 | 48.1163 | −59.8895 | −45.4644 | 5.3909 | 48.1163 |
| 176 | 0 0 0 0 | 95.8578 | −22.0943 | −16.8813 | 5.2636 | 95.8578 |
| 177 | 0 0 0 0 | 71.1427 | 1.3136 | 0.2953 | 16.2008 | 71.1427 |
| 178 | 0 0 0 0 | 64.2561 | −21.1531 | −11.2645 | 18.8833 | 64.2561 |
| 179 | 0 0 0 0 | 46.8236 | −35.3915 | −32.1742 | 20.8832 | 46.8236 |
| 180 | 0 0 0 0 | 75.0675 | 0 | −2.3977 | 21.2822 | 75.0675 |
| 181 | 0 0 0 0 | 92.8383 | 12.3946 | 12.9169 | 18.8847 | 92.8383 |

TABLE 8-continued

Compound data

| | | | | | | |
|---|---|---|---|---|---|---|
| 182 | 0 0 0 0 | 93.5709 | 0 | 0 | 34.7191 | 93.5709 |
| 183 | 0 0 0 0 | 99.5289 | 0 | 2.0346 | 24.4291 | 99.5289 |
| 184 | 0 0 0 0 | 83.8533 | 0 | −0.5506 | 26.0285 | 83.8533 |
| 185 | 0 0 0 0 | 94.548 | −21.6443 | −24.0045 | 0 | 94.548 |
| 186 | 0 0 0 0 | 37.2481 | −37.158 | −17.69 | 15.0968 | 37.2481 |
| 187 | 0 0 0 0 | 51.5472 | −53.6324 | −42.397 | −1.7858 | 51.5472 |
| 188 | 0 0 0 0 | 88.0501 | 0 | 0.7946 | 19.9555 | 88.0501 |
| 189 | 0 0 0 0 | 66.7349 | 13.1405 | 23.7073 | 43.9763 | 66.7349 |
| 190 | 0 0 0 0 | 79.582 | −30.5111 | −25.2626 | 6.3098 | 79.582 |
| 191 | 0 0 0 0 | 96.0338 | −18.0752 | −19.9657 | −4.197 | 96.0338 |
| 192 | 0 0 0 0 | 76.1007 | 0.8898 | 2.9636 | 15.9079 | 76.1007 |
| 193 | 0 0 0 0 | 91.5294 | 3.7365 | 1.9996 | 17.8759 | 91.5294 |
| 194 | 0 0 0 0 | 68.0475 | −2.4257 | 0 | 30.6498 | 68.0475 |
| 195 | 0 0 0 0 | 89.3989 | −7.8811 | −12.0365 | 15.2586 | 89.3989 |
| 196 | 0 0 0 0 | 65.0912 | 0 | 0 | 20.6484 | 65.0912 |
| 197 | 0 0 0 0 | 66.8554 | 5.2461 | 15.7031 | 40.796 | 66.8554 |
| 198 | 0 0 0 0 | 79.0861 | 2.3908 | 0 | 17.574 | 79.0861 |
| 199 | 0 0 0 0 | 78.1385 | 0 | 7.6087 | 32.1891 | 78.1385 |
| 200 | 0 0 0 0 | 46.2423 | −40.8885 | −35.7652 | 1.5723 | 46.2423 |
| 201 | 0 0 0 0 | 69.7901 | −21.5136 | −17.1084 | 8.0866 | 69.7901 |
| 202 | 0 0 0 0 | 74.538 | −3.4095 | −0.6635 | 28.063 | 74.538 |
| 203 | 0 0 0 0 | 51.7897 | −45.9905 | −36.9465 | 8.4225 | 51.7897 |
| 204 | 0 0 0 0 | 70.2936 | 0.8815 | 0.1572 | 20.0962 | 70.2936 |
| 205 | 0 0 0 0 | 50.1627 | −39.3964 | −31.6886 | 12.0722 | 50.1627 |
| 206 | 0 0 0 0 | 91.1628 | 12.1077 | 15.2718 | 28.5203 | 91.1628 |
| 207 | 0 0 0 0 | 73.3009 | 0.545 | 0 | 25.4562 | 73.3009 |
| 208 | 0 0 0 0 | 73.4157 | −7.8355 | −10.7764 | 16.4066 | 73.4157 |
| 209 | 0 0 0 0 | 138.801 | 12.9601 | 10.613 | 18.5675 | 138.801 |
| 210 | 0 0 0 0 | 113.044 | 13.8203 | 9.4299 | 20.2893 | 113.044 |
| 211 | 0 0 0 0 | 87.88 | 0.2296 | 11.6146 | 43.0472 | 87.88 |
| 212 | 0 0 0 0 | 127.53 | 11.1275 | 7.371 | 15.9241 | 127.53 |
| 213 | 0 0 0 0 | 90.1221 | 0 | 6.4924 | 41.084 | 90.1221 |
| 214 | 0 0 0 0 | 101.307 | 13.239 | 16.0649 | 43.8718 | 101.307 |
| 215 | 0 0 0 0 | 83.2597 | 14.2367 | 15.1789 | 40.8331 | 83.2597 |
| 216 | 0 0 0 0 | 71.6749 | 8.2756 | 20.8299 | 43.9905 | 71.6749 |
| 217 | 0 0 0 0 | 65.2014 | 10.407 | 9.2853 | 27.4661 | 65.2014 |
| 218 | 0 0 0 0 | 71.4891 | 13.9594 | 13.1115 | 29.7899 | 71.4891 |
| 219 | 0 0 0 0 | 66.0085 | −8.2231 | −3.0469 | 21.4195 | 66.0085 |
| 220 | 0 0 0 0 | 93.7673 | 7.1434 | 9.5135 | 27.6356 | 93.7673 |
| 221 | 0 0 0 0 | 66.1162 | 6.3785 | 7.8673 | 16.8498 | 66.1162 |
| 222 | 0 0 0 0 | 66.4815 | 9.4439 | 9.7686 | 16.5469 | 66.4815 |

Example 3

In this example, embodiments of small molecules that increase α7 integrin in skeletal muscle are disclosed. Using myogenic cells from mice in which the LacZ reporter gene was inserted into exon 1 of the mouse α7 integrin gene, 403,000 compounds were screened and more than 1500 hits that increased the β-galactosidase reporter were identified. Further evaluation identified 6 compounds that increased α7 integrin at least 1.5-fold in myotubes. Compounds were classified as iron chelating compounds, cell cycle inhibitors and compounds with undefined function. Compounds identified from this screen represent novel molecular probes that can be used to further elucidate regulation of α7β1 integrin expression and signaling in skeletal muscle and may serve as potential therapeutics for the treatment of DMD.

Several therapeutic approaches have been developed with the aim of restoring dystrophin expression and shown efficacy in animal models of DMD. These include virally mediated delivery and expression of dystrophin, myoblast cell transfer and engraftment, exon-skipping and stop-codon read-through. Currently, none of these methods have been approved as therapy for DMD patients. An alternative approach is to target and enhance levels of proteins which modify disease progression and act to partially compensate for the absence of dystrophin. These disease modifiers include utrophin, α7β1 integrin, GalNac, nNos and Adam12.

The α7β1 integrin is a laminin receptor in skeletal muscle that serves to link laminin-211/221 in the basal lamina and the actin cytoskeleton of muscle. The α7β1 integrin has structural and signaling functions that contribute to muscle development and physiology and was originally identified as a marker for muscle differentiation. Studies have shown that enhanced transgenic expression of the α7 integrin in skeletal and cardiac muscle can ameliorate dystrophic pathology and extend the lifespan of mdx/utr$^{-/-}$ mice more than three-fold. Multiple mechanisms appear to contribute to α7 integrin mediated rescue of dystrophin deficient muscle including maintenance of myotendinous and neuromuscular junctions, enhanced muscle hypertrophy and regeneration, and decreased apoptosis and cardiomyopathy. Enhanced α7 integrin also protects muscles against exercise-induced damage. Conversely loss of the α7 integrin in mdx mice results in more severe muscle disease. Together these observations support the idea that the α7β1 integrin is a major disease modifier in DMD.

To translate transgenic mouse studies into potential therapies for DMD, a drug discovery program to identify chemical probes that increase α7 integrin in skeletal muscle was initiated. A report on the generation and characterization of an α7 integrin knockout line of mice in which the LacZ gene is inserted into intron 1, downstream of the endogenous α7 integrin promoter has been reported. Thus, β-galactosidase functions as a reporter for α7 integrin expression in these animals. Primary myogenic cells were isolated from a heterozygous mouse (α7βgal$^{+/-}$) so that the cells express α7 integrin and also report for transcription of the integrin. The myogenic reporter cells were designated α7βgal$^{+/-}$ and were used to identify two molecules, valproic acid and laminin-111, in preliminary screens and have been successfully tested in mouse models of DMD.

To identify further small molecules that increase α7 integrin in skeletal muscle, a muscle cell-based assay to screen 403,000 compounds including FDA approved drugs and the large compound libraries at the National Chemical and Genomics Center (NCGC) was used. Several compounds that increase the α7 integrin with known mechanisms of action including iron chelators, microtubule inhibitors, cell cycle inhibitors and steroid-like molecules were identified. Additionally, several small molecules with unknown biological activities were identified. Overall, the results identified novel small molecules that increase the α7 integrin in cultured muscle cells and may serve as molecular probes to further dissect signaling pathways that regulate the α7β1 integrin in skeletal muscle. These small molecules could potentially be developed as novel therapeutics in the treatment of Duchenne and other fatal muscular dystrophies.

Cell Culture:

C2C12 myoblasts and myotubes were grown as previously described. α7$^{+/LacZ}$ myoblasts were originally isolated and maintained as described. Briefly, myoblasts were grown and maintained in DMEM without phenol red (Sigma) containing 20% FBS (Atlanta Biologicals), 1% Penicillin/Streptomycin (P/S) (GIBCO)+L-Glutamine (GIBCO). Myoblasts were maintained below 70% confluence until use in assay. Myoblasts were differentiated into myotubes in DMEM without phenol red, 1% horse-serum (Atalanta Biologicals), and 1% P/S+L-Glutamine. All cells were incubated at 37° C. with 5% $CO_2$. Assays were performed on myoblasts and myotubes between passages 8 and 14.

Compound Libraries:

Four compound libraries were screened using our muscle cell based assay: 1) Prestwick Chemical and Microsource Spectrum Libraries (BioFocus DPI, Leiden Netherlands with facilities in UK, Basel, Heidelberg) (Overington et al., 2006). 2) DIVERSet library (Chembridge Corp., San Diego, Calif.) and compounds from the ChemDiv library. 3) LOPAC library (Sigma-RPI) consists of 1280 pharmaceutically active compounds. 4) MLSMR-Molecular Libraries Small Molecule Repository.

Myoblast α7$^{+/LacZ}$ Integrin FDG Assay:

A total of 5000 α7βgal$^{+/-}$ myoblasts were dispensed in 1.00 μL growth media using a 12-well multi-pipette (Rainin) onto Nunc black sided TC coated 96-well plate. After 24 hours up to 1 μl of compound in DMSO was added to the myoblast plates from pre-made working drug plates using a 1 μl 96-well pin tool or using an 8-well automatic multi-channel pipette. Each working drug plate contained a column of a positive control (sodium butyrate (Fluka) or SU9516 (Tocris)) and at least one column containing DMSO alone. After incubating for 48 hours the media was aspirated, and cells were lysed with 50 μL of Mammalian Protein Extraction Reagent (MPER) (Thermo) per well followed by incubation at room temperature for 10 minutes. β-galactosidase (βgal) activity in each well was quantified by adding 50 μL of FDG assay solution (20% 0.1M sodium phosphate buffer pH 7.0 (Sigma), 0.2% 1M $MgCl_2$ (Sigma), 0.2% 20 mM fluorescein di-galactoside (FDG) (Marker Gene Technologies)) and incubating the plates in the dark for 20 minutes at room temperature. Stop solution (2×TE) was then added (100 μl/well) and plates were read for fluorescence on the Victor V (Perkin-Elmer) with an excitation filter at 485 nm, an emission filter at 535 nm, and a 0.1 s/well count time.

Myotube α7 Integrin FDG Assay:

A total of 25,000 α7βgal$^{+/-}$ myoblasts were dispensed in 100 μL growth media. After 24 hours, growth media was aspirated, wells were washed with 200 μL PBS, and 100 μL/well of differentiation media was added. Differentiation media was changed daily between 72 and 120 hours, and up to 1 μL compounds in DMSO were added as previously described once wells contained differentiated myotubes. The FDG fluorescence assay was performed as described in the myoblast screen with the one notable exception being the incubation after FDG solution addition being shortened from 20 minute to 5 minutes at RT due to the higher levels of βgal in myotubes.

qHTS of the LOPAC Library and MLSMR:

A total of 250 α7LacZ$^{+/-}$ myoblasts at passage 13 were dispensed using a mulitdrop (Thermo) into black low base tissue culture treated microclear aurora plates in 6 μl media containing DMEM without phenol, 5% FBS, 1× GluMax and 1× Penicillin/Streptomycin. The plates were incubated 16-24 hours at 37 C., 5% CO2, 95% humidity covered with low evaporation stainless steel lids from Kalypsys. Compounds were then dispensed using a Kalypsys pintool to deliver 23 nl/well compounds in DMSO (diluted into 6 μl resulting in a 1:260 dilution of compound). The positive control compound used was the cdk2 inhibitor SU9516 (Tocris) (identified in the initial LOPAC screen). The plates were incubated for 48 hours at 37 C., 5% CO2, 95% humidity using the same stainless steel lids. After incubation with compound, 5 μl of the media was aspirated using the Kalypsys washer/dispenser and 3 μl of the Mammalian Protein Extraction Reagent (MPER) lysis buffer (Thermo Fisher) was added. The plates were spun at 2000 rpm to remove bubbles and an initial capture was acquired on the Viewlux (Perkin Elmer) with excitation at 480 nm and emission at 540 nm for 25 seconds to omit any auto fluorescent compounds. The plates were then incubated for 10 minutes at room temperature. After incubation, 3 μl of 125 μM FDG (Marker Gene Technologies) diluted in PBS with 2 mM $MgCl_2$ and 0.2% β-mercaptoethanol (BME) was added, the plates were then centrifuged at 2000 rpms and incubated for 30 minutes at room temperature. The plates were again read on the Viewlux with excitation at 480 nm and emission at 540 nm for 25 seconds.

CMV-LacZ Secondary Screen:

In order to determine compounds that acted to stabilize β-gal in myogenic cells, a CMV-LacZ C2C12 cell line was used in a secondary screen. The EGFP gene from the pEGFP (Clontech) vector was replaced by LACZ PCR product with digests of the vector/PCR product performed using EcoRI (NEB) and NodI (NEB) and ligated using T4 DNA Ligase (NEB) following standard procedures to produce the CMV-LACZ vector. The LACZ gene was generated by PCR from the pBK-RSV (Stratagene) vector using primers LACZ EcoRI F- and LACZ NotI R-. The CMV-LACZ vector was then digested with AfiII (NEB) to linearize the construct, which was then transfected in C2C12 myoblasts using Lipofectamine 2000 (Invitrogen) following the manufacturer's instructions. Stable cell lines were selected in growth medium containing G418 (Life Technologies) at 1.5 mg/ml. Clonal lines were selected and screened for βgal levels using the myoblast FDG assay. C2C12 cell lines with the highest βgal expression were used to screen cherry picked compounds, following the same procedures defined above for the myoblast and myotube screens. Compounds were determined to have failed this secondary assay if signal was elevated above the average DMSO+2× standard deviation (~30%) for two separate data points.

Western Blotting:

C2C12 myotubes were treated for 48 hours with each hit compound, washed with PBS, then scraped and pelleted using standard procedures. Cell pellets were resuspended in RIPA buffer and protein concentration determined by BCA. Approximately 10 μg of protein was loaded per lane and separated on 8% SDS-PAGE gels and transferred to nitrocellulose using standard conditions. Blots were probed using α7A and α7B integrin specific rabbit polyclonal antibody as previously described and normalized to α-tubulin.

Statistical Analysis and Curve-Fitting:

Statistical analysis was performed using Graphpad Prism software and unpaired t-test comparison against the DMSO control treatment group. Graphpad prism software was also used to fit curves using nonlinear regression analysis with log (agonist) vs. response with a variable slope. A constraint equal to 1 was placed on the bottom of the curve and either 2 or 2.5 at the top (when needed) in order to produce appropriate $EC_{50}$ values.

Figure 4D:
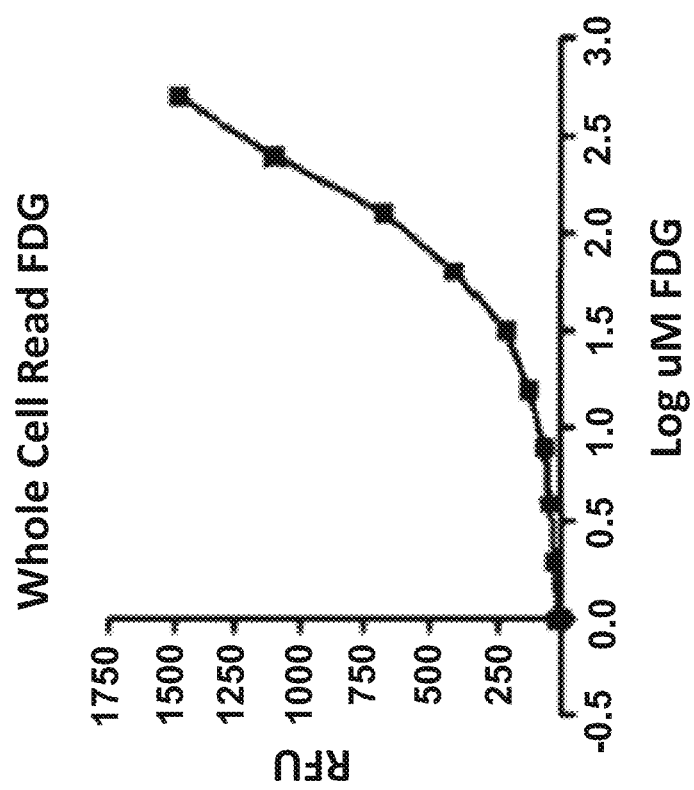
(FIG. 4D) The α7$^{+/LacZ}$ myotube assay response with varying levels of FDG in the FDG Buffer.

Generation and Validation of $\alpha 7^{+/LacZ}$ Integrin Myoblast Assay:

In order identify α7 Integrin enhancing compounds, an assay based on $\alpha 7^{+/LacZ}$ mouse derived primary myoblasts and myotubes was developed. Heterozygous myoblasts were used in order to maintain a copy of the Itga7 gene for normal myogenic cell adhesion and signaling. The second Itga7 gene allele had exon 1 replaced by the LacZ gene, providing a reporter for α7 integrin transcription and maintaining the endogenous promoter, enhancer, and chromatin environment. By deriving primary muscle cells, myogenic cells capable of differentiating into myotubes and in which the μ-gal reporter levels accurately mimicked the α7 integrin protein levels during this developmental process were produced. Several rounds of pre-plating were performed with the myogenic line used for the screen in order to remove fibroblasts, leaving a relatively pure population of myogenic cells.

α7 Integrin Muscle Cell-Based Assay:

Assessing the growth rate of myogenic cells in a 96-well format was carried out. For the myoblast assay, it was determined that plating 5000 $\alpha 7^{+/LacZ}$ cells led to a confluence of ~80% at the time of fluorescence quantification. Limiting the confluence to less than 80% helped prevent entry into a differentiated state in this assay which may affect LacZ expression. For the myotube assay, it was determined that plating 25,000 myoblasts led to a confluence of around 95% after 24 hours allowing myogenic differentiation to proceed. Next, the linearity of fluorescence for the assay was determined for various amounts of purified E. coli β-galactosidase using the FDG assay solution (FIG. 4A). This displayed a linear response that was comparable to levels observed in the $\alpha 7^{+/LacZ}$ myoblasts. Finally, as library compounds are normally solubilized in DMSO, the effects of DMSO on our assay were examined for both myoblasts and myotubes (FIG. 4B). In myoblasts, DMSO concentrations of up to 0.5% had no significant effect on the assay compared to cells without DMSO addition (FIG. 4C). At 1% DMSO, there was a 10% decrease in overall fluorescent signal in the assay, which was considered to be within acceptable range (FIG. 4C). The effect of DMSO on the myotube assay was more robust, where 0.5% DMSO decreased fluorescence by ~12% and 1% DMSO displayed ~25% decrease in overall fluorescence (FIG. 4B). Greater than 1% DMSO resulted in reduced fluorescence and therefore 1% DMSO in media was determined to be the maximum acceptable level for myotubes. The levels of FDG were optimized to 125 μM which was used in the MLSMR screen and subsequent verification assays (FIG. 4D).

For our preliminary screens, sodium butyrate was determined to increase β-galactosidase levels with treatments of ~1.5 mM. In initial studies with sodium butyrate a Z' factor of 0.6, which is considered a strong assay for drug discovery, was calculated and thus a myotube screen of the Prestwick Chemical at 0.2 ug/mL and Microsource Spectrum Libraries at 10 μM was initiated. As these libraries are relatively small, myotubes were initially screened because they are the ideal therapeutic target for α7 Integrin elevation. Using a 1.2 fold increase over DMSO control as the minimum cutoff, 24 compounds in the Prestwick chemical library and 30 compounds in the Microsource spectrum library were identified. These corresponded to a hit percentage of 2.1% and 1.5% of the libraries. After secondary and counter screens, the compounds that increased α7 integrin were classified as either iron chelators or a cholesterol analog. The iron chelators identified in the screen were Ciclopirox ethanolamine, deferoxamine, and 2,2-Dipyridyl which all displayed positive dose-response curves in myotubes. The cholesterol analog compound. 5alpha-cholestan-3β-ol-6-one, also displayed a positive dose-response curve.

This initial success led us to attempt a larger scale high-throughput screen (HTS) using the DIVERSet library of compounds with sodium butyrate as a positive control. Due to the number of compounds in the DIVERSet library (~50,000), a myoblast screen was performed. This screen generated several more "hits" which upon secondary screens were narrowed down to three compounds annotated: 1001, 1002, and 1003. After further studies, these compounds and analogs were either less robust or too toxic to move forward with further studies.

Figure 5A:
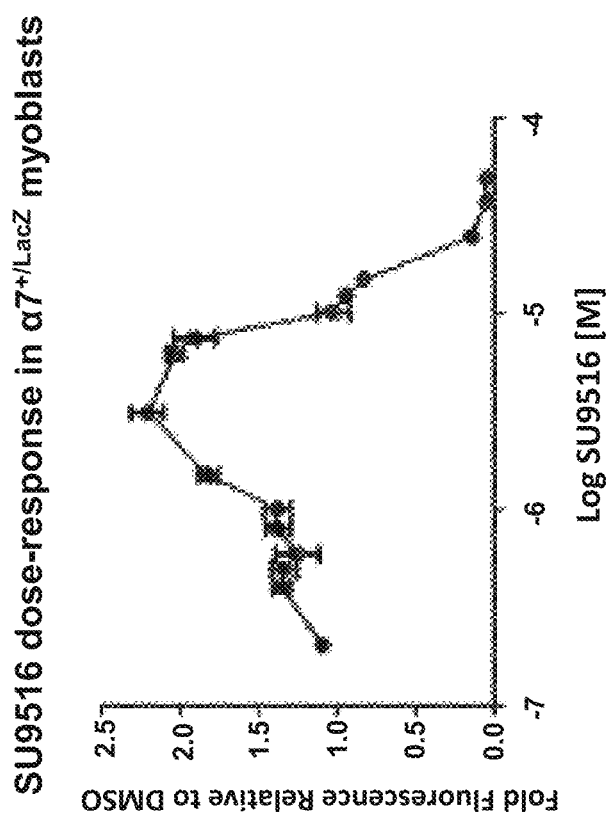

Primary Screen of LOPAC Library and the MLSMR:

The assay was adapted for a high-throughput screen with the fully automated Kalypsys robotic system using 1536 well plates at NCGC. A preliminary screen of the LOPAC library with 1001 (DIVERSet) as a positive control was used to develop the new conditions for this assay, comparing offline to online results and reducing myoblasts plated to 2000 cells/well for the 384-well format. This screen produced several "hit" compounds including Sodium Nitroprusside dihydrate, a Nitric oxide donor, and two cdk2 inhibitors SU9516 and CK2 inhibitor 2. SU9516 gave a relatively robust response of around 2.1-fold, relative to DMSO alone. There was still a relatively high variability in DMSO background signal (~30%) even using SU9516 as a positive control. However, as SU9516 was the most reproducibly active drug that had been identified it was selected as a positive control for the qHTS. To this end a dose-response curve SU9516 treatment of myoblasts and myotubes was generated (FIGS. 5A and 5B).

Using SU9516 as a positive plate control and DMSO as a negative control, the assay was then used to screen the Molecular Libraries Small Molecule Repository (MLSMR) of 368,680 compounds at NIH Chemical Genomics Center (NCGC) using concentrations at 0.08 μM, 0.4 μM, 2 μM, and 10 μM. Around 1500 compounds were cherry picked as "hits" based on previously defined curve classifications (FIG. 6).

Offline Confirmation and β-Galactosidase Stability Secondary Screen:

From the 1500 cherry picked "hits" two pools were chosen for further off-line myoblast, myotube and secondary screening. The first pool consisted of 166 compounds, which were still active in a subsequent online myoblast screening of the original 1500 cherry picks (Tables 9-12). The second pool consisted of the top 197 compounds, which had not been repeatedly active in subsequent screens (Tables 9-12). Finally, as SU9516 had proven to be a highly reliable positive control, 44 analogs, based on the SU9516 platform, were selected from the MLSMR library or from separate stock compounds and screened. The secondary screen consisted of a CMV-LACZ stably transfected C2C12 myoblast line with consistent β-Galactosidase activity (Tables 9-16, and Table 17). The assays were used the original 96-well format and new dose-response curves for myoblasts (N=3-6 replicates for each data point), myotubes (N=3-6 replicates for data point), and CMV-LacZ secondary assay (N=2 replicates for each data point) using concentrations of 0.5 μM, 1 μM, 10 μM, 20 μM, and 40 μM (Tables 9-16). A cutoff of greater than 25% relative to DMSO was used to exclude compounds (Table 17). Almost one fifth of the compounds from the initial 197 top "hits" worked exclusively in myotubes assay and not in myoblasts. Together, this data suggested that during the primary screen some of the cells in the assay had differentiated into myotubes. This trend was not observed in the 166 NCGC compounds where almost one third worked exclusively in myoblasts. Again, during the transition from on-line to off-line screening many of the compounds from both groups (54% and 69%, Table 17) failed to achieve the minimum cutoff of 25% increase over DMSO levels in either myoblasts or myotubes. In addition the majority of compounds, which showed activity in the β-galactosidase stabilizing secondary screen, did not show activity in either of the $\alpha 7^{+/LacZ}$ based assays (Table 17, full results in Tables 9-12). These results suggest some of these compounds may not be actually stabilizing or catalyzing the β-galactosidase enzymatic reaction but instead may be activating the CMV promoter in the C2C12 cells.

As SU9516 was used as our positive control, it was used to potentially represent a platform that could be modified to produce other "hit" compounds off-line screens with 44 SU9516 analogs were performed. The myoblast, myotube, and secondary CMV-LacZ assays were performed as previously described and results from this screen are summarized in Table 17 (Full results in Tables 13-16). Surprisingly, many of them, as with SU9516 itself, showed activity in the C2C12 CMV-LACZ myoblasts and myotubes. Most of the compounds had activity in the β-galactosidase stabilizing screen also had no response in the primary screen suggesting that they were not β-galactosidase stabilizers but instead activators of CMV or the region of CMV-LACZ stable integration within this cell line. This result also suggests that SU9516 was likely activating both the ITGA7 promoter and the CMV-promoter by inhibition or activation of separate signaling pathways. With reference to Tables 9-16 below, values of less than about 0.9 correspond to less desirable compounds as compounds with such values were toxic at the indicated concentration value; values of 0.9 to about 1.1 indicate compounds with some activity (substantially similar to the DMSO background); and values greater than about 1.2 indicate compounds that have desirable activity as these values indicate compounds exhibiting an activity about 20% above the background.

TABLE 9

Burkin Assay in Myoblasts

|  | 40 uM | 20 uM | 10 uM | 5 uM | 1 uM | 0.5 uM |
| --- | --- | --- | --- | --- | --- | --- |
| MLS000591667-01 | 1.1351 | 0.86235 | 1.088 | 1.13163 | 1.03356 | 0.99007 |
| MLS000568234-01 | 1.01115 | 1.10558 | 1.37321 | 1.13643 | 1.03188 | 1.09422 |
| MLS000689562-01 | 0.88167 | 0.95366 | 1.22402 | 1.01263 | 1.014 | 1.07412 |
| MLS000732652-01 | 0.87916 | 1.0346 | 1.2648 | 0.97202 | 1.19119 | 1.17557 |
| MLS001240181-01 | 1.19808 | 1.15299 | 1.07353 | 1.4585 | 1.08072 | 1.08233 |
| MLS001211139-01 | 1.21551 | 1.218 | 0.96826 | 1.06491 | 1.13586 | 1.2392 |
| MLS001030268-01 | 0.60686 | 0.72598 | 0.87162 | 1.48967 | 1.14329 | 1.23909 |
| MLS000912699-01 | 0.43922 | 0.6724 | 0.9298 | 0.93216 | 1.03847 | 1.11521 |
| MLS001125260-01 | 0.90571 | 1.02411 | 0.96159 | 0.98381 | 1.11006 | 1.20955 |
| MLS000717689-01 | 0.98659 | 0.95999 | 1.03846 | 1.03203 | 1.04195 | 1.15829 |
| MLS001197665-01 | 1.18868 | 1.09447 | 0.95234 | 1.01544 | 1.06912 | 1.06224 |
| MLS001075922-01 | 0.64637 | 0.56776 | 0.2869 | 0.60386 | 1.29157 | 1.2085 |
| MLS001124046-01 | 1.07367 | 1.10106 | 1.01243 | 1.07966 | 1.15704 | 1.06118 |
| MLS001197220-01 | 1.0836 | 1.11129 | 0.92184 | 1.84318 | 1.28622 | 1.2811 |
| MLS001221318-01 | 1.07461 | 1.05387 | 0.99442 | 1.00961 | 1.28345 | 1.11823 |
| MLS000947910-01 | 1.01847 | 1.04651 | 1.0429 | 1.03277 | 1.18767 | 1.02381 |
| MLS001215795-01 | 0.71873 | 0.74097 | 0.77762 | 0.93196 | 1.20673 | 1.14257 |
| MLS002163670-01 | 0.7779 | 0.89724 | 0.94682 | 1.01239 | 1.23366 | 1.11688 |
| MLS001200149-01 | 0.98756 | 1.02136 | 0.99804 | 1.0782 | 1.15573 | 1.03945 |
| MLS001359861-01 | 0.91135 | 0.87253 | 0.93239 | 0.94838 | 0.93763 | 0.93526 |
| MLS000710669-01 | 0.82425 | 1.84768 | 0.99409 | 1.0722 | 1.04969 | 1.02525 |
| MLS001035690-01 | 1.09083 | 1.05474 | 0.98721 | 1.18564 | 1.15072 | 1.05147 |
| MLS001030621-01 | 1.00997 | 1.00129 | 1.16138 | 1.15044 | 1.15833 | 1.00359 |
| MLS001083082-01 | 0.94677 | 1.01412 | 1.02292 | 1.05814 | 0.95159 | 0.90356 |
| MLS000045588-01 | 0.89188 | 1.00313 | 0.91698 | 1.07484 | 1.10703 | 1.01584 |
| MLS001216939-01 | 0.78651 | 0.86335 | 0.98283 | 1.11114 | 1.2827 | 1.12283 |
| MLS001163859-01 | 0.92799 | 0.92082 | 1.02427 | 1.05488 | 1.09001 | 0.97855 |
| MLS000683232-01 | 1.65393 | 1.82061 | 1.77787 | 1.6445 | 1.19868 | 1.23351 |
| MLS001170856-01 | 0.71333 | 0.92168 | 1.24442 | 0.97435 | 0.86511 | 0.94996 |
| MLS002667707-01 | 0.83137 | 0.93474 | 1.23469 | 1.01997 | 0.91716 | 1.0156 |
| MLS001200665-01 | 1.02863 | 1.14332 | 1.24505 | 1.00302 | 0.8539 | 0.89824 |
| MLS002161853-01 | 0.9354 | 1.07259 | 1.1978 | 0.93857 | 0.82784 | 0.85687 |
| MLS002163101-01 | 0.97754 | 0.94568 | 1.25085 | 0.96995 | 0.94422 | 0.95515 |
| MLS000062431-01 | 0.9038 | 1.78859 | 1.20925 | 1.01602 | 0.95817 | 0.9542 |
| MLS000028160-01 | 0.85354 | 1.10681 | 0.85212 | 0.98053 | 0.98728 | 1.03731 |
| MLS002248819-01 | 0.76886 | 0.81835 | 1.0849 | 1.06786 | 1.11265 | 1.12574 |
| MLS000780654-01 | 0.91656 | 1.11208 | 0.94286 | 0.92349 | 0.92297 | 0.97875 |
| MLS000760876-01 | 0.95041 | 1.10218 | 0.91131 | 1.81188 | 0.98558 | 1.0287 |

TABLE 9-continued

Burkin Assay in Myoblasts

| | 40 uM | 20 uM | 10 uM | 5 uM | 1 uM | 0.5 uM |
|---|---|---|---|---|---|---|
| MLS000677675-01 | 0.95543 | 1.00416 | 1.02813 | 0.98734 | 1.06053 | 1.09282 |
| MLS000113985-01 | 0.12198 | 0.17793 | 0.48041 | 0.78982 | 1.01847 | 1.06463 |
| MLS001182368-01 | 0.89517 | 1.00108 | 0.89449 | 0.91403 | 1.21452 | 1.08093 |
| MLS001212882-01 | 1.04785 | 1.06823 | 0.9069 | 1.04855 | 1.06975 | 1.0132 |
| MLS001004364-01 | 0.93735 | 0.97287 | 0.95313 | 1.03485 | 1.10452 | 1.0917 |
| MLS000736846-01 | 0.95628 | 1.0406 | 1.01151 | 1.06976 | 1.2858 | 1.21826 |
| MLS001098105-01 | 1.13456 | 1.07472 | 0.97405 | 0.99364 | 1.02871 | 0.94487 |
| MLS000678673-01 | 1.13357 | 1.17252 | 0.96866 | 1.04367 | 1.05388 | 0.93249 |
| MLS000925023-01 | 0.41794 | 0.77654 | 0.79566 | 0.95232 | 1.03462 | 0.99596 |
| MLS001212319-01 | 0.78199 | 0.85293 | 0.88263 | 0.94115 | 1.02595 | 1.04963 |
| MLS000779126-01 | 0.93895 | 0.91244 | 0.81956 | 0.92292 | 1.11482 | 1.01879 |
| MLS000948055-01 | 0.58675 | 0.82128 | 0.8986 | 1.13571 | 1.05347 | 1.32788 |
| MLS000110418-01 | 0.8889 | 1.00365 | 1.11988 | 1.24866 | 1.07925 | 1.3095 |
| MLS000693704-01 | 0.80188 | 0.84732 | 0.94181 | 1.1427 | 1.15286 | 1.42821 |
| MLS001225512-01 | 1.28384 | 1.10796 | 0.88323 | 1.17276 | 0.91313 | 1.1596 |
| MLS001006798-01 | 1.01583 | 1.11843 | 1.00833 | 1.13293 | 0.92818 | 1.19095 |
| MLS000711491-01 | 0.57934 | 0.79492 | 1.02377 | 1.02034 | 1.0159 | 1.21405 |
| MLS000582947-01 | 0.77374 | 0.9417 | 0.98066 | 0.94304 | 0.96323 | 1.23612 |
| MLS000531177-01 | 0.80079 | 1.01406 | 1.62515 | 1.06657 | 0.92304 | 0.88259 |
| MLS001202389-01 | 0.25563 | 0.58161 | 1.1004 | 1.00911 | 0.94807 | 0.9323 |
| MLS000536064-01 | 0.45011 | 0.54402 | 1.04652 | 0.73332 | 0.80395 | 0.80279 |
| MLS000586245-01 | 1.02068 | 1.03337 | 1.24403 | 1.11633 | 1.04937 | 0.99033 |
| MLS001061374-01 | 0.67743 | 0.87297 | 1.16907 | 0.98264 | 0.84475 | 0.84766 |
| MLS000675441-01 | 0.89965 | 0.90155 | 1.24817 | 1.04359 | 0.8764 | 0.93971 |
| MLS001200396-01 | 0.4794 | 0.48269 | 1.1321 | 0.53784 | 0.92449 | 0.88271 |
| MLS001165937-01 | 0.68201 | 1.03268 | 1.70065 | 1.27472 | 0.89489 | 0.86889 |
| MLS000325736-01 | 0.88542 | 0.91197 | 1.16957 | 1.42277 | 0.78755 | 0.77572 |
| MLS001215357-01 | 0.53275 | 0.9203 | 1.48859 | 0.88374 | 0.93 | 1.03703 |
| MLS000588210-01 | 0.96107 | 1.13586 | 0.98164 | 0.90019 | 0.97069 | 1.05483 |
| MLS000764729-01 | 0.72603 | 0.9581 | 0.96935 | 0.98159 | 1.0582 | 1.08805 |
| MLS000689492-01 | 0.96521 | 1.08264 | 0.94309 | 0.93998 | 0.90795 | 1.07297 |
| MLS001000299-01 | 0.77383 | 0.93971 | 0.97497 | 0.95516 | 0.99529 | 1.08932 |
| MLS000393762-01 | 0.46958 | 0.59613 | 0.69566 | 0.77991 | 0.94283 | 0.97379 |
| MLS001130011-01 | 0.91554 | 1.03734 | 0.97619 | 1.37412 | 0.89472 | 0.97145 |
| MLS001229477-01 | 0.90194 | 0.96342 | 0.94542 | 1.36703 | 0.82957 | 0.87031 |
| MLS000707378-01 | 1.49252 | 1.31687 | 1.07579 | 1.02429 | 1.04559 | 1.00348 |
| MLS000573208-01 | 0.62351 | 1.63233 | 0.81207 | 0.95231 | 1.01493 | 1.03104 |
| MLS001167281-01 | 0.86182 | 0.88689 | 0.97761 | 1.07478 | 1.18016 | 1.08931 |
| MLS000053342-01 | 1.02205 | 1.0354 | 0.86681 | 0.97655 | 1.08832 | 1.22195 |
| MLS002171615-01 | 0.61782 | 0.70899 | 0.88587 | 0.97469 | 0.94068 | 1.05229 |
| MLS001005712-01 | 0.76395 | 0.87627 | 0.87827 | 0.92598 | 1.17003 | 1.1047 |
| MLS001176153-01 | 1.12011 | 1.14544 | 0.87665 | 0.91849 | 1.04463 | 1.06004 |
| MLS000735021-01 | 0.99412 | 1.02509 | 0.97651 | 0.99818 | 0.92462 | 0.94018 |
| MLS000767397-01 | 0.97544 | 1.61335 | 0.93339 | 1.47579 | 0.83903 | 0.88624 |
| MLS001196572-01 | 0.9345 | 0.93622 | 0.94826 | 1.22354 | 0.76263 | 0.88263 |
| MLS000393966-01 | 0.96498 | 0.99041 | 1.07573 | 1.79279 | 0.96263 | 0.94947 |
| MLS001034810-01 | 0.84068 | 0.8996 | 1.19071 | 1.37466 | 0.99747 | 1.02099 |
| MLS001165394-01 | 1.00709 | 1.03548 | 0.95105 | 1.15909 | 1.20071 | 1.14858 |
| MLS000089464-01 | 0.39111 | 0.56309 | 0.7825 | 0.93396 | 0.98019 | 0.99651 |
| MLS000698617-01 | 0.89657 | 0.84622 | 0.93172 | 1.06001 | 1.00295 | 1.00774 |
| MLS001175021-01 | 0.95749 | 0.97466 | 0.90603 | 0.88063 | 0.98034 | 0.92001 |
| MLS001166758-01 | 0.61737 | 0.72753 | 0.82445 | 0.97363 | 0.73944 | 0.82402 |
| MLS001008109-01 | 0.83059 | 0.82603 | 0.86263 | 1.00193 | 0.78003 | 0.84815 |
| MLS001181936-01 | 0.32845 | 0.50999 | 0.82189 | 0.85734 | 0.75618 | 0.84427 |
| MLS000560266-01 | 0.55892 | 0.83206 | 1.13014 | 1.02573 | 0.85564 | 0.95298 |
| MLS001215074-01 | 0.59739 | 0.73389 | 0.97384 | 0.94307 | 0.9004 | 1.02349 |
| MLS001215123-01 | 0.52524 | 0.665 | 1.15451 | 1.1241 | 0.97081 | 1.07545 |
| MLS001033255-01 | 0.82795 | 0.98503 | 1.12416 | 1.01684 | 0.93725 | 1.01302 |
| MLS001160611-01 | 0.92674 | 0.97495 | 1.11549 | 1.00379 | 0.97673 | 1.1058 |
| MLS001006302-01 | 0.94141 | 0.97305 | 1.17248 | 0.95352 | 0.93033 | 1.12331 |
| MLS001123876-01 | 0.88436 | 0.93393 | 1.09536 | 1.43977 | 0.82637 | 1.04105 |
| MLS001122698-01 | 0.83886 | 0.9061 | 0.96519 | 1.00842 | 0.85728 | 0.98289 |
| MLS000755214-01 | 0.86097 | 0.84475 | 0.96348 | 0.97565 | 1.02077 | 1.07667 |
| MLS000731285-01 | 0.60769 | 0.60402 | 0.7344 | 0.77267 | 0.92346 | 1.06384 |
| MLS000776409-01 | 0.34443 | 0.50867 | 0.98382 | 0.93888 | 1.00738 | 1.1194 |
| MLS001221908-01 | 0.56836 | 1.43328 | 0.88118 | 0.93061 | 0.95314 | 1.05089 |
| MLS000419286-01 | 0.71995 | 0.7945 | 0.8951 | 0.91739 | 1.00244 | 1.16649 |
| MLS000554416-01 | 0.82485 | 1.08704 | 0.9591 | 0.99152 | 1.0679 | 1.21133 |
| MLS000073150-01 | 1.06802 | 1.13888 | 0.90898 | 0.92622 | 1.0875 | 1.26179 |
| MLS000663185-01 | 0.83278 | 0.92216 | 0.93123 | 1.39854 | 0.97437 | 1.10863 |
| MLS001078811-01 | 0.74109 | 1.68071 | 0.89103 | 0.95834 | 0.99261 | 0.9376 |
| MLS002694363-01 | 0.70661 | 0.75811 | 1.08986 | 1.04452 | 1.06141 | 1.06241 |
| MLS000689218-01 | 1.03748 | 1.07006 | 1.05082 | 1.13165 | 1.17068 | 1.06835 |
| MLS001215294-01 | 0.20458 | 0.20253 | 0.61411 | 0.76405 | 1.00264 | 0.97828 |
| MLS001183575-01 | 0.53384 | 0.69163 | 0.79465 | 0.89805 | 1.00931 | 0.96443 |
| MLS000393567-01 | 0.87054 | 0.83339 | 0.93251 | 0.97236 | 1.05083 | 1.03233 |

TABLE 9-continued

Burkin Assay in Myoblasts

| | 40 uM | 20 uM | 10 uM | 5 uM | 1 uM | 0.5 uM |
|---|---|---|---|---|---|---|
| MLS000546316-01 | 1.02675 | 1.02594 | 1.12291 | 1.16412 | 1.22254 | 1.15942 |
| MLS000912258-01 | 0.37249 | 0.63513 | 0.84251 | 1.2722 | 0.90885 | 0.84356 |
| MLS000850522-01 | 0.88047 | 0.8743 | 1.00276 | 1.30679 | 0.93316 | 0.79932 |
| MLS001197779-01 | 0.75302 | 0.84665 | 0.98695 | 1.28053 | 1.0032 | 0.91613 |
| MLS001095705-01 | 0.72839 | 0.79174 | 0.969 | 1.29549 | 0.87876 | 0.78726 |
| MLS000912562-01 | 0.55515 | 0.69112 | 0.92532 | 1.03872 | 0.92904 | 0.76968 |
| MLS000092785-01 | 0.6509 | 0.78329 | 0.93433 | 1.1703 | 1.03537 | 0.95442 |
| MLS000418650-01 | 0.94454 | 0.91042 | 0.96326 | 1.12987 | 1.06885 | 0.91564 |
| MLS000860966-01 | 1.11657 | 1.24227 | 1.12552 | 1.22473 | 0.95061 | 0.8092 |
| MLS001180929-01 | 1.1941 | 1.10157 | 1.05028 | 1.04982 | 1.0555 | 1.07667 |
| MLS000564564-01 | 0.97011 | 0.94044 | 1.0834 | 1.04244 | 0.94502 | 0.99186 |
| MLS001164432-01 | 0.66217 | 0.7137 | 1.06663 | 1.09125 | 1.1813 | 1.24825 |
| MLS000621451-01 | 1.08838 | 1.0713 | 1.11408 | 1.06613 | 1.01829 | 1.06548 |
| MLS000078709-01 | 0.26162 | 0.51714 | 0.80516 | 0.81574 | 0.996 | 1.06264 |
| MLS000688267-01 | 1.10743 | 1.0466 | 0.91328 | 1.35814 | 1.10445 | 1.09233 |
| MLS001006516-01 | 0.48019 | 0.69276 | 0.79316 | 0.8796 | 1.13422 | 1.09738 |
| MLS001095033-01 | 1.0618 | 1.12466 | 0.96135 | 0.96322 | 1.18613 | 1.28147 |
| MLS000072290-01 | 0.22377 | 0.39842 | 0.6517 | 0.73337 | 1.19579 | 1.40542 |
| MLS000036988-01 | 0.65813 | 0.90234 | 0.82559 | 0.86568 | 1.0825 | 1.18898 |
| MLS001217935-01 | 0.58698 | 0.80022 | 0.89296 | 0.91061 | 1.07572 | 1.16224 |
| MLS000777780-01 | 0.72314 | 0.91334 | 1.24779 | 0.94395 | 1.05647 | 1.13609 |
| MLS001174740-01 | 0.54139 | 0.96576 | 1.18066 | 0.85119 | 1.19298 | 1.22104 |
| MLS000392555-01 | 1.22568 | 1.31366 | 0.97342 | 1.30012 | 1.10052 | 1.2055 |
| MLS000693795-01 | 1.24042 | 1.18741 | 0.97277 | 1.02032 | 1.24179 | 1.1137 |
| MLS000684034-01 | 0.30855 | 0.42247 | 0.62584 | 0.78721 | 1.01964 | 0.99899 |
| MLS001172822-01 | 0.9597 | 0.98696 | 0.90137 | 0.96623 | 1.35133 | 1.23301 |
| MLS000052969-01 | 0.75911 | 0.82915 | 0.83559 | 0.96455 | 1.35174 | 1.24959 |
| MLS001217212-01 | 1.06402 | 0.99668 | 0.99332 | 0.97848 | 1.17844 | 1.09519 |
| MLS001004864-01 | 0.88826 | 1.10454 | 1.02341 | 1.10852 | 1.19287 | 1.1396 |
| MLS001116535-01 | 1.26741 | 1.23894 | 0.93856 | 0.99796 | 1.11141 | 1.09197 |
| MLS001165424-01 | 1.22991 | 1.17612 | 0.95477 | 0.99659 | 1.2222 | 1.15184 |
| MLS001116079-01 | 1.34036 | 1.24425 | 0.9749 | 1.02479 | 1.08671 | 1.02952 |
| MLS001198271-01 | 1.0038 | 1.08798 | 1.03423 | 1.29177 | 1.00045 | 1.03412 |
| MLS001167798-01 | 1.00561 | 1.05069 | 1.06388 | 1.27705 | 1.16574 | 1.05836 |
| MLS000710288-01 | 0.59627 | 0.86808 | 1.1778 | 1.3928 | 1.30459 | 1.16807 |
| MLS000734270-01 | 0.98726 | 0.97392 | 0.95501 | 1.21022 | 1.04793 | 1.0135 |
| MLS000858981-01 | 1.00476 | 1.0113 | 1.01009 | 1.18572 | 0.999 | 0.95297 |
| MLS000698826-01 | 1.02313 | 0.99365 | 0.95981 | 1.24627 | 1.00831 | 1.01911 |
| MLS001000874-01 | 0.95449 | 1.00725 | 0.86772 | 1.07723 | 1.03283 | 1.17509 |
| MLS000682750-01 | 1.10263 | 1.12414 | 1.07554 | 1.22927 | 1.02005 | 1.20347 |
| MLS001090787-01 | 1.22203 | 1.26522 | 1.45989 | 1.26261 | 0.97343 | 1.14195 |
| MLS002636056-01 | 0.82025 | 0.93768 | 1.22389 | 1.03743 | 1.06589 | 1.15719 |
| MLS002170630-01 | 0.67353 | 0.78253 | 1.21616 | 1.0982 | 0.97082 | 1.12201 |
| MLS002162890-01 | 0.49245 | 0.694 | 1.26109 | 1.1338 | 1.03367 | 1.10651 |
| MLS001105912-01 | 0.46309 | 0.60252 | 1.24569 | 1.02884 | 1.05749 | 1.16179 |
| MLS001007892-01 | 0.49826 | 0.72245 | 1.22958 | 1.01568 | 1.03672 | 1.12717 |
| MLS000089748-01 | 0.17663 | 0.24025 | 0.73549 | 0.86559 | 1.16763 | 1.14515 |
| MLS000912726-01 | 1.02179 | 1.1258 | 1.02001 | 0.98384 | 1.17723 | 1.27931 |
| MLS000086970-01 | 0.78111 | 0.8541 | 0.87225 | 0.85834 | 1.07424 | 0.98177 |
| MLS000420298-01 | 0.92353 | 1.11099 | 1.10015 | 1.08324 | 1.24343 | 1.37886 |
| MLS001147478-01 | 0.82145 | 0.9651 | 1.19218 | 1.0569 | 1.09145 | 1.14192 |
| MLS000090135-01 | 0.39561 | 0.60292 | 1.01787 | 0.98804 | 1.16609 | 1.22735 |
| MLS001179717-01 | 0.05093 | 0.30517 | 0.67937 | 0.83575 | 0.86405 | 0.91197 |
| MLS000683234-01 | 1.21046 | 1.06733 | 1.15246 | 1.13392 | 0.83414 | 1.18747 |
| MLS000695955-01 | 1.03417 | 0.96102 | 1.06308 | 1.08042 | 0.87081 | 0.90171 |
| MLS001125488-01 | 0.92319 | 0.9073 | 0.87883 | 0.9899 | 0.97552 | 0.93329 |
| MLS000768008-01 | 0.87872 | 0.78367 | 0.87683 | 0.89762 | 0.96178 | 0.9886 |
| MLS000913117-01 | 0.05713 | 0.19517 | 0.67292 | 0.91381 | 0.91552 | 0.90847 |
| MLS000860538-01 | 0.97828 | 0.958 | 1.11473 | 1.07765 | 1.03288 | 1.02022 |
| MLS001177259-01 | 0.77735 | 0.76937 | 0.91654 | 0.97354 | 0.98957 | 0.96057 |
| MLS000861434-01 | 0.93215 | 0.87769 | 0.97717 | 0.91327 | 1.02784 | 0.94636 |
| MLS000047918-01 | 0.78033 | 0.80348 | 1.0006 | 0.94829 | 0.91191 | 0.87328 |
| MLS000389484-01 | 0.61319 | 0.73315 | 0.8706 | 0.85238 | 0.76721 | 0.78483 |
| MLS001217673-01 | 0.80793 | 0.83254 | 0.92563 | 0.93529 | 0.83431 | 0.84936 |
| MLS000389677-01 | 0.60885 | 0.66194 | 0.79763 | 0.84263 | 0.88312 | 0.53248 |
| MLS001208858-01 | 0.84248 | 0.85481 | 0.87594 | 0.88923 | 1.00324 | 0.9851 |
| MLS000333610-01 | 0.77941 | 0.79748 | 0.91885 | 1.04819 | 0.92531 | 0.8664 |
| MLS001117351-01 | 0.4323 | 0.71365 | 0.74454 | 0.77183 | 1.10521 | 1.10312 |
| MLS000682883-01 | 0.73791 | 0.82691 | 0.91923 | 1.01077 | 0.96331 | 0.94759 |
| MLS001095231-01 | 0.72802 | 0.91969 | 0.86365 | 0.92419 | 0.96824 | 0.96919 |
| MLS000721584-01 | 0.7628 | 0.86626 | 0.98462 | 1.02979 | 0.85252 | 0.933 |
| MLS001183429-01 | 0.33287 | 0.56663 | 0.73733 | 0.78206 | 0.66516 | 0.75919 |
| MLS002158881-01 | 1.21172 | 1.11559 | 1.01779 | 0.98858 | 0.83776 | 0.88812 |
| MLS001165749-01 | 0.77107 | 0.96276 | 0.93419 | 1.03408 | 1.05712 | 1.04807 |
| MLS001237320-01 | 0.81867 | 0.92872 | 0.84952 | 0.91452 | 0.98478 | 0.97334 |
| MLS000763405-01 | 1.083 | 1.469 | 1.53163 | 1.46329 | 1.03014 | 0.96126 |

TABLE 9-continued

Burkin Assay in Myoblasts

| | 40 uM | 20 uM | 10 uM | 5 uM | 1 uM | 0.5 uM |
|---|---|---|---|---|---|---|
| MLS000538580-01 | 0.02896 | 0.03863 | 0.53063 | 0.8691 | 0.90971 | 0.96452 |
| MLS001033202-01 | 0.77044 | 0.84083 | 0.92815 | 0.99521 | 0.91528 | 0.66817 |
| MLS001216260-01 | 0.89335 | 0.87813 | 0.87981 | 0.8531 | 0.98403 | 1.0145 |
| MLS000085522-01 | 0.74815 | 0.97285 | 0.95306 | 1.11804 | 0.87205 | 0.99272 |
| MLS000702680-01 | 0.62643 | 0.69252 | 0.89075 | 0.86233 | 0.8804 | 0.84503 |
| MLS001212998-01 | 1.29981 | 1.36467 | 1.54392 | 1.45225 | 1.19984 | 1.19252 |
| MLS001160885-01 | 0.79137 | 1.02135 | 0.91473 | 0.94021 | 0.93557 | 1.05034 |
| MLS001122718-01 | 0.93319 | 0.99226 | 0.90919 | 1.03265 | 1.04066 | 1.1056 |
| MLS000027478-01 | 0.81604 | 0.91452 | 0.92087 | 0.97213 | 0.90438 | 0.95522 |
| MLS001177364-01 | 0.83857 | 1.00465 | 0.90148 | 0.96554 | 0.98693 | 1.08229 |
| MLS001179695-01 | 0.80683 | 0.89235 | 0.98712 | 0.87525 | 0.94414 | 1.03309 |
| MLS002251986-01 | 0.91837 | 0.97926 | 0.86667 | 0.95123 | 0.92314 | 1.04571 |
| MLS001166704-01 | 0.43935 | 0.57467 | 0.76522 | 0.84987 | 1.16515 | 1.10905 |
| MLS001196422-01 | 1.00409 | 1.24784 | 1.33031 | 1.22893 | 0.9784 | 0.74578 |
| MLS001179624-01 | 0.88278 | 0.87902 | 0.93143 | 0.95146 | 0.99629 | 0.99296 |
| MLS001223425-01 | 1.1318 | 1.22256 | 1.14626 | 1.05531 | 1.08325 | 1.05664 |
| MLS001117140-01 | 0.94202 | 0.9222 | 0.90096 | 0.90913 | 1.06544 | 1.02935 |
| MLS001110618-01 | 1.08304 | 0.97133 | 1.00452 | 0.9228 | 1.02989 | 0.95251 |
| MLS001223482-01 | 0.98024 | 1.28967 | 1.02296 | 1.0127 | 1.09469 | 1.06378 |
| MLS000680049-01 | 0.63536 | 0.74931 | 0.9727 | 0.96933 | 1.10296 | 0.99975 |
| MLS001212498-01 | 1.39711 | 1.28613 | 1.31206 | 1.18111 | 1.20238 | 1.05365 |
| MLS001124732-01 | 0.65809 | 0.68925 | 0.81246 | 0.8622 | 1.07116 | 1.12082 |
| MLS000526364-01 | 1.02864 | 1.11416 | 1.08517 | 1.04544 | 0.95015 | 0.97473 |
| MLS000767227-01 | 0.92827 | 0.91325 | 0.91067 | 0.85772 | 0.80731 | 1.02529 |
| MLS000703499-01 | 0.10433 | 0.44649 | 0.76322 | 0.9278 | 1.01689 | 0.70927 |
| MLS001167169-01 | 0.90615 | 0.81331 | 0.93783 | 0.95467 | 0.8858 | 1.03215 |
| MLS001198693-01 | 0.91638 | 0.93507 | 0.91367 | 0.92293 | 0.54265 | 0.96167 |
| MLS001219345-01 | 0.92275 | 0.98071 | 1.01406 | 1.04565 | 1.11947 | 0.30269 |
| MLS001211651-01 | 1.02624 | 0.99093 | 0.97202 | 1.01085 | 1.12405 | 1.06095 |
| MLS000806880-01 | 1.05558 | 0.99571 | 0.95237 | 1.00906 | 1.12862 | 1.09682 |
| MLS001223567-01 | 0.86396 | 0.85795 | 0.92033 | 0.96076 | 1.08244 | 1.04444 |
| MLS001005283-01 | 0.93009 | 0.89649 | 0.89081 | 0.93463 | 0.85822 | 0.87024 |
| MLS001218427-01 | 0.30387 | 0.22324 | 0.76631 | 0.83344 | 0.94853 | 0.9466 |
| MLS001139288-01 | 0.93365 | 1.08484 | 0.92246 | 0.86341 | 0.97087 | 0.98227 |
| MLS000696445-01 | 0.80698 | 0.81296 | 0.88069 | 0.86702 | 0.56209 | 1.01258 |
| MLS001218795-01 | 0.98756 | 0.93531 | 0.91165 | 0.86087 | 0.95964 | 1.02373 |
| MLS000419555-01 | 0.79662 | 0.94775 | 1.02881 | 1.06624 | 1.20411 | 1.18538 |
| MLS001225507-01 | 0.88802 | 0.86847 | 0.8292 | 0.90357 | 0.94438 | 1.0374 |
| MLS000663651-01 | 1.04765 | 0.95036 | 0.95509 | 0.98337 | 1.05878 | 1.14296 |
| MLS000706349-01 | 0.65331 | 0.85838 | 0.84341 | 0.85931 | 0.97973 | 1.08607 |
| MLS000393110-01 | 0.71005 | 1.01204 | 1.08776 | 1.07374 | 0.92729 | 0.90455 |
| MLS000574647-01 | 0.83429 | 0.89851 | 0.95152 | 0.96407 | 1.02749 | 1.08127 |
| MLS000532969-01 | 1.77036 | 1.94964 | 1.66961 | 1.43381 | 1.25091 | 1.2092 |
| MLS001125260-01 | 0.84255 | 0.87384 | 0.88933 | 0.9248 | 1.02145 | 1.07071 |
| MLS000122749-01 | 0.94804 | 1.18542 | 1.11587 | 1.02606 | 1.03955 | 1.11255 |
| MLS001150751-01 | 0.84542 | 1.07873 | 0.95726 | 0.99415 | 1.059 | 1.11416 |
| MLS001221867-01 | 0.89431 | 0.96155 | 0.92196 | 0.92746 | 1.02402 | 1.00113 |
| MLS001147727-01 | 0.90442 | 1.12838 | 0.88917 | 1.02852 | 1.03907 | 1.21211 |
| MLS000688437-01 | 0.80643 | 0.8203 | 0.90766 | 0.82332 | 0.88782 | 0.89005 |
| MLS001211976-01 | 0.89518 | 0.94171 | 0.91545 | 0.90182 | 0.94602 | 0.95829 |
| MLS002161350-01 | 0.82621 | 0.822 | 0.95139 | 0.95314 | 0.92361 | 0.94036 |
| MLS001077207-01 | 1.14734 | 1.01291 | 1.06263 | 1.05309 | 1.0107 | 0.96989 |
| MLS001209245-01 | 1.03855 | 1.09982 | 1.07082 | 1.02132 | 1.13168 | 1.03871 |
| MLS000737953-01 | 1.23263 | 1.14945 | 1.07964 | 1.00275 | 0.96727 | 0.89998 |
| MLS000552080-01 | 0.88548 | 0.93327 | 1.089 | 1.05564 | 0.97843 | 0.96895 |
| MLS000737204-01 | 0.74718 | 0.87311 | 0.93361 | 0.91643 | 0.98155 | 0.90109 |
| MLS000579238-01 | 0.9117 | 1.10725 | 1.30359 | 1.16711 | 1.11338 | 0.96109 |
| MLS001181671-01 | 0.89104 | 0.81134 | 0.86384 | 0.87588 | 0.96504 | 1.05191 |
| MLS001167424-01 | 0.81643 | 0.7995 | 0.90704 | 0.89245 | 1.42763 | 0.99036 |
| MLS000094770-01 | 0.6762 | 0.79989 | 0.98661 | 0.94914 | 0.96764 | 1.02063 |
| MLS001123810-01 | 0.87288 | 0.8853 | 0.97786 | 0.97821 | 0.95241 | 0.97668 |
| MLS000532078-01 | 1.07709 | 1.09043 | 0.94314 | 0.94396 | 1.07555 | 1.09068 |
| MLS000585616-01 | 0.93184 | 0.93498 | 0.97673 | 1.00788 | 0.94346 | 0.68079 |
| MLS000553673-01 | 0.88921 | 0.9043 | 1.0007 | 1.03788 | 0.89516 | 1.00886 |
| MLS001175592-01 | 0.94054 | 0.97307 | 0.90064 | 0.93232 | 0.88593 | 0.89891 |
| MLS001033255-01 | 0.79904 | 0.79618 | 0.95423 | 0.95091 | 0.9407 | 0.94675 |
| MLS000733703-01 | 0.8463 | 0.86346 | 0.87341 | 0.89191 | 0.95923 | 0.98802 |
| MLS001096269-01 | 1.19809 | 1.0523 | 1.02918 | 0.94134 | 1.01068 | 1.04248 |
| MLS001162872-01 | 0.7773 | 0.78298 | 0.904 | 0.90246 | 0.94902 | 0.95468 |
| MLS000584511-01 | 1.07248 | 1.04995 | 1.08732 | 1.03293 | 0.88848 | 0.5425 |
| MLS001166325-01 | 1.03177 | 0.97718 | 0.94529 | 0.9487 | 0.9268 | 1.01725 |
| MLS000122180-01 | 0.91163 | 1.00352 | 0.96652 | 0.97257 | 0.84241 | 0.80232 |
| MLS001157804-01 | 1.10384 | 1.05163 | 1.11684 | 0.99798 | 0.93852 | 0.87895 |
| MLS000693729-01 | 0.91945 | 0.91361 | 0.90877 | 0.86473 | 0.7902 | 0.90691 |
| MLS001220669-01 | 0.76127 | 0.87013 | 0.9605 | 0.90157 | 0.94259 | 1.00023 |
| MLS001214461-01 | 0.76704 | 0.84718 | 0.81234 | 0.89639 | 0.92407 | 1.06371 |

TABLE 9-continued

Burkin Assay in Myoblasts

| | 40 uM | 20 uM | 10 uM | 5 uM | 1 uM | 0.5 uM |
|---|---|---|---|---|---|---|
| MLS000081838-01 | 0.92338 | 0.98223 | 0.92525 | 0.96114 | 1.04698 | 1.0627 |
| MLS002402866-01 | 0.76886 | 0.8943 | 0.93757 | 0.9113 | 1.1052 | 1.03727 |
| MLS001200980-01 | 0.92013 | 0.95613 | 0.95438 | 1.05452 | 0.92555 | 0.99175 |
| MLS001174719-01 | 0.52655 | 0.75243 | 0.84804 | 1.01314 | 1.04779 | 1.05338 |
| MLS001175449-01 | 0.75639 | 1.06596 | 0.99486 | 1.04541 | 1.03595 | 1.0562 |
| MLS001172577-01 | 0.94305 | 1.0212 | 1.0758 | 1.14243 | 0.96541 | 0.99596 |
| MLS001122792-01 | 0.80584 | 0.99893 | 0.8643 | 0.91298 | 0.87873 | 0.97016 |
| MLS001216405-01 | 0.76668 | 0.92023 | 0.92084 | 0.9945 | 0.97845 | 1.13166 |
| MLS000673766-01 | 0.99188 | 0.91 | 1.0253 | 0.92796 | 1.06126 | 1.02043 |
| MLS000912614-01 | 0.77984 | 0.73821 | 0.93996 | 0.95339 | 1.08794 | 0.95511 |
| MLS001194551-01 | 1.39229 | 1.17648 | 1.29698 | 1.11537 | 1.20463 | 1.09593 |
| MLS001214704-01 | 1.04984 | 0.9848 | 1.18552 | 1.07694 | 1.29585 | 1.11409 |
| MLS001219159-01 | 0.95198 | 0.91989 | 0.96435 | 0.91609 | 1.059 | 0.95972 |
| MLS001060549-01 | 0.94107 | 0.77307 | 1.07213 | 1.01176 | 1.20369 | 1.05617 |
| MLS000850824-01 | 1.06134 | 0.98611 | 1.07604 | 1.07622 | 1.27474 | 1.17361 |
| MLS000879190-01 | 1.12798 | 1.09398 | 1.37657 | 1.18531 | 1.34461 | 1.09674 |
| MLS001163140-01 | 0.98293 | 0.93502 | 1.09843 | 0.99656 | 1.21719 | 1.01896 |
| MLS000046123-01 | 0.98939 | 1.00216 | 1.00659 | 0.95652 | 0.98085 | 1.049 |
| MLS000086970-01 | 0.93423 | 1.01907 | 0.95467 | 1.60052 | 1.19781 | 1.01404 |
| MLS000388722-01 | 0.94068 | 0.91005 | 1.1175 | 1.1052 | 1.1187 | 0.93002 |
| MLS000676974-01 | 0.51838 | 0.66732 | 1.09948 | 0.98998 | 1.13674 | 1.10496 |
| MLS000772580-01 | 0.72509 | 0.79384 | 0.8513 | 0.85541 | 0.97361 | 0.84867 |
| MLS000698686-01 | 0.82518 | 0.84559 | 1.07491 | 1.05367 | 1.01783 | 1.03691 |
| MLS001162337-01 | 0.81495 | 0.87886 | 1.07141 | 1.09144 | 1.12717 | 1.12285 |
| MLS001204005-01 | 1.1735 | 1.23109 | 1.23509 | 1.02172 | 1.15194 | 1.0842 |
| MLS000721525-01 | 0.98502 | 0.99363 | 1.00993 | 0.98343 | 1.08578 | 1.08628 |
| MLS000525404-01 | 1.79482 | 1.4553 | 1.28085 | 1.12043 | 1.08413 | 0.99959 |
| MLS000772194-01 | 1.14873 | 1.09796 | 1.08185 | 1.05483 | 1.05904 | 1.09583 |
| MLS000775793-01 | 0.98952 | 0.9292 | 1.07565 | 1.10917 | 1.07613 | 1.10346 |
| MLS000710130-01 | 0.86888 | 0.83263 | 1.03606 | 1.00611 | 1.10306 | 0.96656 |
| MLS001146463-01 | 0.80609 | 0.73177 | 0.92926 | 0.90269 | 0.97806 | 1.02615 |
| MLS000712769-01 | 0.78927 | 0.76968 | 0.92863 | 0.94757 | 1.05857 | 1.05487 |
| MLS000334464-01 | 1.07573 | 0.8957 | 1.14233 | 1.17793 | 1.11026 | 1.12515 |
| MLS000862690-01 | 0.97527 | 0.87171 | 1.00387 | 1.00872 | 1.02652 | 1.02904 |
| MLS001179267-01 | 0.94996 | 0.93048 | 0.9902 | 0.97969 | 1.03143 | 0.98302 |
| MLS000683174-01 | 0.80586 | 1.02775 | 1.01393 | 1.01994 | 0.91756 | 1.01961 |
| MLS000913052-01 | 1.20186 | 1.11329 | 1.06715 | 1.07591 | 1.03833 | 1.11596 |
| MLS001080869-01 | 0.84846 | 0.97296 | 0.9857 | 1.14722 | 1.03572 | 1.14407 |
| MLS000332693-01 | 0.92254 | 0.89498 | 1.09531 | 1.06767 | 0.99365 | 1.03957 |
| MLS001141113-01 | 0.55984 | 0.91514 | 1.07109 | 1.07883 | 1.058 | 1.22948 |
| MLS001176611-01 | 0.91345 | 0.83982 | 1.07215 | 1.09667 | 0.99398 | 1.04935 |
| MLS001202627-01 | 0.21788 | 0.54268 | 0.77391 | 0.99233 | 1.08133 | 1.17187 |
| MLS000765108-01 | 1.02593 | 1.04146 | 1.11307 | 1.20183 | 1.1197 | 1.17146 |
| MLS000937079-01 | 0.99561 | 1.02838 | 1.14674 | 1.05254 | 0.89583 | 1.16289 |
| MLS001215742-01 | 0.81646 | 0.76822 | 1.10465 | 1.04044 | 0.92602 | 0.88704 |
| MLS001217045-01 | 1.10891 | 1.05719 | 1.11177 | 1.08675 | 0.96972 | 0.88104 |
| MLS001196946-01 | 0.08385 | 0.11943 | 0.61881 | 0.79887 | 0.97976 | 0.95406 |
| MLS001216714-01 | 0.27369 | 1.08646 | 1.13942 | 1.04321 | 0.97056 | 1.018 |
| MLS000772430-01 | 0.89631 | 0.88124 | 1.04602 | 1.00717 | 0.93622 | 0.97283 |
| MLS000693370-01 | 0.93667 | 0.95143 | 1.06427 | 0.88727 | 0.80004 | 0.86381 |
| MLS000769322-01 | 0.95504 | 1.00606 | 1.0771 | 0.96529 | 0.93537 | 0.95348 |
| MLS000721030-01 | 1.12244 | 1.02526 | 1.16581 | 1.02742 | 0.93485 | 0.9673 |
| MLS001176897-01 | 0.94746 | 0.94581 | 0.99783 | 0.90579 | 0.94565 | 0.9342 |
| MLS000774940-01 | 0.77609 | 0.85802 | 1.04275 | 1.09508 | 0.89283 | 0.93089 |
| MLS001030746-01 | 0.96367 | 0.93385 | 1.07333 | 1.06913 | 0.8373 | 0.91954 |
| MLS003126425-01 | 0.44013 | 1.12959 | 1.254 | 1.28169 | 1.1398 | 1.14604 |
| MLS001217697-01 | 1.0127 | 0.88306 | 1.15767 | 1.18252 | 1.11591 | 1.09067 |
| MLS000516719-01 | 0.96515 | 0.91967 | 1.06775 | 1.0321 | 1.04756 | 1.00574 |
| MLS001165323-01 | 0.47791 | 0.87431 | 0.92404 | 0.88215 | 0.94909 | 0.97044 |
| MLS001220803-01 | 0.99059 | 0.95026 | 0.95106 | 0.88777 | 1.0343 | 0.96878 |
| MLS001163121-01 | 0.91572 | 0.80739 | 0.99067 | 0.94885 | 1.01191 | 1.04852 |
| MLS001060561-01 | 0.63183 | 0.79502 | 0.88777 | 0.82662 | 0.92837 | 0.99611 |
| MLS001139515-01 | 0.85269 | 0.83359 | 1.15988 | 1.05338 | 0.98522 | 0.92246 |
| MLS001149811-01 | 0.61724 | 1.00026 | 1.02244 | 1.01027 | 0.88883 | 0.64967 |
| MLS000733700-01 | 0.87206 | 0.9227 | 0.86573 | 0.90585 | 1.0257 | 0.93354 |
| MLS001177045-01 | 0.95693 | 1.03087 | 1.0259 | 1.0025 | 1.03211 | 0.84633 |
| MLS000693747-01 | 0.91746 | 0.87957 | 1.08763 | 1.0596 | 1.03615 | 1.11428 |
| MLS001175556-01 | 0.80176 | 0.89561 | 0.88558 | 0.92019 | 0.86252 | 0.92004 |
| MLS001175473-01 | 0.86983 | 0.899 | 0.87154 | 0.87321 | 0.37213 | 0.53313 |
| MLS002156278-01 | 0.82456 | 0.86044 | 0.96531 | 1.00963 | 0.96419 | 0.85974 |
| MLS000707281-01 | 0.79693 | 0.83587 | 0.88542 | 0.89346 | 0.97563 | 0.95067 |
| MLS000591198-01 | 0.47304 | 0.77654 | 0.95931 | 1.03702 | 0.92511 | 1.00578 |
| MLS000714175-01 | 0.96263 | 0.99361 | 1.06 | 1.1625 | 0.97498 | 0.53831 |
| MLS002163386-01 | 0.93876 | 1.01374 | 0.88796 | 1.03415 | 0.9023 | 1.0508 |
| MLS000761297-01 | 0.95256 | 1.07174 | 1.05527 | 1.12127 | 1.07133 | 1.0693 |
| MLS002245351-01 | 0.86569 | 0.90007 | 0.97044 | 1.03385 | 1.03691 | 1.08244 |

TABLE 9-continued

Burkin Assay in Myoblasts

| | 40 uM | 20 uM | 10 uM | 5 uM | 1 uM | 0.5 uM |
|---|---|---|---|---|---|---|
| MLS000718886-01 | 0.81389 | 0.91243 | 0.96613 | 1.08727 | 0.93943 | 1.05198 |
| MLS002156485-01 | 1.02644 | 1.05206 | 0.87521 | 0.92779 | 0.9382 | 1.05917 |
| MLS001140657-01 | 0.79783 | 0.85676 | 0.87677 | 0.95283 | 0.96198 | 0.9918 |
| MLS002157024-01 | 1.08144 | 1.09694 | 0.85235 | 0.96094 | 0.97128 | 1.01144 |
| MLS000721730-01 | 0.93424 | 0.82698 | 0.88242 | 0.81574 | 0.81973 | 0.83765 |
| MLS000705922-01 | 0.87835 | 0.88922 | 0.72832 | 0.72819 | 1.02 | 0.96273 |
| MLS000724709-01 | 0.55365 | 0.48598 | 0.77902 | 0.73891 | 0.95538 | 0.98992 |
| MLS002161757-01 | 1.15126 | 1.00861 | 0.91351 | 0.91126 | 0.89196 | 0.96138 |
| MLS002164687-01 | 0.81941 | 0.83778 | 0.84902 | 0.69489 | 0.81935 | 0.77498 |
| MLS001060533-01 | 1.21969 | 1.39744 | 1.10126 | 1.03286 | 0.99152 | 0.90492 |
| MLS000685139-01 | 0.98483 | 0.98933 | 0.77595 | 0.84163 | 0.6285 | 0.82342 |
| MLS001217286-01 | 1.06759 | 1.00563 | 0.82726 | 0.76705 | 0.8506 | 0.74275 |
| MLS001221619-01 | 0.89756 | 0.96481 | 0.67637 | 0.73674 | 0.76333 | 0.68552 |
| MLS001219621-01 | 0.54233 | 0.78837 | 0.75418 | 0.72486 | 0.80633 | 0.86421 |
| MLS001166156-01 | 0.34807 | 0.75715 | 0.76012 | 0.75432 | 0.90852 | 0.8005 |
| MLS000534926-01 | 0.42215 | 0.59957 | 0.88325 | 0.85863 | 0.94733 | 1.52217 |
| MLS000548725-01 | 0.07694 | 0.51687 | 0.76446 | 0.89891 | 0.88938 | 0.91317 |
| MLS000374261-01 | 0.83211 | 0.83763 | 0.71381 | 0.72479 | 0.77583 | 0.7676 |
| MLS000123454-01 | 1.01341 | 1.51865 | 0.86209 | 0.78618 | 0.8234 | 0.8934 |
| MLS000625140-01 | 0.68287 | 0.75893 | 0.78335 | 0.87481 | 0.8709 | 0.88394 |
| MLS001214443-01 | 0.9313 | 0.9132 | 0.81732 | 0.7787 | 0.80738 | 0.92033 |

TABLE 10

Burkin Assay in Myotubes

| | 40 uM | 20 uM | 10 uM | 5 uM | 1 uM | 0.5 uM |
|---|---|---|---|---|---|---|
| MLS000591667-01 | 0.69646 | 0.67806 | 0.99863 | 1.07156 | 1.1434 | 1.00531 |
| MLS000568234-01 | 0.97051 | 0.86942 | 1.08971 | 0.96419 | 1.16742 | 1.07977 |
| MLS000689562-01 | 0.85465 | 0.72357 | 1.0159 | 0.97883 | 1.03466 | 1.08068 |
| MLS000732652-01 | 0.73092 | 0.67974 | 1.14125 | 1.1938 | 1.11599 | 1.09214 |
| MLS001240181-01 | 0.79047 | 0.88714 | 0.96827 | 1.64271 | 1.214 | 1.17431 |
| MLS001211139-01 | 0.75468 | 0.82834 | 0.94255 | 1.00287 | 1.28848 | 1.16726 |
| MLS001030268-01 | 0.76063 | 0.62773 | 0.92494 | 1.21276 | 1.16147 | 1.07576 |
| MLS000912699-01 | 0.65181 | 0.52169 | 0.93901 | 0.92519 | 0.93756 | 1.17498 |
| MLS001125260-01 | 0.74508 | 0.76341 | 1.09105 | 0.96768 | 1.20801 | 1.28483 |
| MLS000717689-01 | 0.71346 | 0.82829 | 1.07589 | 1.04848 | 0.90065 | 1.11085 |
| MLS001197665-01 | 0.95828 | 1.00065 | 0.99899 | 0.97302 | 1.06784 | 1.11547 |
| MLS001075922-01 | 0.82425 | 1.06745 | 0.62896 | 0.65563 | 1.14344 | 1.29247 |
| MLS001124046-01 | 0.91979 | 0.89276 | 1.01603 | 1.41708 | 1.09565 | 1.14517 |
| MLS001197220-01 | 0.83097 | 0.90004 | 1.00438 | 1.25409 | 1.3061 | 1.32659 |
| MLS001221318-01 | 0.7186 | 0.80714 | 0.95914 | 0.92662 | 1.08244 | 1.13276 |
| MLS000947910-01 | 0.95151 | 0.96285 | 1.03459 | 0.99998 | 1.10147 | 1.13447 |
| MLS001215795-01 | 0.88728 | 0.9147 | 0.91066 | 0.86305 | 1.19109 | 1.29108 |
| MLS002163670-01 | 0.73497 | 0.85264 | 1.07165 | 0.97782 | 1.29363 | 1.22297 |
| MLS001200149-01 | 0.83633 | 0.92859 | 1.09373 | 1.06886 | 1.07233 | 1.26026 |
| MLS001359861-01 | 0.80395 | 1.0337 | 0.876 | 0.90881 | 1.18375 | 1.09515 |
| MLS000710669-01 | 1.0073 | 0.99667 | 0.90001 | 1.05381 | 1.16308 | 1.04515 |
| MLS001035690-01 | 0.92376 | 0.97197 | 0.93577 | 1.07274 | 1.07159 | 1.11088 |
| MLS001030621-01 | 0.72029 | 0.7954 | 0.94292 | 0.99904 | 0.94925 | 0.97239 |
| MLS001083082-01 | 0.93703 | 0.89872 | 1.05034 | 1.07008 | 0.94106 | 1.03453 |
| MLS000045588-01 | 0.95463 | 1.06301 | 1.03566 | 1.135 | 1.09854 | 1.07688 |
| MLS001216939-01 | 0.47431 | 0.85294 | 1.06002 | 1.06991 | 1.18531 | 1.19276 |
| MLS001163859-01 | 1.05788 | 1.11822 | 1.24934 | 1.38468 | 1.28077 | 1.13173 |
| MLS000683232-01 | 1.31969 | 1.4149 | 1.44782 | 1.27158 | 1.2778 | 1.13572 |
| MLS001170856-01 | 1.02912 | 0.77626 | 1.06447 | 0.91001 | 0.74357 | 0.82959 |
| MLS002667707-01 | 0.7617 | 0.80494 | 0.95401 | 0.89392 | 1.01022 | 0.99551 |
| MLS001200665-01 | 0.88772 | 0.83653 | 1.12552 | 1.09065 | 0.84612 | 1.03137 |
| MLS002161853-01 | 0.93534 | 0.91896 | 1.15981 | 0.98887 | 0.80923 | 0.87612 |
| MLS002163101-01 | 0.97609 | 0.77823 | 1.30157 | 1.10149 | 0.90746 | 1.04549 |
| MLS000062431-01 | 0.88412 | 0.76433 | 1.1989 | 1.17804 | 0.84151 | 0.95709 |
| MLS000028160-01 | 0.81118 | 0.90493 | 0.95982 | 0.91617 | 1.10188 | 1.08464 |
| MLS002248819-01 | 0.85083 | 0.92428 | 1.24039 | 1.06554 | 1.19767 | 1.11701 |
| MLS000080654-01 | 0.62169 | 0.74219 | 0.97069 | 0.90438 | 1.09159 | 1.06711 |
| MLS000760876-01 | 0.89931 | 0.86336 | 0.9755 | 1.24882 | 1.25578 | 1.2427 |
| MLS000677675-01 | 0.68734 | 0.66754 | 1.04369 | 1.08103 | 1.20496 | 1.27844 |
| MLS000113985-01 | 0.66792 | 0.76552 | 0.99254 | 0.99189 | 1.03688 | 0.98825 |
| MLS001182368-01 | 0.91934 | 0.90974 | 1.02027 | 1.2117 | 1.0792 | 1.04351 |
| MLS001212882-01 | 0.91073 | 0.84206 | 0.8877 | 0.90721 | 1.02311 | 0.98143 |
| MLS001004364-01 | 1.05525 | 0.88751 | 0.86169 | 0.90474 | 1.10504 | 1.09276 |
| MLS000736846-01 | 0.96729 | 0.87764 | 0.93964 | 1.00375 | 1.14446 | 1.13093 |
| MLS001098105-01 | 0.84588 | 0.81422 | 0.83539 | 0.91598 | 1.05323 | 1.05204 |

TABLE 10-continued

Burkin Assay in Myotubes

| | 40 uM | 20 uM | 10 uM | 5 uM | 1 uM | 0.5 uM |
|---|---|---|---|---|---|---|
| MLS000678673-01 | 0.78099 | 0.86554 | 0.96062 | 0.97673 | 0.98018 | 0.97725 |
| MLS000925023-01 | 0.73184 | 0.80043 | 0.8784 | 0.89694 | 1.23995 | 1.16045 |
| MLS001212319-01 | 0.63105 | 0.73964 | 0.92007 | 0.94764 | 1.13867 | 1.13422 |
| MLS000779126-01 | 0.77678 | 0.88319 | 0.87581 | 0.91457 | 1.01779 | 0.98357 |
| MLS000948055-01 | 0.75145 | 0.98002 | 0.8264 | 0.90529 | 1.05415 | 1.06716 |
| MLS000110418-01 | 0.88548 | 0.99394 | 0.943 | 1.01658 | 1.0975 | 1.07264 |
| MLS000693704-01 | 0.82627 | 0.9587 | 0.92299 | 1.00259 | 1.0787 | 0.93149 |
| MLS001225512-01 | 0.74015 | 0.84309 | 0.82346 | 0.97987 | 1.05854 | 0.92901 |
| MLS001006798-01 | 0.88856 | 0.97456 | 0.89057 | 1.05957 | 1.04218 | 0.93455 |
| MLS000711491-01 | 0.57898 | 0.67103 | 0.94615 | 0.9629 | 1.06241 | 1.06977 |
| MLS000582947-01 | 0.79101 | 1.10221 | 0.97595 | 1.01969 | 1.15528 | 0.90028 |
| MLS000531177-01 | 0.90051 | 0.80069 | 1.16345 | 1.05071 | 0.73291 | 0.82589 |
| MLS001202389-01 | 0.55936 | 0.64125 | 1.05346 | 0.99362 | 0.93925 | 0.9181 |
| MLS000536064-01 | 0.7073 | 0.76421 | 1.13143 | 0.95394 | 0.95554 | 0.90458 |
| MLS000586245-01 | 1.02629 | 0.94257 | 1.17916 | 1.04311 | 0.9584 | 1.00329 |
| MLS001061374-01 | 0.81546 | 0.73205 | 1.18149 | 1.00437 | 1.09204 | 1.05776 |
| MLS000675441-01 | 0.71678 | 0.74757 | 1.11902 | 0.95908 | 1.07053 | 0.85516 |
| MLS001200396-01 | 0.71138 | 0.6408 | 1.26379 | 0.98293 | 0.94875 | 0.93009 |
| MLS001165937-01 | 0.72485 | 1.00559 | 1.52391 | 1.21196 | 1.16352 | 0.96798 |
| MLS000325736-01 | 0.69718 | 0.6582 | 1.16824 | 1.02677 | 0.80167 | 0.91355 |
| MLS001215357-01 | 0.69286 | 0.75605 | 0.88397 | 0.90573 | 0.81367 | 0.9366 |
| MLS000588210-01 | 0.95653 | 0.97629 | 0.91553 | 0.94662 | 0.95586 | 0.94246 |
| MLS000764729-01 | 0.60751 | 0.68098 | 0.97198 | 1.00794 | 1.08392 | 1.05496 |
| MLS000689492-01 | 0.75436 | 0.88357 | 0.92917 | 0.93108 | 1.13846 | 1.15571 |
| MLS001000299-01 | 0.55782 | 0.793 | 0.91625 | 0.87644 | 1.00592 | 0.92249 |
| MLS000393762-01 | 0.70455 | 0.77047 | 1.00696 | 0.97947 | 0.92497 | 0.94021 |
| MLS001130011-01 | 0.7512 | 0.78831 | 1.0699 | 0.88339 | 0.99521 | 0.95531 |
| MLS001229477-01 | 0.8339 | 0.83764 | 0.90149 | 0.97022 | 0.93677 | 0.80147 |
| MLS000707378-01 | 1.05105 | 1.04623 | 1.24093 | 0.88992 | 0.85116 | 0.87159 |
| MLS000573208-01 | 0.59664 | 0.82393 | 1.04515 | 0.97999 | 1.00715 | 0.94525 |
| MLS001167281-01 | 0.83453 | 0.82926 | 1.14202 | 1.07436 | 1.05393 | 1.06349 |
| MLS000053342-01 | 1.11028 | 1.04947 | 1.03003 | 1.00173 | 1.01051 | 1.05896 |
| MLS002171615-01 | 0.83027 | 0.84318 | 0.99471 | 0.97089 | 1.16975 | 1.10717 |
| MLS001005712-01 | 0.74045 | 0.78848 | 0.93903 | 0.94721 | 1.17289 | 0.87044 |
| MLS001176153-01 | 0.98183 | 0.92376 | 1.10591 | 0.95378 | 1.02681 | 1.00708 |
| MLS000735021-01 | 0.85229 | 0.84443 | 1.00585 | 0.91367 | 1.00886 | 1.01265 |
| MLS000767397-01 | 1.01365 | 0.99933 | 1.0608 | 1.00428 | 0.94806 | 0.92939 |
| MLS001196572-01 | 0.71815 | 0.98051 | 0.92943 | 1.14827 | 0.88824 | 0.92363 |
| MLS000393966-01 | 1.01539 | 1.23304 | 0.95462 | 1.30422 | 0.84361 | 0.85472 |
| MLS001034810-01 | 0.75928 | 1.00003 | 1.16544 | 1.40257 | 1.06959 | 1.03516 |
| MLS001165394-01 | 1.03397 | 1.18823 | 0.98536 | 1.23914 | 1.13467 | 1.06778 |
| MLS000089464-01 | 0.83732 | 0.95449 | 0.99169 | 1.12764 | 1.02877 | 1.06322 |
| MLS000698617-01 | 0.79633 | 1.09199 | 0.94496 | 1.13858 | 1.07472 | 1.19659 |
| MLS001175021-01 | 0.87883 | 0.97988 | 0.99128 | 1.05123 | 1.0167 | 1.06135 |
| MLS001166758-01 | 0.87545 | 0.98563 | 0.89787 | 0.98565 | 1.02671 | 1.0327 |
| MLS001008109-01 | 0.61033 | 0.82635 | 0.93355 | 1.18189 | 0.91465 | 0.92469 |
| MLS001181936-01 | 0.73871 | 0.58684 | 1.02387 | 0.98561 | 0.76335 | 0.91972 |
| MLS000560266-01 | 0.60594 | 0.67057 | 1.18475 | 1.03662 | 0.88245 | 0.98908 |
| MLS001215074-01 | 0.84879 | 0.75046 | 1.13207 | 1.04996 | 0.83074 | 0.78865 |
| MLS001215123-01 | 0.816 | 0.69382 | 1.13745 | 1.04903 | 0.90099 | 0.94663 |
| MLS001033255-01 | 1.23171 | 0.83368 | 1.24617 | 1.08579 | 0.81878 | 0.90997 |
| MLS001160611-01 | 1.23985 | 0.83969 | 1.16888 | 1.00621 | 0.86282 | 0.94515 |
| MLS001006302-01 | 1.07828 | 0.78349 | 1.21228 | 1.03871 | 0.93734 | 0.98217 |
| MLS001123876-01 | 1.00321 | 0.71141 | 1.23169 | 1.1689 | 0.81926 | 0.86603 |
| MLS001122698-01 | 0.85722 | 0.92091 | 1.03016 | 0.95745 | 0.90389 | 0.91311 |
| MLS000755214-01 | 0.8312 | 0.96553 | 1.0353 | 0.93209 | 0.96607 | 1.00954 |
| MLS000731285-01 | 0.19528 | 0.68996 | 0.94092 | 0.86954 | 0.96101 | 0.85441 |
| MLS000776409-01 | 0.80563 | 0.89489 | 0.92835 | 0.88195 | 1.02936 | 0.89249 |
| MLS001221908-01 | 0.74062 | 0.81797 | 0.96928 | 0.88901 | 0.95887 | 1.19709 |
| MLS000419286-01 | 0.193 | 0.45703 | 0.94796 | 0.87898 | 0.8124 | 0.9511 |
| MLS000554416-01 | 0.49152 | 0.68156 | 0.93336 | 0.83662 | 0.9261 | 0.91456 |
| MLS000073150-01 | 0.85596 | 0.83687 | 0.94757 | 0.9467 | 0.92051 | 1.11147 |
| MLS000663185-01 | 1.11786 | 0.77913 | 1.0708 | 0.97669 | 0.81366 | 0.96799 |
| MLS001078811-01 | 0.45984 | 0.63069 | 0.8773 | 0.98157 | 0.90642 | 0.91635 |
| MLS002694363-01 | 0.41079 | 0.66943 | 0.87872 | 0.91782 | 1.01024 | 0.99095 |
| MLS000689218-01 | 0.96764 | 1.00798 | 0.98295 | 0.96996 | 1.08276 | 0.96628 |
| MLS001215294-01 | 0.8079 | 0.80622 | 0.82158 | 0.89346 | 1.10597 | 1.04694 |
| MLS001183575-01 | 0.68676 | 0.73778 | 0.79376 | 0.81721 | 0.96813 | 1.0887 |
| MLS000393567-01 | 0.92366 | 0.8607 | 0.88565 | 0.90647 | 0.99533 | 0.88817 |
| MLS000546316-01 | 1.17565 | 0.85707 | 1.09939 | 1.06571 | 1.17392 | 1.13749 |
| MLS000912258-01 | 0.71931 | 0.87695 | 0.96307 | 1.14382 | 0.85708 | 0.92635 |
| MLS000850522-01 | 0.93236 | 0.94157 | 0.92633 | 1.10981 | 0.90575 | 0.9439 |
| MLS001197779-01 | 0.91301 | 0.82374 | 0.92492 | 1.10225 | 0.96099 | 1.03803 |
| MLS001095705-01 | 0.79366 | 0.94108 | 0.8798 | 1.07342 | 0.94627 | 0.9916 |
| MLS000912562-01 | 0.70243 | 0.88725 | 0.8748 | 0.92895 | 0.85822 | 0.89803 |
| MLS000092785-01 | 0.82253 | 0.82933 | 0.85855 | 1.02029 | 0.96616 | 1.02722 |

TABLE 10-continued

Burkin Assay in Myotubes

| | 40 uM | 20 uM | 10 uM | 5 uM | 1 uM | 0.5 uM |
|---|---|---|---|---|---|---|
| MLS000418650-01 | 0.75932 | 0.75808 | 0.96539 | 1.03182 | 1.00364 | 1.08596 |
| MLS000860966-01 | 0.89269 | 1.05975 | 1.10725 | 1.1137 | 0.82114 | 0.92753 |
| MLS001180929-01 | 1.13472 | 0.86586 | 1.02995 | 0.96426 | 0.92563 | 0.89896 |
| MLS000564564-01 | 1.08968 | 0.80854 | 1.05291 | 0.94262 | 0.94023 | 0.95865 |
| MLS001164432-01 | 0.84639 | 0.71209 | 0.99848 | 0.98784 | 0.95093 | 0.89821 |
| MLS000621451-01 | 1.02447 | 0.83274 | 1.07136 | 0.92535 | 0.8932 | 0.94711 |
| MLS000078709-01 | 0.48942 | 0.63113 | 0.98985 | 0.95354 | 0.82363 | 0.83742 |
| MLS000688267-01 | 1.13079 | 0.88079 | 1.10089 | 1.13158 | 0.83733 | 0.9011 |
| MLS001006516-01 | 0.71268 | 0.71266 | 0.90855 | 0.92575 | 0.87139 | 0.92612 |
| MLS001095033-01 | 0.91577 | 0.89377 | 0.92979 | 0.94401 | 0.94882 | 0.99586 |
| MLS000072290-01 | 0.17841 | 0.47499 | 0.84049 | 0.90961 | 1.12146 | 1.10865 |
| MLS000036988-01 | 0.10401 | 0.41718 | 0.82226 | 0.80994 | 0.75767 | 0.85532 |
| MLS001217935-01 | 0.52464 | 0.78867 | 1.08057 | 0.88116 | 1.01763 | 0.90754 |
| MLS000777780-01 | 0.77559 | 0.88145 | 0.93933 | 0.86968 | 0.98371 | 1.04663 |
| MLS001174740-01 | 0.70642 | 0.78226 | 0.90166 | 0.85739 | 0.86868 | 0.90778 |
| MLS000392555-01 | 0.93005 | 0.93498 | 0.97413 | 1.10516 | 0.96637 | 0.96465 |
| MLS000693795-01 | 0.95128 | 1.00214 | 0.93842 | 0.9381 | 0.91713 | 0.83969 |
| MLS000684034-01 | 0.73851 | 0.74026 | 0.80757 | 0.83826 | 0.95363 | 0.97308 |
| MLS001172822-01 | 0.78582 | 0.84656 | 0.86099 | 0.85134 | 0.93148 | 0.94964 |
| MLS000052969-01 | 0.55483 | 0.66209 | 0.876 | 0.91836 | 1.05823 | 0.91311 |
| MLS001217212-01 | 0.73655 | 0.76634 | 0.87723 | 0.88308 | 0.83859 | 0.82329 |
| MLS001004864-01 | 0.37599 | 0.60748 | 0.96185 | 0.97835 | 1.02518 | 0.949 |
| MLS001116535-01 | 0.83664 | 0.89931 | 0.85528 | 0.89286 | 1.00307 | 0.95003 |
| MLS001165424-01 | 0.76414 | 0.77905 | 0.83154 | 0.89381 | 0.85679 | 0.87714 |
| MLS001116079-01 | 0.96857 | 0.90267 | 0.90118 | 0.95586 | 0.95017 | 0.95237 |
| MLS001198271-01 | 0.82169 | 0.90557 | 0.98564 | 1.11296 | 0.9334 | 1.0083 |
| MLS001167798-01 | 0.72315 | 0.79831 | 0.93824 | 1.11791 | 0.92426 | 1.05071 |
| MLS000710288-01 | 0.8202 | 1.02449 | 0.95983 | 1.08387 | 0.95749 | 1.07633 |
| MLS000734270-01 | 0.81021 | 0.85578 | 0.90807 | 1.08322 | 0.89746 | 0.941 |
| MLS000858981-01 | 0.81733 | 0.85258 | 0.89224 | 1.05483 | 0.88365 | 1.02668 |
| MLS000698826-01 | 0.78436 | 0.95754 | 0.90009 | 1.08025 | 0.87178 | 1.00839 |
| MLS001000874-01 | 0.81807 | 0.92657 | 0.92162 | 1.0731 | 0.86464 | 0.9357 |
| MLS000682750-01 | 0.70644 | 1.00201 | 0.88388 | 1.07253 | 0.99385 | 0.99573 |
| MLS001090787-01 | 1.5544 | 1.20894 | 1.19518 | 1.08299 | 1.16762 | 1.05405 |
| MLS002636056-01 | 1.16657 | 0.90453 | 1.02703 | 0.92033 | 1.08895 | 0.96193 |
| MLS002170630-01 | 1.0714 | 0.88566 | 1.12282 | 0.96974 | 1.07532 | 1.03038 |
| MLS002162890-01 | 0.80295 | 0.7452 | 1.1501 | 0.93508 | 1.18455 | 1.05063 |
| MLS001105912-01 | 1.00319 | 0.82995 | 1.1322 | 0.94666 | 1.06085 | 0.94833 |
| MLS001007892-01 | 0.98876 | 0.83431 | 1.07453 | 0.97418 | 1.01306 | 0.90462 |
| MLS000089748-01 | 0.74149 | 0.77148 | 0.80258 | 0.8675 | 0.91388 | 1.04302 |
| MLS000912726-01 | 0.82375 | 0.82313 | 0.88602 | 0.88182 | 0.8889 | 1.06575 |
| MLS000086970-01 | 0.97145 | 0.96119 | 0.95762 | 0.86446 | 1.08763 | 1.00334 |
| MLS000420298-01 | 1.00617 | 0.91001 | 0.90053 | 0.94527 | 1.0464 | 0.95384 |
| MLS001147478-01 | 0.87441 | 0.8876 | 1.04143 | 0.99327 | 0.96771 | 1.07626 |
| MLS000090135-01 | 0.82149 | 0.8015 | 0.9078 | 0.87471 | 0.95976 | 1.04209 |
| MLS001179717-01 | 0.26634 | 0.5137 | 0.6812 | 0.74398 | 1.02658 | 0.8788 |
| MLS000683234-01 | 1.63139 | 1.41362 | 1.27328 | 1.09078 | 1.05264 | 0.9165 |
| MLS000695955-01 | 1.38633 | 1.23243 | 1.32243 | 1.14659 | 1.03159 | 0.94502 |
| MLS001125488-01 | 1.2197 | 1.14304 | 1.31932 | 1.11918 | 1.15129 | 1.03181 |
| MLS000768008-01 | 1.2867 | 1.09811 | 1.27255 | 1.10984 | 1.17937 | 1.07276 |
| MLS000913117-01 | 0.39105 | 0.49497 | 0.66235 | 0.96547 | 1.20782 | 1.08965 |
| MLS000860538-01 | 0.94028 | 0.96352 | 1.41241 | 1.31905 | 1.10205 | 0.98501 |
| MLS001177259-01 | 0.92374 | 0.81869 | 1.04363 | 0.99884 | 1.05301 | 0.94799 |
| MLS000861434-01 | 1.05784 | 0.87623 | 1.10144 | 0.97878 | 1.06594 | 0.95931 |
| MLS000047918-01 | 0.94474 | 0.96731 | 0.87188 | 0.8995 | 0.91346 | 1.40284 |
| MLS000389484-01 | 0.69458 | 0.86703 | 0.64333 | 0.8638 | 0.7793 | 0.92918 |
| MLS001217673-01 | 1.07849 | 1.09479 | 0.95155 | 0.96989 | 0.74898 | 0.88943 |
| MLS000389677-01 | 0.95301 | 0.64209 | 0.99562 | 1.10906 | 0.91563 | 1.00483 |
| MLS001208858-01 | 1.00672 | 1.09983 | 1.06192 | 1.10431 | 0.99771 | 1.09459 |
| MLS000333610-01 | 0.90959 | 0.87418 | 0.99324 | 1.00287 | 1.03921 | 0.98596 |
| MLS001117351-01 | 0.69855 | 0.76687 | 0.94632 | 0.83154 | 0.99239 | 1.02475 |
| MLS000682883-01 | 1.09375 | 1.10243 | 1.00996 | 0.99357 | 1.09503 | 0.81158 |
| MLS001095231-01 | 0.83555 | 0.98635 | 0.96948 | 1.02204 | 0.93816 | 1.00477 |
| MLS000721584-01 | 0.9927 | 0.91547 | 0.88669 | 0.88021 | 0.98327 | 0.91477 |
| MLS001183429-01 | 0.26288 | 0.4076 | 0.733 | 0.85574 | 0.82302 | 0.80419 |
| MLS002158881-01 | 1.00118 | 1.20183 | 0.77262 | 0.67034 | 0.86523 | 0.89603 |
| MLS001165749-01 | 0.73418 | 0.7808 | 1.12222 | 1.1624 | 1.07825 | 0.95317 |
| MLS001237320-01 | 0.97868 | 0.99122 | 0.65538 | 1.03546 | 1.05525 | 0.98786 |
| MLS000763405-01 | 1.37591 | 1.45481 | 1.1121 | 1.21073 | 1.13948 | 1.03273 |
| MLS000538580-01 | 0.18248 | 0.92803 | 0.47741 | 0.8641 | 1.02508 | 1.08678 |
| MLS001033202-01 | 0.98604 | 1.05145 | 1.0906 | 1.04232 | 1.01895 | 1.05691 |
| MLS001216260-01 | 0.93478 | 0.91445 | 1.06046 | 1.15971 | 0.98935 | 1.00499 |
| MLS000085522-01 | 0.556 | 1.02941 | 0.92486 | 0.87196 | 0.8415 | 0.96218 |
| MLS000702680-01 | 0.74641 | 0.80744 | 0.77734 | 0.96778 | 0.91962 | 1.01629 |
| MLS001212998-01 | 1.05241 | 1.4472 | 1.44543 | 1.4553 | 1.10305 | 1.14344 |
| MLS001160885-01 | 0.92003 | 1.01751 | 1.14627 | 1.10829 | 0.95686 | 1.00027 |

TABLE 10-continued

Burkin Assay in Myotubes

| | 40 uM | 20 uM | 10 uM | 5 uM | 1 uM | 0.5 uM |
|---|---|---|---|---|---|---|
| MLS001122718-01 | 0.98039 | 1.08947 | 1.10635 | 1.06877 | 0.94347 | 1.01133 |
| MLS000027478-01 | 0.91147 | 0.98536 | 0.9583 | 0.984 | 0.90435 | 1.0222 |
| MLS001177364-01 | 0.6717 | 1.12523 | 1.21312 | 1.23479 | 0.95193 | 1.03584 |
| MLS001179695-01 | 0.85456 | 0.92985 | 0.99222 | 1.19881 | 0.94899 | 1.05344 |
| MLS002251986-01 | 0.91124 | 0.98819 | 1.08822 | 1.07325 | 0.95152 | 1.12062 |
| MLS001166704-01 | 0.81001 | 0.79177 | 1.06471 | 0.89357 | 1.26767 | 1.166 |
| MLS001196422-01 | 0.97494 | 1.09481 | 1.3198 | 1.19044 | 1.14189 | 0.97577 |
| MLS001179624-01 | 0.21827 | 0.89035 | 1.10439 | 1.04824 | 0.97089 | 0.9052 |
| MLS001223425-01 | 1.18449 | 1.14219 | 1.37641 | 0.91422 | 1.22038 | 1.07959 |
| MLS001117140-01 | 1.0628 | 1.08703 | 1.37473 | 1.09477 | 1.11707 | 0.93188 |
| MLS001110618-01 | 0.94634 | 1.0381 | 1.25185 | 1.11356 | 1.06727 | 0.95258 |
| MLS001223482-01 | 0.96702 | 1.13235 | 1.52904 | 1.26854 | 1.14804 | 1.06047 |
| MLS000680049-01 | 0.43791 | 0.87306 | 1.22022 | 1.04721 | 1.05615 | 0.88755 |
| MLS001212498-01 | 1.15666 | 1.15759 | 1.34193 | 1.10705 | 1.11751 | 0.94103 |
| MLS001124732-01 | 0.78881 | 0.87194 | 0.89636 | 0.87591 | 1.02949 | 1.0065 |
| MLS000526364-01 | 0.91621 | 1.35752 | 0.89076 | 1.03293 | 0.89526 | 0.96484 |
| MLS000767227-01 | 0.9434 | 0.77748 | 0.84403 | 0.96445 | 0.89975 | 0.85931 |
| MLS000703499-01 | 0.44935 | 1.10118 | 0.85178 | 1.05913 | 0.88093 | 0.97252 |
| MLS001167169-01 | 0.62616 | 1.3902 | 0.96963 | 1.04119 | 0.93745 | 0.89248 |
| MLS001198693-01 | 1.11598 | 0.93192 | 0.95144 | 1.01113 | 0.90482 | 0.95996 |
| MLS001219345-01 | 0.92318 | 0.71463 | 1.0424 | 1.07784 | 0.98891 | 0.94156 |
| MLS001211651-01 | 1.02681 | 1.07588 | 1.02524 | 1.11572 | 0.91297 | 0.85432 |
| MLS000806880-01 | 0.93527 | 1.05733 | 0.99601 | 0.90936 | 0.87308 | 0.735 |
| MLS001223567-01 | 0.99314 | 0.99913 | 0.92396 | 0.8636 | 0.99783 | 0.95334 |
| MLS001005283-01 | 0.75963 | 0.9432 | 0.91413 | 0.85832 | 0.99512 | 0.98114 |
| MLS001218427-01 | 0.42896 | 0.33115 | 0.60544 | 0.84638 | 0.7974 | 0.80515 |
| MLS001139288-01 | 0.78077 | 1.31295 | 0.97767 | 0.98285 | 0.85249 | 0.92343 |
| MLS000696445-01 | 0.84334 | 0.58427 | 0.62501 | 0.9714 | 0.86366 | 0.86019 |
| MLS001218795-01 | 0.96063 | 0.9463 | 0.99909 | 0.97775 | 0.9363 | 0.96478 |
| MLS000419555-01 | 1.01948 | 1.01177 | 1.09286 | 1.14975 | 1.01818 | 1.05246 |
| MLS001225507-01 | 0.95391 | 1.17494 | 1.00225 | 1.01286 | 0.67411 | 0.93211 |
| MLS000663651-01 | 0.96476 | 1.01671 | 1.00729 | 1.10579 | 0.90988 | 0.94596 |
| MLS000706349-01 | 0.92386 | 1.07347 | 0.9294 | 0.97383 | 1.00814 | 1.19252 |
| MLS000393110-01 | 0.81734 | 0.67258 | 0.98158 | 1.02232 | 0.92759 | 1.13888 |
| MLS000574647-01 | 0.82187 | 1.00598 | 0.85961 | 1.00656 | 0.86456 | 0.93501 |
| MLS000532969-01 | 1.46962 | 1.64768 | 1.35295 | 1.52016 | 1.03395 | 1.1906 |
| MLS001125260-01 | 0.90862 | 0.90566 | 0.94019 | 1.02222 | 0.86628 | 1.00234 |
| MLS000122749-01 | 0.93057 | 1.25564 | 1.13138 | 1.09637 | 0.99818 | 1.04233 |
| MLS001150751-01 | 0.5343 | 1.0842 | 1.02303 | 1.25375 | 0.95035 | 1.0993 |
| MLS001221867-01 | 0.9915 | 1.01963 | 0.93743 | 0.95928 | 0.94218 | 0.97278 |
| MLS001147727-01 | 0.96519 | 1.10951 | 0.97163 | 1.10077 | 0.78772 | 0.99369 |
| MLS000684437-01 | 1.03392 | 0.99294 | 1.10191 | 1.12359 | 1.19436 | 1.07625 |
| MLS001211976-01 | 1.1302 | 1.09895 | 1.19884 | 1.24128 | 1.2336 | 1.03242 |
| MLS002161350-01 | 1.11602 | 1.04912 | 0.98699 | 0.77831 | 1.17667 | 0.98443 |
| MLS001077207-01 | 1.20734 | 1.00773 | 1.14894 | 1.42157 | 1.06141 | 0.9848 |
| MLS001209245-01 | 0.57286 | 0.68765 | 0.99794 | 0.96674 | 1.24547 | 1.11315 |
| MLS000737953-01 | 0.53393 | 1.00681 | 1.22632 | 1.24139 | 1.13455 | 0.96648 |
| MLS000552080-01 | 0.92859 | 1.0378 | 1.23976 | 1.21445 | 1.14993 | 0.96716 |
| MLS000737204-01 | 0.66817 | 0.8815 | 1.11988 | 1.0331 | 1.17335 | 1.04251 |
| MLS000579238-01 | 0.77083 | 0.856 | 1.10409 | 1.01011 | 1.10886 | 0.9507 |
| MLS001181671-01 | 0.98779 | 0.98542 | 1.21954 | 1.33701 | 0.90946 | 1.07118 |
| MLS001167424-01 | 0.97794 | 1.0277 | 0.7848 | 1.36476 | 0.95956 | 1.04607 |
| MLS000094770-01 | 0.71187 | 0.81748 | 0.82301 | 1.31662 | 1.00014 | 1.13971 |
| MLS001123810-01 | 0.96938 | 0.95147 | 1.11589 | 1.41658 | 0.9657 | 0.97401 |
| MLS000532078-01 | 1.04337 | 1.07767 | 1.11359 | 1.239 | 1.07805 | 1.0727 |
| MLS000585616-01 | 0.96223 | 1.03062 | 1.14727 | 1.58056 | 0.95754 | 0.99906 |
| MLS000553673-01 | 1.13447 | 1.08812 | 1.16112 | 1.30384 | 0.89228 | 0.87494 |
| MLS001175592-01 | 1.04727 | 0.64453 | 1.03403 | 0.69108 | 0.986 | 0.96848 |
| MLS001033255-01 | 1.03969 | 0.86833 | 0.99699 | 1.21268 | 0.95257 | 0.96782 |
| MLS000733703-01 | 0.894 | 0.9957 | 1.14714 | 0.87792 | 1.12841 | 1.06336 |
| MLS001096269-01 | 0.91223 | 1.13461 | 1.11864 | 1.30716 | 1.08849 | 0.99921 |
| MLS001162872-01 | 0.88763 | 1.03393 | 1.03106 | 0.83691 | 1.05081 | 1.12992 |
| MLS000584511-01 | 1.04063 | 1.00352 | 1.16335 | 1.2189 | 1.05102 | 1.0682 |
| MLS001166325-01 | 1.0054 | 0.95925 | 1.06467 | 1.11151 | 1.04905 | 1.05671 |
| MLS000122180-01 | 0.94955 | 0.9557 | 0.74557 | 1.02716 | 0.93405 | 1.00577 |
| MLS001157804-01 | 1.18827 | 1.06942 | 1.08307 | 1.03088 | 1.01331 | 1.04505 |
| MLS000693729-01 | 1.05588 | 0.9682 | 1.14413 | 1.11873 | 0.77074 | 0.82188 |
| MLS001220669-01 | 1.01145 | 1.00318 | 1.03797 | 1.0117 | 0.97798 | 0.97225 |
| MLS001244461-01 | 0.88438 | 1.08667 | 0.94574 | 1.07181 | 0.95864 | 1.20656 |
| MLS000081838-01 | 1.03597 | 1.22502 | 0.87042 | 0.90024 | 1.01752 | 0.74245 |
| MLS002402866-01 | 0.92366 | 1.07525 | 1.00041 | 1.181 | 1.25798 | 1.09045 |
| MLS001200980-01 | 0.9712 | 1.01483 | 1.21582 | 1.12144 | 1.02235 | 1.0669 |
| MLS001174719-01 | 0.73741 | 0.97712 | 1.03422 | 1.12778 | 1.00054 | 1.13473 |
| MLS001175449-01 | 0.80412 | 1.15115 | 0.93663 | 1.15584 | 1.01599 | 1.1188 |
| MLS001172577-01 | 0.73236 | 1.14005 | 1.10122 | 1.13147 | 1.0349 | 1.12157 |
| MLS001122792-01 | 0.85223 | 1.06818 | 0.6414 | 1.10175 | 1.03173 | 1.19222 |

TABLE 10-continued

Burkin Assay in Myotubes

| | 40 uM | 20 uM | 10 uM | 5 uM | 1 uM | 0.5 uM |
|---|---|---|---|---|---|---|
| MLS001216405-01 | 0.87057 | 0.93866 | 0.96422 | 1.12433 | 0.99268 | 1.12759 |
| MLS000673766-01 | 0.87173 | 0.82722 | 0.92763 | 0.89603 | 0.98625 | 0.96802 |
| MLS000912614-01 | 0.78553 | 0.77496 | 1.05484 | 1.10265 | 1.02407 | 1.04186 |
| MLS001194551-01 | 1.28081 | 1.20915 | 1.09418 | 1.04262 | 1.01038 | 1.0169 |
| MLS001214704-01 | 1.15847 | 1.05612 | 1.10982 | 1.07011 | 1.11315 | 0.97637 |
| MLS001219159-01 | 0.95074 | 0.94742 | 1.06395 | 0.80696 | 0.99654 | 0.861 |
| MLS001060549-01 | 0.91344 | 0.93911 | 1.11095 | 0.97834 | 1.07101 | 0.81811 |
| MLS000850824-01 | 1.20693 | 1.14342 | 1.0727 | 0.98997 | 1.09142 | 0.90829 |
| MLS000879190-01 | 0.8486 | 1.08434 | 0.91319 | 1.05175 | 1.13391 | 0.96497 |
| MLS001163140-01 | 1.01076 | 0.96509 | 1.1264 | 0.92815 | 1.03471 | 0.92359 |
| MLS000046123-01 | 0.92032 | 0.92679 | 0.86499 | 0.89047 | 0.93893 | 0.98024 |
| MLS000086970-01 | 0.88711 | 0.93125 | 0.96054 | 1.086 | 0.92199 | 0.95281 |
| MLS000388722-01 | 0.9404 | 0.80013 | 1.04165 | 1.03216 | 0.93686 | 0.92252 |
| MLS000676974-01 | 0.54473 | 0.97579 | 0.59939 | 0.70092 | 0.90205 | 0.91712 |
| MLS000772580-01 | 0.85346 | 0.94129 | 0.94737 | 1.32302 | 0.89986 | 0.85101 |
| MLS000698686-01 | 0.97223 | 0.6986 | 0.96603 | 1.01328 | 0.61586 | 0.88382 |
| MLS001162337-01 | 1.01442 | 1.16958 | 0.97377 | 1.00937 | 0.88495 | 0.69861 |
| MLS001204005-01 | 1.15931 | 0.81814 | 1.01778 | 0.76301 | 0.98694 | 0.90311 |
| MLS000721525-01 | 1.04717 | 0.89679 | 0.98056 | 0.66934 | 0.91358 | 0.66465 |
| MLS000525404-01 | 1.34722 | 1.19322 | 1.09097 | 1.11785 | 1.04083 | 1.04334 |
| MLS000772194-01 | 0.76515 | 0.99042 | 1.07217 | 0.96542 | 0.91916 | 0.97818 |
| MLS000775793-01 | 0.9508 | 0.99649 | 0.62239 | 0.87223 | 0.88326 | 0.93913 |
| MLS000710130-01 | 1.06401 | 1.04449 | 0.64515 | 0.61831 | 0.85241 | 0.98109 |
| MLS001146463-01 | 0.84238 | 0.84654 | 0.75138 | 1.21637 | 0.80315 | 0.88271 |
| MLS000712769-01 | 0.98169 | 0.92193 | 0.90375 | 1.2524 | 0.84283 | 0.97463 |
| MLS000334464-01 | 0.66588 | 1.12731 | 0.99178 | 1.00153 | 0.88028 | 0.98611 |
| MLS000862690-01 | 1.0763 | 1.0131 | 0.94809 | 0.59412 | 0.95764 | 1.12516 |
| MLS001179267-01 | 0.51107 | 0.85888 | 0.55899 | 0.89079 | 0.8787 | 0.94697 |
| MLS000683174-01 | 0.98644 | 1.08147 | 0.89073 | 1.00731 | 0.91651 | 1.14461 |
| MLS000913052-01 | 0.82866 | 0.97247 | 1.01326 | 1.05486 | 0.90137 | 1.07299 |
| MLS001080869-01 | 0.98021 | 0.98618 | 0.92569 | 0.97397 | 0.95744 | 1.01118 |
| MLS000332693-01 | 0.92516 | 0.97088 | 0.97983 | 1.09234 | 0.96309 | 1.0441 |
| MLS001141113-01 | 0.812 | 0.88742 | 0.92937 | 1.0538 | 0.85387 | 1.03774 |
| MLS001176611-01 | 0.98456 | 0.96653 | 0.93014 | 1.06623 | 0.66708 | 0.95057 |
| MLS001202627-01 | 0.23353 | 0.93939 | 0.81243 | 1.02515 | 0.76915 | 0.96869 |
| MLS000765108-01 | 0.7072 | 0.9224 | 0.60883 | 1.06063 | 1.01958 | 0.87214 |
| MLS000937079-01 | 0.91968 | 1.14203 | 0.8882 | 0.97562 | 0.63721 | 1.0515 |
| MLS001215742-01 | 0.96872 | 0.83842 | 1.15548 | 0.98031 | 1.10449 | 1.01971 |
| MLS001217045-01 | 1.05145 | 1.11523 | 1.15422 | 0.94 | 1.15574 | 1.00142 |
| MLS001196946-01 | 0.28319 | 0.54647 | 0.94694 | 1.00195 | 1.11272 | 0.99416 |
| MLS001216714-01 | 0.67688 | 0.706 | 1.3235 | 1.1023 | 1.17442 | 1.02706 |
| MLS000772430-01 | 1.04803 | 1.25987 | 1.25362 | 1.04073 | 1.2757 | 1.03466 |
| MLS000693370-01 | 1.245 | 1.15055 | 1.28243 | 1.15793 | 1.13104 | 1.10635 |
| MLS000769322-01 | 1.019 | 1.06721 | 1.16504 | 1.1195 | 1.05468 | 0.96093 |
| MLS000721030-01 | 1.20547 | 1.1412 | 1.2344 | 1.12136 | 1.05053 | 0.97569 |
| MLS001176897-01 | 1.16313 | 1.14489 | 1.19416 | 1.02235 | 1.07267 | 0.95773 |
| MLS000774940-01 | 0.87802 | 1.08429 | 0.99082 | 1.00988 | 0.97774 | 0.9469 |
| MLS001030746-01 | 1.06708 | 0.98862 | 0.94961 | 1.03058 | 0.96919 | 1.04669 |
| MLS003126425-01 | 0.52076 | 0.73725 | 1.6782 | 1.42164 | 1.20322 | 1.10413 |
| MLS001217697-01 | 1.11655 | 1.12294 | 1.19743 | 1.16037 | 0.96777 | 1.20389 |
| MLS000516719-01 | 1.17505 | 1.10738 | 1.18354 | 1.20263 | 1.0239 | 0.86182 |
| MLS001165323-01 | 1.08827 | 1.05423 | 1.15283 | 1.166 | 0.96267 | 0.94685 |
| MLS001220803-01 | 0.96218 | 1.0147 | 1.07507 | 1.17995 | 0.97031 | 0.93451 |
| MLS001163121-01 | 1.09034 | 1.07048 | 1.17333 | 0.93955 | 0.98945 | 1.05191 |
| MLS001060561-01 | 0.93292 | 0.85568 | 0.99768 | 0.98322 | 0.93293 | 0.80472 |
| MLS001139515-01 | 1.01273 | 1.12444 | 0.94878 | 1.01346 | 1.00945 | 0.9636 |
| MLS001149811-01 | 0.54317 | 0.84563 | 0.90865 | 0.94337 | 0.99933 | 0.95702 |
| MLS000773700-01 | 0.47196 | 0.98949 | 0.95155 | 0.71177 | 1.01875 | 1.00839 |
| MLS001177045-01 | 0.96779 | 1.10985 | 1.0851 | 1.02356 | 0.81454 | 1.04675 |
| MLS000693747-01 | 1.0456 | 1.12188 | 0.91107 | 1.43271 | 0.71944 | 1.06136 |
| MLS001175556-01 | 0.75145 | 0.90095 | 0.90127 | 1.09994 | 1.02814 | 0.94901 |
| MLS001175473-01 | 0.79712 | 1.04117 | 0.99773 | 0.8872 | 0.91773 | 0.95559 |
| MLS002156278-01 | 1.02456 | 0.97186 | 0.99244 | 0.69084 | 0.9637 | 1.00503 |
| MLS000707281-01 | 1.14087 | 1.15567 | 0.75052 | 1.05935 | 0.65371 | 1.01094 |
| MLS000591198-01 | 0.70144 | 0.98525 | 0.85477 | 1.00046 | 0.88105 | 1.01695 |
| MLS000714175-01 | 1.02244 | 1.11863 | 1.01289 | 1.13111 | 1.06141 | 1.08575 |
| MLS002163386-01 | 1.01995 | 1.06351 | 1.06415 | 1.11206 | 1.04751 | 1.10384 |
| MLS000761297-01 | 1.09327 | 1.04516 | 1.03348 | 1.15364 | 1.02167 | 1.0906 |
| MLS002245351-01 | 1.03102 | 1.06127 | 1.042 | 1.10724 | 0.94631 | 1.04658 |
| MLS000718886-01 | 0.97849 | 0.93799 | 0.99814 | 1.06782 | 0.95909 | 0.98188 |
| MLS002156485-01 | 1.15603 | 1.05728 | 1.0687 | 1.2005 | 0.98067 | 1.0551 |
| MLS001140657-01 | 0.97076 | 0.9948 | 0.99812 | 1.08308 | 0.95059 | 1.03407 |
| MLS002157024-01 | 1.07674 | 1.18645 | 0.93233 | 1.12188 | 0.88418 | 1.01348 |
| MLS000721730-01 | 1.07097 | 0.87695 | 1.02458 | 0.85627 | 1.06447 | 0.91949 |
| MLS000705922-01 | 1.03921 | 0.90721 | 0.95439 | 0.85107 | 1.13665 | 0.89838 |
| MLS000724709-01 | 0.97675 | 0.885 | 1.00234 | 1.04022 | 1.46739 | 0.99608 |

TABLE 10-continued

Burkin Assay in Myotubes

| | 40 uM | 20 uM | 10 uM | 5 uM | 1 uM | 0.5 uM |
|---|---|---|---|---|---|---|
| MLS002161757-01 | 1.14604 | 0.97951 | 1.06023 | 1.09241 | 1.06958 | 0.8459 |
| MLS002164687-01 | 1.0594 | 1.01681 | 1.36762 | 1.23385 | 1.00235 | 0.85316 |
| MLS001060533-01 | 1.11677 | 1.34224 | 1.51976 | 1.31756 | 1.20754 | 0.94638 |
| MLS000685139-01 | 1.26695 | 1.10202 | 1.24049 | 1.12834 | 0.92023 | 0.87033 |
| MLS001217286-01 | 0.5964 | 1.09526 | 1.21873 | 1.19269 | 0.99106 | 0.76168 |
| MLS001221619-01 | 1.03393 | 0.86027 | 1.01242 | 0.94404 | 0.95568 | 0.82601 |
| MLS001219621-01 | 0.45369 | 0.648 | 0.86159 | 0.8883 | 0.86027 | 0.9394 |
| MLS001166156-01 | 0.44609 | 0.82177 | 0.75916 | 1.07035 | 0.85209 | 1.00131 |
| MLS000534926-01 | 0.85648 | 1.33769 | 0.9622 | 1.00584 | 0.94445 | 1.02592 |
| MLS000548725-01 | 0.22187 | 1.03126 | 0.84619 | 0.9206 | 0.84182 | 0.86975 |
| MLS000374261-01 | 0.44896 | 0.42298 | 0.92885 | 1.13089 | 0.83858 | 0.81441 |
| MLS000123454-01 | 0.88519 | 0.68413 | 1.08253 | 1.04655 | 0.89626 | 1.06673 |
| MLS000625140-01 | 0.65137 | 0.67934 | 0.91312 | 1.11353 | 0.84537 | 0.84836 |
| MLS001214443-01 | 1.08326 | 1.15407 | 1.19298 | 0.94422 | 0.90181 | 0.82616 |

TABLE 11

CMV-LACZ in Myoblasts

| | 40 uM | 20 uM | 10 uM | 5 uM | 1 uM | 0.5 uM |
|---|---|---|---|---|---|---|
| MLS000591667-01 | 1.0593 | 0.8030 | 1.1592 | 1.1587 | 0.7850 | 0.9491 |
| MLS000568234-01 | 0.7322 | 0.8819 | 0.9894 | 0.9043 | 0.9372 | 0.9556 |
| MLS000689562-01 | 1.0619 | 0.9919 | 1.0858 | 0.8060 | 0.7409 | 0.8453 |
| MLS000732652-01 | 0.7856 | 0.9374 | 1.1235 | 1.1327 | 0.7744 | 0.6700 |
| MLS001240181-01 | 0.8907 | 1.0367 | 1.1645 | 0.8408 | 1.0441 | 0.9550 |
| MLS001211139-01 | 0.8744 | 1.0659 | 0.8608 | 0.9500 | 0.7347 | 0.9691 |
| MLS001030268-01 | 0.5556 | 0.7467 | 1.1787 | 1.1347 | 1.1550 | 1.0809 |
| MLS000912699-01 | 0.5204 | 0.8826 | 1.0462 | 0.9111 | 0.8744 | 0.7147 |
| MLS001125260-01 | 1.2270 | 1.0563 | 0.9131 | 1.0114 | 1.0584 | 1.1581 |
| MLS000717689-01 | 0.8996 | 1.0407 | 1.0936 | 1.1129 | 1.0203 | 1.0125 |
| MLS001197665-01 | 1.0267 | 0.9556 | 0.8403 | 0.9214 | 0.8347 | 0.8584 |
| MLS001075922-01 | 1.3037 | 0.9881 | 1.2361 | 1.6332 | 1.3028 | 0.9434 |
| MLS001124046-01 | 1.0807 | 0.9881 | 0.8501 | 0.9307 | 1.2650 | 0.8409 |
| MLS001197220-01 | 1.2844 | 0.9567 | 1.1383 | 0.9355 | 1.1569 | 1.2028 |
| MLS001221318-01 | 1.5641 | 1.0181 | 0.9955 | 1.0999 | 1.0538 | 0.8528 |
| MLS000947910-01 | 1.0500 | 1.0870 | 1.0379 | 0.9452 | 0.9250 | 1.0094 |
| MLS001215795-01 | 0.8256 | 0.8196 | 0.8628 | 1.0974 | 1.1375 | 0.8003 |
| MLS002163670-01 | 1.4715 | 0.8611 | 0.9725 | 0.8671 | 0.8738 | 1.1806 |
| MLS001200149-01 | 1.1552 | 0.9363 | 1.0523 | 0.9489 | 0.9203 | 1.1234 |
| MLS001359861-01 | 1.0330 | 0.9074 | 0.8064 | 0.9009 | 0.9184 | 0.9444 |
| MLS000710669-01 | 0.8778 | 1.1319 | 1.0823 | 1.0325 | 0.9975 | 1.0969 |
| MLS001035690-01 | 0.9178 | 1.3585 | 1.2020 | 0.9910 | 1.0406 | 0.9819 |
| MLS001030621-01 | 0.9063 | 1.0307 | 1.1844 | 1.0494 | 1.0531 | 0.7081 |
| MLS001083082-01 | 0.8144 | 0.9615 | 1.1713 | 1.0409 | 0.9234 | 0.8591 |
| MLS000045588-01 | 1.2167 | 0.8056 | 1.0611 | 1.0245 | 0.8372 | 0.7647 |
| MLS001216939-01 | 1.0644 | 1.1863 | 0.9452 | 1.0913 | 1.1134 | 1.0991 |
| MLS001163859-01 | 0.8104 | 0.7593 | 1.1812 | 1.2009 | 1.1684 | 1.1113 |
| MLS000683232-01 | 0.8237 | 0.6119 | 0.5224 | 0.5638 | 0.7131 | 0.8043 |
| MLS001170856-01 | 0.8389 | 0.8881 | 1.0004 | 0.7938 | 0.9857 | 0.7337 |
| MLS002667707-01 | 1.1226 | 1.0044 | 1.0803 | 1.1897 | 0.6763 | 1.1434 |
| MLS001200665-01 | 0.9937 | 0.7152 | 1.0036 | 0.9398 | 0.9783 | 1.1043 |
| MLS002161853-01 | 0.9348 | 1.0922 | 0.9436 | 0.8819 | 0.8734 | 1.0131 |
| MLS002163101-01 | 1.1556 | 0.9644 | 1.0313 | 1.0262 | 1.0317 | 0.9991 |
| MLS000062431-01 | 1.0993 | 1.0467 | 1.1632 | 0.9848 | 1.1631 | 0.9557 |
| MLS000028160-01 | 0.8600 | 0.8967 | 1.2759 | 0.9378 | 0.9029 | 1.0663 |
| MLS002248819-01 | 1.0270 | 1.7330 | 1.1575 | 1.2604 | 1.2206 | 0.9206 |
| MLS000080654-01 | 0.8815 | 1.0174 | 0.9345 | 1.0703 | 1.4314 | 1.1851 |
| MLS000760876-01 | 0.8504 | 0.9396 | 0.8973 | 0.8293 | 1.0546 | 0.9069 |
| MLS000677675-01 | 1.1578 | 1.0763 | 1.0373 | 0.9905 | 1.1214 | 1.0343 |
| MLS000113985-01 | 0.1841 | 0.2126 | 0.9187 | 1.0836 | 1.0049 | 0.9809 |
| MLS001182368-01 | 1.1615 | 1.2322 | 0.9225 | 1.0528 | 0.8783 | 0.9571 |
| MLS001212882-01 | 1.0326 | 1.3230 | 1.0086 | 0.9792 | 1.1291 | 1.1409 |
| MLS001004364-01 | 1.0441 | 1.0263 | 0.9011 | 1.0438 | 1.0643 | 0.9117 |
| MLS000736846-01 | 1.0174 | 1.3459 | 1.1101 | 1.0269 | 1.0386 | 1.1009 |
| MLS001098105-01 | 0.8704 | 1.0381 | 0.9421 | 0.9282 | 0.8054 | 1.4689 |
| MLS000678673-01 | 0.9656 | 0.8674 | 0.8991 | 1.0561 | 1.1914 | 1.2106 |
| MLS000925023-01 | 0.3278 | 0.5504 | 0.8397 | 0.9762 | 0.9629 | 1.0703 |
| MLS001212319-01 | 1.0259 | 1.2056 | 0.8600 | 1.0840 | 1.2040 | 0.9129 |
| MLS000779126-01 | 0.7441 | 0.9944 | 0.7610 | 0.9637 | 0.9994 | 0.9751 |
| MLS000948055-01 | 0.5522 | 0.5407 | 1.0993 | 1.0787 | 0.9674 | 0.7540 |
| MLS000110418-01 | 0.7141 | 0.8926 | 0.9455 | 1.0913 | 0.9989 | 0.8871 |
| MLS000693704-01 | 1.0567 | 0.7996 | 0.9977 | 0.9522 | 1.1157 | 0.8989 |

TABLE 11-continued

CMV-LACZ in Myoblasts

| | 40 uM | 20 uM | 10 uM | 5 uM | 1 uM | 0.5 uM |
|---|---|---|---|---|---|---|
| MLS001225512-01 | 1.0111 | 0.8237 | 1.4266 | 1.1655 | 1.0843 | 0.9597 |
| MLS001006798-01 | 0.8263 | 0.9622 | 1.0189 | 1.1509 | 1.0326 | 0.8334 |
| MLS000711491-01 | 0.7800 | 1.5063 | 1.0199 | 0.9088 | 1.1060 | 1.0889 |
| MLS000582947-01 | 0.8819 | 0.7811 | 1.0067 | 1.1273 | 0.8991 | 0.9691 |
| MLS000531177-01 | 0.9422 | 1.2952 | 0.8958 | 1.0150 | 1.5065 | 1.0785 |
| MLS001202389-01 | 0.5081 | 0.6115 | 0.8920 | 1.0084 | 1.1108 | 1.0237 |
| MLS000536064-01 | 2.4896 | 2.5396 | 1.3388 | 2.0402 | 0.7412 | 0.9105 |
| MLS000586245-01 | 0.7674 | 0.7726 | 1.0505 | 0.9258 | 0.8985 | 0.9034 |
| MLS001061374-01 | 1.1037 | 0.9744 | 0.9793 | 1.0601 | 1.1702 | 0.7117 |
| MLS000675441-01 | 0.7437 | 0.8656 | 0.8690 | 0.8800 | 0.9289 | 1.0332 |
| MLS001200396-01 | 0.9011 | 0.7252 | 1.2107 | 1.0212 | 0.9157 | 1.0489 |
| MLS001165937-01 | 0.4007 | 0.4526 | 0.7441 | 0.8816 | 0.7788 | 0.7295 |
| MLS000325736-01 | 1.0537 | 1.0111 | 1.0696 | 0.9758 | 0.9135 | 0.7862 |
| MLS001215357-01 | 0.4719 | 1.2467 | 1.0378 | 0.8575 | 1.2686 | 1.1560 |
| MLS000588210-01 | 0.9000 | 1.0307 | 0.9316 | 0.7808 | 0.9782 | 1.2908 |
| MLS000764729-01 | 0.7504 | 1.1200 | 0.8880 | 1.0259 | 0.9520 | 0.9865 |
| MLS000689492-01 | 1.0026 | 1.0141 | 0.8653 | 1.0863 | 1.0252 | 0.9363 |
| MLS001000299-01 | 1.0107 | 1.1522 | 0.8248 | 0.9901 | 1.2745 | 1.4188 |
| MLS000393762-01 | 0.4467 | 0.3793 | 1.0198 | 1.0114 | 0.9351 | 0.9560 |
| MLS001130011-01 | 0.8311 | 0.7837 | 1.1138 | 1.0011 | 0.7695 | 1.1702 |
| MLS001229477-01 | 0.8800 | 1.0674 | 1.1311 | 1.1078 | 1.1345 | 1.0283 |
| MLS000707378-01 | 0.6548 | 0.8667 | 0.8072 | 0.8309 | 1.0883 | 1.0175 |
| MLS000573208-01 | 0.9289 | 0.6626 | 0.8678 | 1.1030 | 0.9594 | 1.0197 |
| MLS001167281-01 | 0.7467 | 0.9256 | 1.1951 | 0.9684 | 1.1289 | 1.0114 |
| MLS000053342-01 | 0.9930 | 0.9811 | 0.8785 | 1.0865 | 1.0397 | 1.0289 |
| MLS002171615-01 | 0.6726 | 1.2159 | 0.9905 | 0.9273 | 1.3505 | 1.0498 |
| MLS001005712-01 | 1.0230 | 1.0241 | 0.9125 | 0.8934 | 1.2385 | 1.0188 |
| MLS001176153-01 | 1.0763 | 0.9322 | 0.9140 | 0.8976 | 1.4588 | 1.2729 |
| MLS000735021-01 | 0.9767 | 1.2130 | 0.9907 | 0.9756 | 1.1646 | 0.8683 |
| MLS000767397-01 | 1.1433 | 0.8485 | 0.9687 | 0.9910 | 1.0646 | 1.2748 |
| MLS001196572-01 | 1.0778 | 1.0767 | 0.9456 | 1.0605 | 1.3172 | 1.0105 |
| MLS000393966-01 | 0.9156 | 1.0411 | 0.8087 | 1.1744 | 1.0625 | 0.9249 |
| MLS001034810-01 | 0.7030 | 1.1193 | 0.9459 | 1.0948 | 0.9538 | 0.9698 |
| MLS001165394-01 | 0.9570 | 0.8663 | 0.9792 | 1.0941 | 1.0015 | 1.0655 |
| MLS000089464-01 | 0.5274 | 0.7500 | 1.1969 | 0.9372 | 0.9160 | 0.9117 |
| MLS000698617-01 | 1.0356 | 1.1670 | 1.0603 | 1.1399 | 0.9852 | 1.3409 |
| MLS001175021-01 | 1.0907 | 1.1070 | 0.9395 | 0.9282 | 1.0729 | 1.1772 |
| MLS001166758-01 | 0.3481 | 0.6126 | 1.0661 | 1.1998 | 1.0175 | 0.9357 |
| MLS001008109-01 | 0.7619 | 0.8730 | 1.2178 | 0.9228 | 1.1138 | 0.9542 |
| MLS001181936-01 | 0.6130 | 0.7863 | 0.8296 | 0.7292 | 0.9273 | 0.8487 |
| MLS000560266-01 | 1.0484 | 1.1095 | 0.9991 | 0.9405 | 0.8123 | 0.9030 |
| MLS001215074-01 | 1.1432 | 1.1277 | 1.0294 | 1.1754 | 0.7800 | 0.7877 |
| MLS001215123-01 | 1.0098 | 1.2639 | 1.1943 | 1.0888 | 0.8837 | 1.0530 |
| MLS001033255-01 | 0.7905 | 1.1919 | 1.0219 | 0.8766 | 1.0723 | 0.7590 |
| MLS001160611-01 | 1.0389 | 0.8144 | 1.0340 | 1.0117 | 0.8157 | 1.2070 |
| MLS001006302-01 | 0.7646 | 0.9502 | 1.0767 | 0.8911 | 0.7663 | 0.9343 |
| MLS001123876-01 | 0.7333 | 0.9618 | 0.9871 | 0.9251 | 1.0263 | 0.8260 |
| MLS001122698-01 | 1.0639 | 1.0404 | 0.8608 | 0.7759 | 1.1003 | 1.1513 |
| MLS000755214-01 | 0.8172 | 1.0835 | 1.0994 | 0.9281 | 1.1650 | 1.0190 |
| MLS000731285-01 | 0.6572 | 0.9582 | 0.8436 | 1.0851 | 1.0853 | 1.1747 |
| MLS000776409-01 | 0.2105 | 1.3344 | 0.9052 | 0.8929 | 0.9103 | 1.1220 |
| MLS001221908-01 | 0.6789 | 0.9726 | 0.7908 | 0.9357 | 0.7607 | 0.9663 |
| MLS000419286-01 | 0.6295 | 0.9368 | 0.8022 | 0.9701 | 0.7960 | 0.9960 |
| MLS000554416-01 | 0.8611 | 1.1077 | 1.1123 | 0.8594 | 1.3983 | 1.1310 |
| MLS000073150-01 | 0.9000 | 0.9491 | 0.9954 | 0.8193 | 1.8970 | 1.0753 |
| MLS000663185-01 | 0.9347 | 0.9211 | 0.8567 | 0.9688 | 1.1477 | 1.1390 |
| MLS001078811-01 | 0.9014 | 0.8393 | 0.6873 | 0.7927 | 1.2290 | 1.2397 |
| MLS002694363-01 | 0.5698 | 1.0123 | 1.0392 | 0.7616 | 1.2840 | 1.1110 |
| MLS000689218-01 | 1.6337 | 1.2835 | 1.0813 | 0.8689 | 1.2273 | 1.1977 |
| MLS001215294-01 | 0.4116 | 0.3302 | 1.3412 | 0.8138 | 1.2817 | 1.2983 |
| MLS001183575-01 | 0.8856 | 1.2825 | 0.7762 | 0.8972 | 1.2440 | 1.1603 |
| MLS000393567-01 | 1.1319 | 1.0175 | 0.8148 | 0.6593 | 1.1373 | 1.2117 |
| MLS000546316-01 | 1.5049 | 1.3463 | 1.2440 | 0.8090 | 1.1373 | 1.0623 |
| MLS000912258-01 | 0.8621 | 1.1074 | 1.0171 | 0.9071 | 1.1693 | 1.1073 |
| MLS000850522-01 | 1.0091 | 0.8358 | 0.8671 | 0.8809 | 1.3763 | 0.8880 |
| MLS001197779-01 | 1.1267 | 0.9846 | 0.6490 | 0.7604 | 1.2563 | 0.8987 |
| MLS001095705-01 | 1.1723 | 1.1400 | 0.7229 | 0.6476 | 1.2293 | 1.2060 |
| MLS000912562-01 | 0.8747 | 1.0302 | 0.6246 | 0.7103 | 0.9150 | 0.8680 |
| MLS000092785-01 | 0.3235 | 1.1004 | 0.7351 | 0.9882 | 1.1653 | 0.8600 |
| MLS000418650-01 | 1.1323 | 1.1523 | 0.8344 | 1.0080 | 0.9533 | 0.9237 |
| MLS000860966-01 | 0.7600 | 0.6232 | 0.8424 | 0.7918 | 1.0900 | 0.9370 |
| MLS001180929-01 | 0.6163 | 0.9811 | 0.8753 | 0.8251 | 0.9288 | 0.8571 |
| MLS000564564-01 | 0.8844 | 1.0422 | 0.9091 | 0.9399 | 1.0092 | 0.9117 |
| MLS001164432-01 | 1.1289 | 1.1059 | 1.3183 | 1.1387 | 0.7842 | 0.9600 |
| MLS000621451-01 | 1.1926 | 1.2493 | 1.3023 | 0.9255 | 1.1579 | 1.0388 |
| MLS000078709-01 | 0.4830 | 0.6919 | 1.0163 | 0.9270 | 0.7008 | 0.8167 |

TABLE 11-continued

CMV-LACZ in Myoblasts

| | 40 uM | 20 uM | 10 uM | 5 uM | 1 uM | 0.5 uM |
|---|---|---|---|---|---|---|
| MLS000688267-01 | 1.0774 | 1.1407 | 0.8935 | 0.9129 | 1.1579 | 1.0950 |
| MLS001006516-01 | 0.6589 | 0.4956 | 0.9076 | 0.9829 | 0.8858 | 1.0038 |
| MLS001095033-01 | 0.9811 | 0.9359 | 1.0269 | 0.9043 | 0.9179 | 0.9488 |
| MLS000072290-01 | 0.2915 | 0.3911 | 1.3303 | 1.4390 | 0.9000 | 1.0579 |
| MLS000036988-01 | 0.6578 | 0.8796 | 1.0435 | 0.9702 | 1.0846 | 1.0767 |
| MLS001217935-01 | 0.5381 | 0.7859 | 1.0465 | 1.0175 | 1.1167 | 1.1729 |
| MLS000777780-01 | 0.9463 | 1.3393 | 1.0126 | 0.9893 | 0.9063 | 0.8779 |
| MLS001174740-01 | 0.4578 | 0.4293 | 0.9490 | 1.0046 | 0.9721 | 1.2750 |
| MLS000392555-01 | 1.2007 | 0.9559 | 0.9799 | 0.9342 | 0.7638 | 0.8954 |
| MLS000693795-01 | 0.8730 | 0.8526 | 0.9207 | 0.9554 | 1.1104 | 0.9100 |
| MLS000684034-01 | 0.3100 | 0.5374 | 1.0568 | 1.2045 | 1.1492 | 1.2525 |
| MLS001172822-01 | 1.2767 | 0.9285 | 1.0904 | 1.1375 | 1.0617 | 0.9304 |
| MLS000052969-01 | 0.6800 | 1.1522 | 1.0444 | 0.9976 | 1.0529 | 0.8950 |
| MLS001217212-01 | 0.9459 | 1.1137 | 1.0626 | 1.0711 | 0.9179 | 1.1804 |
| MLS001004864-01 | 0.9933 | 1.2930 | 1.0417 | 1.2276 | 0.9288 | 1.2650 |
| MLS001116535-01 | 1.1263 | 1.1815 | 1.0580 | 1.0944 | 1.1779 | 1.0167 |
| MLS001165424-01 | 1.2074 | 1.2730 | 1.0078 | 1.0607 | 0.9796 | 1.1754 |
| MLS001116079-01 | 0.9078 | 1.0448 | 1.0228 | 0.9306 | 1.0492 | 1.0950 |
| MLS001198271-01 | 1.2089 | 0.9944 | 0.8516 | 1.2105 | 1.0883 | 1.0204 |
| MLS001167798-01 | 1.1452 | 1.2196 | 1.1494 | 1.1822 | 0.7750 | 1.0342 |
| MLS000710288-01 | 0.9063 | 1.1193 | 1.2515 | 1.0737 | 0.9325 | 1.0338 |
| MLS000734270-01 | 0.9548 | 1.0122 | 0.9468 | 0.9337 | 0.8379 | 0.9296 |
| MLS000858981-01 | 0.9696 | 0.9985 | 0.9009 | 1.1687 | 0.9696 | 0.9229 |
| MLS000698826-01 | 1.2519 | 1.2944 | 0.9013 | 0.8824 | 0.9717 | 0.9942 |
| MLS001000874-01 | 1.1100 | 1.0556 | 1.0295 | 0.8886 | 1.0442 | 1.1029 |
| MLS000682750-01 | 1.0404 | 1.1433 | 0.9934 | 0.8717 | 1.0467 | 0.9679 |
| MLS001090787-01 | 0.5907 | 0.7533 | 0.8594 | 0.9700 | 0.9754 | 0.9196 |
| MLS002636056-01 | 0.8270 | 1.1173 | 1.2571 | 1.0394 | 0.9021 | 0.9392 |
| MLS002170630-01 | 0.7387 | 0.8233 | 0.9628 | 0.9890 | 0.8054 | 0.9954 |
| MLS002162890-01 | 0.9507 | 0.7603 | 0.9939 | 0.9701 | 0.8713 | 0.8392 |
| MLS001105912-01 | 0.3873 | 0.5323 | 0.9597 | 1.0003 | 1.0321 | 1.0725 |
| MLS001007892-01 | 0.4953 | 0.6390 | 1.1495 | 1.0511 | 0.8108 | 0.9338 |
| MLS000089748-01 | 0.4437 | 0.3140 | 0.9905 | 1.0665 | 0.8592 | 1.2129 |
| MLS000912726-01 | 1.0643 | 1.0257 | 1.0325 | 1.0182 | 0.9692 | 1.1004 |
| MLS000086970-01 | 0.8880 | 1.0197 | 0.9068 | 0.8994 | 1.0504 | 0.9925 |
| MLS000420298-01 | 1.1930 | 0.9807 | 1.0482 | 0.8414 | 0.9383 | 1.2808 |
| MLS001147478-01 | 0.8747 | 1.0513 | 1.2999 | 1.2105 | 0.8808 | 1.0721 |
| MLS000090135-01 | 0.3653 | 0.6017 | 0.9296 | 0.9731 | 0.9421 | 1.0896 |

TABLE 12

CMV1: AB305V-LACZ in Myotubes

| | 40 uM | 20 uM | 10 uM | 5 uM | 1 uM | 0.5 uM |
|---|---|---|---|---|---|---|
| MLS000591667-01 | 0.8800 | 0.8929 | 1.0152 | 1.0824 | 1.0726 | 0.8600 |
| MLS005568234-01 | 0.9141 | 0.9918 | 0.9074 | 1.0764 | 1.2622 | 1.3844 |
| MLS000689562-01 | 0.9788 | 0.9824 | 0.8105 | 1.0300 | 0.8652 | 0.9474 |
| MLS000732652-01 | 1.0329 | 0.8518 | 1.0697 | 1.0614 | 0.8859 | 1.1615 |
| MLS001240181-01 | 1.1376 | 1.0976 | 0.9955 | 1.0895 | 1.0511 | 0.9519 |
| MLS001211139-01 | 1.0224 | 0.8259 | 1.0196 | 1.1755 | 0.8948 | 0.9281 |
| MLS001030268-01 | 0.9506 | 0.9365 | 1.1128 | 1.1318 | 1.1711 | 0.8830 |
| MLS000912699-01 | 0.5365 | 0.9235 | 1.1310 | 0.9419 | 0.9859 | 0.8089 |
| MLS001125260-01 | 0.9212 | 1.0000 | 1.0994 | 0.9614 | 1.0993 | 1.0074 |
| MLS000717689-01 | 0.9129 | 0.9576 | 0.9569 | 0.9686 | 1.0956 | 0.8415 |
| MLS001197665-01 | 1.0741 | 1.0047 | 1.2593 | 0.9771 | 0.8756 | 0.9415 |
| MLS001075922-01 | 0.8388 | 1.0282 | 1.2173 | 1.2947 | 1.0533 | 1.0222 |
| MLS001124046-01 | 0.9812 | 1.0906 | 1.0202 | 0.8395 | 1.0156 | 1.0193 |
| MLS001197220-01 | 1.0271 | 0.9659 | 0.9289 | 0.9682 | 0.9356 | 0.8896 |
| MLS001221318-01 | 0.8576 | 1.2212 | 0.9944 | 1.1337 | 1.4059 | 1.0037 |
| MLS000947910-01 | 1.0082 | 1.0165 | 0.8930 | 1.2332 | 0.8348 | 1.0333 |
| MLS001215795-01 | 1.1035 | 1.3929 | 1.0250 | 0.9309 | 1.0207 | 0.9363 |
| MLS002163670-01 | 1.1235 | 1.1659 | 0.8898 | 0.9788 | 1.2044 | 0.9237 |
| MLS001200149-01 | 0.9424 | 0.8318 | 0.8176 | 0.9974 | 0.9933 | 0.8378 |
| MLS001359861-01 | 0.9412 | 0.9976 | 1.1230 | 0.9547 | 0.9533 | 0.8978 |
| MLS000710669-01 | 1.1824 | 0.8682 | 1.2372 | 0.9690 | 0.8881 | 0.9341 |
| MLS001035690-01 | 1.0976 | 1.1976 | 1.1317 | 1.1552 | 0.8644 | 1.0474 |
| MLS001030621-01 | 1.0141 | 0.9024 | 1.0546 | 0.9872 | 0.7970 | 0.7844 |
| MLS001083082-01 | 1.1165 | 1.0282 | 0.9776 | 0.9984 | 1.0326 | 0.9615 |
| MLS000045588-01 | 0.9424 | 1.0494 | 0.9776 | 1.2294 | 0.8607 | 0.9059 |
| MLS001216939-01 | 0.9659 | 1.1518 | 1.2568 | 1.1826 | 0.9748 | 1.0311 |
| MLS001163859-01 | 1.2482 | 1.0965 | 1.1727 | 1.0856 | 1.1326 | 0.8756 |
| MLS000683232-01 | 0.8365 | 0.8835 | 1.0086 | 0.8743 | 0.7752 | 0.8200 |

TABLE 12-continued

| CMV1: AB305V-LACZ in Myotubes | | | | | | |
|---|---|---|---|---|---|---|
| | 40 uM | 20 uM | 10 uM | 5 uM | 1 uM | 0.5 uM |
| MLS001170856-01 | 0.8753 | 1.1518 | 1.0562 | 1.0074 | 0.9105 | 1.1095 |
| MLS002667707-01 | 1.1071 | 1.1576 | 1.0227 | 0.9449 | 1.0590 | 0.8905 |
| MLS001200665-01 | 1.2706 | 1.1800 | 0.9662 | 1.1274 | 0.9695 | 1.1543 |
| MLS002161853-01 | 1.0647 | 1.2341 | 0.9103 | 1.1122 | 0.8352 | 1.0524 |
| MLS002163101-01 | 1.5447 | 0.9212 | 0.8407 | 0.8302 | 1.1400 | 1.0533 |
| MLS000062431-01 | 1.2047 | 0.8812 | 0.9690 | 0.9004 | 0.9743 | 0.9133 |
| MLS000028160-01 | 1.1976 | 1.0471 | 0.9249 | 1.0348 | 1.0362 | 1.0524 |
| MLS002248819-01 | 1.1929 | 0.9847 | 1.1534 | 1.1171 | 0.9505 | 1.0819 |
| MLS000080654-01 | 1.4259 | 1.1871 | 1.0399 | 1.0335 | 1.0086 | 1.1229 |
| MLS000760876-01 | 1.2565 | 0.9482 | 0.9789 | 1.1074 | 1.1010 | 1.0248 |
| MLS000677675-01 | 1.2494 | 0.9918 | 1.0091 | 1.0578 | 0.9962 | 0.8619 |
| MLS000113985-01 | 1.0482 | 1.0541 | 1.0241 | 1.0031 | 1.0638 | 1.0629 |
| MLS001182368-01 | 1.0318 | 0.9953 | 0.8690 | 0.8931 | 1.0619 | 0.8667 |
| MLS001212882-01 | 1.3024 | 1.1471 | 1.1133 | 1.0963 | 0.8705 | 1.0238 |
| MLS001004364-01 | 1.1824 | 1.2824 | 0.9480 | 0.8978 | 1.0095 | 0.9210 |
| MLS000736846-01 | 1.2788 | 1.1000 | 1.1737 | 1.0250 | 0.9714 | 0.8438 |
| MLS001098105-01 | 1.2553 | 0.9671 | 1.3183 | 0.9211 | 1.2543 | 0.9248 |
| MLS000678673-01 | 1.1835 | 0.9635 | 0.9367 | 0.7918 | 1.0286 | 1.1229 |
| MLS000925023-01 | 1.1106 | 1.1565 | 0.8859 | 1.1638 | 1.1333 | 0.7505 |
| MLS001212319-01 | 1.0706 | 0.9965 | 0.9253 | 0.9525 | 0.8152 | 1.1524 |
| MLS000779126-01 | 1.1671 | 0.9988 | 1.0467 | 1.0257 | 1.2162 | 0.9495 |
| MLS000948055-01 | 1.0753 | 1.2212 | 1.1022 | 1.2519 | 0.9638 | 1.0895 |
| MLS000110418-01 | 1.3647 | 1.0459 | 0.9599 | 0.9617 | 0.9000 | 1.0333 |
| MLS000693704-01 | 1.0600 | 1.1647 | 1.0812 | 1.1170 | 0.8695 | 0.8571 |
| MLS001225512-01 | 0.8871 | 1.2482 | 1.0077 | 0.9459 | 1.0381 | 1.0162 |
| MLS001006798-01 | 1.0976 | 0.9953 | 1.0267 | 1.2236 | 0.9648 | 1.0419 |
| MLS000711491-01 | 0.9929 | 1.1318 | 0.8645 | 0.9993 | 0.9095 | 0.9495 |
| MLS000582947-01 | 1.0247 | 1.0729 | 0.9127 | 0.9280 | 0.9610 | 0.8848 |
| MLS000531177-01 | 1.1522 | 0.9244 | 0.8917 | 0.8757 | 1.0411 | 1.1989 |
| MLS001202389-01 | 0.9311 | 1.0900 | 1.1312 | 1.0432 | 1.1821 | 1.1558 |
| MLS000536064-01 | 1.0233 | 1.2344 | 1.1027 | 0.8894 | 1.0389 | 0.9705 |
| MLS000586245-01 | 1.2656 | 1.2267 | 1.1338 | 0.9511 | 1.0800 | 1.0611 |
| MLS001061374-01 | 1.0489 | 1.1689 | 0.8498 | 1.1237 | 1.1000 | 1.2568 |
| MLS000675441-01 | 0.9822 | 0.9578 | 1.0337 | 1.0460 | 1.1032 | 1.0074 |
| MLS001200396-01 | 0.9733 | 0.9644 | 0.7738 | 0.8987 | 0.8442 | 0.9137 |
| MLS001165937-01 | 0.7222 | 0.7678 | 0.7827 | 0.8619 | 0.9663 | 0.9305 |
| MLS000325736-01 | 0.9889 | 0.8244 | 0.9324 | 0.9630 | 0.8968 | 0.9263 |
| MLS001215357-01 | 1.0667 | 1.3622 | 1.1192 | 1.1407 | 1.1400 | 1.1547 |
| MLS000588210-01 | 1.1656 | 1.1322 | 1.0815 | 0.9182 | 1.0853 | 1.1263 |
| MLS000764729-01 | 1.1900 | 0.9656 | 0.9634 | 1.0779 | 1.1432 | 1.0358 |
| MLS000689492-01 | 0.9267 | 1.0444 | 1.0940 | 1.0504 | 1.2400 | 1.0853 |
| MLS001000299-01 | 1.0744 | 0.9544 | 0.9029 | 1.0658 | 1.3158 | 0.6411 |
| MLS000393762-01 | 1.0578 | 1.0800 | 1.0049 | 1.0005 | 0.9326 | 0.8653 |
| MLS001130011-01 | 1.0156 | 0.8367 | 0.8998 | 0.9057 | 1.0211 | 0.9358 |
| MLS001229477-01 | 0.9611 | 0.9622 | 0.9587 | 0.9250 | 1.1095 | 1.0126 |
| MLS000707378-01 | 0.9167 | 0.9689 | 1.0300 | 0.9294 | 1.3937 | 1.0537 |
| MLS000573208-01 | 0.9478 | 0.9633 | 0.8913 | 1.1765 | 1.3021 | 0.9547 |
| MLS001167281-01 | 0.9722 | 1.1089 | 0.9727 | 0.8948 | 1.0789 | 1.0663 |
| MLS000053342-01 | 1.1344 | 1.3044 | 0.9187 | 0.9033 | 0.9863 | 0.9947 |
| MLS002171615-01 | 1.0711 | 1.0111 | 0.9582 | 0.9989 | 0.7874 | 0.9863 |
| MLS001005712-01 | 1.3167 | 1.1133 | 0.8075 | 0.9623 | 1.0379 | 1.0684 |
| MLS001176153-01 | 1.0878 | 1.0256 | 0.9388 | 0.7944 | 0.9832 | 0.8316 |
| MLS000735021-01 | 1.0778 | 1.0378 | 0.9616 | 0.9548 | 1.0221 | 1.0105 |
| MLS000767397-01 | 1.0067 | 1.0144 | 0.9519 | 0.9425 | 1.0368 | 0.8737 |
| MLS001196572-01 | 1.1422 | 1.1456 | 1.0223 | 0.9853 | 0.9379 | 0.9632 |
| MLS000393966-01 | 1.1167 | 1.0378 | 1.1877 | 0.8958 | 1.3516 | 0.9358 |
| MLS001034810-01 | 1.1344 | 1.0578 | 1.0965 | 0.9578 | 1.7389 | 1.1000 |
| MLS001165394-01 | 0.9544 | 1.0344 | 0.9045 | 0.9589 | 1.1558 | 0.9232 |
| MLS000089464-01 | 1.0178 | 1.3067 | 0.9529 | 0.9400 | 1.3716 | 0.9716 |
| MLS000698617-01 | 1.0111 | 1.0011 | 0.9614 | 0.9014 | 1.0842 | 1.1221 |
| MLS001175021-01 | 0.9733 | 1.1378 | 0.7979 | 0.9049 | 0.9621 | 1.0611 |
| MLS001166758-01 | 0.9867 | 1.1044 | 0.9444 | 0.9780 | 0.7474 | 0.9958 |
| MLS001008109-01 | 1.0600 | 1.0756 | 0.9289 | 0.9839 | 1.0168 | 1.0621 |
| MLS001181936-01 | 1.0280 | 0.9020 | 1.0274 | 0.9246 | 0.9886 | 1.0705 |
| MLS000560266-01 | 0.9470 | 1.0520 | 1.0224 | 1.0253 | 1.0000 | 0.9724 |
| MLS001215074-01 | 0.9930 | 0.8700 | 0.8583 | 0.8364 | 0.9238 | 0.8752 |
| MLS001215123-01 | 1.1030 | 1.0710 | 1.2929 | 1.1153 | 1.1457 | 1.1657 |
| MLS001033255-01 | 0.7740 | 0.9930 | 1.0297 | 0.9525 | 1.1438 | 1.1038 |
| MLS001160611-01 | 0.9190 | 1.0240 | 0.9661 | 0.8306 | 1.2419 | 0.9762 |
| MLS001006302-01 | 0.9720 | 0.9010 | 1.0122 | 0.9398 | 0.9143 | 1.0229 |
| MLS001123876-01 | 1.0300 | 0.9880 | 0.9279 | 0.9002 | 1.4943 | 0.8962 |
| MLS001122698-01 | 1.0110 | 1.0340 | 1.1482 | 1.2038 | 1.0133 | 1.0019 |
| MLS000755214-01 | 1.0190 | 0.9280 | 1.0591 | 1.0763 | 0.8600 | 0.9543 |
| MLS000731285-01 | 0.6450 | 1.0310 | 1.3012 | 1.4794 | 1.0562 | 1.2048 |
| MLS000776409-01 | 1.1540 | 1.1040 | 1.1035 | 1.0186 | 0.9752 | 1.0552 |
| MLS001221908-01 | 0.8850 | 1.0770 | 1.1838 | 0.9745 | 0.9171 | 0.8562 |

TABLE 12-continued

| CMV1: AB305V-LACZ in Myotubes | | | | | | |
|---|---|---|---|---|---|---|
| | 40 uM | 20 uM | 10 uM | 5 uM | 1 uM | 0.5 uM |
| MLS000419286-01 | 0.7830 | 0.8530 | 1.1581 | 1.0268 | 1.1867 | 0.9990 |
| MLS000554416-01 | 0.7060 | 0.8760 | 0.9798 | 0.8969 | 0.9629 | 1.0019 |
| MLS000073150-01 | 1.0390 | 0.9750 | 1.1088 | 1.2058 | 1.0848 | 1.0752 |
| MLS000663185-01 | 1.1270 | 0.9540 | 0.8722 | 0.9322 | 0.9800 | 1.0924 |
| MLS001078811-01 | 0.6710 | 1.0510 | 0.9981 | 1.1571 | 0.9086 | 0.8486 |
| MLS002694363-01 | 0.7460 | 0.9870 | 0.9775 | 1.1420 | 1.1800 | 1.0695 |
| MLS000689218-01 | 1.7990 | 1.4900 | 1.2135 | 1.3684 | 0.9514 | 0.9657 |
| MLS001215294-01 | 1.4470 | 1.2800 | 1.4324 | 1.1438 | 1.0800 | 0.8838 |
| MLS001183575-01 | 1.1230 | 0.8230 | 0.9136 | 0.7726 | 0.8657 | 0.9648 |
| MLS000393567-01 | 0.9100 | 1.0160 | 0.9858 | 0.9322 | 0.9524 | 1.0400 |
| MLS000546316-01 | 1.2640 | 1.0190 | 1.0825 | 1.0040 | 1.0019 | 1.2590 |
| MLS000912258-01 | 1.0350 | 1.0760 | 1.2253 | 1.1251 | 0.9162 | 0.9743 |
| MLS000850522-01 | 1.0200 | 1.0580 | 1.0751 | 1.1090 | 0.8933 | 0.8848 |
| MLS001197779-01 | 1.0540 | 1.0630 | 1.0983 | 1.0456 | 1.1705 | 1.1286 |
| MLS001095705-01 | 1.0800 | 1.2020 | 1.3164 | 1.1898 | 0.9933 | 0.9486 |
| MLS000912562-01 | 1.2780 | 1.2090 | 1.1674 | 0.9602 | 0.8924 | 1.0905 |
| MLS000092785-01 | 1.0500 | 1.0400 | 1.0738 | 1.0185 | 1.0143 | 0.9105 |
| MLS000418650-01 | 1.2260 | 1.1180 | 1.1746 | 1.0198 | 1.2819 | 1.0086 |
| MLS000860966-01 | 0.7920 | 0.9190 | 0.8601 | 0.9632 | 1.0743 | 0.8229 |
| MLS001180929-01 | 1.0274 | 1.1347 | 1.0084 | 1.0533 | 0.7876 | 0.8848 |
| MLS005564564-01 | 1.0411 | 0.9779 | 1.1848 | 1.0689 | 0.9924 | 0.8267 |
| MLS001164432-01 | 1.1179 | 1.1358 | 1.2418 | 0.9500 | 1.3543 | 0.9248 |
| MLS000621451-01 | 0.9695 | 0.9853 | 1.1398 | 1.0177 | 0.9295 | 1.1114 |
| MLS000078709-01 | 1.7737 | 1.0853 | 0.8743 | 0.9348 | 0.9257 | 1.0133 |
| MLS000688267-01 | 1.1505 | 0.9505 | 1.2248 | 0.9634 | 1.1333 | 0.8648 |
| MLS001006516-01 | 0.9484 | 0.9032 | 0.8542 | 0.9283 | 0.9257 | 0.9581 |
| MLS001095033-01 | 1.0358 | 1.0326 | 1.0031 | 1.0230 | 1.0867 | 1.2895 |
| MLS000072290-01 | 1.0653 | 1.3484 | 1.1459 | 1.3265 | 1.1495 | 0.9362 |
| MLS000036988-01 | 0.5021 | 0.7116 | 1.0868 | 0.8979 | 0.8905 | 0.9867 |
| MLS001217935-01 | 0.9495 | 1.0547 | 0.9648 | 1.1473 | 1.1381 | 0.9705 |
| MLS000777780-01 | 1.0474 | 0.9316 | 0.8808 | 1.0471 | 0.8838 | 0.8914 |
| MLS001174740-01 | 0.8863 | 1.0568 | 1.0520 | 0.9101 | 0.9267 | 0.8533 |
| MLS000392555-01 | 0.9326 | 1.1537 | 0.8568 | 1.0094 | 0.9676 | 1.0257 |
| MLS000693795-01 | 1.0716 | 1.0453 | 1.0774 | 1.1780 | 1.0314 | 0.9771 |
| MLS000684034-01 | 1.0105 | 1.2347 | 1.1903 | 1.1407 | 0.9810 | 1.0962 |
| MLS001172822-01 | 0.6358 | 1.1768 | 1.1819 | 1.2505 | 1.0514 | 1.2590 |
| MLS000052969-01 | 0.9726 | 0.9800 | 0.8406 | 1.0651 | 1.1714 | 0.9152 |
| MLS001217212-01 | 1.0105 | 1.1842 | 1.0832 | 0.9795 | 0.9610 | 1.0190 |
| MLS001004864-01 | 0.8884 | 0.9653 | 0.9501 | 1.0697 | 0.9610 | 0.9657 |
| MLS001116535-01 | 1.0011 | 0.9800 | 1.2856 | 1.0648 | 0.8771 | 1.2552 |
| MLS001165424-01 | 0.8558 | 1.0316 | 1.1758 | 1.0571 | 1.1248 | 0.9152 |
| MLS001116079-01 | 1.0811 | 0.9063 | 1.1374 | 1.0227 | 0.8152 | 1.3543 |
| MLS001198271-01 | 1.0053 | 1.1053 | 0.9957 | 0.9907 | 1.0686 | 0.9933 |
| MLS001167798-01 | 1.2800 | 1.3337 | 1.2238 | 1.1987 | 0.9295 | 0.9143 |
| MLS000710288-01 | 0.8905 | 0.9400 | 1.1225 | 1.0717 | 1.1133 | 1.0371 |
| MLS000734270-01 | 0.9095 | 1.1158 | 1.0885 | 1.1042 | 1.0038 | 1.0019 |
| MLS000858981-01 | 1.0000 | 1.0421 | 0.9781 | 1.0786 | 0.8419 | 1.0257 |
| MLS000698826-01 | 1.0789 | 1.0505 | 0.9634 | 1.1232 | 1.0200 | 1.2010 |
| MLS001000874-01 | 1.0947 | 1.1484 | 0.9960 | 1.1124 | 1.1590 | 1.0943 |
| MLS000682750-01 | 1.0579 | 1.1189 | 1.0939 | 1.1285 | 0.9638 | 1.0248 |
| MLS001090787-01 | 0.9450 | 0.8990 | 1.1178 | 1.0126 | 0.9055 | 1.0009 |
| MLS002636056-01 | 1.1160 | 1.4090 | 1.1613 | 1.0269 | 1.2636 | 0.9855 |
| MLS002170630-01 | 0.8580 | 0.9710 | 0.9248 | 1.2068 | 1.0036 | 0.8136 |
| MLS002162890-01 | 1.0170 | 1.0140 | 1.0530 | 1.1237 | 1.0191 | 1.0682 |
| MLS001105912-01 | 1.8130 | 1.1910 | 1.0857 | 0.9313 | 0.9618 | 1.1391 |
| MLS001007892-01 | 1.0540 | 1.2170 | 0.9543 | 1.0066 | 0.9291 | 1.1673 |
| MLS000089748-01 | 1.2820 | 1.3800 | 0.9813 | 1.1104 | 0.9809 | 0.9527 |
| MLS000912726-01 | 1.0150 | 1.2060 | 1.1041 | 0.9111 | 0.9264 | 0.8527 |
| MLS000086970-01 | 0.9880 | 0.9870 | 0.9738 | 1.1136 | 0.8855 | 0.9673 |
| MLS000420298-01 | 1.1250 | 1.3660 | 1.2388 | 1.0338 | 0.8527 | 0.9573 |
| MLS001147478-01 | 0.9510 | 1.0810 | 1.2959 | 0.8937 | 1.3827 | 1.3536 |
| MLS000090135-01 | 1.1840 | 1.1100 | 1.0114 | 0.7503 | 1.1036 | 1.0155 |
| MLS001179717-01 | 0.48286 | 0.57476 | 0.81333 | 1.084 | | |
| MLS000683234-01 | 0.93 | 0.69524 | 0.81111 | 0.82044 | | |
| MLS000695955-01 | 0.93 | 0.99238 | 0.896 | 0.78933 | | |
| MLS001125488-01 | 0.87238 | 1.1819 | 0.96756 | 0.74711 | | |
| MLS000768008-01 | 0.94286 | 1.02762 | 0.96444 | 0.82756 | | |
| MLS000913117-01 | 0.65381 | 0.59381 | 0.82622 | 0.80356 | | |
| MLS000860538-01 | 0.96667 | 1.01667 | 0.96133 | 1.00133 | | |
| MLS001177259-01 | 1.10048 | 0.85429 | 0.73156 | 0.94622 | | |
| MLS000861434-01 | 0.8381 | 0.84286 | 0.80267 | 0.88444 | | |
| MLS000047918-01 | 1.05 | 1.03762 | 0.8 | 0.93733 | | |
| MLS000389484-01 | 2.78095 | 1.11571 | 0.83867 | 0.85244 | | |
| MLS001217673-01 | 0.93524 | 1.16095 | 0.94089 | 0.936 | | |
| MLS000389677-01 | 0.76095 | 1.01857 | 0.74178 | 0.81422 | | |
| MLS001208858-01 | 0.92381 | 0.94714 | 0.80178 | 0.944 | | |

TABLE 12-continued

| CMV1: AB305V-LACZ in Myotubes | | | | | | |
|---|---|---|---|---|---|---|
| | 40 uM | 20 uM | 10 uM | 5 uM | 1 uM | 0.5 uM |
| MLS000333610-01 | 0.99476 | 0.94286 | 0.78667 | 0.832 | | |
| MLS001117351-01 | 0.89524 | 1.1481 | 1.08756 | 1.01644 | | |
| MLS000682883-01 | 0.89667 | 1.08667 | 1.08356 | 0.93333 | | |
| MLS001095231-01 | 0.62286 | 0.9181 | 0.74089 | 1.03511 | | |
| MLS000721584-01 | 1.1019 | 1.13333 | 0.90711 | 0.95733 | | |
| MLS001183429-01 | 0.58095 | 0.91048 | 0.944 | 0.84356 | | |
| MLS002158881-01 | 0.80952 | 0.86429 | 0.82667 | 0.79244 | | |
| MLS001165749-01 | 1.03762 | 1.02429 | 0.92844 | 0.82711 | | |
| MLS001237320-01 | 1.08238 | 0.98952 | 0.75689 | 0.95822 | | |
| MLS000763405-01 | 0.80238 | 0.82429 | 0.876 | 1.04978 | | |
| MLS000538580-01 | 0.27048 | 0.38381 | 0.57289 | 0.66133 | | |
| MLS001033202-01 | 1.19952 | 0.82143 | 0.99333 | 0.96578 | | |
| MLS001216260-01 | 0.83667 | 1.08952 | 1.03111 | 0.85156 | | |
| MLS000085522-01 | 0.95095 | 0.77333 | 0.98044 | 1.092 | | |
| MLS000702680-01 | 1.18143 | 1.23286 | 1.10711 | 1.00756 | | |
| MLS001212998-01 | 0.78333 | 0.9719 | 0.90844 | 0.78 | | |
| MLS001160885-01 | 0.8319 | 0.90952 | 0.90089 | 1.16711 | | |
| MLS001122718-01 | 0.89 | 0.95667 | 0.96622 | 0.88622 | | |
| MLS000027478-01 | 0.97905 | 0.94429 | 0.924 | 0.94889 | | |
| MLS001177364-01 | 0.97429 | 1.05286 | 0.95778 | 1.26222 | | |
| MLS001179695-01 | 1.04714 | 1.17524 | 1.09467 | 1.18311 | | |
| MLS002251986-01 | 0.97762 | 0.82381 | 0.96089 | 0.98311 | | |
| MLS001166704-01 | 1.0685 | 1.4595 | 1.1553 | 1.08848 | | |
| MLS001196422-01 | 0.856 | 0.8295 | 0.89309 | 0.89631 | | |
| MLS001179624-01 | 0.4965 | 0.452 | 0.8788 | 0.86037 | | |
| MLS001223425-01 | 1.0095 | 0.979 | 1.03502 | 0.95622 | | |
| MLS001117140-01 | 1.1745 | 1.3785 | 1.12442 | 0.95069 | | |
| MLS001110618-01 | 0.4765 | 1.0555 | 0.93364 | 0.89539 | | |
| MLS001223482-01 | 0.8095 | 0.858 | 0.79309 | 0.90691 | | |
| MLS000680049-01 | 0.4315 | 1.4405 | 1.10599 | 1.12719 | | |
| MLS001212498-01 | 0.8475 | 0.749 | 0.78387 | 0.84977 | | |
| MLS001124732-01 | 0.972 | 1.07 | 1.01567 | 1.02488 | | |
| MLS000526364-01 | 1.1865 | 1.1735 | 0.953 | 0.95069 | | |
| MLS000767227-01 | 1.1815 | 0.9975 | 1.09954 | 1.02396 | | |
| MLS000703499-01 | 0.769 | 0.689 | 0.99677 | 0.93134 | | |
| MLS001167169-01 | 1.103 | 1.085 | 1.00876 | 0.93226 | | |
| MLS001198693-01 | 1.112 | 1.025 | 0.92581 | 1.09171 | | |
| MLS001219345-01 | 1.0255 | 1.0075 | 0.86313 | 1.18802 | | |
| MLS001211651-01 | 0.977 | 0.8465 | 0.84332 | 0.87143 | | |
| MLS000806880-01 | 1.0655 | 0.9145 | 1.12995 | 0.96544 | | |
| MLS001223567-01 | 1.012 | 1.241 | 0.89309 | 1.00184 | | |
| MLS001005283-01 | 1.1425 | 1.032 | 0.90507 | 0.90046 | | |
| MLS001218427-01 | 0.6965 | 34.571 | 15.1793 | 1.20922 | | |
| MLS001139288-01 | 1.0825 | 1.096 | 1.04654 | 1.24654 | | |
| MLS000696445-01 | 0.924 | 1.122 | 1.01106 | 1.26774 | | |
| MLS001218795-01 | 0.989 | 1.2115 | 1.02258 | 0.9553 | | |
| MLS000419555-01 | 1.22 | 1.2165 | 1.21475 | 1.21982 | | |
| MLS001225507-01 | 0.8805 | 0.8655 | 0.99401 | 1.04009 | | |
| MLS000663651-01 | 0.861 | 0.949 | 0.9788 | 0.96359 | | |
| MLS000706349-01 | 1.1355 | 1.0245 | 0.9553 | 0.94654 | | |
| MLS000393110-01 | 0.8895 | 1.0745 | 0.96728 | 1.10323 | | |
| MLS000574647-01 | 1.0095 | 0.962 | 0.93641 | 0.91659 | | |
| MLS000532969-01 | 0.8385 | 0.8525 | 0.88295 | 0.77051 | | |
| MLS001125260-01 | 1.175 | 1.0765 | 1.06498 | 0.96452 | | |
| MLS000122749-01 | 1.0025 | 0.808 | 1.06267 | 1.02166 | | |
| MLS001150751-01 | 0.889 | 0.992 | 0.83364 | 0.91336 | | |
| MLS001221867-01 | 1.0745 | 1.0515 | 0.98341 | 0.99539 | | |
| MLS001147727-01 | 1.1835 | 1.2365 | 0.90691 | 1.11982 | | |
| MLS000688437-01 | 1.05088 | 1.02982 | 0.93462 | 1.23248 | | |
| MLS001211976-01 | 1.01404 | 0.96974 | 0.99786 | 0.8547 | | |
| MLS002161350-01 | 1.04561 | 0.88465 | 0.96795 | 0.90598 | | |
| MLS001077207-01 | 0.78246 | 0.86623 | 1.0359 | 0.95214 | | |
| MLS001209245-01 | 0.99518 | 0.96623 | 0.96752 | 0.85684 | | |
| MLS000737953-01 | 0.90965 | 0.94781 | 1.22393 | 0.82735 | | |
| MLS000552080-01 | 0.80439 | 0.95219 | 1.0688 | 1.19658 | | |
| MLS000737204-01 | 0.3807 | 0.57719 | 0.80684 | 1.02906 | | |
| MLS000579238-01 | 0.9443 | 0.83026 | 0.87179 | 0.81453 | | |
| MLS001181671-01 | 0.93772 | 1.03026 | 0.92009 | 0.88034 | | |
| MLS001167424-01 | 0.99254 | 1.15702 | 0.97179 | 0.74915 | | |
| MLS000094770-01 | 0.84211 | 0.94123 | 0.9406 | 0.80812 | | |
| MLS001123810-01 | 0.93465 | 1.15921 | 0.81496 | 0.8812 | | |
| MLS000532078-01 | 0.86228 | 0.9443 | 0.89145 | 0.79103 | | |
| MLS000585616-01 | 0.87939 | 0.90965 | 0.7906 | 0.90256 | | |
| MLS000553673-01 | 0.91272 | 1.00526 | 0.96026 | 0.80214 | | |
| MLS001175592-01 | 1.01842 | 0.96491 | 1.03077 | 0.94701 | | |
| MLS001033255-01 | 1.23553 | 1.01272 | 1.04487 | 0.84231 | | |

TABLE 12-continued

| | CMV1: AB305V-LACZ in Myotubes | | | | | |
|---|---|---|---|---|---|---|
| | 40 uM | 20 uM | 10 uM | 5 uM | 1 uM | 0.5 uM |
| MLS000733703-01 | 0.79649 | 0.95833 | 0.86538 | 1.1188 | | |
| MLS001096269-01 | 0.77544 | 0.9864 | 0.74017 | 1.08974 | | |
| MLS001162872-01 | 0.97939 | 1.06096 | 1.08376 | 0.78547 | | |
| MLS000584511-01 | 0.74781 | 0.87105 | 0.8735 | 0.83547 | | |
| MLS001166325-01 | 0.87851 | 0.89693 | 0.97949 | 0.77265 | | |
| MLS000122180-01 | 1.00702 | 0.8136 | 0.88077 | 0.77735 | | |
| MLS001157804-01 | 1.06974 | 1.05044 | 0.98419 | 0.70299 | | |
| MLS000693729-01 | 0.87895 | 0.90307 | 1.05684 | 0.97222 | | |
| MLS001220669-01 | 1.00044 | 1.0114 | 0.77009 | 0.82735 | | |
| MLS001214461-01 | 0.95658 | 0.91667 | 0.93632 | 0.81368 | | |
| MLS000081838-01 | 0.96974 | 1.01842 | 0.88889 | 0.91752 | | |
| MLS002402866-01 | 0.7307 | 0.83202 | 0.79658 | 0.87393 | | |
| MLS001200980-01 | 1.0886 | 0.92719 | 0.95684 | 0.87821 | | |
| MLS001174719-01 | 1.10789 | 0.92544 | 0.83205 | 0.85513 | | |
| MLS001175449-01 | 0.86711 | 0.88904 | 0.90342 | 0.85342 | | |
| MLS001172577-01 | 0.96272 | 1.02895 | 0.86197 | 0.89444 | | |
| MLS001122792-01 | 0.72544 | 0.99693 | 0.96752 | 0.81368 | | |
| MLS001216405-01 | 1.07982 | 1.34474 | 0.80085 | 0.91923 | | |
| MLS000673766-01 | 1.04045 | 1.10955 | 0.96316 | 0.98469 | | |
| MLS000912614-01 | 1.01227 | 0.97 | 1.16603 | 1.01818 | | |
| MLS001194551-01 | 0.78091 | 1.04682 | 0.94593 | 0.82727 | | |
| MLS001214704-01 | 0.91364 | 0.93273 | 1.27847 | 0.88517 | | |
| MLS001219159-01 | 1.02318 | 0.96364 | 0.93158 | 0.93541 | | |
| MLS001060549-01 | 1.075 | 0.88136 | 0.89522 | 1.32153 | | |
| MLS000850824-01 | 0.94591 | 0.99455 | 0.99234 | 0.88517 | | |
| MLS000879190-01 | 0.46273 | 0.84955 | 1.04737 | 0.99091 | | |
| MLS001163140-01 | 1.18955 | 0.91591 | 1.06124 | 1.02871 | | |
| MLS000046123-01 | 1.07636 | 1.14455 | 1.08421 | 0.91244 | | |
| MLS000086970-01 | 0.82727 | 0.93955 | 1.18565 | 0.95407 | | |
| MLS000388722-01 | 0.86682 | 1.08455 | 1.06699 | 0.95694 | | |
| MLS000676974-01 | 0.46 | 1.08273 | 0.45742 | 1.07656 | | |
| MLS000772580-01 | 1.08773 | 1.02909 | 1.0933 | 0.89856 | | |
| MLS000698686-01 | 0.88636 | 0.88636 | 0.97273 | 0.83636 | | |
| MLS001162337-01 | 1.05 | 0.84909 | 0.95933 | 0.99043 | | |
| MLS001204005-01 | 0.78136 | 1.01818 | 1.13636 | 0.94019 | | |
| MLS000721525-01 | 0.91273 | 0.84091 | 1.03636 | 0.86603 | | |
| MLS000525404-01 | 0.74955 | 0.84136 | 0.87273 | 0.76029 | | |
| MLS000772194-01 | 0.99682 | 1.05636 | 0.92344 | 1.06842 | | |
| MLS000775793-01 | 1.02136 | 0.93227 | 1.01196 | 0.85502 | | |
| MLS000710130-01 | 0.93364 | 0.98636 | 0.86459 | 0.81435 | | |
| MLS001146463-01 | 1.14091 | 1.06045 | 0.93923 | 1.07416 | | |
| MLS000712769-01 | 0.85818 | 0.91409 | 1.07129 | 0.96507 | | |
| MLS000334464-01 | 0.96364 | 0.98773 | 1.07751 | 1.30144 | | |
| MLS000862690-01 | 1.01818 | 0.93227 | 0.89426 | 0.86842 | | |
| MLS001179267-01 | 0.55545 | 0.61409 | 0.8244 | 0.90909 | | |
| MLS000683174-01 | 1.23773 | 1.035 | 1.0866 | 1.15646 | | |
| MLS000913052-01 | 0.92 | 0.91545 | 1.28708 | 1.11531 | | |
| MLS001080869-01 | 1.01045 | 0.99273 | 0.91531 | 0.93493 | | |
| MLS000332693-01 | 0.93045 | 0.88045 | 0.97943 | 1.24402 | | |
| MLS001141113-01 | 1.91273 | 0.98227 | 1.38278 | 1.13397 | | |
| MLS001176611-01 | 0.785 | 1.03364 | 1.23541 | 0.92871 | | |
| MLS001202627-01 | 0.735 | 0.93455 | 0.9555 | 0.92344 | | |
| MLS000765108-01 | 0.97 | 0.99273 | 1.09856 | 1.17656 | | |
| MLS000937079-01 | 0.96818 | 0.96409 | 0.99234 | 1.08708 | | |
| MLS001215742-01 | 0.98509 | 0.92544 | 1.1034 | 1.02596 | | |
| MLS001217045-01 | 0.91272 | 0.92719 | 0.98213 | 0.96128 | | |
| MLS001196946-01 | 3.9614 | 2.7886 | 1.12979 | 0.9817 | | |
| MLS001216714-01 | 3.63333 | 1.41711 | 0.98 | 0.91617 | | |
| MLS000772430-01 | 1.03684 | 0.89561 | 0.90936 | 0.8183 | | |
| MLS000693370-01 | 1.1136 | 0.99474 | 0.96213 | 0.9783 | | |
| MLS000769322-01 | 1.09079 | 1.11842 | 1.01957 | 0.86085 | | |
| MLS000721030-01 | 0.79167 | 0.92763 | 0.96553 | 1.11106 | | |
| MLS001176897-01 | 1.04649 | 1.12149 | 0.79702 | 1.00851 | | |
| MLS000774940-01 | 1.00526 | 1.17105 | 0.86043 | 0.95404 | | |
| MLS001030746-01 | 0.99123 | 1.09781 | 0.87574 | 0.97915 | | |
| MLS003126425-01 | 0.71228 | 0.74298 | 0.89021 | 1.35447 | | |
| MLS001217697-01 | 0.73947 | 0.76404 | 0.86468 | 1.20043 | | |
| MLS000516719-01 | 1.07193 | 1.10307 | 1.11404 | 0.88936 | | |
| MLS001165323-01 | 1.48772 | 1.31535 | 0.9 | 1.07234 | | |
| MLS001220803-01 | 1.04956 | 1.09079 | 1.06426 | 1.11489 | | |
| MLS001163121-01 | 0.92105 | 0.87807 | 0.82936 | 0.85064 | | |
| MLS001060561-01 | 0.64254 | 0.93728 | 1.00213 | 0.93957 | | |
| MLS001139515-01 | 0.96009 | 0.92368 | 0.76043 | 0.94043 | | |
| MLS001149811-01 | 1.65044 | 1.12193 | 1.04766 | 0.9566 | | |
| MLS000773700-01 | 0.40921 | 0.92895 | 1.1166 | 1.12553 | | |
| MLS001177045-01 | 1.11798 | 1.05833 | 1.11021 | 0.92383 | | |

TABLE 12-continued

CMV1: AB305V-LACZ in Myotubes

| | 40 uM | 20 uM | 10 uM | 5 uM | 1 uM | 0.5 uM |
|---|---|---|---|---|---|---|
| MLS000693747-01 | 1.04298 | 0.9693 | 0.95234 | 0.99617 | | |
| MLS001175556-01 | 1.10263 | 0.91579 | 1.05277 | 1.11277 | | |
| MLS001175473-01 | 1.06579 | 0.95921 | 0.85872 | 0.89617 | | |
| MLS002156278-01 | 1.03114 | 0.96667 | 1.09574 | 0.86936 | | |
| MLS000707281-01 | 0.95263 | 0.94737 | 0.92553 | 0.87064 | | |
| MLS000591198-01 | 0.45307 | 0.83377 | 0.93191 | 0.96809 | | |
| MLS000714175-01 | 0.97105 | 1.12412 | 1.09745 | 0.93191 | | |
| MLS002163386-01 | 1.06623 | 0.94649 | 1.19617 | 0.97489 | | |
| MLS000761297-01 | 0.88289 | 0.99298 | 0.81064 | 0.99106 | | |
| MLS002245351-01 | 0.9307 | 1.00921 | 1.00128 | 0.83064 | | |
| MLS000718886-01 | 0.83553 | 0.87982 | 0.98043 | 0.97872 | | |
| MLS002156485-01 | 0.94825 | 1.11491 | 0.95234 | 0.94681 | | |
| MLS001140657-01 | 1.075 | 1.05044 | 1.04596 | 1.05319 | | |
| MLS002157024-01 | 0.83333 | 1.05921 | 0.85532 | 1.14638 | | |
| MLS000721730-01 | 1.03067 | 0.93111 | 0.92069 | 0.85043 | | |
| MLS000705922-01 | 0.99467 | 0.93022 | 0.9306 | 0.87759 | | |
| MLS000724709-01 | 1.12533 | 1.05378 | 0.88276 | 0.84224 | | |
| MLS002161757-01 | 1.256 | 1.15289 | 1.10216 | 0.91897 | | |
| MLS002164687-01 | 1.11333 | 0.968 | 0.92198 | 0.7625 | | |
| MLS001060533-01 | 0.68711 | 0.77156 | 0.77888 | 0.83578 | | |
| MLS000685139-01 | 0.93867 | 1.03111 | 1.03621 | 0.93621 | | |
| MLS001217286-01 | 0.36044 | 0.39911 | 1.22672 | 0.95991 | | |
| MLS001221619-01 | 1.78133 | 1.51333 | 1.32069 | 1.17155 | | |
| MLS001219621-01 | 1.29022 | 1.132 | 1.06293 | 0.94914 | | |
| MLS001166156-01 | 0.52267 | 0.77956 | 0.91983 | 0.87069 | | |
| MLS000534926-01 | 0.844 | 0.95467 | 0.96897 | 0.97241 | | |
| MLS000548725-01 | 0.332 | 0.87289 | 1.12629 | 0.97888 | | |
| MLS000374261-01 | 0.50356 | 0.448 | 0.8319 | 0.82457 | | |
| MLS000123454-01 | 1.05467 | 0.87956 | 0.93233 | 0.93534 | | |
| MLS000625140-01 | 1.016 | 1.10667 | 1.03621 | 0.91724 | | |
| MLS001214443-01 | 0.90222 | 0.95067 | 1.07241 | 0.97371 | | |

TABLE 13

Burkin Assay in Myoblasts

| | 40 uM | 20 uM | 10 uM | 5 uM | 1 uM | 0.5 uM |
|---|---|---|---|---|---|---|
| MLS000763074-01 | 0.60851 | 0.65857 | 1.13427 | 0.843 | 1.06668 | 1.19903 |
| MLS000564846-01 | 0.75904 | 0.74063 | 0.87038 | 0.80671 | 0.84376 | 0.83593 |
| MLS001202366-01 | 0.24561 | 0.48734 | 0.74576 | 0.87622 | 0.96981 | 1.00673 |
| MLS001182278-01 | 0.84246 | 0.76628 | 1.17046 | 1.06287 | 1.0742 | 1.21321 |
| MLS001196427-01 | 0.87626 | 0.81017 | 0.97767 | 0.93838 | 1.03303 | 1.01962 |
| MLS001202425-01 | 0.34448 | 0.74647 | 0.86448 | 0.96729 | 1.21932 | 1.2214 |
| MLS001214276-01 | 0.02694 | 0.20219 | 0.32354 | 0.62344 | 1.22246 | 1.32758 |
| MLS000682748-01 | 0.24723 | 0.46691 | 0.765 | 0.89229 | 1.16212 | 1.259 |
| MLS000834756-01 | 1.08092 | 1.06424 | 1.17192 | 1.22657 | 1.09843 | 1.05646 |
| MLS001202402-01 | 0.32496 | 0.64813 | 1.08015 | 0.92555 | 0.90338 | 1.05088 |
| MLS001214264-01 | 0.23942 | 0.78788 | 0.70087 | 0.74298 | 0.84644 | 0.8908 |
| MLS000391588-01 | 0.30047 | 0.78036 | 0.81758 | 0.91191 | 1.01537 | 1.06962 |
| MLS001013431-01 | 0.33625 | 0.45216 | 0.53107 | 0.70768 | 1.00039 | 1.20211 |
| MLS001163848-01 | 0.14441 | 0.29703 | 0.31406 | 0.48542 | 0.89062 | 1.00231 |
| MLS000327715-01 | 0.57757 | 0.90154 | 1.02899 | 1.14772 | 1.09422 | 1.37572 |
| MLS001214300-01 | 0.02593 | 0.18472 | 0.35298 | 0.80412 | 0.93656 | 1.21103 |
| MLS000834755-01 | 0.79619 | 1.19253 | 1.15647 | 1.08036 | 1.07782 | 1.27365 |
| MLS001163860-01 | 0.23471 | 0.17222 | 0.49218 | 0.57932 | 0.84566 | 0.94942 |
| MLS000710233-01 | 0.17433 | 0.17232 | 0.56369 | 0.80665 | 1.15918 | 1.17028 |
| MLS002702497-01 | 0.04886 | 0.05588 | 0.18885 | 0.17496 | 0.55454 | 0.78041 |
| MLS000546982-01 | 0.88835 | 1.05267 | 1.07821 | 1.27207 | 1.15498 | 0.87993 |
| MLS001197838-01 | 0.86478 | 0.89105 | 1.04838 | 1.05318 | 1.19792 | 1.25617 |
| MLS001202354-01 | 0.42755 | 0.51598 | 1.07323 | 1.03576 | 1.02304 | 1.07717 |
| MLS001202330-01 | 0.64675 | 0.83048 | 0.93405 | 0.95578 | 1.02782 | 0.97384 |
| MLS001182377-01 | 0.61764 | 0.87441 | 0.90613 | 0.91503 | 1.04505 | 1.17882 |
| MLS000834757-01 | 1.02067 | 1.11712 | 0.96506 | 1.12452 | 1.00317 | 1.0102 |
| MLS001202634-01 | 0.93072 | 0.99395 | 1.31203 | 1.14099 | 1.10045 | 1.20777 |
| MLS001194544-01 | 0.50277 | 0.79143 | 1.14522 | 1.02036 | 0.99063 | 1.04429 |
| MLS000554109-01 | 0.89366 | 0.9611 | 1.09535 | 1.06742 | 1.04915 | 0.99289 |
| NCGC00263072-01 | 0.98868 | 1.10983 | 1.04886 | 1.01335 | 1.24172 | 1.27253 |
| NCGC00263071-01 | 0.53023 | 0.69803 | 0.78353 | 0.9185 | 1.13222 | 1.35429 |
| NCGC00263039-01 | 0.81077 | 0.99561 | 1.02563 | 1.02082 | 0.91594 | 1.1697 |
| NCGC00164631-03 | 0.01283 | 0.01408 | 0.01373 | 0.32241 | 1.03203 | 0.83726 |
| NCGC00179302-02 | 0.80668 | 0.84305 | 0.71633 | 0.60599 | 1.0859 | 1.06101 |

TABLE 13-continued

Burkin Assay in Myoblasts

| | 40 uM | 20 uM | 10 uM | 5 uM | 1 uM | 0.5 uM |
|---|---|---|---|---|---|---|
| NCGC00241113-01 | 0.9168 | 0.95936 | 0.86618 | 0.9062 | 1.05675 | 1.01086 |
| NCGC00094381-04 | 0.64658 | 0.77957 | 0.63974 | 0.7317 | 1.05336 | 1.03555 |
| NCGC00015546-04 | 0.14966 | 0.19368 | 0.21399 | 0.37707 | 0.92282 | 0.89229 |
| NCGC00094381-03 | 0.52027 | 0.6668 | 0.65793 | 0.73271 | 0.9952 | 0.93685 |
| NCGC00094381-05 | 0.75776 | 0.88787 | 0.7145 | 0.75321 | 0.98039 | 0.94327 |
| NCGC00015545-02 | 0.18236 | 0.30858 | 0.31898 | 0.59598 | 1.32546 | 1.17517 |
| NCGC00164631-04 | 0.01361 | 0.01476 | 0.08696 | 0.52898 | 1.01135 | 1.02287 |
| NCGC00094112-04 | 0.34285 | 0.45094 | 0.49426 | 0.57218 | 0.99267 | 1.01949 |
| NCGC00242500-01 | 0.01945 | 0.01841 | 0.58791 | 0.87045 | 1.07607 | 1.05199 |
| NCGC00015545-07 | 0.242 | 0.30684 | 0.56798 | 0.84629 | 1.12041 | 1.07252 |

TABLE 14

Burkin Assay in Myotubes

| | 40 uM | 20 uM | 10 uM | 5 uM | 1 uM | 0.5 uM |
|---|---|---|---|---|---|---|
| MLS000763074-01 | 0.26221 | 0.19215 | 0.90703 | 1.04266 | 1.12824 | 1.0274 |
| MLS000564846-01 | 0.75294 | 0.70065 | 1.07066 | 1.00195 | 0.95569 | 0.88356 |
| MLS001202366-01 | 0.51046 | 0.52721 | 0.91937 | 1.08888 | 1.09876 | 1.11392 |
| MLS001182278-01 | 0.64876 | 0.56532 | 1.41234 | 1.40178 | 1.11835 | 1.1969 |
| MLS001196427-01 | 0.93648 | 0.79418 | 1.13545 | 1.02154 | 1.01999 | 0.91943 |
| MLS001202425-01 | 0.35401 | 0.51782 | 0.80333 | 0.9499 | 1.20487 | 1.14828 |
| MLS001214276-01 | 0.07736 | 0.23625 | 0.69453 | 0.9019 | 1.19651 | 1.16185 |
| MLS000682748-01 | 0.62062 | 0.74301 | 1.08485 | 1.14662 | 1.21063 | 0.98015 |
| MLS000834756-01 | 0.91886 | 0.94946 | 0.9214 | 1.09476 | 1.18855 | 1.07853 |
| MLS001202402-01 | 0.37173 | 0.59069 | 1.0295 | 0.96293 | 0.89618 | 0.96279 |
| MLS001214264-01 | 0.71731 | 0.71648 | 1.05756 | 0.90726 | 0.89746 | 0.95761 |
| MLS000391588-01 | 0.66403 | 0.76307 | 0.93558 | 0.89942 | 0.95626 | 1.07272 |
| MLS001013431-01 | 0.70692 | 0.7376 | 0.85055 | 0.85067 | 1.0097 | 1.23758 |
| MLS001163848-01 | 0.48759 | 0.68784 | 0.74688 | 0.95866 | 1.04499 | 1.0964 |
| MLS000327715-01 | 1.11892 | 1.19159 | 1.11494 | 1.30229 | 1.02522 | 0.88377 |
| MLS001214300-01 | 0.31784 | 0.74468 | 0.87335 | 1.09139 | 1.03917 | 1.01853 |
| MLS000834755-01 | 0.81603 | 0.96865 | 0.98675 | 1.00334 | 1.23201 | 1.26329 |
| MLS001163860-01 | 1.20854 | 0.86198 | 1.13792 | 0.92233 | 0.94035 | 1.00928 |
| MLS000710233-01 | 0.62947 | 0.69332 | 0.86883 | 0.93307 | 1.033 | 1.11028 |
| MLS002702497-01 | 0.38389 | 0.45669 | 0.78137 | 0.76924 | 0.74901 | 0.84142 |
| MLS000546982-01 | 0.71115 | 0.85558 | 0.99622 | 1.14451 | 1.03799 | 1.04819 |
| MLS001197838-01 | 0.99815 | 0.86987 | 1.09145 | 1.00443 | 0.98105 | 1.00877 |
| MLS001202354-01 | 0.57849 | 0.5824 | 1.06858 | 0.95451 | 0.90225 | 0.84594 |
| MLS001202330-01 | 0.62071 | 0.63028 | 1.01709 | 0.91234 | 0.91736 | 0.97095 |
| MLS001182377-01 | 0.91488 | 0.86542 | 0.9389 | 0.93717 | 1.02095 | 1.01535 |
| MLS000834757-01 | 0.94642 | 0.99887 | 0.95369 | 1.02962 | 0.94297 | 1.01879 |
| MLS001202634-01 | 1.28943 | 0.94727 | 1.13854 | 0.9675 | 1.1156 | 0.99278 |
| MLS001194544-01 | 0.76105 | 0.754 | 1.06983 | 1.00203 | 0.9995 | 0.96112 |
| MLS000554109-01 | 1.04819 | 0.84256 | 0.98744 | 0.96115 | 1.05362 | 0.88389 |
| NCGC00263072-01 | 0.88975 | 0.93047 | 0.95374 | 0.96945 | 1.00581 | 0.98195 |
| NCGC00263071-01 | 0.65683 | 0.68367 | 0.77685 | 0.86036 | 0.89218 | 0.86806 |
| NCGC00263039-01 | 0.59697 | 0.74735 | 0.86326 | 0.98314 | 0.95574 | 0.96891 |
| NCGC00164631-03 | 0.07758 | 0.09031 | 0.18808 | 0.55055 | 0.94454 | 0.95119 |
| NCGC00179302-02 | 0.68712 | 0.68199 | 0.79125 | 0.81812 | 0.93769 | 0.93491 |
| NCGC00241113-01 | 0.63117 | 0.74575 | 0.76777 | 0.84894 | 1.10523 | 1.07764 |
| NCGC00094381-04 | 0.93082 | 0.76798 | 0.87417 | 0.83691 | 0.94176 | 0.8006 |
| NCGC00015546-04 | 0.79646 | 0.78811 | 0.82527 | 0.85291 | 1.05081 | 0.9443 |
| NCGC00094381-03 | 1.15097 | 0.94969 | 1.02446 | 0.90148 | 0.93337 | 0.8564 |
| NCGC00094381-05 | 1.13784 | 1.05028 | 1.31892 | 1.04722 | 0.93095 | 0.92337 |
| NCGC00015545-02 | 0.35192 | 0.49594 | 0.55162 | 0.69213 | 0.91177 | 0.91301 |
| NCGC00164631-04 | 0.08093 | 0.08218 | 0.21321 | 0.77386 | 0.99976 | 0.97606 |
| NCGC00094112-04 | 0.34997 | 0.68129 | 0.62896 | 0.7596 | 0.81588 | 0.74019 |
| NCGC00242500-01 | 0.21319 | 0.652 | 0.75336 | 0.94215 | 0.93914 | 0.99743 |
| NCGC00015545-07 | 0.49755 | 0.66539 | 0.74573 | 0.87208 | 1.08023 | 1.12579 |

TABLE 15

| | CMV-LACZ in Myoblasts | | | | | |
|---|---|---|---|---|---|---|
| | 40 uM | 20 uM | 10 uM | 5 uM | 1 uM | 0.5 uM |
| MLS000763074-01 | 1.6644 | 1.2981 | 1.1966 | 1.1447 | 0.8256 | 0.8431 |
| MLS000564846-01 | 1.0885 | 1.2363 | 1.3619 | 0.9379 | 0.8172 | 0.9922 |
| MLS001202366-01 | 0.3322 | 0.7222 | 1.3214 | 1.0533 | 0.6431 | 0.7656 |
| MLS001182278-01 | 0.5959 | 1.0519 | 0.9778 | 0.9823 | 0.9491 | 0.7466 |
| MLS001196427-01 | 0.9563 | 0.7144 | 1.1811 | 0.9957 | 1.0356 | 0.7219 |
| MLS001202425-01 | 0.6233 | 0.9081 | 1.1386 | 0.8675 | 1.0919 | 1.0625 |
| MLS001214276-01 | 0.1781 | 1.2922 | 1.2231 | 1.3014 | 0.8731 | 0.9516 |
| MLS000682748-01 | 0.2419 | 0.3893 | 0.9959 | 1.0215 | 0.9666 | 0.9075 |
| MLS000834756-01 | 1.1889 | 0.8022 | 1.0917 | 1.2652 | 1.0422 | 0.8709 |
| MLS001202402-01 | 0.4819 | 0.7204 | 0.7598 | 0.8771 | 1.0106 | 1.0546 |
| MLS001214264-01 | 0.4856 | 0.3870 | 0.9233 | 1.3058 | 1.1383 | 1.0657 |
| MLS000391588-01 | 1.1119 | 1.4307 | 1.0968 | 0.9885 | 0.7411 | 1.0009 |
| MLS001013431-01 | 0.6670 | 0.5904 | 0.6673 | 0.8366 | 1.0640 | 0.9906 |
| MLS001163848-01 | 2.2215 | 2.1030 | 1.0762 | 0.9336 | 0.9620 | 1.1146 |
| MLS000327715-01 | 1.0648 | 1.3181 | 1.0060 | 0.9664 | 1.1731 | 1.2294 |
| MLS001214300-01 | 0.1793 | 0.4007 | 1.1047 | 0.7949 | 0.9403 | 1.0446 |
| MLS000834755-01 | 0.9133 | 0.9007 | 0.9834 | 0.9591 | 1.0400 | 1.0317 |
| MLS001163860-01 | 0.6488 | 0.3425 | 1.1417 | 0.9610 | 0.8230 | 0.9350 |
| MLS000710233-01 | 0.8779 | 0.8530 | 0.8509 | 0.8263 | 0.8263 | 1.0173 |
| MLS002702497-01 | 0.2779 | 0.2593 | 3.6076 | 2.6344 | 1.0213 | 0.8643 |
| MLS000546982-01 | 1.3937 | 0.9512 | 1.0785 | 0.9273 | 1.2640 | 1.0877 |
| MLS001197838-01 | 0.9437 | 1.1615 | 1.1118 | 1.0010 | 0.9954 | 0.7904 |
| MLS001202354-01 | 0.7437 | 0.8378 | 0.9170 | 0.9669 | 0.9521 | 1.2275 |
| MLS001202330-01 | 0.7619 | 0.9511 | 0.9082 | 1.0099 | 0.9325 | 0.7417 |
| MLS001182377-01 | 0.4170 | 0.4441 | 0.9294 | 0.9113 | 1.1646 | 1.1229 |
| MLS000834757-01 | 1.1026 | 0.8115 | 1.0942 | 0.9101 | 0.9300 | 1.0367 |
| MLS001202634-01 | 0.9217 | 1.0817 | 1.0990 | 1.1287 | 1.0071 | 1.0500 |
| MLS001194544-01 | 0.7383 | 0.8983 | 1.0363 | 0.9068 | 0.7213 | 0.8975 |
| MLS000554109-01 | 0.9650 | 0.9853 | 0.9457 | 0.9003 | 1.1863 | 1.1083 |
| NCGC00263072-01 | 1.2880 | 1.1540 | 1.1158 | 1.0035 | 0.9983 | 1.2383 |
| NCGC00263071-01 | 0.6430 | 0.7803 | 0.9908 | 1.2012 | 1.2813 | 1.0800 |
| NCGC00263039-01 | 0.9543 | 0.9740 | 0.9335 | 1.0522 | 1.1700 | 1.0746 |
| NCGC00164631-03 | 0.1767 | 0.1830 | 0.2763 | 0.7817 | | 0.8658 |
| NCGC00179302-02 | 1.2873 | 1.0247 | 1.6628 | 2.4679 | | 1.1867 |
| NCGC00241113-01 | 3.3097 | 2.7827 | 1.1352 | 1.1634 | | 1.4142 |
| NCGC00094381-04 | 0.9697 | 0.9330 | 0.9770 | 1.1366 | | 1.0763 |
| NCGC00015546-04 | 0.5873 | 0.8083 | 1.2439 | 1.4889 | | 1.1442 |
| NCGC00094381-03 | 1.0253 | 0.7777 | 1.0089 | 0.8667 | | 0.9504 |
| NCGC00094381-05 | 0.8220 | 0.7147 | 0.8606 | 0.9614 | | 0.8383 |
| NCGC00015545-02 | 0.2480 | 0.2907 | 0.8475 | 0.9440 | | 1.0179 |
| NCGC00164631-04 | 0.1827 | 0.2323 | 0.4405 | 0.6842 | | 0.8225 |
| NCGC00094112-04 | 0.3627 | 0.4403 | 1.0782 | 1.0309 | 1.1779 | 1.1721 |
| NCGC00242500-01 | 0.4237 | 0.3570 | 2.4909 | 1.6977 | 1.1446 | 1.1021 |
| NCGC00015545-07 | 0.3383 | 0.5257 | 0.8603 | 0.7896 | 1.1950 | 1.2967 |

TABLE 16

| | CMV-LACZ in Myotubes | | | | | |
|---|---|---|---|---|---|---|
| | 40 uM | 20 uM | 10 uM | 5 uM | 1 uM | 0.5 uM |
| MLS000763074-01 | 1.9682 | 1.7671 | 0.9645 | 1.0487 | 0.8593 | 1.0089 |
| MLS000564846-01 | 1.0094 | 1.2012 | 0.8711 | 1.1234 | 1.0444 | 0.8304 |
| MLS001202366-01 | 1.0847 | 0.8329 | 0.9927 | 0.8072 | 1.0570 | 0.9844 |
| MLS001182278-01 | 1.1212 | 1.0224 | 1.0297 | 1.0327 | 1.0126 | 0.9674 |
| MLS001196427-01 | 0.9000 | 0.9918 | 0.9282 | 0.8423 | 1.0704 | 0.9363 |
| MLS001202425-01 | 0.9976 | 0.9918 | 1.0423 | 1.1496 | 1.0185 | 0.8793 |
| MLS001214276-01 | 0.4976 | 0.5259 | 11.1000 | 2.0151 | 0.9141 | 0.7733 |
| MLS000682748-01 | 1.1071 | 1.1753 | 0.9205 | 0.8790 | 0.8459 | 0.9356 |
| MLS000834756-01 | 2.2953 | 2.0788 | 1.1713 | 1.1994 | 1.0059 | 0.9859 |
| MLS001202402-01 | 0.8129 | 0.8847 | 0.8015 | 0.9237 | 0.8695 | 0.9200 |
| MLS001214264-01 | 1.4482 | 1.2424 | 1.1534 | 0.9411 | 1.1905 | 1.1210 |
| MLS000391588-01 | 0.9094 | 0.9212 | 0.9740 | 1.0019 | 1.0010 | 0.8400 |
| MLS001013431-01 | 1.2059 | 1.0682 | 0.9162 | 0.9388 | 1.1257 | 0.8638 |
| MLS001163848-01 | 6.8624 | 6.7729 | 4.2586 | 1.1937 | 0.9638 | 1.2133 |
| MLS000327715-01 | 1.4871 | 1.2200 | 0.9983 | 1.1289 | 1.0562 | 1.1762 |
| MLS001214300-01 | 0.7118 | 6.2635 | 1.0956 | 1.0550 | 0.8924 | 0.9819 |
| MLS000834755-01 | 0.8789 | 1.2989 | 1.1048 | 1.0514 | 1.2863 | 0.5547 |
| MLS001163860-01 | 1.4490 | 1.3880 | 1.2757 | 1.1250 | 1.1562 | 1.0352 |
| MLS000710233-01 | 1.1380 | 1.1130 | 1.0698 | 0.9060 | 0.9410 | 0.8781 |
| MLS002702497-01 | 0.6550 | 0.6520 | 6.3598 | 7.0726 | 2.2829 | 1.1181 |
| MLS000546982-01 | 1.3290 | 1.0160 | 1.1265 | 1.0159 | 0.8467 | 1.0438 |

TABLE 16-continued

CMV-LACZ in Myotubes

| | 40 uM | 20 uM | 10 uM | 5 uM | 1 uM | 0.5 uM |
|---|---|---|---|---|---|---|
| MLS001197838-01 | 1.0063 | 0.8547 | 1.1637 | 0.9701 | 1.0038 | 1.0305 |
| MLS001202354-01 | 0.7863 | 0.7000 | 1.0340 | 0.8910 | 0.9200 | 1.0676 |
| MLS001202330-01 | 0.8242 | 0.9168 | 0.8717 | 0.9600 | 0.9562 | 0.8314 |
| MLS001182377-01 | 1.0263 | 1.0305 | 1.0589 | 0.9608 | 0.8105 | 0.7762 |
| MLS000834757-01 | 1.3600 | 1.0789 | 1.1047 | 1.0546 | 0.8695 | 1.0238 |
| MLS001202634-01 | 0.9340 | 0.9750 | 0.9661 | 1.2348 | 1.0073 | 0.9582 |
| MLS001194544-01 | 0.9400 | 0.9800 | 0.9739 | 0.9683 | 1.1318 | 1.0764 |
| MLS000554109-01 | 0.9950 | 0.9100 | 1.1355 | 1.1559 | 0.9491 | 1.2682 |
| NCGC00263072-01 | 1.0230 | 0.9190 | 1.0660 | 1.0396 | 0.8536 | 1.0945 |
| NCGC00263071-01 | 0.9160 | 1.0840 | 0.9779 | 1.0165 | 1.2909 | 0.9845 |
| NCGC00263039-01 | 1.0510 | 0.8580 | 0.9982 | 0.9481 | 0.9727 | 0.9645 |
| NCGC00164631-03 | 0.7680 | 0.6690 | 0.3964 | 0.8420 | 1.2736 | 1.2682 |
| NCGC00179302-02 | 1.1410 | 1.0030 | 0.9196 | 1.1533 | 0.9736 | 0.9618 |
| NCGC00241113-01 | 0.9520 | 0.9790 | 1.0724 | 0.9410 | 1.3227 | 0.8627 |
| NCGC00094381-04 | 8.1220 | 3.8710 | 1.1010 | 1.2849 | 1.4927 | 1.0845 |
| NCGC00015546-04 | 1.0700 | 1.0230 | 1.1513 | 1.0553 | 1.1427 | 1.1555 |
| NCGC00094381-03 | 18.6030 | 10.9800 | 1.5444 | 1.1125 | 1.2227 | 0.9227 |
| NCGC00094381-05 | 18.0610 | 6.8950 | 2.8305 | 1.2069 | 0.8773 | 1.0045 |
| NCGC00015545-02 | 0.4770 | 0.5490 | 0.5058 | 0.7586 | 0.9536 | 0.8627 |
| NCGC00164631-04 | 0.6690 | 0.6490 | 0.3804 | 0.8803 | 0.9164 | 1.1336 |
| NCGC00094112-04 | 0.5420 | 0.7190 | 0.7933 | 0.8123 | 0.8864 | 1.0409 |
| NCGC00242500-01 | 7.0800 | 5.2430 | 3.3039 | 2.2432 | 1.9682 | 1.2482 |
| NCGC00015545-07 | 0.5470 | 0.7010 | 0.8393 | 0.9434 | 1.1036 | 1.0736 |

TABLE 17

407 compounds chosen from the initial 1500 MLSMR "hit" compounds and the results from the Burkin lab rescreening in myoblasts (MB), myotubes (MT), and β-Gal stabilizing assay

| 407 compounds chosen for Burkin Lab evaluation | MB >25% increase over DMSO | MT >25% increase over DMSO | Both MB and MT >25% increase over DMSO | β-Gal Stabilizing or CMV activating | Less than 25% max increase in both MB and MT |
|---|---|---|---|---|---|
| NCGC repeatedly active (166) | 52 (31%) | 12 (7.2%) | 10 (6%) | 2* (1.2%) | 90 (54%) |
| Original top hits (197) | 6 (3%) | 37 (18.8%) | 12 (6.1%) | 6** (3%) | 136 (69%) |
| SU9516 platform Analogs (44) | 6 (13.6%) | 1 (2.3%) | 3 (6.8%) | 12*** (27.3%) | 15 (34%) |

*Neither of the β-Gal stabilizing compounds gave a >25% in α7$^{+/LacZ}$ MB or MT assays
**1 β-gal stabilizer also increased MT >25% over DMSO
***1 β-gal stabilizer also increased MB >25% over DMSO Top Hits from the Screen Next the top 6 compounds for activation of ITGA7 in myotubes, based on maximum response (Table 18) were selected and the screen was performed with a larger number of concentrations in order to achieve more accurate dose-response curves (FIGS. 7A-7F). From these dose-response curves, GraphPad Prism nonlinear-regression analysis was used to determine the $EC_{50}$ in myotubes (Table 18). The maximum predicted increase was calculated as the maximum increase generated in the α7$^{+/LacZ}$ multiplied by 2 due to the single allelic copy of the LacZ reporter (FIGS. 7A-7F).

TABLE 18

Summary of the top 6 compounds found to be effective in myotubes.

| Compound Name | MW | Known effects | Online Screen Score | Online Screen Fold-change | EC50 α7$^{+/LacZ}$ MT | MT FOLD INCREASE |
|---|---|---|---|---|---|---|
| SU9516 | 241.3 | Cdk2 inhibitor | | | $6.0 \times 10^{-6}$ M | 2.4 |
| MLS000532969 | 236.3 | NA | 44 | 1.7 | $2.2 \times 10^{-6}$ M | 2.0 |
| MLS003126425 | 399.4 | NA | 43 | 1.9 | $7.0 \times 10^{-6}$ M | 2.0 |
| MLS001060533 | 483.3 | NA | 42 | 1.9 | $4.7 \times 10^{-6}$ M | 1.5 |
| MLS000683232 | 257.2 | NA | | | $5.3 \times 10^{-6}$ M | 1.7 |
| MLS000683234 | 237.3 | NA | 46 | 2.6 | $2.7 \times 10^{-5}$ M | 1.7 |

SU9516 Increases α7 Integrin Protein in C2C12 Myotubes

Figure 8A:
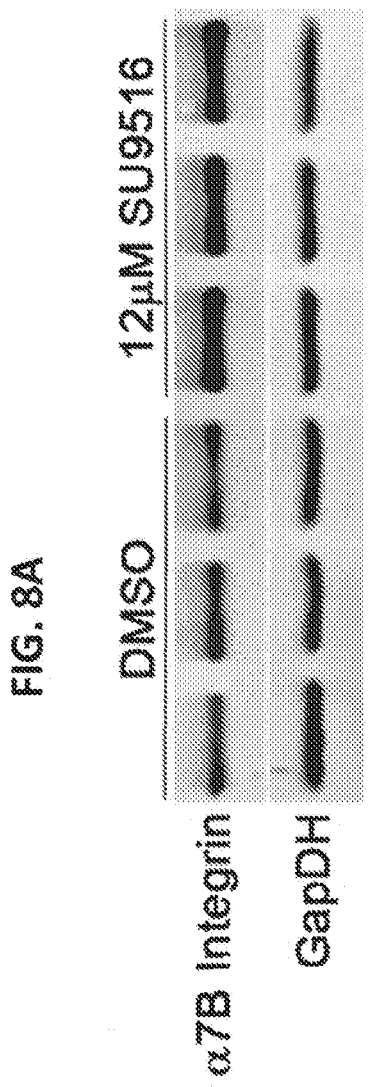
FIGS. 8A and 8B provide results obtained for C2C12 myotubes treated with DMSO (n=3) or 12 μM SU9516 (n=3), which were examined for α7 Integrin protein levels by western blotting (FIG. 8A) wherein GapDH protein levels were used as a loading normalization control and the α7 Integrin/GapDH levels were quantitated and graphed for both DMSO and SU9516 treatments (FIG. 8B).
Figure 8B:
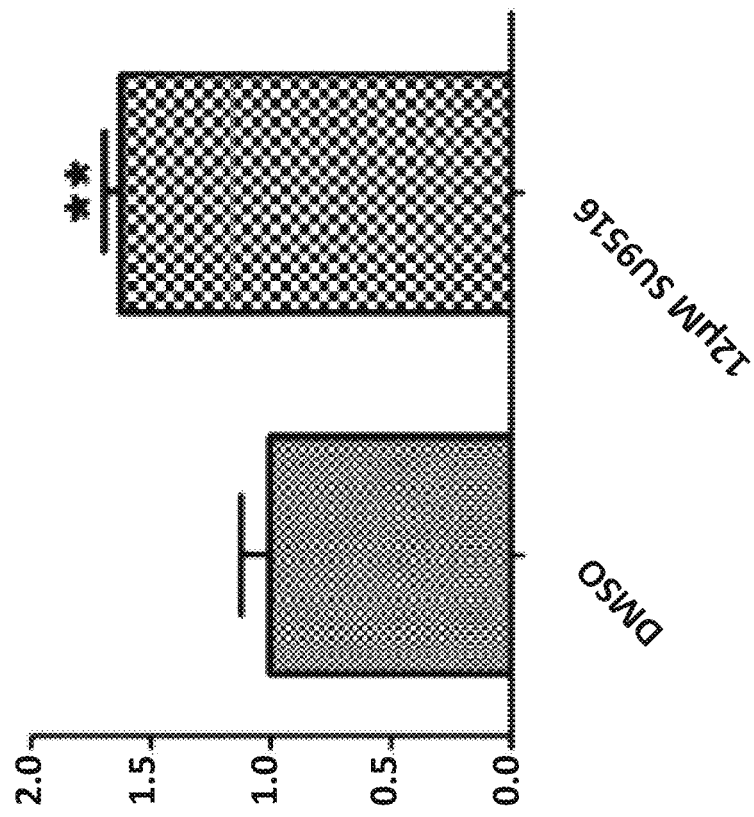
Figure 9:
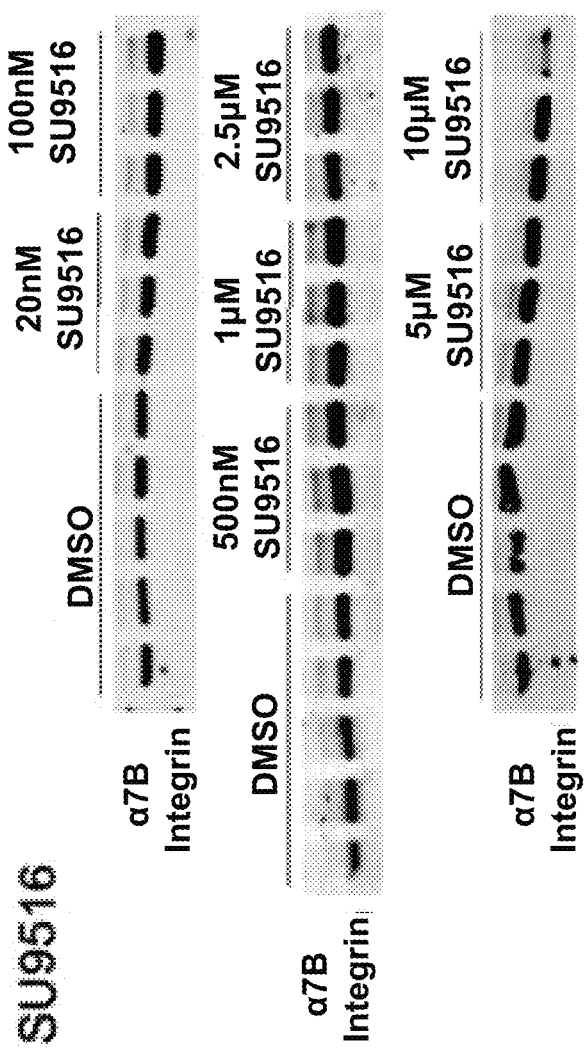
FIG. 9 is an image of results obtained for various different compounds disclosed herein and their effects on α7 integrin levels in human DMD myotubes.
Figure 9:
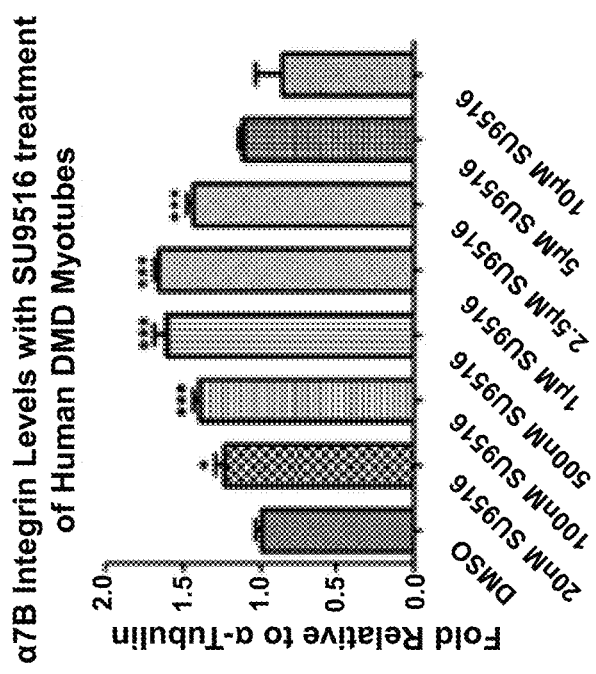
Figure 9:
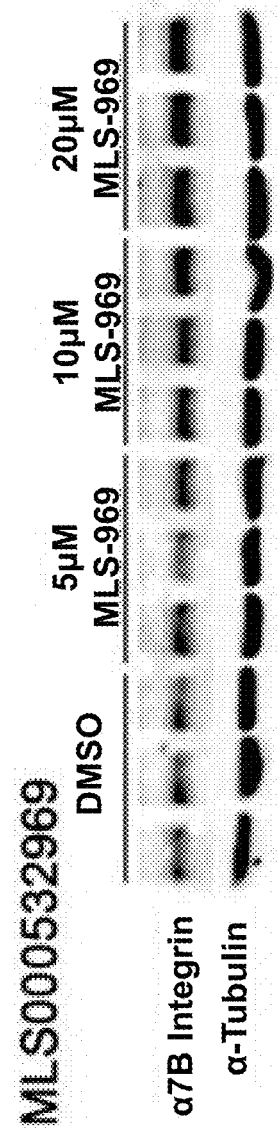
Figure 9:
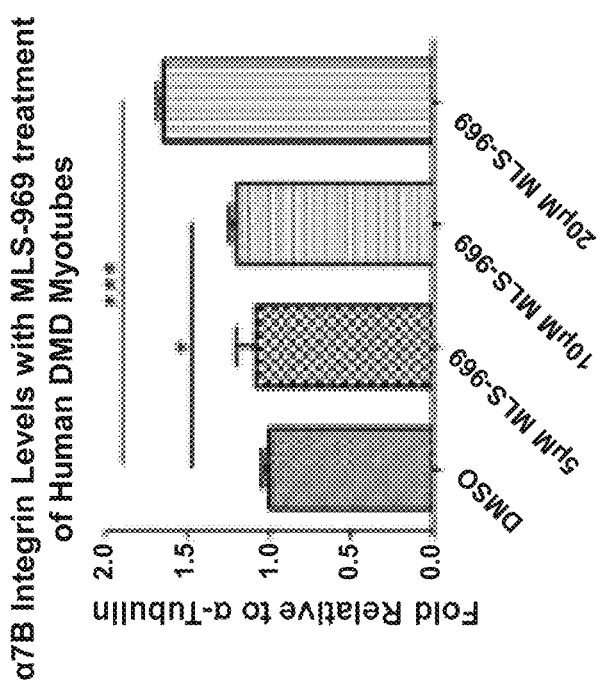
Figure 9:
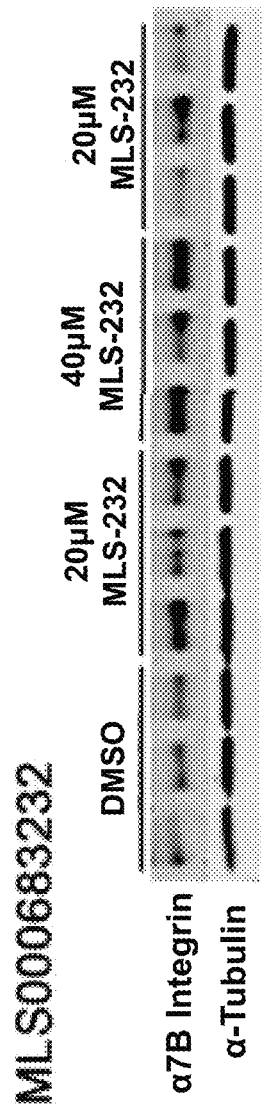
Figure 9:
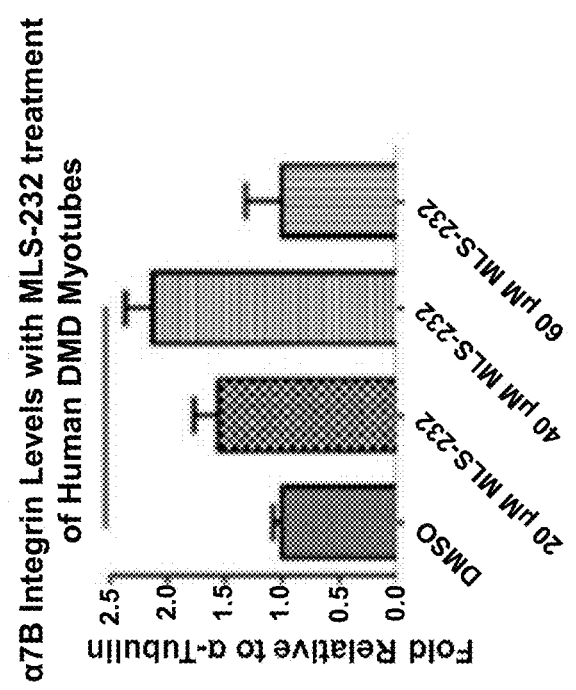
Figure 9:
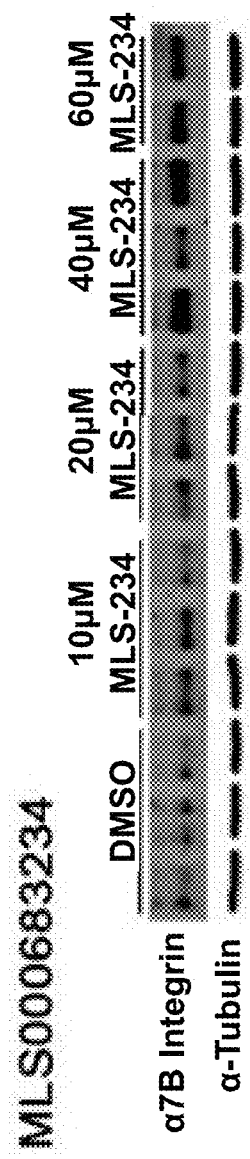
Figure 9:
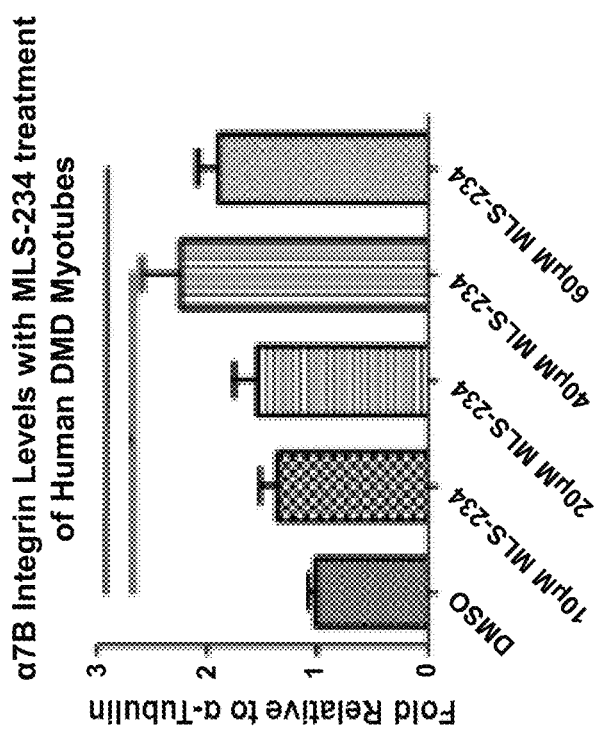
Figure 9:
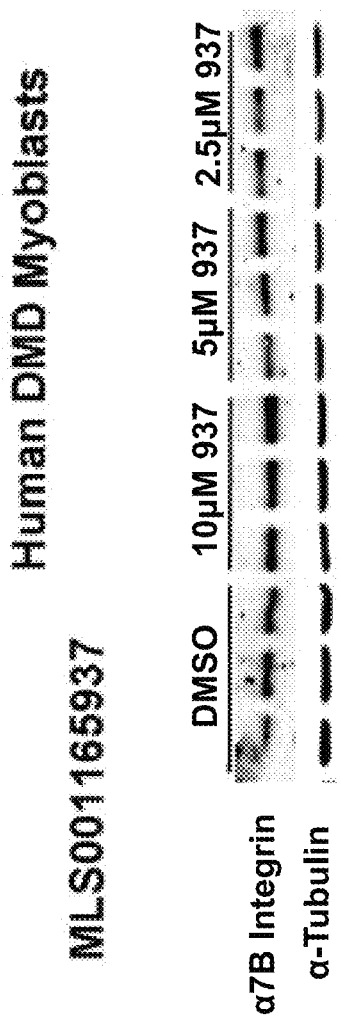
Figure 9:
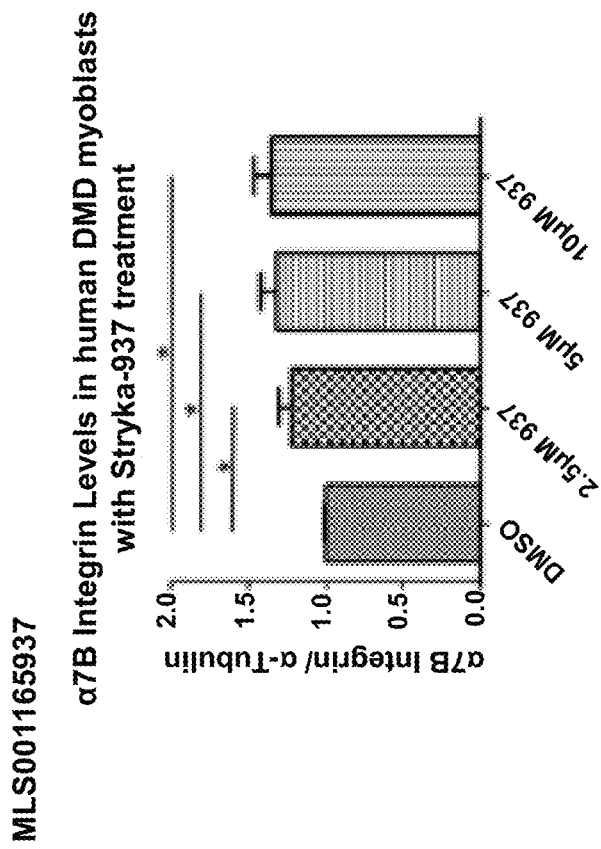

In order to confirm the on-target activity of SU9516, C2C12 myotubes were treated with either DMSO control or 12 μM SU9516 for 48 hours. Western blot analysis of the myotube protein extracts were then performed for α7B Integrin and normalized to GAPDH (FIGS. 8A and 8B). SU9516 treated myotubes displayed an increase of approximately 1.6-fold in α7 Integrin protein levels compared to DMSO treated controls (FIGS. 8A and 8B). These results confirm the myogenic cell-based assay had successful identified novel small molecules that would target an increase in α7 integrin in skeletal muscle.

Duchenne muscular dystrophy is a fatal neuromuscular disease for which there is currently no cure and limited treatment options. Studies have shown that the α7β1 integrin is a major modifier of disease progression in mouse models of DMD. Loss of the α7 integrin in dystrophin deficient mdx mice results in more severe muscle disease, while transgenic or viral mediated expression of the α7 integrin can rescue mouse models of DMD. These results support the hypothesis that the α7β1 integrin is major modifier of disease progression in DMD. In support of the idea that drug-based modulation of α7β1 integrin in skeletal muscle may serve as a therapeutic avenue for DMD, it has been shown that prednisone, the current front line therapy for DMD, acts to increase laminin-α2 and α7β1 integrin in the muscles of mdx mice, GRMD dog and DMD patient cells. Together these preclinical studies indicate the α7 integrin is a "druggable" target for the treatment of DMD.

In this study a muscle cell-based assay was used to identify small molecules that promote an increase in α7 integrin in myogenic cells. A screen of FDA-approved and novel compound libraries identified several chemical platforms which may be promising for the treatment of DMD. From the FDA-approved libraries it was identified that the Fe-chelating compounds Ciciopirox and Deferoxamine as α7β1 integrin enhancers. In addition 2,2-dipyridyl which is within this same compound family was tested using the muscle cell-based assay and was confirmed to also increase α7 integrin levels. Since Ciclopirox, deferoxamine and 2,2-dipyridyl have been shown to increase stability of the transcription factor hypoxia inducible factor-1 (HIF-1) by preventing its breakdown, bioinformatic analysis was performed on the α7 integrin promoter. Analysis of a 2.8 kb fragment of the proximal α7 integrin promoter sequence using MATINSPECTOR (Genomatix) revealed the presence of a HIF-1 binding site and flanking sequences that promote HIF-1 binding. These results indicate Ciclopirox, Deferoxamine and 2,2-dipyridyl act to increase α7 integrin gene expression by inhibiting proteosomal breakdown of HIF-1 in muscle cells resulting in increased cellular levels of HIF-1 protein in skeletal muscle. Interestingly, increased HIF-1 levels are associated with increased angiogenesis and therefore not only would these drugs increase membrane stability through increased α7 integrin gene expression, but they may also increase muscle vascularization, improving blood flow and reducing the ischemia associated with dystrophic muscle.

To identify small novel molecular probes that increase the α7 integrin in skeletal muscle, the MLSMR at the National Chemical and Genomics Center (NCGC) at NIH was screened. Using the muscle cell-based assay 380,000 compounds in the Molecular Library and Small Molecule Repository (MLSMR) were screened using dose-response quantitative high through-put screening (qHTS). From the primary screen, 1,500 hit compounds were identified as actives. Analysis of these compounds using the hierarchical cluster approach revealed 321 clusters in which 17 clusters contained more than 10 compounds and 210 singletons. From these studies 500 compounds were cherry-picked for further testing which included confirmation of activity in the primary screening assay and secondary assays which included β-galactosidase reporter stabilizer, myostatin and cell-toxicity assays. In addition primary HTS active compounds were tested to determine if they increased β-galactosidase reporter in myoblasts and myotubes. From these counter-screens seven novel hit compounds were selected for further analysis to determine whether they increase the α7 integrin in a dose-dependent fashion. Analysis in mouse and DMD human muscle cells revealed that all seven increased both α7 integrin transcript and protein levels. These compounds gave a maximal increase in α7 integrin protein in human DMD muscle cells which would be in the therapeutic range as predicted from transgenic mouse studies.

Studies of the seven novel α7 integrin enhancing compounds showed that two molecular platforms are related, while the other compounds are unrelated to each other. One compound, SU9156 which was used as a positive control in the screen is currently in clinical trials as a potential anti-cancer therapeutic. SU9516 (3-[1-(3H-imidazol-4-yl)-meth-(Z)-ylidene]-5-methoxy-1,3-dihydro-indol-2-one) is a 3-substituted-indolinone compound that binds to cdk2 and selectively inhibits its catalytic kinase activity. X-ray crystallography studies showed that the small molecule compound inhibited cdk2/cyclin A through competitive inhibition of ATP. In human leukemic cells, SU9516 caused the pronounced down-regulation of the anti-apoptotic protein Mcl-1 through transcriptional repression, increased proteasomal degradation, inhibition of RNA Pol II CTD phosphorylation and oxidative damage. Thus, SU9516 has demonstrated its potential as a viable pharmacological drug for the development of anti-neoplastic therapeutics and has reached clinical trials for the same. The molecular mechanism by which SU9516 enhances integrin is currently unknown. SU9516 has also been reported to inhibit glycogen synthase kinase 3β (GSK-3β), which is involved in normal cell death. Levels of inactive p-S9-GSK3β are reduced and total GSK3β is elevated in the muscles of patients with myotonic dystrophy type 1 (DM1). Inhibition of GSK3β in both DM1 cell culture and mouse models reduced muscle weakness and myotonia in DM1 mice. Hence, compounds normalizing GSK3β activity might be beneficial for improving muscle function in patients with DM1.

Using a novel muscle cell-based assay an exhaustive screen of small molecule compound libraries has been conducted and identified several FDA-approved and novel molecules that increase α7 integrin in skeletal muscle. These small molecules can serve as molecular probes to dissect the signaling pathways that regulate levels of the α7β1 integrin in skeletal muscle. In addition these molecules may serve as platforms to develop novel therapeutics that target an increase in α7 integrin for the treatment of muscular dystrophy.

Example 4

This example describes methods for identifying and analyzing suitable analog compounds useful for the methods and assays disclosed herein. In one embodiment, Stryka-969 was identified as a top "hit" from of the over 400,000 compounds screened using the assay disclosed herein due to its efficacy, large range of potency, and its lack of cellular toxicity (REF paper in prep). The chemical structure of Stryka-969 along with the dose-response curve generated in ITGA7$^{+/LacZ}$ myotubes is illustrated FIG. 7B. While Stryka-969 also functions equally well in myoblasts, the therapeutic target for enhanced α7 integrin protein are differentiated myofibers and thus this example focuses primarily on the Stryka-969 analogs function in ITGA7$^{+/LacZ}$ myotubes. The maximum increase of ~2-fold should translate into a 3-fold change in ITGA7 transcription due to the heterogenetic nature of the assay and single reporter. This increase is well within the therapeutic range previously reported for dystrophic mice.

Figure 10:
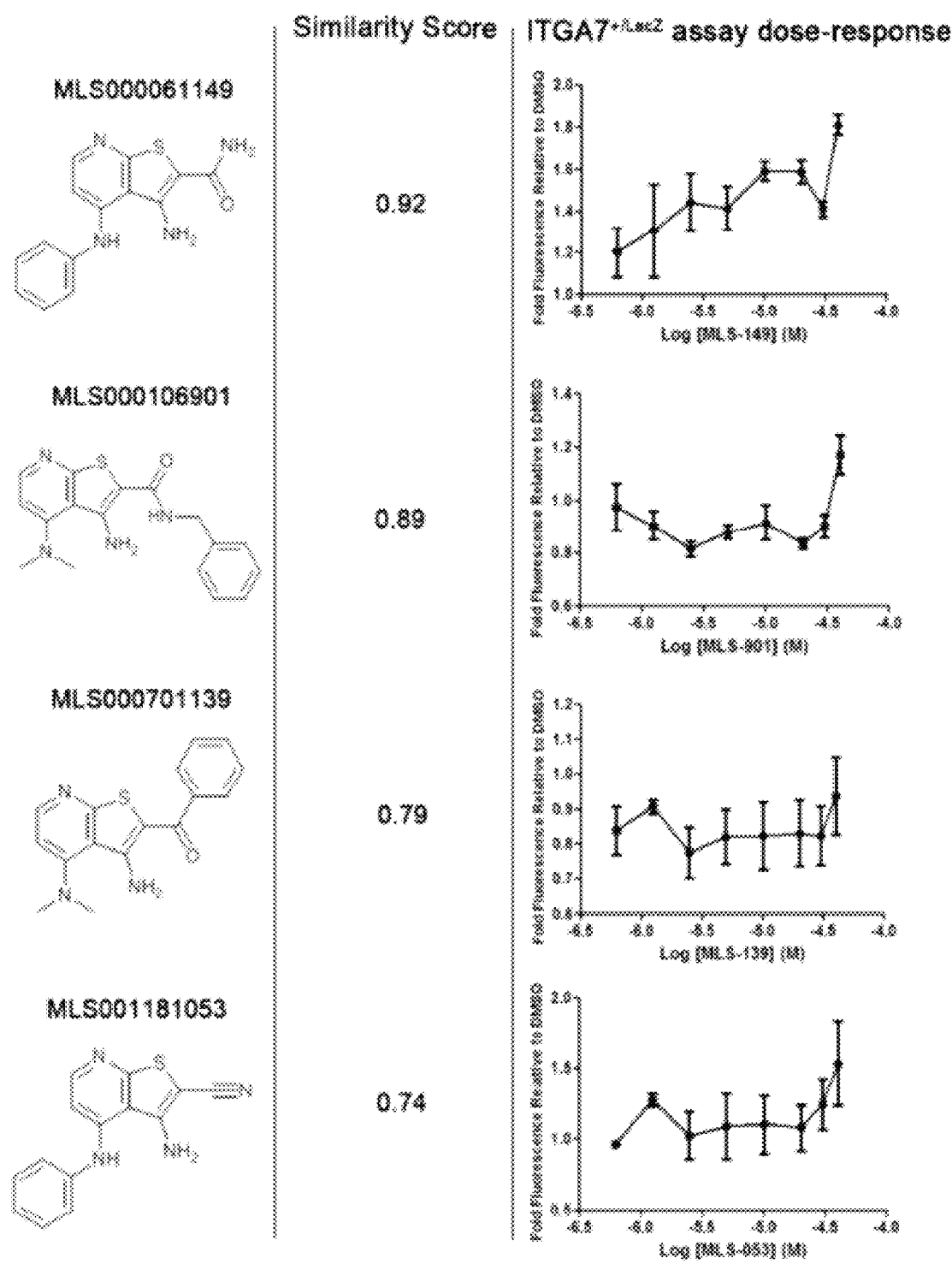
FIG. 10 is an image illustrating chemical structures and names, similarity score relative to Stryka-969, and ITGA7$^{+/LacZ}$ myotube dose-response for 4 compounds with similar structures to Stryka-969.

FIG. 10 illustrates results obtained from some analogs of Stryka-969. These compounds were scored based on their structural similarity to Stryka-969 using the Tanimoto coefficient which measures the similarity between two. These compounds were then used to treat ITGA7$^{+/LacZ}$ myotubes at eight different concentrations in order to produce dose-response curves (FIG. 10; n=3/concentration). The dose-response results suggest that the amide group may help increase α7 Integrin. This group is maintained in MLS000061149, which displays similar activity in the Burkin assay to the parent compound Stryka-969 (FIG. 10). The other compounds were less similar to Stryka-969 and displayed little to no relevant response (FIG. 10). Together, these studies indicate that SAR analysis will further elucidate the functional groups capable of maximizing the α7 integrin enhancing activity of this compound platform.

Figure 11:
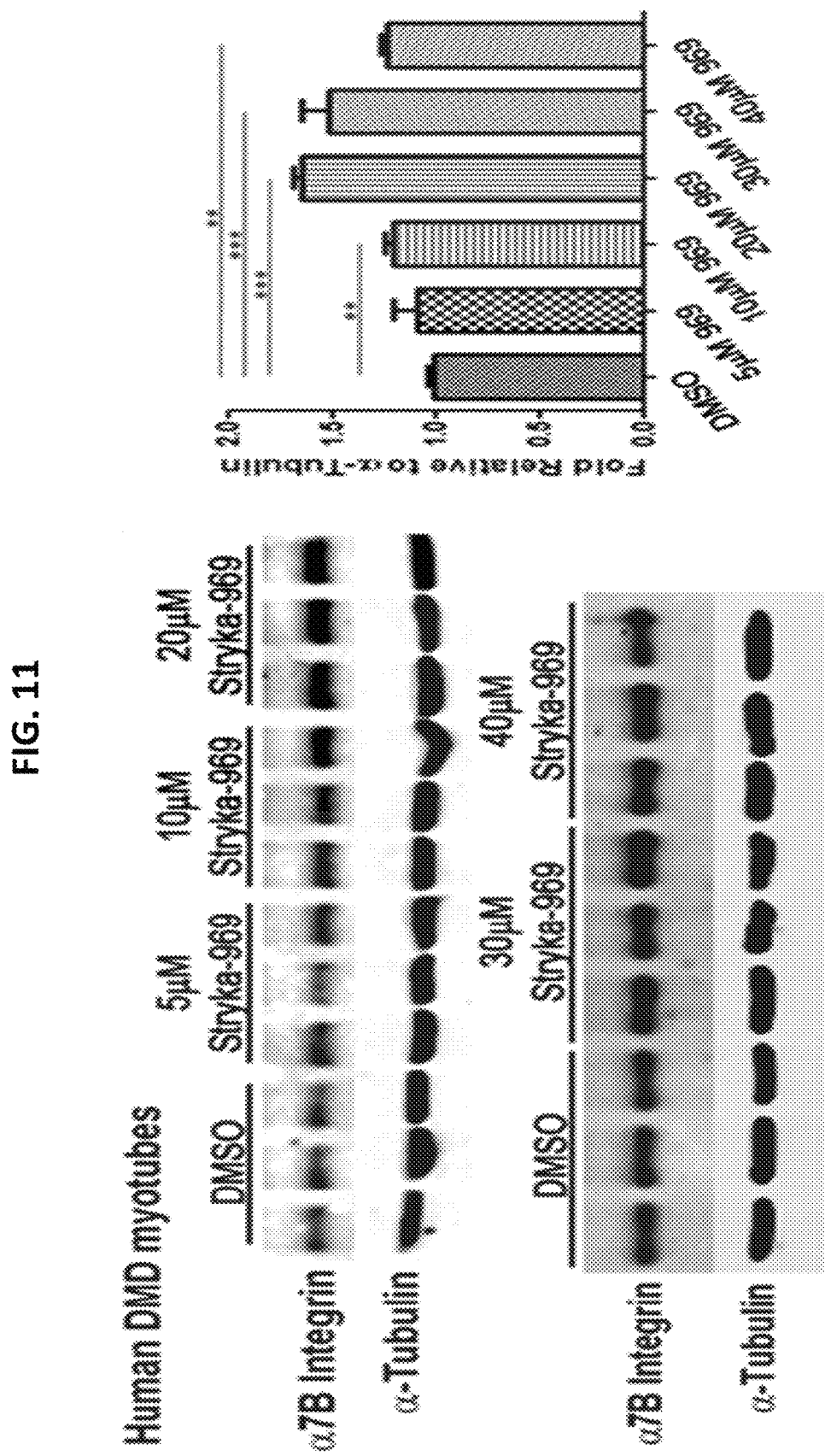
FIG. 11 is an image of a Western blot analysis for α7 Integrin and α-tubulin, quantitated and graphed wherein significance was determined by unpaired t-test with  p<0.01 and * p<0.001.

To assess the on-target effects of Stryka-969, cultured telomerase-expressing Human DMD myotubes were used. After a minimum of 10 days of differentiation, myotubes were treated with either DMSO or varying concentrations of Stryka-969. After 48 hours the media was aspirated and the myotubes were washed in PBS and then scraped into ice-cold RIPA buffer with protease inhibitors. After protein concentration was determined by BCA, standard. SDS-PAGE and western blotting procedures for α7B Integrin and α-Tubulin were followed. A maximum increase of ~1.7-fold over DMSO levels with a treatment of 20 μM Stryka-969 (FIG. 11) was obtained. This shows that Stryka-969 is an α7 integrin enhancing compound with strong therapeutic potential for the treatment of DMD patients.

Pre-clinical assessment of therapeutic small molecules, including ADMET studies, can help to prioritize small molecules with the highest therapeutic value. A step to ensuring that small molecules will be therapeutically on-target in patients is to use cultured Human patient cells for assessment. This ensures that given biologic availability has a conserved mechanism of action between species and the treatment should effectively produce the desired effect in the specific tissue.

Briefly, either 1 mg or 5 mg of each analog are suspended in DMSO at 10 μM concentration. Working plates are made to give a minimum of 8-point dose response per compound. Drugs are added to ITGA7$^{+/LacZ}$ myotubes for 48 hours, at which time the FDG assay is performed as previously described. Using such analogs of Stryka-969 that achieve a minimum of 1.5-fold increase in the Burkin Lab ITGA7$^{+/LacZ}$ based assay, 6 cm plates with cultured Human DMD myotubes are treated with a range of concentrations based on the dose-response discussed above (n=3/concentration). After 48 hours the myotubes are washed and lysed for western blot analysis. Several proteins, including α7B and β1A Integrins, Laminin-β2, and utrophin levels, are assessed using standard western blotting techniques. If compounds fail to produce a minimum of 1.5-fold α7 integrin increase they may be eliminated from further studies. The behavior of Stryka-969 on the cultured Human DMD myotubes discussed herein indicates that analogs of this compound may lead to increased α7 integrin in the Human cells. Western blots using a broad range of concentrations can be used to avoid missing an optimal dose for a small molecule, which could occur if the EC$_{100}$ concentration from the initial assay for use in the human DMD myotubes is solely relied upon.

The activity of other α7 integrin compounds also can be determined using β-galactosidase cleavage of the non-fluorescent compound fluorescein di-β-D-galactopyranoside (FDG) to fluorescein in both myoblasts and myotubes. For myoblast assays using analog compounds, 1×10$^4$ cells are plated on 96 well black well culture plates and cells grown for 24 hours. The parent and analog compounds are added and the FDG bioassay is performed 48 hours after the addition of compounds. For myotube assays. 2.5×10$^5$ myoblasts on 96 well black cell culture plates are grown for 24 hours. Cell differentiation medium is added daily and after 7 days of differentiation, and compounds are added to myotubes and incubated for 48 hours. β-galactosidase levels are then be quantified using the FDG assay. These assays re performed in triplicate for each compound screened. For each assay the parent compound and analogs are added to cells with a dose range from 0.5-20 μM in DMSO and a DMSO only control is added for each assay. The dose curve class and EC$_{50}$ for each compound is calculated, plotted and compared to the profile of the parent hit molecule. Analog molecules that show activity (both positive and negative) in myoblasts and myotubes inform the SAR for each molecular platform series. In parallel microsome and plasma stability, permeability and solubility of confirmed lead compounds able to increase α7 integrin in myotubes is also evaluated to help determine the best templates for further pharmacokinetic evaluation. Lead compounds are selected for further studies based on the most potent activity in myotubes (the target tissue) and optimal physical and structural drug-like properties in accordance with Lipinski's Rules.

Positive analogs are then assessed to determine whether they increase α7 integrin transcript and protein using mouse C2C12 and human DMD myogenic cells. For myotube analysis, C2C12 and DMD myoblasts are differentiated in DMEM supplemented with 2% horse serum and 50U/ml of penicillin/streptomycin. Compounds or DMSO are added to C2C12 and DMD myoblasts and myotubes at EC$_{100}$ dose calculated from the FDG screen above. All studies are done in triplicate, and RNA is extracted using TriZol reagent. RNA is reverse transcribed to cDNA using a Superscript II kit (Invitrogen). Primer sequences are used that specifically amplify mouse or human transcripts using SYBR Green technology and quantitative RT-PCR, and reactions carried out in an ABI Prism 7000 Sequence Detection System. The C$_T$ value and a standard curve from a dilution series of cDNA from non-treated cells is calculated by the accompanying ABI Prism 7000 SDS software. Transcripts are normalized to 18S rRNA transcript and reported as fold change from control cells. Experiments are performed in triplicate and statistical significance (p<0.05) determined using ANOVA.

Immunoblot analysis is used to assess the protein level expression in treated and control cells. C2C12 and human DMD myoblasts and myotubes are cultured in triplicate experiments and treated with lead compounds or DMSO as described above. Cells are harvested using a cell scraper and extracted proteins. Extracted protein is quantified by a Bradford assay. Equal amounts of total protein are separated on SDS-PAGE gels at 40 mA for 1 hour and protein is transferred to nitrocellulose membranes. Blots are incubated with Ponceau S to confirm equal protein loading. Rabbit anti-α7 integrin antibodies, A2-345 and B2-347, at 1:500 with will be used to detect mouse and human α7A and α7B integrin respectively. Bands are scanned with an Odyssey Infrared Imaging System. Blots are re-probed with an anti-GAPDH to normalize band intensities for protein loading. A LiCoR Odyssey scanner and software is used to quantify band intensities and statistical significance (p<0.05) is determined using ANOVA.

The pharmacokinetic properties of the compounds having desirable drug-like structures are analyzed for in vivo activity. Three 8-week-old C57Bl/6 mice by will be treated by intraperiontoneal injection (i.p) with either the control solute or the compounds under investigation at the $EC_{100}$ determined in the examples discussed above. At 0 mins (before administration) and then 30 mins, 1 hr, 2 hrs, 4 hrs, 8 hrs, 12 hrs and 24 hrs after compound administration, 50 μL of blood is collected by retro-orbital bleeds and serum isolated by centrifugation. After administration, animals re observed and signs of toxicity including weight loss, convulsions, uncoordinated movement, torpidity, temperature changes, dispenia or death. In a separate series of pharmacokinetic experiments to assess muscle tissue levels of analogs, three 8-week-old C57Bl/6 mice are treated control solute or the compounds at the same time points listed above. At each time point mice are humanely euthanized by CO2 inhalation and the gastroenemius, TA, heart, intestine and diaphragm muscles dissected for analysis. The muscle and intestine is extracted to determine the levels of each lead analog within the tissue.

Purified compounds serve as a control to identify the small molecule signature after LC-MS/MS analysis. Pharmacokinetic profiles include: serum half-life ($t_{1/2}$), Volume of distribution ($V_d$), drug concentration in serum ($C_0$ or $C_{SS}$), Elimination rate constant ($k_e$), Clearance (CL), Bioavailability (f), peak serum concentration ($C_{max}$) and time to reach $C_{max}$ ($t_{max}$). A lead compound with a suitable pharmacokinetic profile is then selected for further studies. Formulation is developed with the objective of developing a lead α7 integrin enhancing compound that can be orally administered. For experimental rigor, samples will be coded before analysis so those collecting data are blinded to the treatment group.

The pharmacokinetic profile for the lead compound identified above and the calculated optimal dose are used to determine if the on-target in vivo activity of the drug increases α7 integrin into the therapeutic range as determined by transgenic mouse studies. Off-target activity of the lead compound also will be examined. Three week-old mdx mice are administered with a suitable lead compound as determined using the above examples, or a vehicle by oral gavage daily for 14 days using dosing determined in pharmacokinetic studies. C57Bl/10 mice are included as wild-type controls. A minimum of 22 male mdx mice per experimental and control group are used as determined by Power analysis (Power=0.8, α=0.05 and r=0.5). Mice are weighed weekly and behavioral changes recorded. Mice are euthanized at 5 weeks-of-age and Tibialis anterior (TA), gastroenemius, diaphragm and cardiac muscles harvested. Expression of α7 and β1 integrin is quantified by qRT-PCR and western blots as discussed herein. For off-target activity, transcript levels of integrin α3, α5, α6 and extracellular matrix genes are quantified. Primers are used that specifically amplify these mouse transcripts using SYBR Green technology and quantitative RT-PCR reactions performed in an ABI Prism 7000 Sequence Detection System. The $C_T$ value for each is calculated using ABI Prism 7000 SDS software and transcripts normalized to 18S rRNA and reported as fold change from control tissue. Experiments are performed in triplicate and statistical significance (p<0.05) determined using ANOVA. Transcripts that change >2-fold are confirmed by western blot analysis.

To determine if the lead compound shows therapeutic benefit, a preliminary muscle histology study also is performed. Before harvesting tissue, mice are injected with Evans Blue dye (EBD) and histology performed for EBD uptake, percentage of myofibers with centrally located nuclei, inflammation, myofiber cross-sectional area and fibrosis as previously described. For experimental rigor, samples are coded before analysis so those collecting data will blinded to the treatment group. Data analyzed by ANOVA and a p-value<0.05 will be considered statistically significant.

These examples can be used to determine the PK/PD of a lead α7 integrin enhancing compound. The lead compound with favorable PK/PD is then assessed for on-target efficacy and off-target activity.

Statements of the Disclosure

Paragraph 1. A method for treating a subject with muscular dystrophy, comprising administering an effective amount of an α7β1 integrin modulatory agent to the subject with muscular dystrophy, wherein the α7β1 integrin modulatory agent is selected from any one or more of Formulas 1-16 and/or any one of or more of the compounds disclosed in Tables 1-16 and 18 and wherein the α7β1 integrin modulatory agent increases α7β1 integrin expression or activity as compared to α7β1 integrin expression or activity prior to treatment, thereby treating the subject with muscular dystrophy.

Paragraph 2. The method disclosed in the preceding paragraph, wherein the muscular dystrophy is merosin deficient congenital muscular dystrophy Type 1A (MDC1A), merosin deficient congenital muscular dystrophy Type 1D (MDC1D), limb-girdle muscular dystrophy (LGMD), Duchenne muscular dystrophy (DMD), Fukuyama congenital muscular dystrophy (FCMD) or Facioscapulohumeral muscular dystrophy (FHMD).

Paragraph 3. The method disclosed in any one of the preceding paragraphs wherein the muscular dystrophy is DMD, MDC1A or FCMD.

Paragraph 4. The method disclosed in any one of the preceding paragraphs, wherein the muscular dystrophy is DMD.

Paragraph 5. The method disclosed in any one of the preceding paragraphs, wherein the α7β1 integrin modulatory agent is administered with an additional therapeutic agent.

Paragraph 6. The method disclosed in the preceding paragraph, wherein the additional therapeutic agent is a costameric protein, a growth factor, satellite cells, stem cells, myocytes or an additional α7β1 integrin modulatory agent.

Paragraph 7. The method disclosed in paragraph 6, wherein the additional α7β1 integrin modulatory agent is laminin-111, a laminin-111 fragment, valproic acid, or a valproic acid analog, a different compound selected from Formulas 1-16 and/or Tables 1-16 and 18.

Paragraph 8. The method disclosed in any one of the preceding paragraphs, further comprising selecting a subject with muscular dystrophy.

Paragraph 9. The method disclosed in the preceding paragraphs, wherein selecting a subject with muscular dystrophy comprises diagnosing the subject with muscular dystrophy prior to administering an effective amount of the α7β1 integrin modulatory agent to the subject.

Paragraph 10. A method of enhancing muscle regeneration, repair, or maintenance in a subject, comprising:

administering an effective amount of an α7β1 integrin modulatory agent to the subject in need of muscle regeneration, repair, or maintenance, wherein the α7β1 integrin modulatory agent is selected from any one or more of Formulas 1-16 and/or any one of or more of the compounds disclosed in Tables 1-16 and 18 and wherein the α7β1 integrin modulatory agent increases α7β1 integrin expression or activity as compared to α7β1 integrin expression or activity prior to treatment, thereby enhancing muscle regeneration, repair or maintenance in a subject.

Paragraph 11. The method of enhancing muscle regeneration, repair, or maintenance in a subject of the preceding paragraph, wherein the α7β1 modulatory agent is administered prior to the subject experiencing muscle damage or disease.

Paragraph 12. The method of enhancing muscle regeneration, repair, or maintenance in a subject of any one of the preceding paragraphs, wherein the method is a method of enhancing muscle maintenance in a subject.

Paragraph 13. The method of enhancing muscle regeneration, repair, or maintenance in a subject of any one of the preceding paragraphs, wherein the α7β1 integrin modulatory agent is administered to the subject prior to the subject exercising.

Paragraph 14. The method of enhancing muscle regeneration, repair, or maintenance in a subject of any one of the preceding paragraphs, wherein the α7β1 integrin modulatory agent is administered to a subject at risk of acquiring a muscle disease or damage.

Paragraph 15. The method of enhancing muscle regeneration, repair, or maintenance in a subject of any one of the preceding paragraphs, further comprising selecting a subject in need of enhancing muscle regeneration, repair, or maintenance.

Paragraph 16. The method of enhancing muscle regeneration, repair, or maintenance in a subject of the preceding paragraph, wherein selecting a subject in need of enhancing muscle regeneration, repair, or maintenance comprises diagnosing the subject with a condition characterized by impaired muscle regeneration prior to administering an effective amount of the α7β1 integrin modulatory agent to the subject.

Paragraph 17. The method of enhancing muscle regeneration, repair, or maintenance in a subject of any one of the preceding paragraphs, wherein selecting a subject in need of enhancing muscle regeneration, repair, or maintenance comprises diagnosing the subject with a condition characterized by impaired production of a component of α7β1 integrin prior to administering an effective amount of the α7β1 integrin modulatory agent to the subject.

Paragraph 18. The method of enhancing muscle regeneration, repair, or maintenance in a subject of any one of the preceding paragraphs, wherein the α7β1 integrin modulatory agent is administered with an additional therapeutic agent.

Paragraph 19, The method of enhancing muscle regeneration, repair, or maintenance in a subject of the preceding paragraph, wherein the additional therapeutic agent is a costameric protein, a growth factor, satellite cells, stem cells, myocytes or an additional α7β1 integrin modulatory agent.

Paragraph 20. The method of enhancing muscle regeneration, repair, or maintenance in a subject of the preceding paragraph, wherein the additional α7β1 integrin modulatory agent is laminin-111, a laminin-111 fragment, valproic acid, or a valproic acid analog, or a different compound selected from Formulas 1-16 and/or Tables 1-16 and 18.

Paragraph 21. A method of prospectively preventing or reducing muscle injury or damage in a subject, comprising, administering an effective amount of an α7β1 integrin modulatory agent to the subject wherein the α7β1 integrin modulatory agent is selected from any one or more of Formulas 1-16 and/or any one or more of the compounds disclosed in Tables 1-16 and 18 and wherein the α7β1 integrin modulatory agent increases α7β1 integrin expression or activity as compared to α7β1 integrin expression or activity prior to treatment, thereby prospectively preventing or reducing muscle injury or damage in the subject.

Paragraph 22. The method of the preceding paragraph, wherein the subject is at risk of developing a muscle injury or damage.

Paragraph 23. The method of prospectively preventing or reducing muscle injury or damage in a subject in any one of the preceding paragraphs, wherein the α7β1 integrin modulatory agent is administered with an additional therapeutic agent.

Paragraph 24. The method of prospectively preventing or reducing muscle injury or damage in a subject of the preceding paragraph, wherein the additional therapeutic agent is a costameric protein, a growth factor, satellite cells, stem cells, myocytes or an additional α7β1 integrin modulatory agent.

Paragraph 25. The method of prospectively preventing or reducing muscle injury or damage in a subject of the preceding paragraph, wherein the additional α7β1 integrin modulatory agent is laminin-111, laminin-111 fragment, valproic acid, or a valproic acid analog, or a different compound selected from Formulas 1-16 and/or Tables 1-16 and 18.

Paragraph 26. A method of enhancing α7β1 integrin expression, comprising contacting a cell with an effective amount of an α7β1 integrin modulatory agent, wherein the α7β1 integrin modulatory agent is selected from any one or more of Formulas 1-16 and/or any one or more of the compounds disclosed in Tables 1-16 and 18 and wherein the α7β1 integrin modulatory agent increases α7β1 integrin expression in the treated cell relative to α7β1 integrin expression in an untreated cell, thereby enhancing α7β1 integrin expression.

Paragraph 27. The method of the preceding paragraph, wherein the cell is a muscle cell.

Paragraph 28. The method of enhancing α7β1 integrin expression of any of the preceding paragraphs, wherein the muscle cell is present in a mammal, and wherein contacting the cell with an agent comprises administering the agent to the mammal.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating a subject with muscular dystrophy, comprising administering an effective amount of an α7β1 integrin modulatory agent to the subject with muscular dystrophy, wherein the α7β1 integrin modulatory agent is MLS000534926-01

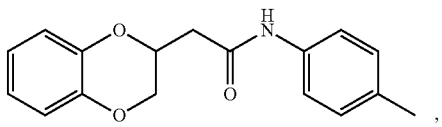 [SMILES: Cc1ccc(NC(=O)CC2COc3ccccc3O2)cc1]

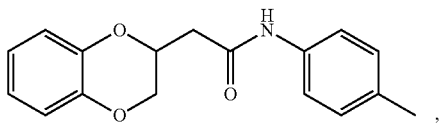 [SMILES: Cc1ccc(NC(=O)CC2COc3ccccc3O2)cc1]

and wherein the α7β1 integrin modulatory agent increases α7β1 integrin expression or activity as compared to α7β1 integrin expression or activity prior to treatment, thereby treating the subject with muscular dystrophy.

2. The method of claim 1, wherein the muscular dystrophy is merosin deficient congenital muscular dystrophy Type 1A (MDC1A), merosin deficient congenital muscular dystrophy Type 1D (MDC1D), limb-girdle muscular dystrophy (LGMD), Duchenne muscular dystrophy (DMD), Fukuyama congenital muscular dystrophy (FCMD) or Facioscapulohumeral muscular dystrophy (FHMD).

3. The method of claim 2, wherein the muscular dystrophy is DMD, MDC1A or FCMD.

4. The method of claim 2, wherein the muscular dystrophy is DMD.

5. The method of claim 1, wherein the α7β1 integrin modulatory agent is administered with an additional therapeutic agent.

6. The method of claim 5, wherein the additional therapeutic agent is a costameric protein, a growth factor, satellite cells, stem cells, myocytes or an additional α7β1 integrin modulatory agent.

7. The method of claim 6, wherein the additional α7β1 integrin modulatory agent is laminin-111, a laminin-111 fragment, valproic acid, or a valproic acid analog.

8. The method of claim 1, further comprising selecting a subject with muscular dystrophy.

9. The method of claim 8, wherein selecting a subject with muscular dystrophy comprises diagnosing the subject with muscular dystrophy prior to administering an effective amount of the α7β1 integrin modulatory agent to the subject.

10. A method of enhancing muscle regeneration, repair, or maintenance in a subject, comprising:
administering an effective amount of an α7β1 integrin modulatory agent to the subject in need of muscle regeneration, repair, or maintenance, wherein the α7β1 integrin modulatory agent is MLS000534926-01 wherein the α7β1 integrin modulatory agent increases α7β1 integrin expression or activity as compared to α7β1 integrin expression or activity prior to treatment, thereby enhancing muscle regeneration, repair or maintenance in a subject.

11. The method of claim 10, wherein the α7β1 modulatory agent is administered prior to the subject experiencing muscle damage or disease.

12. The method of claim 10, wherein the method is a method of enhancing muscle maintenance in a subject.

13. The method of claim 12, wherein the α7β1 integrin modulatory agent is administered to the subject prior to the subject exercising.

14. The method of claim 13, wherein the α7β1 integrin modulatory agent is administered to a subject at risk of acquiring a muscle disease or damage.

15. The method of claim 10, further comprising selecting a subject in need of enhancing muscle regeneration, repair, or maintenance.

16. The method of claim 15, wherein selecting a subject in need of enhancing muscle regeneration, repair, or maintenance comprises diagnosing the subject with a condition characterized by impaired muscle regeneration prior to administering an effective amount of the α7β1 integrin modulatory agent to the subject.

17. The method of claim 15, wherein selecting a subject in need of enhancing muscle regeneration, repair, or maintenance comprises diagnosing the subject with a condition characterized by impaired production of a component of α7β1 integrin prior to administering an effective amount of the α7β1 integrin modulatory agent to the subject.

18. The method of claim 10, wherein the α7β1 integrin modulatory agent is administered with an additional therapeutic agent.

19. The method of claim 18, wherein the additional therapeutic agent is a costameric protein, a growth factor, satellite cells, stem cells, myocytes or an additional α7β1 integrin modulatory agent.

20. The method of claim 19, wherein the additional α7β1 integrin modulatory agent is laminin-111, a laminin-111 fragment, valproic acid, or a valproic acid analog.

* * * * *